United States Patent
Kim

(10) Patent No.: US 11,953,501 B2
(45) Date of Patent: Apr. 9, 2024

(54) COMPOSITIONS AND METHODS TO DETECT GASTROINTESTINAL DISEASE

(71) Applicant: The Board of Supervisors of Louisiana State University and Agricultural and Mechanical College, Baton Rouge, LA (US)

(72) Inventor: Sunyoung Kim, New Orelans, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

(*) Notice: Subject to any disclaimer, the term of this patent is extended or adjusted under 35 U.S.C. 154(b) by 227 days.

(21) Appl. No.: 17/428,416

(22) PCT Filed: Feb. 4, 2020

(86) PCT No.: PCT/US2020/016646
§ 371 (c)(1),
(2) Date: Aug. 4, 2021

(87) PCT Pub. No.: WO2020/163381
PCT Pub. Date: Aug. 13, 2020

(65) Prior Publication Data
US 2023/0036392 A1    Feb. 2, 2023

Related U.S. Application Data

(63) Continuation-in-part of application No. 16/267,120, filed on Feb. 4, 2019, now Pat. No. 11,493,515, which is a continuation-in-part of application No. PCT/US2017/045588, filed on Aug. 4, 2017.

(60) Provisional application No. 62/524,306, filed on Jun. 23, 2017, provisional application No. 62/467,487, filed on Mar. 6, 2017, provisional application No. 62/378,820, filed on Aug. 24, 2016, provisional application No. 62/371,131, filed on Aug. 4, 2016.

(51) Int. Cl.
*G01N 33/53* (2006.01)
*G01N 33/573* (2006.01)

(52) U.S. Cl.
CPC ..... *G01N 33/573* (2013.01); *G01N 2333/916* (2013.01); *G01N 2800/065* (2013.01); *G01N 2800/52* (2013.01)

(58) Field of Classification Search
None
See application file for complete search history.

(56) References Cited

U.S. PATENT DOCUMENTS

| | | |
|---|---|---|
| 10,781,470 B2 | 9/2020 | Malo |
| 2004/0157306 A1 | 8/2004 | Plowman et al. |
| 2008/0038759 A1 | 2/2008 | Keren et al. |
| 2010/0093552 A1 | 4/2010 | Panja |
| 2011/0142817 A1 | 6/2011 | Brands et al. |
| 2011/0206654 A1 | 8/2011 | Hodin et al. |
| 2012/0253771 A1* | 10/2012 | Col .................. G16Z 99/00 703/11 |

FOREIGN PATENT DOCUMENTS

EP    0274198    11/1989

OTHER PUBLICATIONS

Torzewski et al., Animal Models of C-Reactive Protein, Hindawl Publishing Corporation, Mediators of Inflammation, vol. 2014, 2014, pp. 1-7 (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992. (Year: 1992).*
Whitehouse et al., The Protective Role of Intestinal Alkaline Phosphatase in Necrotizing Enterocolitis, Journal or Surgical Research 163,2010, pp. 79-85. (Year: 2010).*
Beck et al., The Markov Process in Medical Prognosis, Med Decis Making vol. 3, No. 4, pp. 419-458, 1983. (Year: 1983).*
Molnar et al., Intestinal alkaline phosphatase in the colonic mucosa of children with inflammatory bowel disease, World Journal of Gastroenterology, Jul. 2012, vol. 18, Issue 25, pp. 3254-3259. (Year: 2012).*
Afrazi A, Sodhi CP, RichardsonW, et al. New insights into the pathogenesis and treatment of necrotizing enterocolitis: Toll-like receptors and beyond. Pediatr Res. 2011;69(3):183-188.
**Al-Rashida and Iqbal. Inhibition of alkaline phosphatase: an emerging new drug target. Minireviews in Medicinal Chemistry 15, 41-51, 2015.
**Amer M D, Hedlund E, Rochester J, Caplan M S. Platelet-activating factor concentration in the stool of human newborns: effects of enteral feeding and neonatal necrotizing enterocolitis. Biol Neonate. 2004; 85:159-66.
Arboleya, S., et al., Establishment and development of intestinal microbiota in preterm neonates. FEMS Microbiol Ecol, 2012. 79(3): p. 763-72.
Arboleya, S., et al., Intestinal microbiota development in preterm neonates and effect of perinatal antibiotics. J Pediatr, 2015. 166(3): p. 538-44.
Attridge JT, Herman AC, Gurka MJ, Griffin MP, McGahren ED, Gordon PV. Discharge outcomes of extremely low birth weight infants with spontaneous intestinal perforations. J Perinatol. 2006;26(1):49-54.
Bale JR, Chock PB, Huang CY. The nature of negative cooperativity in alkaline phosphatase: kinetic patterns contrary to the flip-flop model. J Biol Chem. 1980;255(18):8424-8430.
**Ballance, W. A., Dahms, B. B., Shenker, N. & Kliegman, R. M. Pathology of neonatal necrotizing enterocolitis: a ten-year experience. J Pediatr 117, S6-13 (1990).
Bates, D., et al., Fitting Linear Mixed-Effects Models Using lme4. Journal of Statistical Software, 2015. 67(1): p. 1-48.

(Continued)

*Primary Examiner* — Gary Counts
(74) *Attorney, Agent, or Firm* — Baker, Donelson, Bearman, Caldwell & Berkowitz, PC

(57) ABSTRACT

This invention comprises compositions and methods to determine the prognosis of necrotizing enterocolitis.

4 Claims, 53 Drawing Sheets

(56) References Cited

OTHER PUBLICATIONS

Battersby C, Longford N, Costeloe K, Modi N; UK Neonatal Collaborative Necrotising Enterocolitis Study Group. Development of a gestational age-specific case definition for neonatal necrotizing enterocolitis. JAMA Pediatr. 2017;171(3):256-263.
\*\*Bell M J, Ternberg J L, Feigin R D, Keating J P, Marshall R, Barton L, Brotherton T. Neonatal necrotizing enterocolitis. Therapeutic decisions based upon clinical staging. Ann Surg. 1978; 187:1-7.
Benjamin, D.K., Jr., et al., Safety and transparency of pediatric drug trials. Arch Pediatr Adolesc Med, 2009. 163(12): p. 1080-6.
\*\*Biesterveld B E, Koehler S M, Heinzerling N P, Rentea R M, Fredrich K, Welak S R, Gourlay D M. Intestinal alkaline phosphatase to treat necrotizing enterocolitis. J Surg Res. 2015; 196:235-40.
\*\*Bobkova, Ekaterina V., Tina Kiffer-Moreira, and Eduard A. Sergienko. "Modulators of intestinal alkaline phosphatase." Phosphatase Modulators. Humana Press, Totowa, NJ, 2013. 135-144.
Bokodi, G., et al., Association of interferon gamma T+874A and interleukin 12 p40 promoter CTCTAA/GC polymorphism with the need for respiratory support and perinatal complications in low birthweight neonates. Arch Dis Child Fetal Neonatal Ed, 2007. 92(1): p. F25-9.
\*\*Borgers M. The cytochemical application of new potent inhibitors of alkaline phosphatases. Journal of Histochemistry & Cytochemistry 21, 812-824.
Bose, A.K. and K.A. Janes, A high-throughput assay for phosphoprotein-specific phosphatase activity in cellular extracts. Mol Cell Proteomics, 2013. 12(3): p. 797-806, 1973.
Bossuyt PM, Cohen JF, Gatsonis CA, Korevaar DA; STARD group. STARD 2015: updated reporting guidelines for all diagnostic accuracy studies. Ann Transl Med. 2016;4(4):85.
Boycott, K.M., et al., Rare-disease genetics in the era of next-generation sequencing: discovery to translation. Nat Rev Genet, 2013. 14(10): p. 681-91.
Bradford, M.M., A rapid and sensitive method for the quantitation of microgram quantities of protein utilizing the principle of protein-dye binding. Anal Biochem, 1976. 72: p. 248-54.
Breslow, N. and D. Clayton, Approximate inference in generalized linear mixed models. Journal of the American Statistical Association, 1993. 88(421): p. 9-25.
Brody JP, Williams BA, Wold BJ, Quake SR. Significance and statistical errors in the analysis of DNA microarray data. Proc Natl Acad Sci U S A. 2002;99(20):12975-12978.
Buhimschi CS, Bhandari V, Hamar BD, et al. Proteomic profiling of the amniotic fluid to detect inflammation, infection, and neonatal sepsis. PLoS Med. 2007;4(1):e18. doi:10.1371/journal.pmed. 0040018.
Buhimschi CS, Buhimschi IA, Abdel-Razeq S, et al. Proteomic biomarkers of intraamniotic inflammation: relationship with funisitis and early-onset sepsis in the premature neonate. Pediatr Res. 2007;61(3):318-324. doi:10.1203/01.pdr.0000252439.48564.37.
Burnette WN. "Western blotting": electrophoretic transfer of proteins from sodium dodecyl sulfatepolyacrylamide gels to unmodified nitrocellulose and radiographic detection with antibody and radioiodinated protein A. Anal Biochem. 1981;112(2):195-203.
Center for Disease Control and Prevention. CDC/NHSN surveillance definitions for specific types of infections. In 2018 NHSN Patient Safety Component Manual. US Department of Health and Human Services National Healthcare SafetyNetwork, 2018 edition:17. 11-17.30.
\*\*Cetinkaya M, Ozkan H, Koksal N, Akaci O, Ozgur T. Comparison of the efficacy of serum amyloid A, C-reactive protein, and procalcitonin in the diagnosis and follow-up of necrotizing enterocolitis in premature infants. J. Pediatr Surg. 2011; 46:1482-9.
Chaaban H, Shin M, Sirya E, Lim YP, Caplan M, Padbury JF. Inter-alpha inhibitor protein level in neonates predicts necrotizing enterocolitis. J Pediatr. 2010;157(5):757-761. doi:10.1016/j.jpeds. 2010.04.075.

Chen, D.T., et al., Strategies for power calculations in predictive biomarker studies in survival data. Oncotarget, 2016. 7(49): p. 80373-80381.
\*\*Chu A, Hageman J R, Caplan M S. Necrotizing enterocolitis: predictive markers and preventive strategies. NeoReviews. 2013; 14:e113-e20.
Cohen JF, Korevaar DA, Altman DG, et al. STARD 2015 guidelines for reporting diagnostic accuracy studies: explanation and elaboration. BMJ Open. 2016;6(11):e012799.
Cole CR, Hansen NI, Higgins RD, et al; Eunice Kennedy Shriver National Institute of Child Health and Human Development's Neonatal Research Network. Bloodstream infections in very low birth weight infants with intestinal failure. J Pediatr. 2012;160(1):54-9.e2.
Collins, M.A., et al., Total protein is an effective loading control for cerebrospinal fluid western blots. J Neurosci Methods, 2015. 251: p. 72-82.
Consortium U. Reorganizing the protein space at the Universal Protein Resource (UniProt). Nucleic Acids Res. 2012;40(Database issue):D71-75.
Cooper, G.M. and J. Shendure, Needles in stacks of needles: finding disease-causal variants in a wealth of genomic data. Nat Rev Genet, 2011. 12(9): p. 628-40.
Corazziari E, Staiano A, Miele E, Greco L, Italian Society of Pediatric Gastroenterology H, Nutrition. Bowel frequency and defecatory patterns in children: a prospective nationwide survey. Clin Gastroenterol Hepatol. 2005;3(11):1101-1106.
\*\*Coursey C A, Hollingsworth C L, Wriston C, Beam C, Rice H, Bisset G, 3rd. Radiographic predictors of disease severity in neonates and infants with necrotizing enterocolitis. AJR Am J Roentgenol. 2009; 193:1408-13.
Cummings JH, Branch W, Jenkins DJ, Southgate DA, Houston H, James WP. Colonic response to dietary fibre from carrot, cabbage, apple, bran. Lancet. 1978;1(8054):5-9.
Cuna, A., L. George, and V. Sampath, Genetic predisposition to necrotizing enterocolitis in premature infants: current knowledge, challenges, and future directions. Semin Fetal Neonatal Med, 2018.
Dang, Q., S. Mazumdar, and P.R. Houck, Sample size and power calculations based on generalized linear mixed models with correlated binary outcomes. Comput Methods Programs Biomed, 2008. 91(2): p. 122-7.
Derikx JP, Evennett NJ, Degraeuwe PL, et al. Urine based detection of intestinal mucosal cell damage in neonates with suspected necrotising enterocolitis. Gut. 2007;56(10):1473-1475.
Di Napoli A, Di Lallo D, Perucci CA, et al. Inter-observer reliability of radiological signs of necrotising enterocolitis in a population of high-risk newborns. Paediatr Perinat Epidemiol. 2004;18(1):80-87. doi:10.1111/j.1365-3016.2003.00517.x.
\*\*Dictionary of Pharmacy, 2004, Dennis B. Worthen, Editor.
Eaton Simon et al: "Current research in necrotizing enterocolitis", Early Human Development, Shannon, IR, vol. 97, Feb. 28, 2016 (Feb. 28, 2016), pp. 33-39, XP029538630, ISSN: 0378-3782, DOI: 10.1016/J.EARLHUMDEV.2016.01.013.
Eaton, S.L., et al., Total protein analysis as a reliable loading control for quantitative fluorescent Western blotting. PLoS One, 2013. 8(8): p. e72457.
\*\*Eliakin R, Mahmood A, Alpers D H. Rat intestinal alkaline phosphatase secretion into lumen and serum is coordinately regulated. Biochim Biophys Acta. 1991; 1091:1-8.
Erickson AR, Cantarel BL, Lamendella R, et al. Integrated metagenomics/metaproteomics reveals human host-microbiota signatures of Crohn's disease. PLoS One. 2012;7(11):e49138.
\*\*Evennett N, Cerigioni E, Hall N J, Pierro A, Eaton S. Smooth muscle actin as a novel serologic marker of severe intestinal damage in rat intestinal ischemia-reperfusion and human necrotizing enterofolitis. J Surg Res. 2014; 191:323-30.
Evennett NJ, Hall NJ, Pierro A, Eaton S. Urinary intestinal fatty acid-binding protein concentration predicts extent of disease in necrotizing enterocolitis. J Pediatr Surg. 2010;45(4):735-740. doi:10. 1016/j.jpedsurg.2009. 09.024.
Evennett NJ, PetrovMS, Mittal A, Windsor JA. Systematic review and pooled estimates for the diagnostic accuracy of serological

(56) References Cited

OTHER PUBLICATIONS markers for intestinal ischemia.World J Surg. 2009;33(7):1374-1383. doi:10.1007/s00268-009-0074-7.
Jilling, T., et al., The roles of bacteria and TLR4 in rat and murine models of necrotizing enterocolitis. J Immunol, 2006. 177(5): p. 3273-82.
Joseph, P.D., J.C. Craig, and P.H. Caldwell, Clinical trials in children. Br J Clin Pharmacol, 2015. 79(3): p. 357-69.
**Kamkpanatkosol, R. et al. The relationship between reticulated platelets, intestinal alkaline phosphatase, and necrotizing enterocolitis. J Pediatr Surg 49, 273-276, doi:10.1016/j.jpedsurg.2013.11.037 (2014).
Kang, B.H., et al., Simultaneous profiling of 194 distinct receptor transcripts in human cells. Sci Signal, 2013. 6(287): p. rs13.
Kaufman D, Fairchild KD. Clinical microbiology of bacterial and fungal sepsis in verylow-birth-weight infants. Clin Microbiol Rev. 2004;17(3):638-680.
Kern, S.E., Challenges in conducting clinical trials in children: approaches for improving performance. Expert Rev Clin Pharmacol, 2009. 2(6): p. 609-617.
**Klemperer, Friedrich W., Joseph M. Miller, and Caroline J. Hill. "The inhibition of alkaline phosphatase by beryllium." Journal of Biological Chemistry 180.1 (1949): 281-8.
Kliegman, R.M. and M.C. Walsh, Neonatal necrotizing enterocolitis: pathogenesis, classification, and spectrum of illness. Curr Probl Pediatr, 1987. 17(4): p. 213-88.
**Knight et al. Non-invasive analysis of intestinal development in preterm and term infants using RNA-sequencing. 2014. Scientific Reports 4, 5453.
**Kosloske A M, Musemeche C A, Ball W S, Jr., Ablin D S, Bhattacharyya N. Necrotizing enterocolitis: value of radiographic findings to predict outcome. AJR A J Roentgenol. 1988; 151:771-4.
**Lalles J P. Luminal ATP: the missing link between intestinal alkaline phosphatase, the gut microbiota, and inflammation? Am J Physiol Gastrointest Liver Pysiol. 2014; 2306:G824-5.
Lalles JP. Intestinal alkaline phosphatase: multiple biological roles in maintenance of intestinal homeostasis and modulation by diet. Nutr Rev. 2010;68:323-32.
Laventhal, N., B.A. Tarini, and J. Lantos, Ethical issues in neonatal and pediatric clinical trials. Pediatr Clin North Am, 2012. 59(5): p. 1205-20.
Le Du, M.H., et al., Crystal structure of alkaline phosphatase from human placenta at 1.8 A resolution. Implication for a substrate specificity. J Biol Chem, 2001. 276(12): p. 9158-65.
Leaphart, C.L., et al., A critical role for TLR4 in the pathogenesis of necrotizing enterocolitis by modulating intestinal injury and repair. J Immunol, 2007. 179(7): p. 4808-20.
Lee, J.S., W.A. Kibbe, and R.L. Grossman, Data harmonization for a molecularly driven health system. Cell, 2018. 174(5): p. 1045-1048.
Lee, J.W., et al., Fit-for-purpose method development and validation for successful biomarker measurement. Pharm Res, 2006. 23(2): p. 312-28.
Leek JT, Scharpf RB, Bravo HC, et al. Tackling the widespread and critical impact of batch effects in high-throughput data. Nat Rev Genet. 2010; 11(10):733-739.
**Lehmann, F. G., Hufnagel, H. & Lorenz-Meyer, H. Fecal intestinal alkaline phosphatase: a parameter for toxic damage of the small intestinal mucosa. Digestion 21, 156-162 (1981).
Levine MN, Raines RT. Sensitive fluorogenic substrate for alkaline phosphatase. Anal Biochem. 2011;418(2):247-252.
**Lichtman J S, Marcobal A, Sonnenburg J L, Elias J E. Host-centric proteomics of stool: a novel strategy focused on intestinal responses to the gut microbiota. Mol Cell Proteomics. 2013; 12:3310-8.
Lin, P.W. and B.J. Stoll, Necrotising enterocolitis. Lancet, 2006. 368(9543): p. 1271-83.
Lin, P.W., T.R. Nasr, and B.J. Stoll, Necrotizing enterocolitis: recent scientific advances in pathophysiology and prevention. Semin Perinatol, 2008. 32(2): p. 70-82.

Livshits MA, Khomyakova E, Evtushenko EG, et al. Isolation of exosomes by differential centrifugation: Theoretical analysis of a commonly used protocol. Sci Rep. 2015;5:17319.
Mahowald MA, Rey FE, Seedorf H, et al. Characterizing a model human gut microbiota composed of members of its two dominant bacterial phyla. Proc Natl Acad Sci U S A. 2009;106(14):5859-5864.
Mai V, Young CM, Ukhanova M, et al. Fecal microbiota in premature infants prior to necrotizing enterocolitis. PLoS One. 2011;6(6):e20647. doi:10.1371/journal.pone.0020647.
**Malo M S. A high level of intestinal alkaline phosphatase is protective against type 2 diabetes mellitus irrespective of obesity. EBioMedicine. 2015; 2:2016-23.
**Malo, M. S. et al. Intestinal alkaline phosphatase preserves the normal homeostasis of gut microbiota. Gut 59, 1476-1484, doi:10.1136/gut.2010.211706 (2010).
**Malo, M.S. et al. Intestinal alkaline phosphatase promotes gut bacterial growth by reducing the concentration of luminal nucleotide triphosphates. Am J Physiol Gastrointest Liver Physiol 306, G826-838, doi:10.1152/ajpgi.00357.2013 (2014).
Marcus, E., Credibility and reproducibility. Cell, 2014. 159(5): p. 965-966.
Marik PE, Taeb AM. SIRS, qSOFA and new sepsis definition. J Thorac Dis. 2017;9(4):943-945. doi:10.21037/jtd.2017.03.125.
Markel, T.A., H. Engelstad, and B.B. Poindexter, Predicting disease severity of necrotizing enterocolitis: how to identify infants for future novel therapies. J Clin Neonatol, 2014. 3(1): p. 1-9.
Mata AG, Rosengart RM. Interobserver variability in the radiographic diagnosis of necrotizing enterocolitis.Pediatrics. 1980;66(1):68-71.
**McFarland, J. Medic. Microbiol. 2005, 54:101-111.
**McLachlan, R., Coakley, J., Murton, L. & Campbell, N. Plasma intestinal alkaline phosphatase isoenzymes in neonates with bowel necrosis. J. Clin Pathol 46, 654-659 (1993).
Miki K, Suzuki H, Iino S, Oda T, Hirano K, Sugiura M. Human fetal intestinal alkaline phosphatase. Clin Chim Acta. 1977;79(1):21-30.
Milani, C., et al., The first microbial colonizers of the human gut: composition, activities, and health implications of the infant gut microbiota. Microbiol Mol Biol Rev, 2017. 81(4).
Molecular Probes Handbook—A Guide to Fluorescent Probes and Labeling Technologies, 11th Edition (2010).
Molnár, Kriszta, et al. "Intestinal alkaline phosphatase in the colonic mucosa of children with inflammatory bowel disease." World journal of gastroenterology: WJG 18.25 (2012): 3254.
Moritz, C.P., Tubulin or Not Tubulin: Heading Toward Total Protein Staining as Loading Control in Western Blots. Proteomics, 2017. 17(20).
Morowitz MJ, Poroyko V, Caplan M, Alverdy J, Liu DC. Redefining the role of intestinal microbes in the pathogenesis of necrotizing enterocolitis. Pediatrics. 2010;125(4):777-785. doi:10.1542/peds.2009-3149.
**Moussa R, Khashana A, Kamel N, Elsharqawy S E. Fecal calprotectin levels in preterm infants with and without feeding intolerance. J. Pediatr (Rio J). 2016.
**Mulivor, R. A., Hannig, V.L. & Harris, H. Developmental change in human intestinal alkaline phosphatase. Proc Natl Acad Sci USA 75, 3909-3912 (1978).
Nanthakumar N, Meng D, Goldstein AM, et al. The mechanism of excessive intestinal inflammation in necrotizing enterocolitis: an immature innate immune response. PLoS One. 2011;6(3):e17776. doi:10.1371/journal.pone.0017776.
Nanthakumar NN, Fusunyan RD, Sanderson I,WalkerWA. Inflammation in the developing human intestine: a possible pathophysiologic contribution to necrotizing enterocolitis. Proc Natl Acad Sci U S A. 2000;97(11): 6043-6048. doi:10.1073/pnas.97.11.6043.
**Narisawa et al. Novel inhibitors of alkaline phosphatase suppress vascular smooth muscle cell calcification. Journal of Bone and Mineral Research 22, 1700-1710, 2007.
**Neal, et al Discovery and validation of a new class of small molecule Toll-like receptor 4 (TLR4) inhibitors. PloS One 12, e65779, 2013.
** Neu, J. & Walker, W. A. Necrotizing enterocolitis. N Engl J Med 364, 255-264, doi: 10.1056/NEJMra1005408 (2011).

(56) References Cited

OTHER PUBLICATIONS

\*\*Ng P C, Ang I L, Chiu R W, Li K, Lam H S, Wong R P, Chui KM, CheungH M, Ng E W,Fok T F, Sung J J, Lo Y M, Poon T C. Host-response biomarkers for diagnosis of late-onset septicemia and necrotizing enterocolitis in preterm infants. J. Clin Invest. 2010; 120:2989-3000.

\*\*Ng P C, Ma T P, Lam H S. The use of laboratory biomarkers for surveillance, diagnosis and prediction of clinical outcomes in neonatal sepsis and necrotizing enterocolitis. Arch Dis Child Fetal Neonatal Ed. 2015; 100:F448-52.

Towbin H, Staehelin T, Gordon J. Electrophoretic transfer of proteins from polyacrylamide gels to nitrocellulose sheets: procedure and some applications. Proc Natl Acad Sci U S A. 1979;76(9):4350-4354.

Tricarico C, Pinzani P, Bianchi S, et al. Quantitative real-time reverse transcription polymerase chain reaction: normalization to rRNA or single housekeeping genes is inappropriate for human tissue biopsies. Anal Biochem. 2002;309(2):293-300.

Tsim, S., et al., Diagnostic and prognostic biomarkers in the rational assessment of mesothelioma (DIAPHRAGM) study: protocol of a prospective, multicentre, observational study. BMJ Open, 2016. 6(11): p. e013324.

\*\*Tuin A. Poelstra. K. de Jager-Krikken A, Bok L, Raaben W, Velders M P, Dijkstra G. Role of alkaline phosphatase in colitis in manand rats. Gut. 2009; 58:379-87.

\*\*Uauy, R. D. et al. Necrotizing enterocolitis in very low birth weight infants: biodemographic and clinical correlates. National Institute of Child Health and Human Development Neonatal Research Network. J Pediatr 119, 630-638 (1991).

Verberkmoes NC, Russell AL, Shah M, et al. Shotgun metaproteomics of the human distal gut microbiota. ISME J. 2009;3(2):179-189.

\*\*Vockley, J., Meyer, L.J. & Harris, H. Differentiation of human adult and fetal intestinal alkalike phosphatases with monoclonal antibodies. Am J. Hum Genet 36, 987-1000 (1984).

Walsh, T., et al., Whole exome sequencing and homozygosity mapping identify mutation in the cell polarity protein GPSM2 as the cause of nonsyndromic hearing loss DFNB82. Am J Hum Genet, 2010. 87(1): p. 90-4.

\*\*Whitehouse J S, Riggle K M, PurpiD P, Mayer A N, Pritchard K A, Jr., Oldham K T, Gourlay D M. The protective role of intestinal alkaline phosphatase in necrotizing enterocolitis. J. Surg Res. 2010; 163:79-85.

Williams, K., et al., Standard 6: age groups for pediatric trials. Pediatrics, 2012. 129(Suppl 3): p. S153-60.

Wynn JL, Polin RA. Progress in the management of neonatal sepsis: the importance of a consensus definition. Pediatr Res. 2018;83(1-1):13-15.

Wynn JL. Defining neonatal sepsis. Curr Opin Pediatr. 2016;28(2):135-140.

\*\*Yang Q, Smith P B, Goldberg R N, Cotton C M. Dynamic change of fecal calprotectin in very low birth weight infants during the first month of life. Neonatology. 2008; 94:267-71.

\*\*Yazji et al Endothelial TLR4 activation impairs intestinal microcirculatory perfusion in necrotizing enterocolitis via eNOS-NO-nitrite signaling. Proceedings of the National Academy of Science USA 110, 9451-9456, 2013.

Yedlin et al. J Biol Chem 256, 5620, 1981.

\*\*Yee W H, Soraisham A S, Shah V S, Aziz K, Yoon W, Lee S K, Canadian Neonatal Network. Incidence and timing of presentation of necrotizing enterocolitis in preterm infants. Pediatric. 2012; 129:e298-304.

\*\*Young C, Sharma R, Handfield M, Mai V, Neu J. Biomarkers for infants at risk for necrotizing enterocolitis: clues to preventing? Pediatr Res. 2009; 65:91R-7R.

Zhi, D. and R. Chen, Statistical guidance for experimental design and data analysis of mutation detection in rare monogenic mendelian diseases by exome sequencing. PLoS One, 2012. 7(2): p. e31358.

Zor, T. and Z. Selinger, Linearization of the Bradford protein assay increases its sensitivity: theoretical and experimental studies. Anal Biochem, 1996. 236(2): p. 302-8.

Fanaro. 2013. Early Human Development 89, S13-S20.

\*\*Fawley, Jr. & Gourlay, D. M. Intestinal alkaline phosphatase: a summary of its role in clinical disease. J Surg Res 202, 225-234, doi:10.1016/j.jss.201.12.008 (2016).

Fernley HN, Walker PG. Kinetic behaviour of calf-intestinal alkaline phosphatase with 4-methylumbelliferyl phosphate. Biochem J. 1965;97(1):95-103.

Fernley HN,Walker PG. Inhibition of alkaline phosphatase by L-phenylalanine. Biochem J. 1970; 116(3): 543-544. doi:10.1042/bj1160543.

Fishman WH, Green S, Inglis NI. L-phenylalanine: an organ specific, stereospecific inhibitor of human intestinal alkaline phosphatase. Nature. 1963;198:685-686.

Fiskerstrand, T., et al., Familial diarrhea syndrome caused by an activating GUCY2C mutation. N Engl J Med, 2012. 366(17): p. 1586-95.

\*\*Fitzbiggons S C., Ching Y, Yu D, Carpenter J, Kenny M, Weldon C, Killehei C, Valim C, Harbor J D, Jaksic T. Mortality of necrotizing enterocolitis expressed by birth weight categories. J. Pediatr Surg. 2009; 44:1072-6.

Flores, R., et al., Collection media and delayed freezing effects on microbial composition of human stool. Microbiome, 2015. 3: p. 33.

Flynn MA, Gehrke C, Maier BR, Tsutakawa RK, Hentges DJ. Effect of diet on fecal nutrients. J Am Diet Assoc. 1977;71(5):521-526.

Fosset, M., D. Chappelet-Tordo, and M. Lazdunski, Intestinal alkaline phosphatase. Physical properties and quaternary structure. Biochemistry, 1974. 13(9): p. 1783-8.

Franklin, A.L., et al., Are immune modulating single nucleotide polymorphisms associated with necrotizing enterocolitis? Sci Rep, 2015. 5: p. 18369.

Garg BD, Sharma D, Bansal A. Biomarkers of necrotizing enterocolitis: a review of literature. J Matern Fetal Neonatal Med. 2018;31(22):3051-3064. doi:10.1080/14767058.2017.1361925.

Genomes Project, C., et al., A map of human genome variation from population-scale sequencing. Nature, 2010. 467(7319): p. 1061-73.

Gephart SM, Gordon PV, Penn AH, et al. Changing the paradigm of defining, detecting, and diagnosing NEC: perspectives on Bell's stages and biomarkers for NEC. Semin Pediatr Surg. 2018;27(1):3-10. doi:10.1053/j.sempedsurg.2017.11.002.

Gephart SM, Spitzer AR, Effken JA, Dodd E, Halpern M, McGrath JM. Discrimination of GutCheck(NEC): a clinical risk index for necrotizing enterocolitis. J Perinatol. 2014;34(6):468-475. doi:10.1038/jp.2014.37.

Ghosh, K., et al., Crystal structure of rat intestinal alkaline phosphatase—role of crown domain in mammalian alkaline phosphatases. J Struct Biol, 2013. 184(2): p. 182-92.

Ghosh, N.K. and W.H. Fishman, L-phenylalanine inhibiton of rat intestinal alkaline phosphatase: a homosteric phenomenon. Arch Biochem Biophys, 1968. 126(2): p. 700-6.

Ghosh, N.K. and W.H. Fishman, On the mechanism of inhibition of intestinal alkaline phosphatase by Lphenylalanine. I. Kinetic studies. J Biol Chem, 1966. 241(11): p. 2516-22.

Gibson, W.T., et al., Mutations in EZH2 cause Weaver syndrome. Am J Hum Genet, 2012. 90(1): p. 110-8.

\*\*Goldberg R F., Austen W G., Jr., Zhang X, Munene G, Mostafa G, Biswas S, McCormack M, Eberlin K R, Nguyen J T, Tatlidede H S, Warren H S, Narisawa S, Millan J L, Hoden R A. Intesttinal alkaline phosphatase is a gut mucosal defense factor maintained by enteral nutrition. Proc Natl Acad Sci USA. 2008; 105:3551-6.

Goldman, J., et al., Development of biomarkers to optimize pediatric patient management: what makes children different? Biomark Med, 2011. 5(6): p. 781-94.

\*\*Gonzalez-Rivera R, Culverhouse R C, HamvasA, Tarr P I, Warner B.B. The age of necrotizing enterocolitis onset: an application of Sartwell's incubation period model. J. Perinat. 2011; 31:519-23.

Good, M., et al., Breast milk protects against the development of necrotizing enterocolitis through inhibition of Toll-like receptor 4 in the intestinal epithelium via activation of the epidermal growth factor receptor. Mucosal Immunol, 2015. 8(5): p. 1166-79.

(56) References Cited

OTHER PUBLICATIONS

Gordon P, Christensen R,Weitkamp JH, Maheshwari A. Mapping the new world of necrotizing enterocolitis (NEC): review and opinion. EJ Neonatol Res. 2012;2(4):145-172.
Gribar, S.C., et al., Reciprocal expression and signaling of TLR4 and TLR9 in the pathogenesis and treatment of necrotizing enterocolitis. J Immunol, 2009. 182(1): p. 636-46.
**Group YICSS. Clinical signs that predict severe illness in children under age 2 months: a multi-centre study. The lancet. 2008; 371:135-42.
Gupta A, Paria A. Etiology and medical management of NEC. Early Hum Dev. 2016;97:17-23.
Guthmann F, Borchers T,Wolfrum C,Wustrack T, Bartholomaus S, Spener F. Plasma concentration of intestinal-and liver-FABP in neonates suffering from necrotizing enterocolitis and in healthy preterm neonates. Mol Cell Biochem. 2002;239(1-2):227-234.
Hackam, D. and M. Caplan, Necrotizing enterocolitis: pathophysiology from a historical context. Semin Pediatr Surg, 2018. 27(1): p. 11-18.
Heath Maya et al: "Association of Intestinal Alkaline Phosphatase With Necrotizing Enterocolitis Among Premature Infants", JAMA Network Open, vol. 2, No. 11, Nov. 1, 2019 (Nov. 1, 2019), p. e1914996, XP055965856, DOI: 10.1001/jamanetworkopen.2019.14996.
**Heinzerling N P, Liedel J L, Welak S R, Fredrich K, Biesterveld B E, Pritchard K A, Jr., Gourlay D M. Intestinal alkaline phosphatase is protective to the preterm rat pup intestine. J. Pediatr Surg. 2014; 49:954-60.
Henthorn PS, Raducha M, Edwards YH, et al. Nucleotide and amino acid sequences of human intestinal alkaline phosphatase: close homology to placental alkaline phosphatase. Proc Natl Acad Sci U S A. 1987;84(5):1234-1238.
Henthorn PS, Raducha M, Kadesch T, Weiss MJ, Harris H. Sequence and characterization of the human intestinal alkaline phosphatase gene. J Biol Chem. 1988;263(24):12011-12019.
Herrmann and Herrman. 2010. Nutrition in Clinical Practice 25, 69-75.
Hintz SR, Kendrick DE, Stoll BJ, et al; NICHD Neonatal Research Network. Neurodevelopmental and growth outcomes of extremely low birth weight infants after necrotizing enterocolitis. Pediatrics. 2005;115(3):696-703.
Hoehn T, Stover B, Buhrer C. Colonic pneumatosis intestinalis in preterm infants: different to necrotizing enterocolitis with a more benign course? Eur J Pediatr. 2001;160(6):369-371. doi:10.1007/s004310100757.
Holman, R.C., et al., Necrotising enterocolitis hospitalisations among neonates in the United States. Paediatric and perinatal epidemiology, 2006. 20(6): p. 498-506.
Hood, R.L., et al., Mutations in SRCAP, encoding SNF2-related CREBBP activator protein, cause Floating-Harbor syndrome. Am J Hum Genet, 2012. 90(2): p. 308-13.
Hornik CP, Benjamin DK, Becker KC, et al. Use of the complete blood cell count in lateonset neonatal sepsis. Pediatr Infect Dis J. 2012;31(8):803-807.
**Horrigan, F.D. & Danovitch, S. H. The origin of human fecal alkaline phosphatase. Am J Dig Dis 19,603-608 (1974).
Hoylaerts, M.F., et al., Mammalian alkaline phosphatase catalysis requires active site structure stabilization via the N-terminal amino acid microenvironment. Biochemistry, 2006. 45(32): p. 9756-66.
Hunter, C.J., et al., Understanding the susceptibility of the premature infant to necrotizing enterocolitis (NEC). Pediatr Res, 2008. 63(2): p. 117-123.
International HapMap, C., et al., Integrating common and rare genetic variation in diverse human populations. Nature, 2010. 467(7311): p. 52-8.
International Search Report for PCT/US20/16646 dated Apr. 30, 2020.
**International Search Report for PCT/US2017/045588 dated Nov. 6, 2017.

International Written Opinion for PCT/US20/16646 dated Apr. 30, 2020.
**International Written Opinion for PCT/US2017/045588 dated Nov. 6, 2017.
Janes KA. An analysis of critical factors for quantitative immunoblotting. Sci Signal. 2015;8(371):rs2.
Jensen, K.J., et al., An ERK-p38 subnetwork coordinates host cell apoptosis and necrosis during coxsackievirus B3 Infection. Cell Host Microbe, 2013. 13(1): p. 67-76.
**Ji J, Ling X B, Zhao Y, Hu Z, Zheng X, Xu Z, Wen Q, Kastenberg Z J, Li P, Abdullah F, Brandt M L, Ehrenkranz R A, Harris M C, Lee T C, Simpson B J, Bowers C, Moss R L, Sylvester K G. A data-driven algorithm integrating clinical and laboratory features for the diagnosis ands prognosis of necrotizing enterocolitis. PLoS One. 2014; 9:e89860.
**Ng, P.C., Chan, K. & & Poon, T C. Biomarkers for prediction and diagnosis of necrotizing enterocolitis. Clin Perinatol 40, 149-159, doi:101016/j.clp.2012.12.005 (2013).
Ng, S.B., et al., Exome sequencing identifies the cause of a mendelian disorder. Nat Genet, 2010. 42(1): p. 30-5.
O'Brien PJ, Herschlag D. Alkaline phosphatase revisited: hydrolysis of alkyl phosphates. Biochemistry. 2002;41(9):3207-3225.
Ohashi, T., Enzyme replacement therapy for lysosomal storage diseases. Pediatr Endocrinol Rev, 2012. 10(Suppl 1): p. 26-34.
Olson, B.J. and J. Markwell, Assays for determination of protein concentration. Curr Protoc Protein Sci, 2007. Chapter 3: p. Unit 3 4.
**Patel R M, Kandefer S, Walch M C, Bell E F, Carlo W A, Laptook A R, Sanchez P J, Shankaran S, Van Meurs K P, Ball M B, Hale E C, Newman N S, Das A, Higgins R D, Stoll B J, Eunice Kennedy Shriver National Institute of Child H, Human Development Neonatal Research Network, Causes and timing of death in extremely premature infants from 2000 through 2011. N Engl J Med. 2015: 372-331-40.
Patel, J.C., et al., Neonatal necrotizing enterocolitis: The long-term perspective/discussion. Amer Surgeon, 1998. 64(6): p. 575.
**Pedregosa F, Varoquaux G, Gramfort A, Michel V, Thirion B, Grisel O, Blondel M, Prettenhofer P, Weiss R, Dubourg V. Scikit-learn: Machine learning in Python. J. Machine Learning Research 2011; 12:2825-30.
Peterson BW, Sharma PK, van der Mei HC, Busscher HJ. Bacterial cell surface damage due to centrifugal compaction. Appl Environ Microbiol. 2012;78(1):120-125.
PetitClerc C. Quantitative fractionation of alkaline phosphatase isoenzymes according to their thermostability. Clin Chem. 1976;22(1):42-48.
**Porstmann, B., Porstmann, T., Nugel, E. & Evers, U. Which of the commonly used marker enzymes gives the best results in colorimetric and fluorimetric enzyme immunoassays: horseradish peroxidase, alkaline phosphatase or bets-galactosidase? J Immunl Methods 79, 27-37 (1985).
**Pourcyrous M, Korones S B, Yang W, Bouldfen T F, Bada H S. C-reactive protein in the diagnosis, management, and prognosis of neonatal necrotizing enterocolitis. Pediatrics. 2005; 116:1064-9.
**Rabinowitz S S, Dzakpasu P, Piecuch S, Leblanc P, Valencia G, Kornecki E. Platelet-activating factor in infants at risk for necrotizing enterocolitis. J Pediatr. 2001; 138-81-6.
Rehan VK, Seshia MM, Johnston B, Reed M, Wilmot D, Cook V. Observer variability in interpretation of abdominal radiographs of infants with suspected necrotizing enterocolitis. Clin Pediatr (Phila). 1999;38(11):637-643. doi:10.1177/000992289903801102.
Rentea et al. Eur J Pediatr Surg 23, 39, 2012.
**Rentea R M, Liedel J L, Welak S R, Cassidy L K, Mayer A N, Pirtchard K A, Jr., Oldham K T, Gourlay D M. Intestinal alkaline phosphatase administration in newborns is protective of gut barrier function in a neonatal necrotizing, enterocolitis rat model. J Pediatr Surg. 2012; 47:1135-42.
Richard, J., et al., Allostery wiring map for kinesin energy transduction and its evolution. J Biol Chem, 2016. 291(40): p. 20932-20945.
**Riggle K M, Rentea R M, Welak S R, Pritchard K A, Jr., Oldham K T, Gourlay D M. Intestinal alkaline phosphatase prevents the systemic inflammatory response associated with necrotizing enterocolitis. J Surg Res. 2013; 180:21-6.

(56) References Cited

OTHER PUBLICATIONS

**Rish I. An empirical study of the naïve Bayes classifier. IJCAI 2001 workshop on empirical methods in artificial intelligence: IBM Net York; 2001. p. 41-6.

Rose, C., et al., The characterization of feces and urine: a review of the literature to inform advanced treatment technology. Crit Rev Environ Sci Technol, 2015. 45(17): p. 1827-1879.

Rusconi, B., M. Good, and B.B. Warner, The microbiome and biomarkers for necrotizing enterocolitis: are we any closer to prediction? J Pediatr, 2017. 189: p. 40-47 e2.

Sampath, V., et al., A functional ATG16L1 (T300A) variant is associated with necrotizing enterocolitis in premature infants. Pediatr Res, 2017. 81(4): p. 582-588.

Sampath, V., et al., Necrotizing enterocolitis is not associated with sequence variants in antioxidant response genes in premature infants. J Pediatr Gastroenterol Nutr, 2016. 62(3): p. 420-3.

Sampath, V., et al., The NFKB1 (g.-24519delATTG) variant is associated with necrotizing enterocolitis (NEC) in premature infants. J Surg Res, 2011. 169(1): p. e51-7.

Schmoor, C., W. Sauerbrei, and M. Schumacher, Sample size considerations for the evaluation of prognostic factors in survival analysis. Stat Med, 2000. 19(4): p. 441-52.

Shah J, Singhal N, da Silva O, et al. Intestinal perforation in very preterm neonates: risk factors and outcomes. J Perinatol. 2015;35(8):595-600.

Sharma R, Tepas JJ III, Hudak ML, et al. Neonatal gut injury and infection rate: impact of surgical debridement on outcome. Pediatr Surg Int. 2005;21(12):977-982.

Sherry, S.T., et al., dbSNP: the NCBI database of genetic variation. Nucleic Acids Res, 2001. 29(1): p. 308-11.

**Shifrin D A, Jr., McConnell R E, Nambiar R, Higginbotham J N, Coffey R J, Tyska M J. Enterocyte microvillus-derivee vesicles detoxify bacterial products and regulate epithelial-microbial interactions. Curr Biol. 2012; 22:627-31.

Shifrin, D.A., Jr. and M.J. Tyska, Ready . . . aim . . . fire into the lumen: a new role for enterocyte microvilli in gut host defense. Gut Microbes, 2012. 3(5): p. 460-2.

**Shulman R J, Buffone G, Wise L. Enteric protein loss in necrotizing enterocolitis as measured by fecal alpha 1-antitrypsin excretion. J Pediatr. 1985; 107:287-9.

Singer M, Deutschman CS, Seymour CW, et al. The third international consensus definitions for sepsis and septic shock (Sepsis-3). JAMA. 2016;315(8):801-810.

**Sisley A C, Desai T R, Hynes K L, Gewertz B L, Dudeja P K. Decrease in mucosal alkaline phosphatase: a potential marker of intestinal reperfusion injury. J Lab Clin Med. 1999; 133:335-41.

Smith, p. B., et al., Safety monitoring of drugs receiving pediatric marketing exclusivity. Pediatrics, 2008. 122(3): p. 628-33.

Sodhi CP, Neal MD, Siggers R, et al. Intestinal epithelial Toll-like receptor 4 regulates goblet cell development and is required for necrotizing enterocolitis in mice. Gastroenterology. 2012;143(3):708-718.e5, e705.

Spinola SM, Cannon JG. Different blocking agents cause variation in the immunologic detection of proteins transferred to nitrocellulose membranes. J Immunol Methods. 1985;81(1):161-165.

**Stedman's Medical Dictionary for the Health Professions and Nursing, 2005, Lippincott Williams & Wilkins.

Stephen AM, Wiggins HS, Cummings JH. Effect of changing transit time on colonic microbial metabolism in man. Gut. 1987;28(5):601-609.

Stewart, C.J., et al., Preterm gut microbiota and metabolome following discharge from intensive care. Sci Rep, 2015. 5: p. 17141.

Stewart, C.J., et al., The preterm gut microbiota: changes associated with necrotizing enterocolitis and infection. Acta Paediatr, 2012. 101(11): p. 1121-7.

Stoll BJ, Hansen N, Fanaroff AA, et al. Late-onset sepsis in very low birth weight neonates: the experience of the NICHD Neonatal Research Network. Pediatrics. 2002;110(2 Pt 1):285-291. doi:10.1542/peds.110.2.285.

Sunyaev, S.R., Inferring causality and functional significance of human coding DNA variants. Hum Mol Genet, 2012. 21(R1): p. R10-7.

**Swittink et al 2017. Metaproteomics reveals functional differences in intestinal microbiota development of pretem infants. Molecular & Cellular Proteomics. DOI: 10.1074/mcp. RA117.000102.

**Sylvester K G, Ling X B, Liu G Y, Kastenberg Z J, Ji J, Hu Z, Wu S, Peng S, Abdullah F, Brandt M L, Ehrenkranz R A, Harris M C, Lee T C, Simpson B J, Bowers C, Moss R L. Urine protein biomarkers for the diagnosis and prognosis of necrotizing enterocolitis in infants. J. Pediatr. 2014; 164:607-12 el-7.

**Sylvester K G, Ling X B,Liu G Y, Kastenberg Z J, Ji J, Hu Z, Peng S, Lau K, Abdullah F, Brandt M L, Ehrenkranz R A, Harris M C, Lee T C, Smpson J, Bowers C, Moss R L. A novel urine peptide biomarker0based algorithm for the prognosis of necrotizing enterocolitis in human infants. Gut. 2014; 63:1284-92.

** Tam A L, Camberos A, Applebaum H. Surgical decision making in necrotizing enterocolitis and focal intestinal perforation: predictive value of radiologic findings. J Pediatr Surg. 2002; 37:1688-91.

**Tayman C, Tonbul A, Kahveci H, Uysal S, Koseoglu B, Tatli M M, Dilmen U. C5a, a complement activation product, is a useful marker in predicting the severity of necrotizing enterocolitis. Tohoku J Exp Med. 2011; 224:143-50.

Terrin G, Stronati L, Cucchiara S, De Curtis M. Serum markers of necrotizing enterocolitis: a systematic review. J Pediatr Gastroenterol Nutr. 2017;65(6):e120-e132. doi:10.1097/MPG.0000000000001588.

**Thomas D W, Henton D H. The use of fecal alkaline phosphatase as an indicator of intestinal damage. Digestion. 1985; 31:82-8.

Thuijls G, Derikx JP, van Wijck K, et al. Non-invasive markers for early diagnosis and determination of the severity of necrotizing enterocolitis. Ann Surg. 2010;251(6):1174-1180. doi:10.1097/SLA.0b013e3181d778c4.

\* cited by examiner

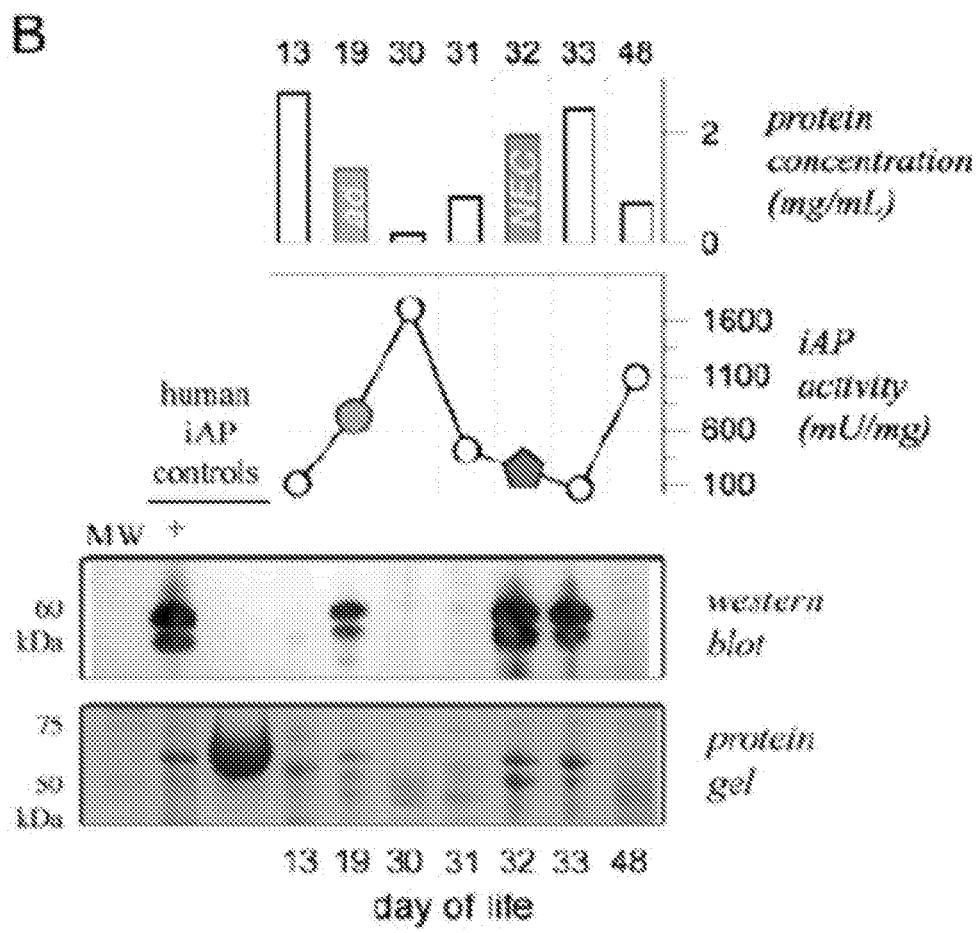
FIG. 1 CON'T

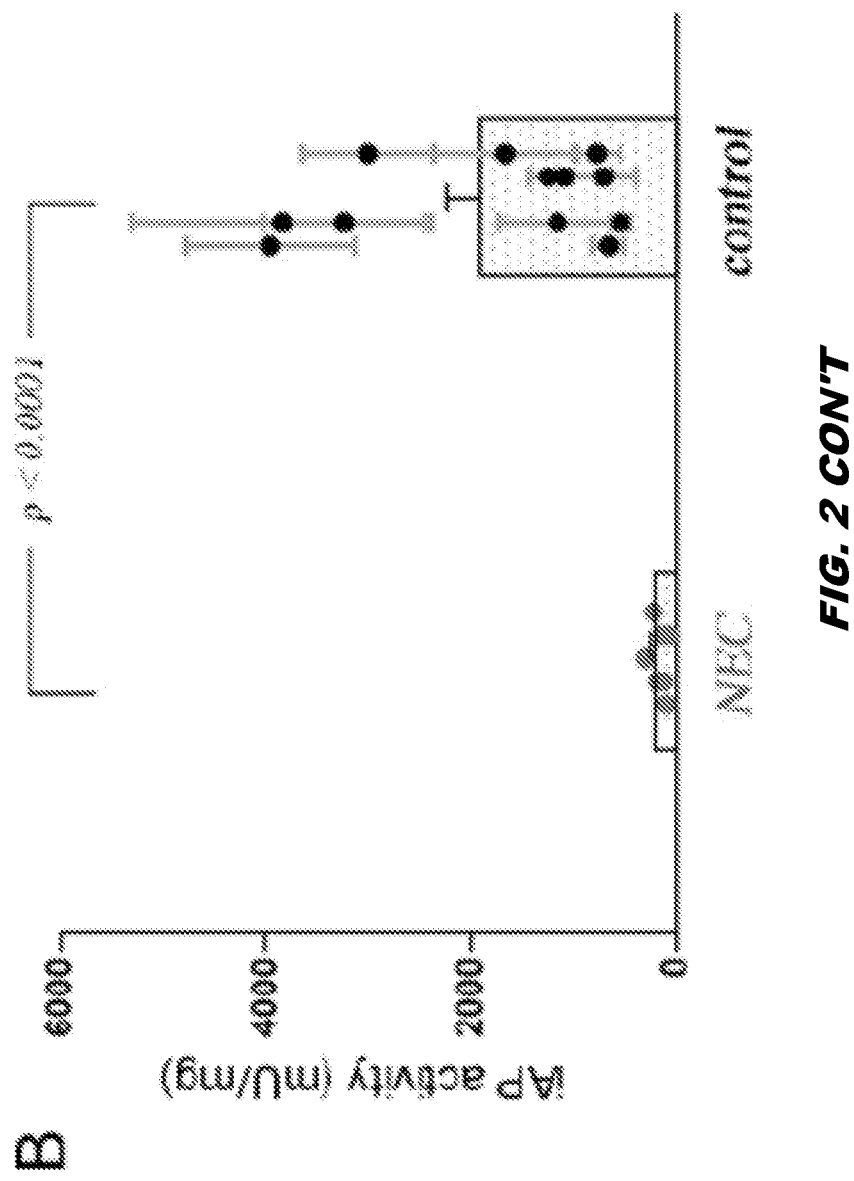
FIG. 2 CON'T

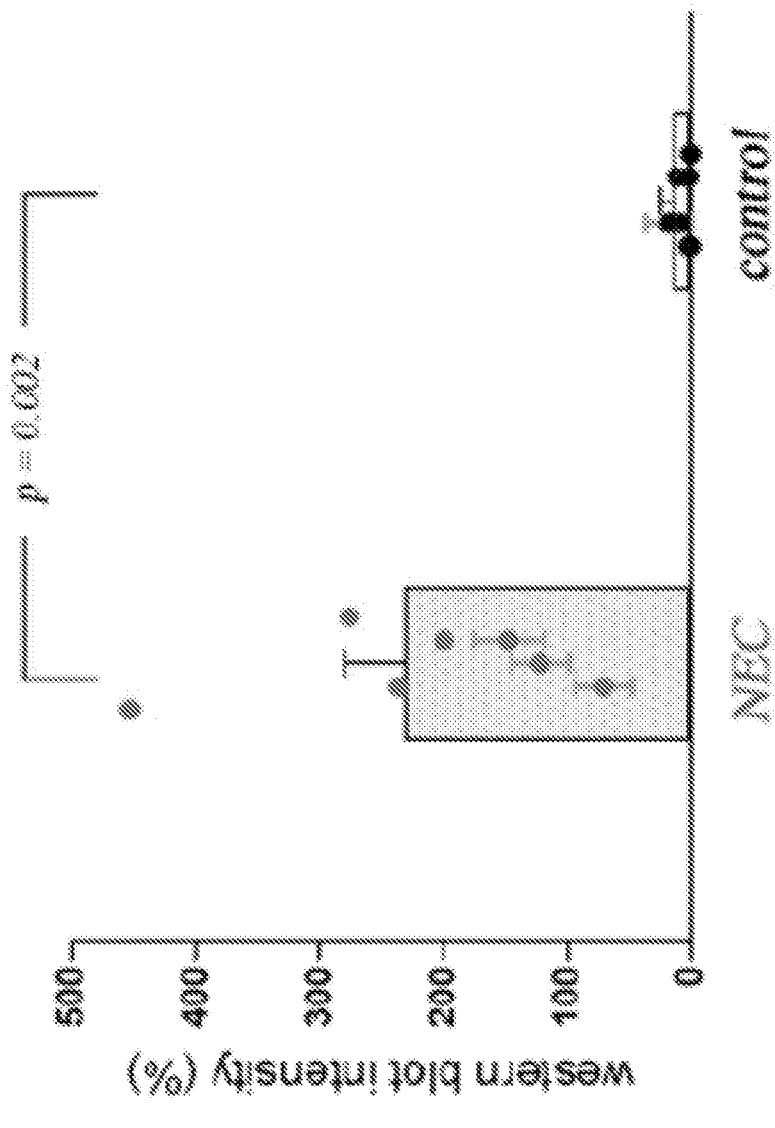
FIG. 2 CON'T

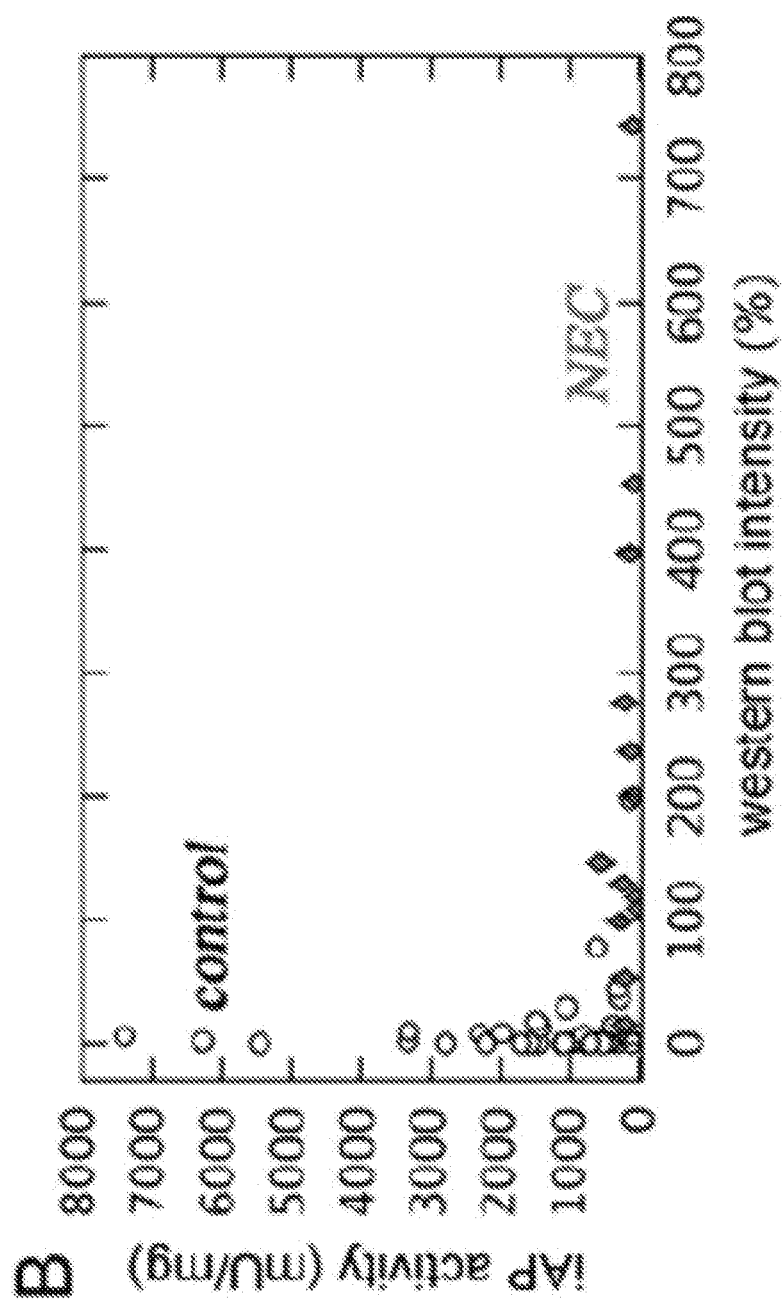
FIG. 3 CON'T

| Physical trait | | NEC Infants (n=6) | Non-NEC Infants (n=12) |
|---|---|---|---|
| Mean gestational age (weeks) | | 29.98 ± 3.32 | 29.87 ± 1.30 |
| Gestational age (weeks) | 23-26 | 1 | 5 |
| | 27-30 | 3 | 2 |
| | 31-34 | 1 | 4 |
| | 35-37 | 1 | 1 |
| Average birth weight (kg) | | 1.19 ± 0.58 | 1.30 ± 0.73 |
| Gender | male | 2 | 5 |
| | female | 4 | 7 |
| Bell Stage (NEC Events= 7) | I | 2 | n/a |
| | II | 2 | n/a |
| | III | 3 | n/a |

*FIG. 4*

Table 1. Demographics of patient enrollment in study.

| Physical trait | | NEC Infants (n=6) | Non-NEC Infants (n=12) |
|---|---|---|---|
| Bell Stage (NEC Events= 7) | I | 2 | n/a |
| | II | 2 | n/a |
| | III | 3 | n/a |
| Gestational age (WGA) | 23-26 | 1 | 5 |
| | 27-30 | 3 | 2 |
| | 31-34 | 1 | 4 |
| | 35-38 | 1 | 1 |
| Average birth weight (kg) | | 1.19 ± 0.58 | 1.30 ± 0.73 |
| Gender | male | 2 | 5 |
| | female | 4 | 7 |

FIG. 6

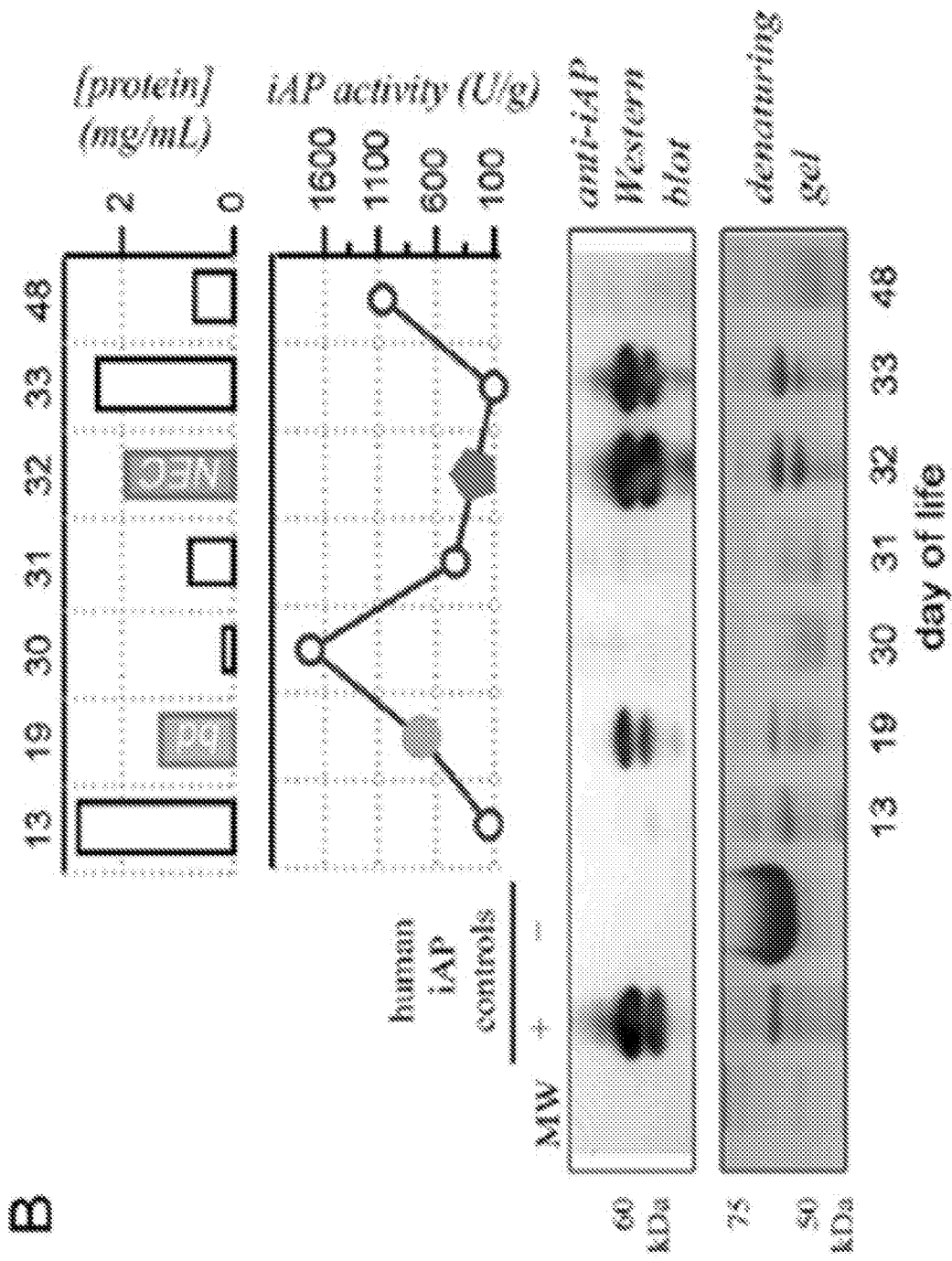
FIG. 10 CON'T

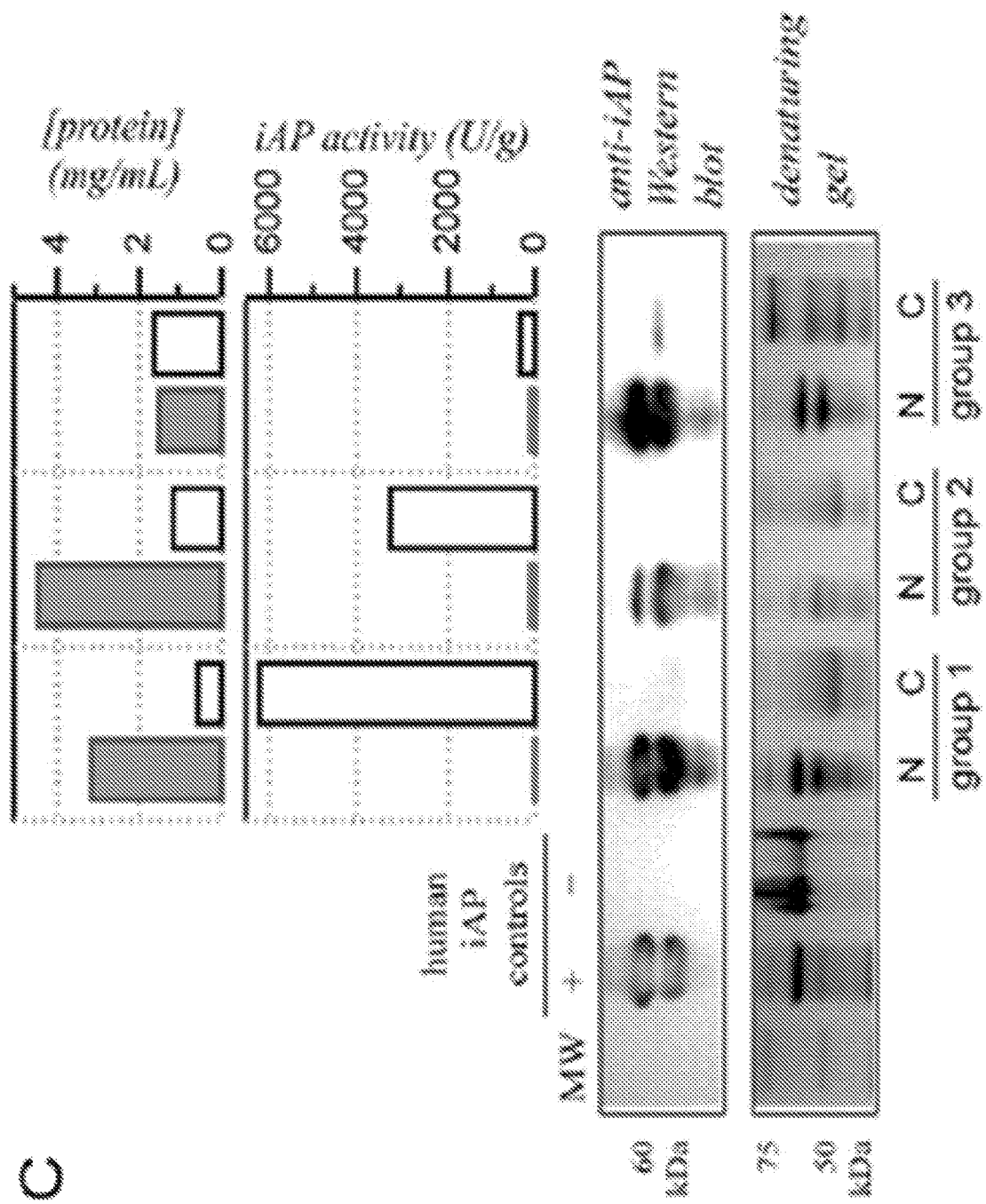
FIG. 10 CON'T

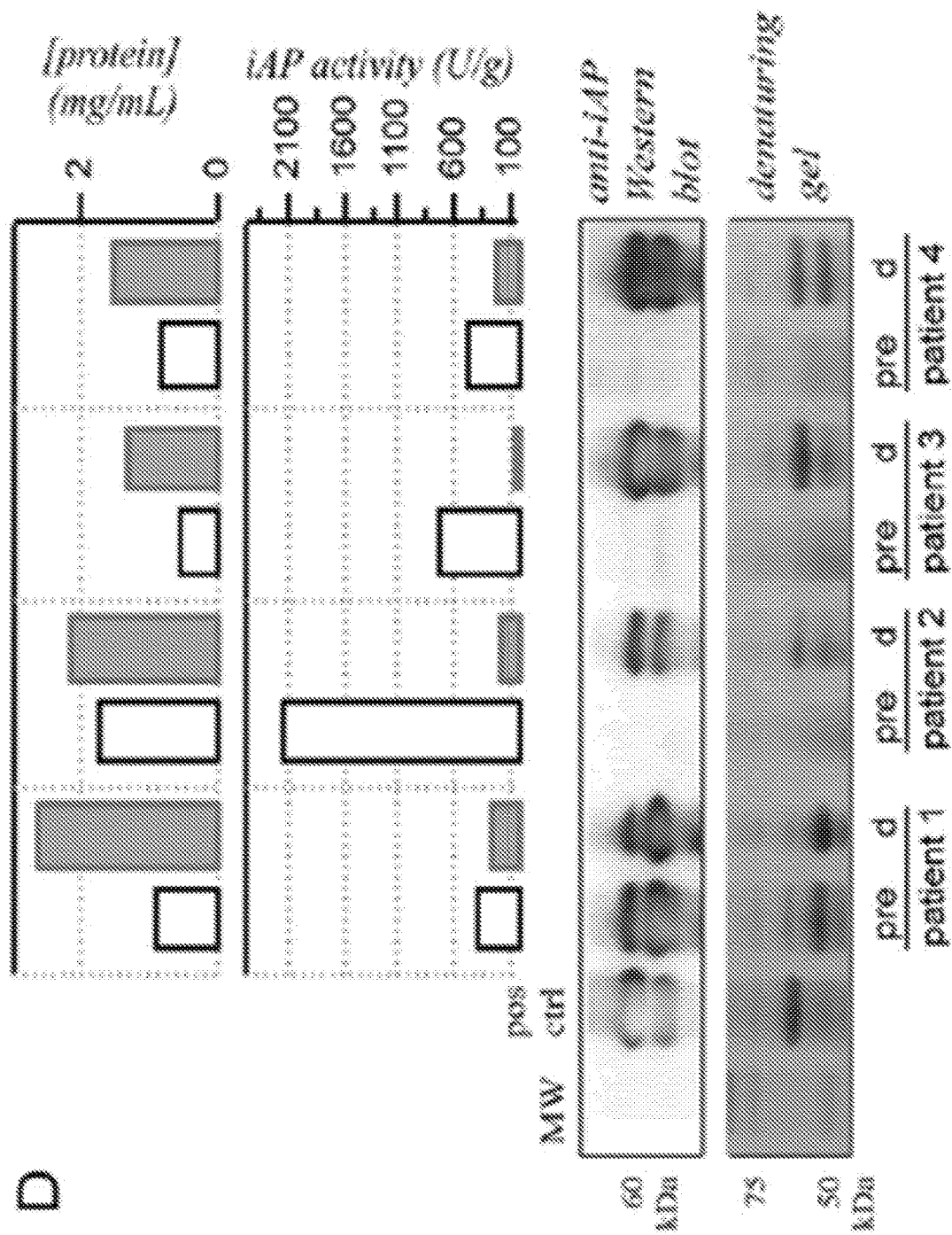
FIG. 10 CON'T

A.

B.
FIG. 11 CON'T
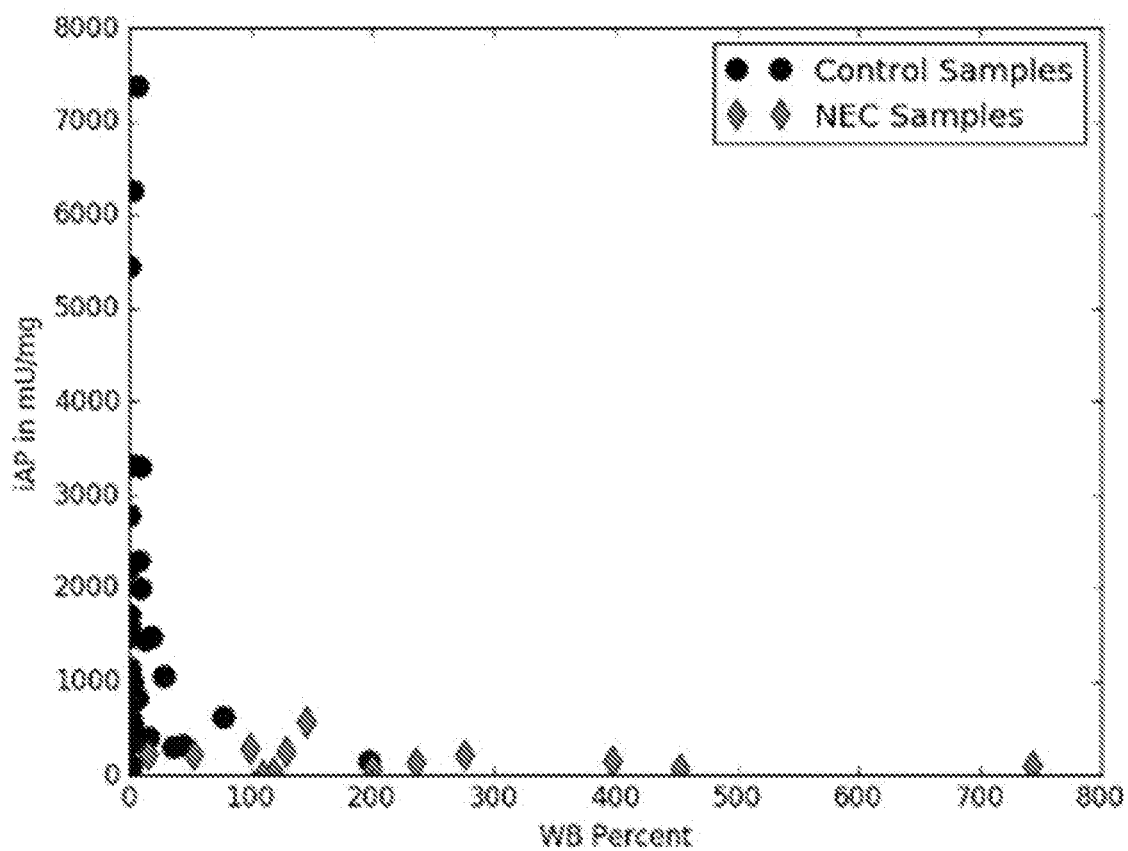

FIG. 11 CON'T
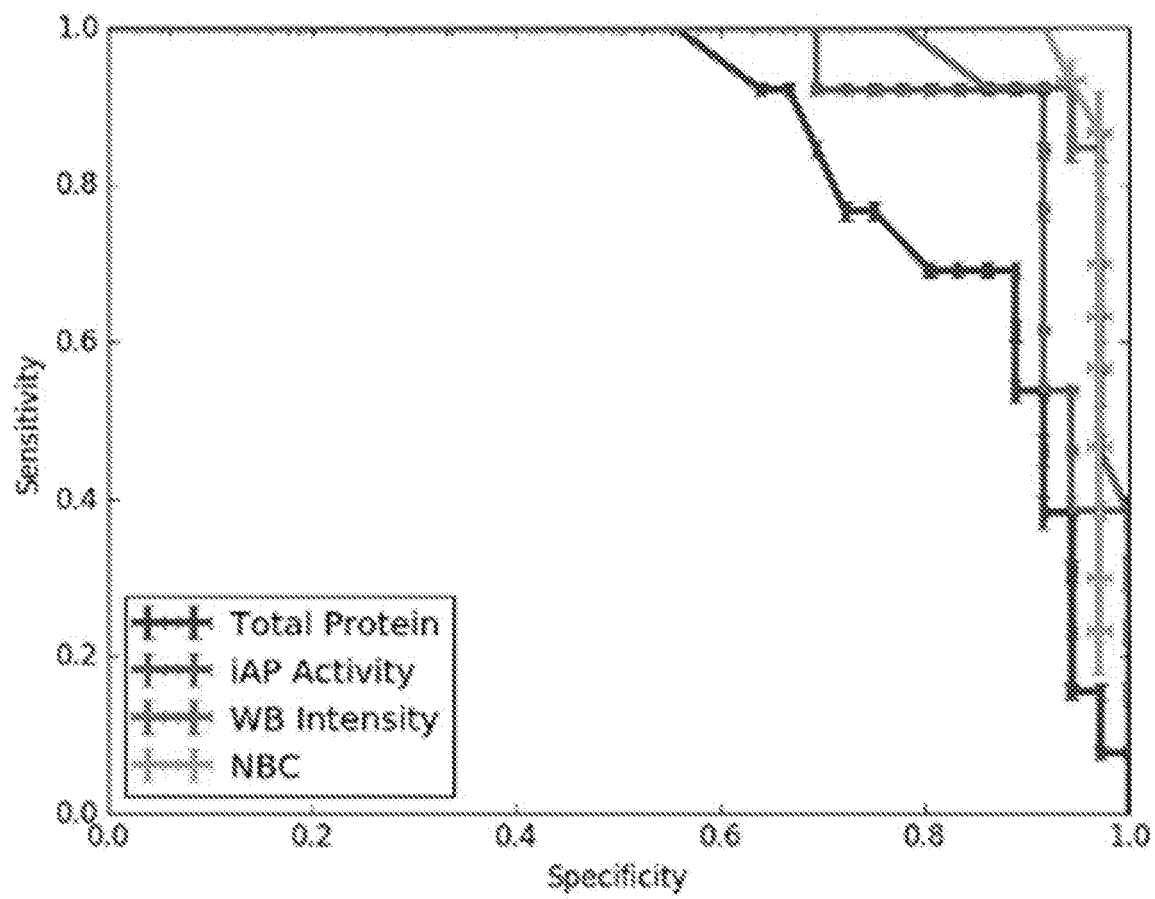

B.
FIG. 12 CON'T
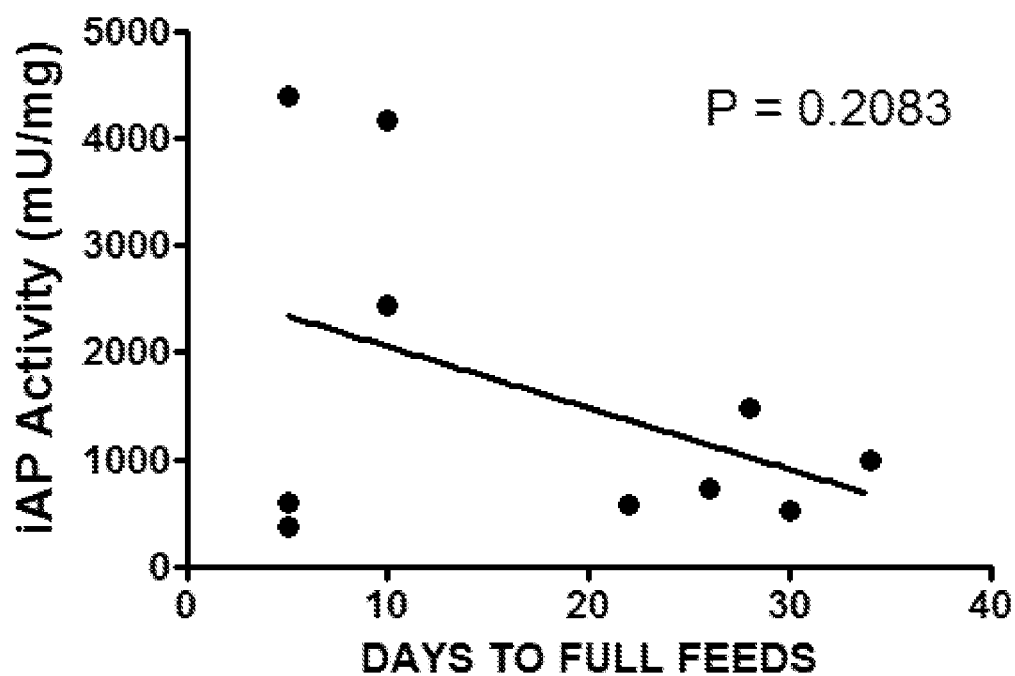

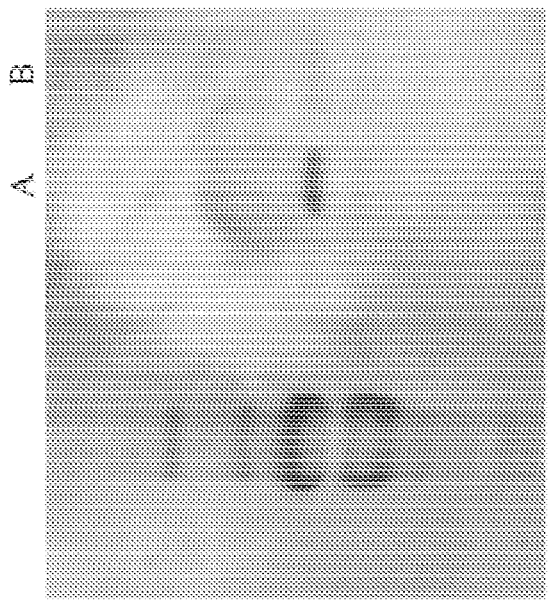
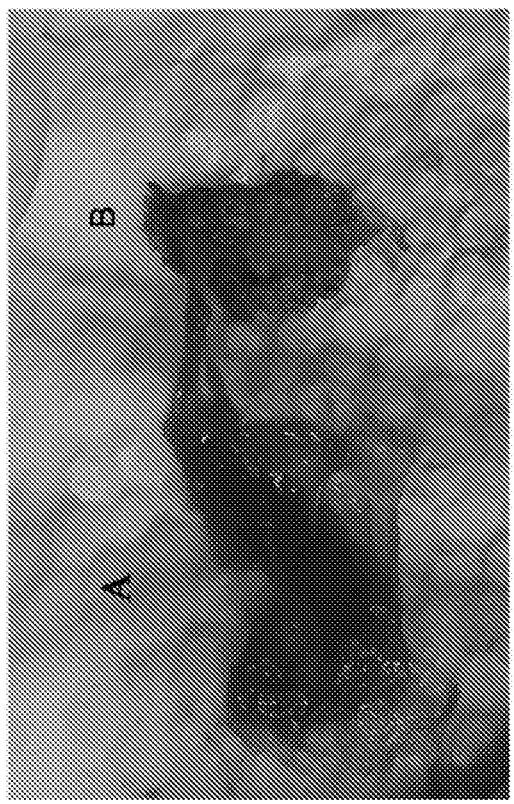
FIG. 13

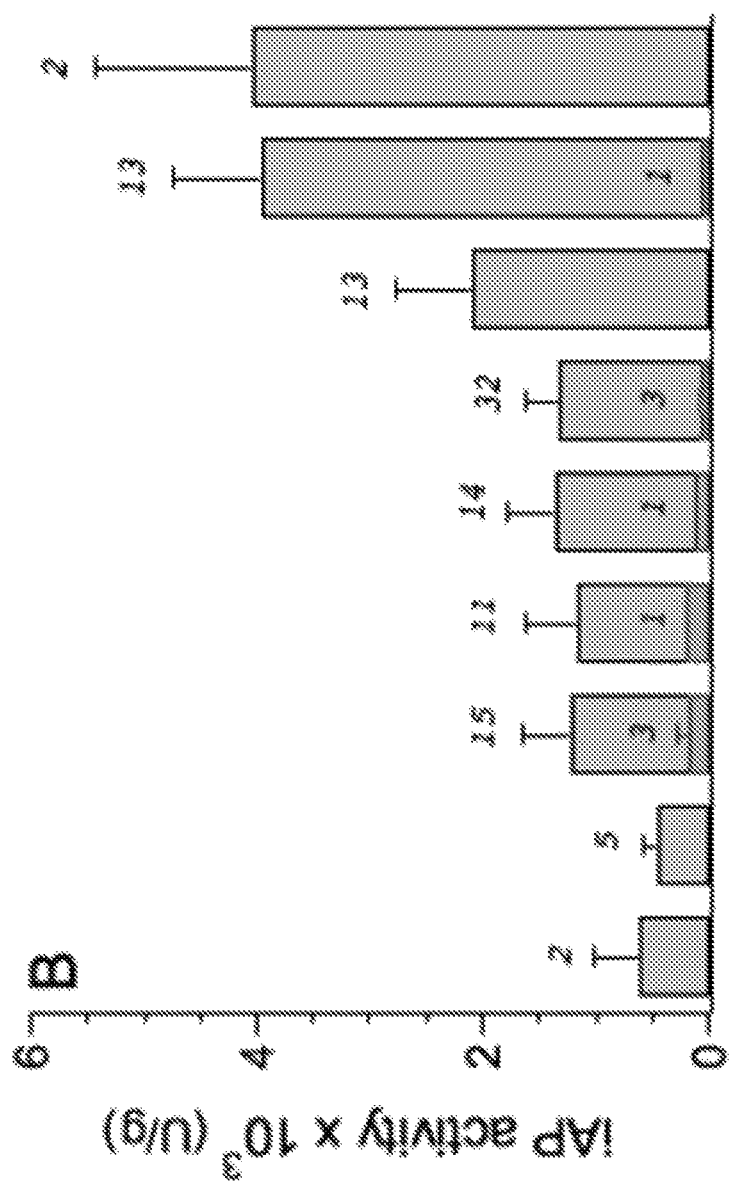
*FIG. 14 CON'T*

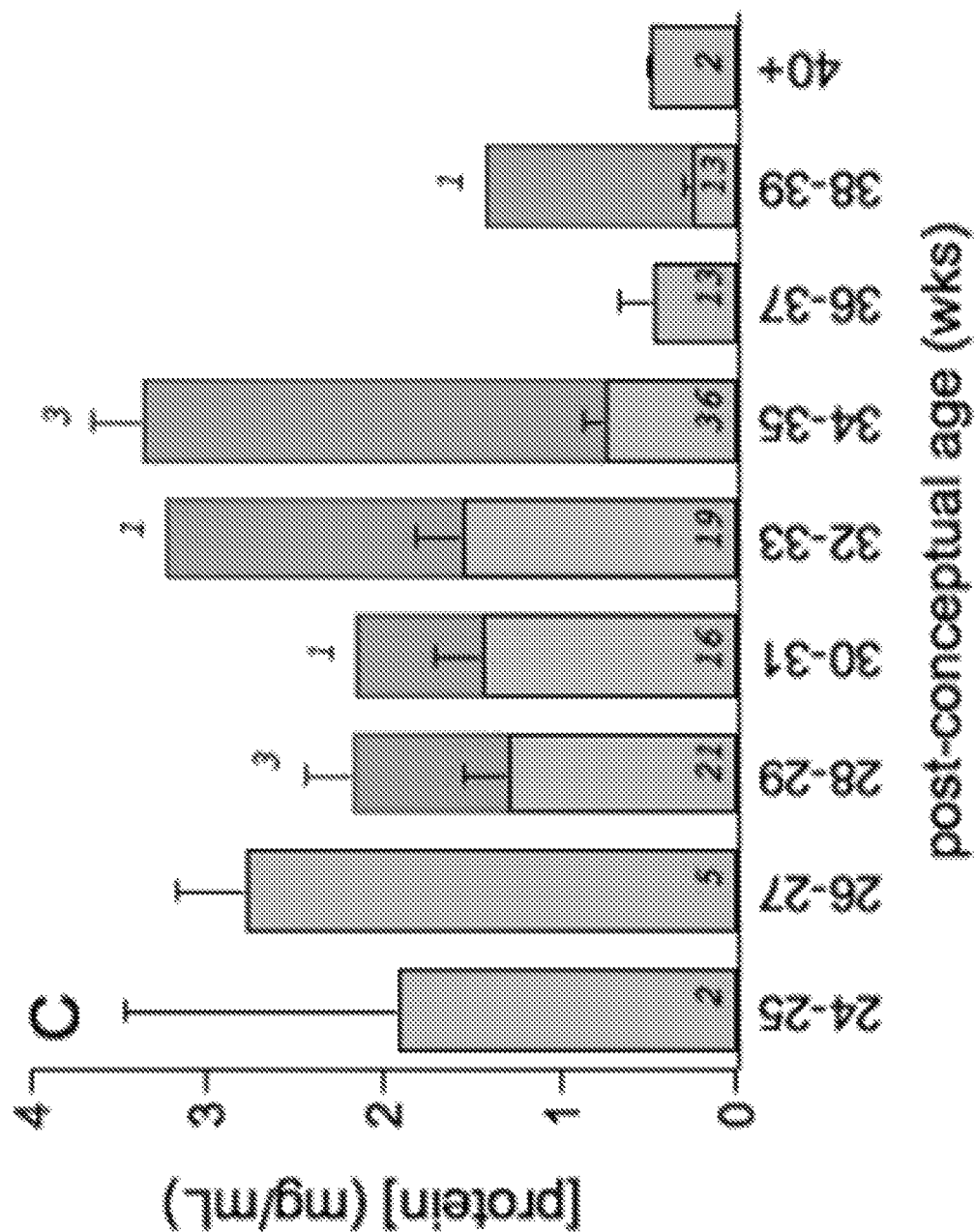
*FIG. 14 CON'T*

Lalles. Jean-Paul in Nutrition Reviews 2010 Vol 68

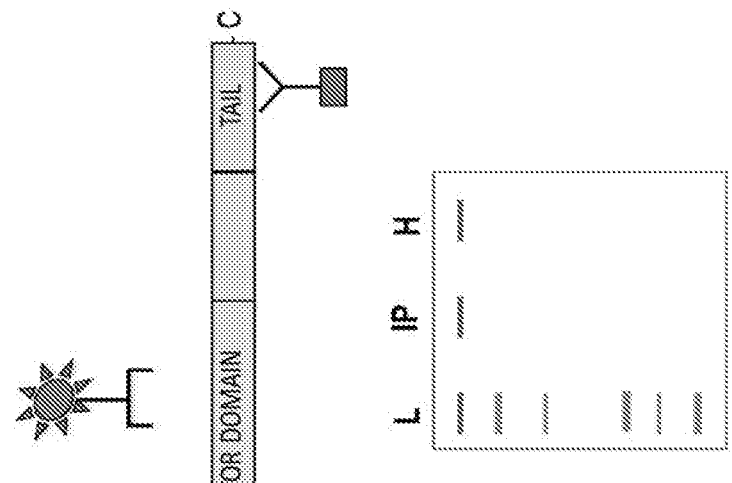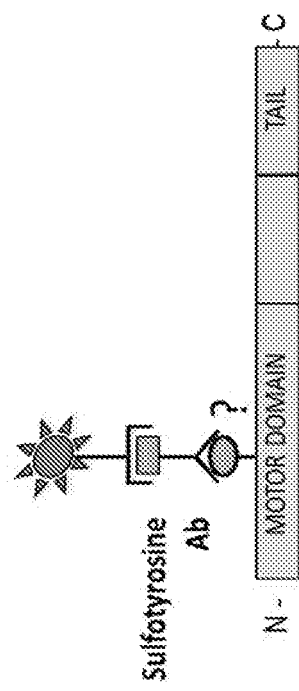
FIG. 23

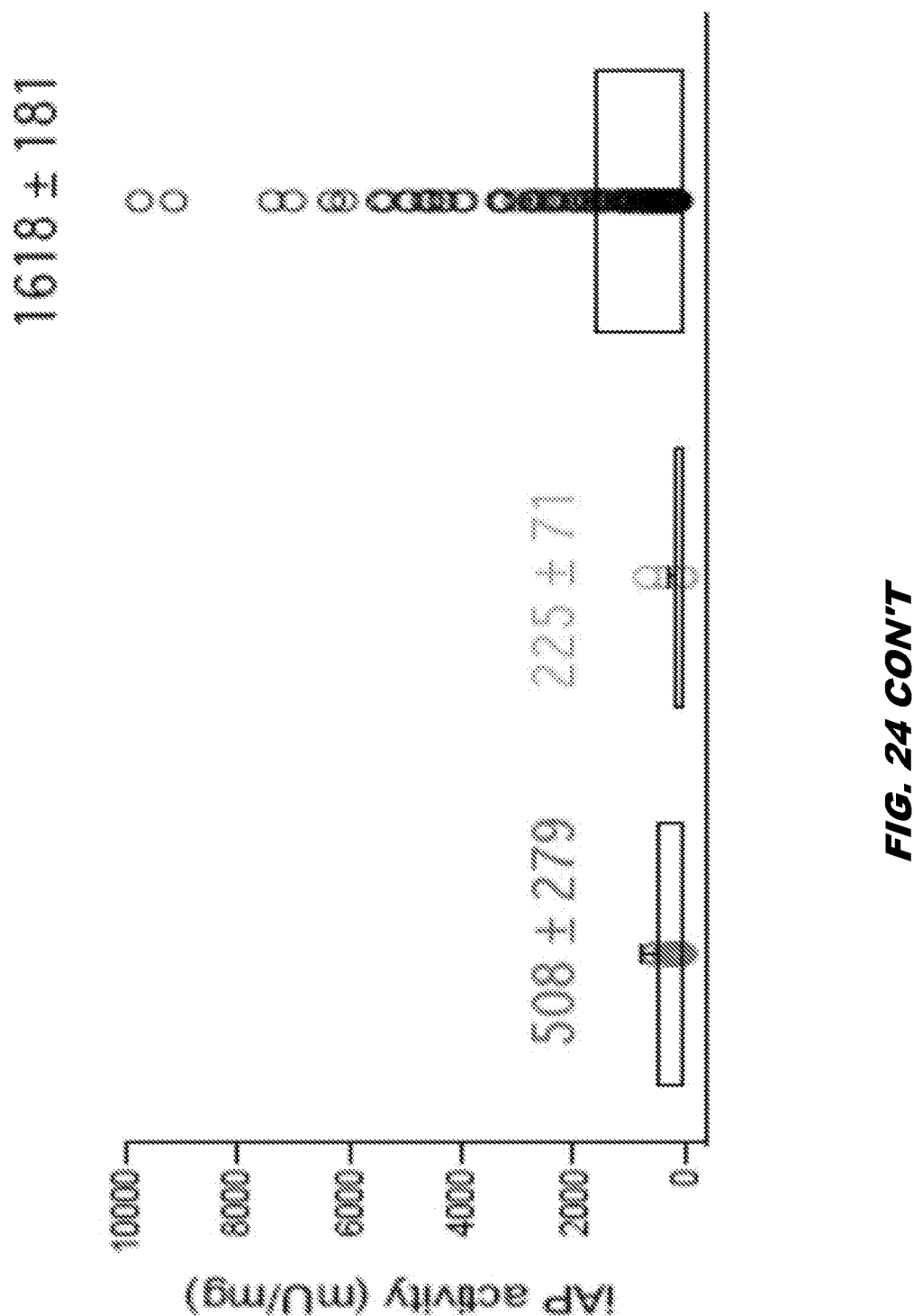
FIG. 24 CON'T

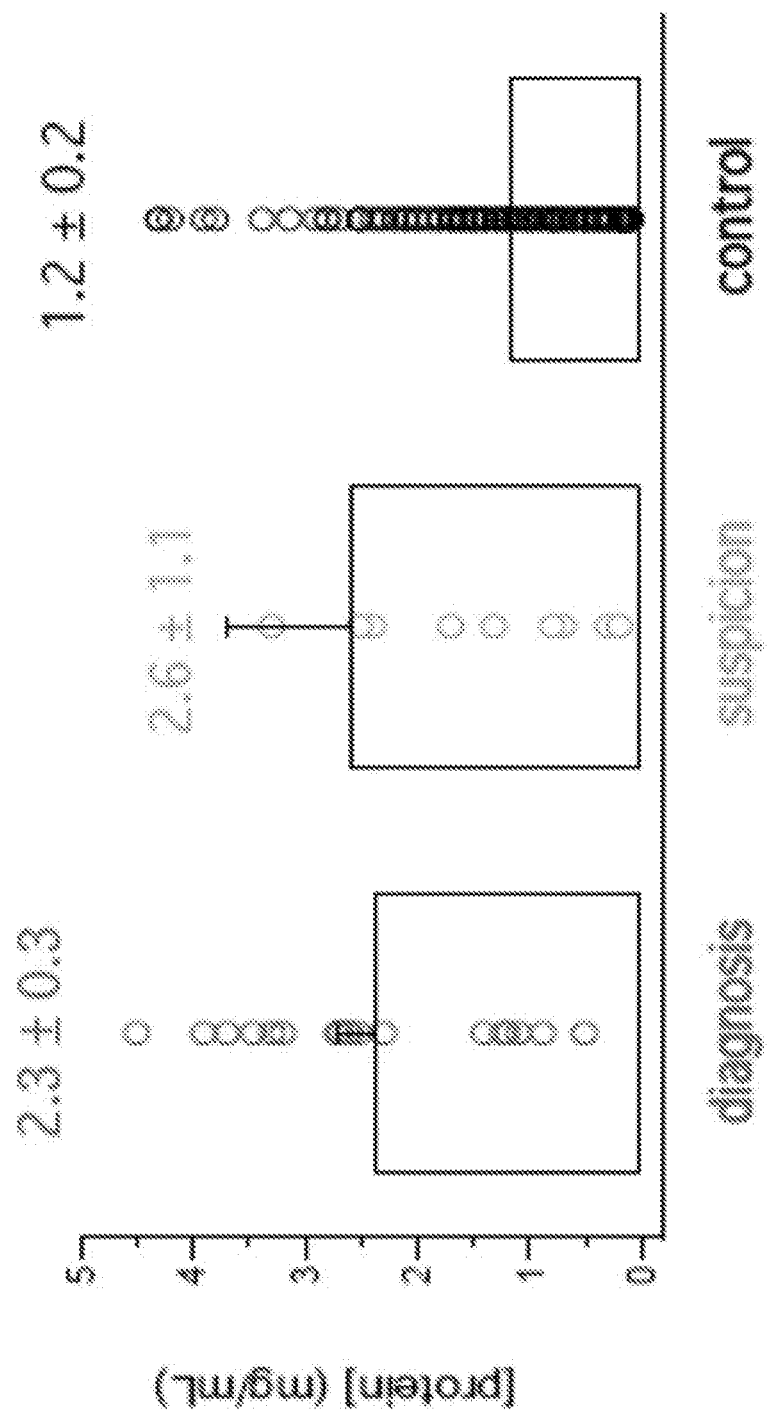
FIG. 24 CON'T

| Simulation scenarios considered for sample size justification | | | |
|---|---|---|---|
| Scenario | $(\beta, \alpha_1, \alpha_2)$ | $P[NEC = 1 \| IAP = 159, \theta]$ (probability of NEC as a function of IAP content in NEC patient group) | $P[NEC = 1 \| IAP = 2, \theta]$ (probability of NEC as a function of IAP content in non-NEC patient group) |
| 1 | (-8.5, 5, 0) | 0.370 | 0.002 |
| 2 | (-8.5, 6, 0) | 0.738 | 0.002 |
| 3 | (-8.5, 5, 1) | 0.933 | 0.002 |
| 4 | (-8.5, 6, 1) | 0.739 | 0.0002 |

FIG. 32

| Power analysis results for different effect sizes | | | | |
|---|---|---|---|---|
| Scenario: $(\beta, \alpha_1, \alpha_2)$ | n = 50 | n = 100 | n = 150 | n = 200 |
| 1: (-8.5, 5, 0) | (.697, —, —) | (.865, —, —) | (.931, —, —) | (.969, —, —) |
| 2: (-8.5, 6, 0) | (.741, —, —) | (.899, —, —) | (.964, —, —) | (.974, —, —) |
| 3: (-8.5, 5, 1) | (.714, .457, .448) | (.908, .822, .819) | (.972, .929, .927) | (.989, .987, .987) |
| 4: (-8.5, 6, 1) | (.707, .437, .432) | (.925, .837, .830) | (.970, .950, .953) | (.987, .982, .982) |

COMPOSITIONS AND METHODS TO DETECT GASTROINTESTINAL DISEASE

GOVERNMENT INTERESTS

This invention was made with government support under Grant No. R01GM097350 awarded by the National Institute of Health. The government has certain rights in the invention.

This application is a National Stage Entry of International Application PCT/US2020/16646, filed on Feb. 4, 2020, which claims priority from U.S. patent application Ser. No. 16/267,120 filed on Feb. 4, 2019, now U.S. Pat. No. 11,493,515, the entire contents of each which are incorporated herein by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to compositions and methods to detect and treat gastrointestinal diseases.

BACKGROUND OF THE INVENTION

Gastrointestinal diseases refer to diseases involving the gastrointestinal tract. For example, necrotizing enterocolitis (NEC) is an acquired gastrointestinal disease often seen in pre-term infants. In NEC, bacteria invade the wall of the intestine, causing local infection and inflammation. NEC is characterized by high mortality and long-term morbidity, including short gut syndrome, recurrent infection, nutritional deficiency and neurodevelopmental delay. Despite an overall net decrease in mortality for premature infants, there has been an increase in NEC-associated deaths. NEC is often difficult to diagnose and manage, due to initial nonspecific symptomatology and rapid deterioration. Clinicians currently rely on radiographic evidence to make the diagnosis in advanced stage of disease.

SUMMARY OF THE INVENTION

The present invention provides a method for determining the prognosis of necrotizing enterocolitis (NEC) in a patient. In embodiments, the method comprises fitting a Markov model using a two state transition matrix and propensity values measured among a plurality of subjects, wherein the two state transition matrix comprises a first state and a second state, wherein the first state comprises a non-necrotizing enterocolitis status, wherein the second state comprises a necrotizing enterocolitis status (NEC), wherein a propensity value is a function of intestinal Alkaline Phosphatase (iAP) activity values and the amount of iAP found in a subject of the plurality of subjects; using a propensity value of the patient and the fitted Markov model to estimate a probability of transitioning from the first state to the second state, wherein the fitted model indicates that an increased propensity level of the patient significantly increases the probability of transitioning from the first state to the second state; treating the patient when the propensity value is greater than or equal to a threshold value of about 0.5.

In embodiments, a propensity value comprises a product of a first value and a second value, wherein the first value comprises one (1) minus a first ratio, wherein the first ratio comprise an iAP activity value of a subject of the plurality of subjects divided by a maximum iAP activity value observed among the plurality of subjects, wherein the second value comprises a second ratio, wherein the second ratio comprises an amount of iAP from an immunoassay value of a subject of the plurality of subjects divided by a maximum amount of iAP from an immunoassay value observed in a sample.

Non-limiting examples of immunoassays comprise western blot analysis, ELISA, or immunoprecipitation. For example, the immunoassay can comprise western blot analysis utilizing a chemiluminescent reporter. In another example, the immunoassay can comprise western blot analysis using a fluorescent reporter. Fluorescent reports can be more linear in response.

In embodiments, the immunoassay readings can be considered a 'mini-ELISA,' as patient sample iAP abundance is quantitated against a 2-point curve. For example, the signal in a patient sample can be compared by ratioing it to the difference between human small intestinal lysate (positive control with the greatest level of iAP or 100%) and bovine iAP (negative control as anti-human iAP antibody does not detect cow iAP or 0%). The maximum WB value in Example 9 is the human small intestinal lysate.

In embodiments, a propensity value comprises a product of a first value and a second value, wherein the first value comprises one (1) minus an iAP activity value of a subject of the plurality of subjects, wherein the second value comprises an amount of iAP from an immunoassay value of a subject of the plurality of subjects.

In embodiments, the plurality of subjects comprises the patient.

In embodiments, treating comprises withholding feeding, administering an antibiotic, or a combination thereof.

In embodiments, the sample is a human small intestinal lysate.

In embodiments, the immunoassay comprises a western blot, an ELISA, or immunoprecipitation.

The present invention provides a method of identifying a subject afflicted with a gastrointestinal (GI) disease. An aspect of the invention is directed to methods for diagnosing a subject with a gastrointestinal disease. Another aspect of the invention is directed to methods for identifying a subject at risk of a gastrointestinal disease. Embodiments as described herein can further identify both early stages of gastrointestinal disease and advanced stages of gastrointestinal disease. Certain embodiments can distinguish between early stage and late stage gastrointestinal disease. For example, embodiments as described herein can diagnose advanced states of inflammation, such as that identified by radiological findings of pneumatosis intestinalis (portal vein or biliary gas). As another example, embodiments can identify early stages of the disease before rampant inflammation of the gut is physiologically evident.

In embodiments, the methods comprise incubating a biological sample from a subject with an agent that binds intestinal alkaline phosphatase (iAP), detecting in the sample iAP-bound agent, and detecting and/or measuring in the sample the amount or activity of iAP in sample, whether bound to the agent or not. In embodiments, the iAP-bound agent is at least one GI disease biomarker comprising AP enzymatic activity of iAP, iAP protein level, iAP dimerization/dissociation, post-translationally modified iAP, total protein, such as total fecal protein, or a combination thereof. In some embodiments, the GI disease biomarker is useful for diagnosing a subject with a gastrointestinal disease, and can also be indicative of a subject afflicted with a gastrointestinal (GI) disease, and/or a subject at risk of developing a GI disease. In some embodiments, a subject afflicted with a gastrointestinal (GI) disease can encompass both early and advanced stages of the disease.

In embodiments, iAP is not bound by an iAP binding agent. For example, a substrate can be provided for the enzyme in the sample, and the change of the substrate is monitored. In one embodiment, iAP is not bound for the activity assay. For example, substrate can be provided for the enzyme in the sample and the change in the enzyme can be monitored. Without being bound by theory, this can also be the same for AP-bound to enzyme where the measured change of substrate in immunoassays is for the protein tethered by the antibody system but also for any free AP in the sample.

The present invention further provides for a method of diagnosing a GI disease in a subject, such as necrotizing enterocolitis, comprising incubating a biological sample from a subject with an agent that binds intestinal alkaline phosphatase (iAP), detecting in the sample iAP-bound agent, and detecting and/or measuring in the sample the amount or activity of iAP-bound agent. In embodiments, the iAP-bound agent is at least one GI disease biomarker comprising iAP enzymatic activity, iAP protein level, iAP dimerization/dissociation, post-translationally modified iAP, total protein, such as total fecal protein, or a combination thereof, and wherein the GI disease biomarker is indicative of a subject afflicted with a gastrointestinal (GI) disease. An iAP-bound agent according to the invention can be iAP bound to its cognate substrate, an antibody that recognizes and binds to iAP, a short peptide sequence that is directed to and binds to iAP, and the like, non-limiting examples of which comprise a small-molecule activator or inhibitor of the catalytic reaction, a metal ion (tungsten is a transition state effector of alkaline phosphatases), an agent that causes allosteric release of products, a labile chemical moiety that serves as a chemical, enzymatic, or photolytic trigger, or a matrix that binds to a tagged form of iAP.

Embodiments can further comprise diagnosing the subject as having a GI disease. For example, a subject can be diagnosed as having a GI disease: if the total protein concentration in the sample is greater than about 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml or 5.0 mg/ml; if the iAP activity is less than about 10 mU/mg, 20 mU/mg, 30 mU/mg, 40 mU/mg, 50 mU/mg, 60 mU/mg, 70 mU/mg, 80 mU/mg, 90 mU/mg, 100 mU/mg, 200 mU/mg, 300 mU/mg, 400 mU/mg, 500 mU/mg, 600 mU/mg, 700 mU/mg, 800 mU/mg, 900 mU/mg, 1000 mU/mg, 1050 mU/mg, 1100 mU/mg, 1150 mU/mg, 1200 mU/mg, 1250 mU/mg, 1300 mU/mg, 1350 mU/mg 100 mU/mg, 1450 mU/mg, 1500 mU/mg, 1600 mU/mg, 1700 mU/mg, 1800 mU/mg, 1900 mU/mg; if the iAP activity is less than about 5 U/mg, 10 U/mg, 50 U/mg, 100 U/mg, 200 U/mg, 300 U/mg, 400 U/mg, 500 U/mg, 600 U/mg, 700 U/mg, 800 U/mg, 900 U/mg, 1000 U/mg; if the level of iAP protein is greater than 0.05%, 1%, 2%, 3%, 4%, 5%, 6%, 7%, 8%, 9%, 10%, 20%, 30%, 40%, 50%, 60%, 70%, 80%, 90%, 100%, 125%, 150%, 175%, 200%, 225%, 250%, 275% of a control sample, or a combination thereof. Without being bound by theory, total protein concentration in the sample as described herein can be for a stool sample in which the fresh weight to buffer is set at 1 g/mL. Otherwise, the skilled artisan knows that one can dilute or concentrate a sample to alter the protein concentration.

In embodiments, a subject can be diagnosed as having a GI disease if the total protein concentration in the sample is greater than about 1.8 mg/ml, if the iAP activity is lower than about 979 mU/mg, if the level of iAP protein is greater than 10.7% of a control sample, or a combination thereof. In some embodiments, a subject can be diagnosed as having a GI disease if the total protein concentration in the sample is greater than about 1.6 mg/ml, if the iAP activity is lower than about 1256 mU/mg, if the level of iAP protein is greater than 4.8% of a control sample, or a combination thereof.

The present invention provides a method of diagnosing a gastrointestinal (GI) disease in a subject comprising obtaining a sample from the subject, detecting the presence of at least one GI disease biomarker in the sample, wherein the GI disease biomarker can comprise intestinal alkaline phosphatase (iAP) protein, comparing the GI disease biomarker profile to that of a profile obtained from a control sample, and treating the subject. In embodiments, the control sample can comprise two or more control samples.

The present invention further provides a method of preventing the progression of a gastrointestinal disease in a subject in need thereof comprising obtaining a sample from the subject, detecting the presence of at least one GI disease biomarker in the sample, wherein the GI disease biomarker can comprise intestinal alkaline phosphatase (iAP) protein, comparing the GI disease biomarker profile to that of a profile obtained from a control sample, and treating the subject. In embodiments, the control sample can comprise two or more control samples.

The present invention further provides a method of ameliorating the symptoms associated with a gastrointestinal disease in a subject in need thereof comprising obtaining a sample from the subject, detecting the presence of at least one GI disease biomarker in the sample, wherein the GI disease biomarker can comprise intestinal alkaline phosphatase (iAP) protein, comparing the GI disease biomarker profile to that of a profile obtained from a control sample, and treating the subject. In embodiments, the control sample can comprise two or more control samples.

In embodiments, treating the subject diagnosed with a GI disease comprises administering an effective amount of antibiotics, probiotics, intravenous fluids, or a combination thereof; withholding oral feeding; administering an iAP replacement composition; an anti-inflammatory; a therapeutic; a small molecule activator and/or effector of catalytic activity; parenteral (or intravenous) nutrition or a combination thereof.

Non-limiting examples of a therapeutic that can be used according to the invention comprise Toll-like receptor (TLR) inhibitors (Neal et al. Discovery and validation of a new class of small molecule Toll-like receptor 4 (TLR4) inhibitors. PloS One 12, e65779) and interruption of eNOS-NO-nitrite signaling (Yazji et al. Endothelial TLR4 activation impairs intestinal microcirculatory perfusion in necrotizing enterocolitis via eNOS-NO-nitrite signaling. Proceeedings of the National Academy of Science USA 110, 9451-9456).

Non-limiting examples of a small molecule effector of catalytic activity comprise levamisole, theophylline, triazole-based compounds, sulfonamide derivatives, phosphatase derivatives, metals, and amino acids (Borgers M. The cytochemical application of new potent inhibitors of alkaline phosphatases. Journal of Histochemistry & Cytochemistry 21, 812-824; Klemperer et al. The inhibition of alkaline phosphatase by beryllium. Journal of Biological Chemistry 180, 281-288; Bobkova et al. Modulators of intestinal alkaline phosphatase. Methods Mol Biol 1053, 135-144; Narisawa et al. Novel inhibitors of alkaline phosphatase suppress vascular smooth muscle cell calcification. Journal of Bone and Mineral Research 22, 1700-1710; al-Rashida and Iqbal. Inhibition of alkaline phosphatase: an emerging new drug target. Minireviews in Medicinal Chemistry 15, 41-51.

Non-limiting examples of such antibiotics comprise Vancomycin, Ampicillin, Zosyn (combination of piperacillin and tazobactam), Gentamycin, Flagyl (metrodniazole generic), Meropenem, Metronidazole, Cefotaxime, Clindamycin, or any combination thereof. In some embodiments, an antifungal agent can further be administered. In other embodiments, the antifungal agent can be Fluconazole, Terconazole, Voriconazole, Posaconazole, Pentamidine, Itraconazole, and Ketoconazole.

Non-limiting examples of probiotic organisms include those in the genera *Lactobacillus, Lactococcus, Bifidobacteria, Pediococcus, Saccharomyces boulardii*, and related bacteria and yeast.

Non-limiting examples of such intravenous fluids comprise saline (such as 0.9% NaCl in water or 0.45% saline in water), Lactated Ringer's (0.9% NaCl with electrolytes and buffer), $D_5W$ (5% dextrose in water), $D_5NS$ (5% dextrose in 0.9% saline), $D_5$ 1/2 NS (5% dextrose in 0.45% saline), $D_5LR$ (5% dextrose in Lactated Ringer's), or Normosol-R. In embodiments, the intravenous fluid solution can be isotonic. In other embodiments, the intravenous fluid solution can be hypotonic.

Non-limiting examples of parenteral (or intravenous) nutrition comprise intravenous dextrose solutions, intravenous amino acid solutions, intravenous fat emulsions, intravenous vitamin and mineral supplements, or a combination thereof.

The anti-inflammatory agents can be selected from a wide variety of steroidal, non-steroidal, and salicylate water-soluble and water-insoluble drugs and their acid addition or metallic salts. Both organic and inorganic salts can be used provided the anti-inflammatory agent maintains its medicament value. The anti-inflammatory agents can be selected from a wide range of therapeutic agents and mixtures of therapeutic agents that can be administered in sustained release or prolonged action form. Non-limiting examples of anti-inflammatory agents comprise ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, and evening primrose oil (containing about 72% linoleic acid and about 9% gamma-linolenic acid). Nonlimiting examples of salicylate anti-inflammatory agents comprise acetylsalicylic acid, mesalamine, salsalate, diflunisal, salicylsalicylic acid, and choline magnesium trisalicylate. Nonlimiting examples of steroidal anti-inflammatory agents comprise flunisolide, triamcinoline, triamcinoline acetonide, beclomethasone diproprionate, betamethasone diproprionate, hydrocortisone, cortisone, dexamethasone, prednisone, methyl prednisolone, and prednisolone.

In embodiments, the gastrointestinal disease can comprise colitis, inflammatory bowel disease (IBD), or a combination thereof. In embodiments, colitis can comprise necrotizing enterocolitis (NEC), adult necrotizing enterocolitis (ANEC), pseudomembranous enterocolitis, infectious colitis, ulcerative colitis, Crohn's disease, ischemic colitis, and radiation colitis.

In embodiments, the sample can comprise a biological sample obtained from subject. For example, the biological sample can be a biological fluid, a biological solid, or a biological semi-solid. In embodiments, the sample can comprise fecal matter, meconium, vomit, peripheral blood, sera, plasma, or urine.

In embodiments, the GI disease biomarker can comprise iAP enzymatic activity, AP enzymatic activity, iAP protein level, iAP dimerization/dissociation, post-translationally modified iAP, total protein, such as total fecal protein, or a combination thereof. In embodiments, the post-translational modification can comprise acetylation, acylation, alkylation, amidation, butyrylation, deamidation, formylation, glypiation, glycosylation, hydroxylation, iodination, ISGylation, lipoylation, malonylation, methylation, myristoylation, palmitoylation, phosphorylation, phosphopantetheinylation, prenylation, propionylation, ribosylation succinylation, sulfation, SUMOylation, or ubiquitination.

In embodiments, the GI disease biomarker can comprise a NEC biomarker.

In embodiments, detecting can comprise an immunoassay, a colorimetric assay, a fluorimetric assay or a combination of both. In embodiments, the immunoassay can comprise a western blot assay, an enzyme-linked immunosorbent assay (ELISA), immunoprecipitation, single molecule immunoassays in femoliter chamber arrays, digital enzyme assays in both single and multiplex forms, or a combination thereof. In embodiments, the detecting comprise contacting the sample with an anti-iAP antibody. In embodiments, the anti-iAP antibody is a polyclonal or monoclonal antibody. In embodiments, detecting can comprise a kinetic assay, an endpoint assay, Bradford assay, a bicinchoninic acid (BCA) assay, a Lowry assay, a pyrogallol red protein dye-binding assay, a Coomassie blue dye-binding assay, or a combination thereof.

In still other embodiments, detecting can comprise techniques known to one skilled in the art, such as mass spectrometry (MS), RNA sequencing, and immunostaining of patient samples. For example, RNA sequencing of intestinal alkaline phosphatase or other alkaline phosphatases is rapid method of detecting molecules, such as iAP (Knight et al. Non-invasive analysis of intestinal development in preterm and term infants using RNA-sequencing. 2014. Scientific Reports 4, 5453).

In embodiments, the assay can detect phosphatase activity. Non-limiting examples of such assays comprise fluorescent, chemiluminescent, or colorimetric dectection methods, an assay to detect ATP hydrolysis and/or products of ATP hydrolysis, or a combination thereof.

In embodiments, detecting can comprise a kinetic assay comprising use of 4-methyllumbelliferyl phosphate, CPD Star (Disodium 2-chloro-5-(4-methoxyspiro[1,2-dioxetane-3,2'-(5-chlorotricyclo[3.3.1.1$^{3,7}$]decanD-4-yl]-1-phenyl phosphate), AttosPho (2'-[2-benzothiazoyl]-6'-hydroxybenzothiazole phosphate [BBTP]), or any other fluorometric or colorimetric signal, an assay to detect ATP hydrolysis and/or products of ATP hydrolysis (for example, malachite green, NADH-coupled, or other proprietary variation), or a combination thereof.

In embodiments, alkaline phosphatase activity, such as intestinal alkaline phosphatase activity, can be directly detected and/or measured by admixing with the biological sample for a period of time chromogenic substrates and/or fluorogenic substrates of alkaline phosphatase, such as iAP. For example, 4-methylumbelliferyl phosphate (MUP) is a fluorogenic substrate for alkaline phosphatases, and alkaline phosphatase mediated hydrolysis of its phosphate substituent yields the blue-fluorescent 4-methylumbelliferyl (excitation/emission ~386/448 nm). In embodiments, the MUP can be directly admixed with the biological sample, such as stool, allowing for the direct dectection of the presence of alkaline phosphatase or the measurement of its activity.

Non-limiting examples of Alkaline phosphatase (AP) substrates comprise AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color), Fluorescein diacetate, 4-Methylumbelliferyl acetate, 4-Methylumbelliferyl casein, 4-Methylumbelliferyl-α-L-arabinopyranoside, 4-Methylumbelliferyl-β-D-fucopyranoside, 4-Methylumbelliferyl-α-L-fucopyranoside, 4-Methylumbelliferyl-β-L-fucopyranoside, 4-Methylumbelliferyl-α-D-galactopyranoside, 4-Methylumbelliferyl-β-D-galactopyranoside, 4-Methylumbelliferyl-α-D-glucopyranoside, 4-Methylumbelliferyl-β-D-glucopyranoside, 4-Methylumbelliferyl-β-D-glucuronide, 4-Methylumbelliferyl nonanoate, 4-Methylumbelliferyl oleate, 4-Methylumbelliferyl phosphate, bis(4-Methylumbelliferyl)phosphate, 4-Methylumbelliferyl pyrophosphate diester, 4-Methylumbelliferyl-β-D-xylopyranoside.

Non-limiting examples of suitable chromogenic substrates for use within the present invention comprise o-Nitrophenyl-β-D-galactopyranoside, p-Nitrophenyl-β-D-galactopyranoside, o-Nitrophenyl-β-D-glucopyranoside, p-Nitrophenyl-α-D-glucopyranoside, p-Nitrophenyl-β-D-glucopyranoside, p-Nitrophenyl-β-D-glucuronide, p-Nitrophenyl phosphate, o-Nitrophenyl-β-D-xylopyranoside, p-Nitrophenyl-α-D-xylopyranoside, p-Nitrophenyl-β-D-xylopyranoside, and Phenolphthalein-β-D-glucuronide.

In embodiments, the method as described herein further comprise diagnosing the subject with a gastrointestinal disease if the protein level of iAP in the sample is at least two standard deviations above the mean protein level of the control sample. In embodiments, the method as described herein further comprise diagnosing the subject with a gastrointestinal disease if the protein level of iAP in the sample is at least 1, 1.5, 2, 2.5, 3, 3.5, 4, 4.5, 5 standard deviations above the mean protein level of the control sample. In embodiments, the control sample can comprise two or more control samples. Embodiments can comprise 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, or 300 mg fresh weight stool/mL sterile water or buffer. For example, embodiments can comprise 200 mg fresh weigh stool/mL sterile water or buffer In embodiments, the method as described herein further comprise diagnosing the subject with a gastrointestinal disease or at risk of a gastrointestinal disease if the protein level of iAP in the sample is greater than 4.8% of the control sample. In other embodiments, the method described herein further comprise diagnosing the subject with a gastrointestinal disease or at risk of a gastrointestinal disease if the protein level of iAP in the sample is greater than 107% of the control sample. In embodiments, the method as described herein further comprise diagnosing the subject with a gastrointestinal disease or at risk of a gastrointestinal disease if the protein level of iAP in the sample is greater than 2.5%, 5%, 10%, 15%, 20%, 25%, 30%, 40%, 50%, 60%, 70%, 80%, 90%, 100%, 125%, 150%, 175%, 200%, 225%, 250%, 275%, 300%, 325%, 350%, 375%, 400% of the control sample.

In embodiments, the method as described herein further comprise diagnosing the subject with a gastrointestinal disease if the level of iAP enzyme activity in the sample is at least two standard deviations below the mean iAP enzyme activity of the control sample. In embodiments, the method as described herein further comprise diagnosing the subject with a gastrointestinal disease if the level of iAP enzyme activity in the sample is at least 1, 1.5, 2, 2.5, 3, 3.5, 4, 4.5, 5 standard deviations above the mean enzyme activity of the control sample. In embodiments, the control sample can comprise two or more control samples. In embodiments, the method as described herein further comprise diagnosing the subject with a gastrointestinal disease or at risk of a gastrointestinal disease if the level of iAP enzyme activity in the sample is lower than about 10 mU/mg, 20 mU/mg, 30 mU/mg, 40 mU/mg, 50 mU/mg, 60 mU/mg, 70 mU/mg, 80 mU/mg, 90 mU/mg, 100 mU/mg, 200 mU/mg, 300 mU/mg, 400 mU/mg, 500 mU/mg, 600 mU/mg, 700 mU/mg, 800 mU/mg, 900 mU/mg, 1000 mU/mg, 1100 mU/mg, 1200 mU/mg, 1300 mU/mg, 1400 mU/mg, 5 U/mg, 10 U/mg, 50 U/mg, 100 U/mg, 300 U/mg, 400 U/mg, 500 U/mg, 600 U/mg, 700 U/mg, 800 U/mg, 900 U/mg, 1000 U/mg, for example less than 979 mU/mg or less than 1256 mU/mg. In embodiments, the method as described herein further comprise diagnosing the subject with a gastrointestinal disease or at risk of a gastrointestinal disease if the level of iAP enzyme activity in the sample is less than 1500 mU/mg, 1000 mU/mg, 500 mU/mg, for example less than 1256 mU/mg.

In embodiments, the method as described herein further comprise diagnosing the subject with a gastrointestinal disease if the fecal protein level in the sample is at least two standard deviations above the mean fecal protein level of the control sample. In embodiments, the method as described herein further comprise diagnosing the subject with a gastrointestinal disease if the fecal protein level in the sample is at least 1, 1.5, 2, 2.5, 3, 3.5, 4, 4.5, 5 standard deviations above the mean fecal protein level of the control sample. In embodiments, the control sample can comprise two or more control samples. In embodiments, the method as described herein further comprise diagnosing the subject with a gastrointestinal disease or at risk of a gastrointestinal disease if the fecal protein level in the sample exceeds 1.6 mg/ml, or for example exceeds 1.8 mg/ml. In embodiments, the method as described herein further comprise diagnosing the subject with a gastrointestinal disease or at risk of a gastrointestinal disease if the fecal protein level in the sample exceeds 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml.

In embodiments, the method as described herein further comprise treating the subject. In embodiments, treating can comprise administering to the subject diagnosed with a gastrointestinal disease an effective amount of antibiotics, probiotics, intravenous fluids, steps to withhold oral feeding, an iAP replacement composition, parenteral (or intravenous) nutrition, or a combination thereof.

In embodiments, the subject can comprise a mammal. In embodiments, the mammal can comprise a dog, cat, horse, cow, pig, or human. In some embodiments, the biomarkers of the invention can be useful for diagnosing colic in horses. In embodiments, the human can comprise an infant. In embodiments, the infant can comprise a preterm infant.

The present invention further provides a method for screening the presence of a signature in a subject, such as a subject at risk of developing a gastrointestinal disease or a subject with a non-symptomatic gastrointestinal disease, comprising obtaining a sample from the subject, measuring at least one GI disease biomarker in the sample, wherein the GI disease biomarker can comprise intestinal alkaline phosphatase (iAP) protein, comparing the GI disease biomarker profile to that of a profile obtained from a control or reference sample, and treating the subject. In embodiments, the control or reference sample can comprise two or more control samples. In embodiments, the sample is a fecal sample.

The present invention further provides a method for identifying a subject at risk for a gastrointestinal disease or a subject with a non-symptomatic gastrointestinal disease comprising obtaining a sample from the subject, measuring at least one GI disease biomarker in the sample, wherein the GI disease biomarker can comprise intestinal alkaline phosphatase (iAP) protein, comparing the GI disease biomarker profile to that of a profile obtained from a control sample, and treating the subject. In embodiments, the control sample can comprise two or more control samples.

In embodiments the gastrointestinal disease can comprise colitis, inflammatory bowel disease (IBD), or a combination thereof. In embodiments, colitis can comprise necrotizing enterocolitis, adult necrotizing enterocolitis (ANEC), pseudomembranous enterocolitis, infectious colitis, ulcerative colitis, Crohn's disease, ischemic colitis, radiation colitis.

In embodiments, the sample can comprise a biological sample obtained from subject. For example, the biological sample can be a biological fluid, a biological solid, or a biological semi-solid. In embodiments, the sample can comprise fecal matter, meconium, vomit, peripheral blood, sera, plasma, or urine.

In embodiments, the GI disease biomarker further can comprise iAP enzymatic activity, total fecal protein, iAP dimerization/dissociation, post-translationally modified iAP, or a combination thereof. In embodiments, the post-translational modification can comprise acetylation, acylation, alkylation, amidation, butyrylation, deamidation, formylation, glypiation, glycosylation, hydroxylation, iodination, ISGylation, lipoylation, malonylation, methylation, myristoylation, palmitoylation, phosphorylation, phosphopantetheinylation, prenylation, propionylation, ribosylation succinylation, sulfation, SUMOylation, or ubiquitination.

In embodiments, measuring can comprise performing an assay to determine total protein concentration, intestinal alkaline phosphatase enzyme activity, intestinal alkaline phosphatase protein concentration, or a combination thereof in the sample. In embodiments, measuring can comprise a Bradford assay, a bicinchoninic acid (BCA) assay, a Lowry assay, a pyrogallol red protein dye-binding assay, a Coomassie blue dye-binding assay, or a combination thereof. In embodiments, measuring can comprise a kinetic assay. In embodiments, the kinetic assay can comprise use of 4-methyllumbelliferyl phosphate, nitrophenyl phosphate, or any other fluorometric or colorimetric signal, an assay to detect ATP hydrolysis, or a combination thereof. In embodiments, measuring can comprise an immunoassay, a colorimetric assay, fluorimetric assay or a combination of both.

In embodiments, the immunoassay can comprise a western blot assay, an enzyme-linked immunosorbent assay, immunoprecipitation or a combination thereof. In embodiments, the assay can comprise an anti-iAP antibody. In embodiments, the anti-iAP antibody is a monoclonal or polyclonal antibody.

In embodiments, methods as disclosed herein can further comprise diagnosing the subject with a gastrointestinal disease when total protein concentration in the sample is at least two standard deviations above the mean of the control sample, the concentration of intestinal alkaline phosphatase protein is at least two standard deviations above the mean of the control sample, intestinal alkaline phosphatase activity is at least two standard deviations below the mean of the control sample, or a combination thereof. In embodiments, methods as disclosed herein can further comprise diagnosing the subject with a gastrointestinal disease when total protein concentration in the sample is at least 1, 1.5, 2, 2.5, 3, 3.5, 4, 4.5, 5 standard deviations above the mean of the control sample, the concentration of intestinal alkaline phosphatase protein is at least 1, 1.5, 2, 2.5, 3, 3.5, 4, 4.5, 5 standard deviations above the mean of the control sample, intestinal alkaline phosphatase activity is at least 1, 1.5, 2, 2.5, 3, 3.5, 4, 4.5, 5 standard deviations below the mean of the control sample, or a combination thereof. In embodiments, the control sample can comprise two or more control samples.

In embodiments, methods as disclosed herein can further comprise treating the subject. In embodiments, treating can comprise administering to the subject diagnosed with a gastrointestinal disease an effective amount of antibiotics, probiotics, intravenous fluids, withholding oral feeding, an iAP replacement composition, an anti-inflammatory, a potential therapeutic, parenteral (or intravenous) nutrition, or a combination thereof.

In embodiments, the subject can be diagnosed with a gastrointestinal disease or at risk of a gastrointestinal disease if the protein concentration in fecal sample is greater than about 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml, for example 1.6 mg/ml, or for example 1.8 mg/ml. In embodiments, the subject can be diagnosed with a gastrointestinal disease or at risk of a gastrointestinal disease if the iAP activity is lower than about 10 mU/mg, 20 mU/mg, 30 mU/mg, 40 mU/mg, 50 mU/mg, 60 mU/mg, 70 mU/mg, 80 mU/mg, 90 mU/mg, 100 mU/mg, 200 mU/mg, 300 mU/mg, 400 mU/mg, 500 mU/mg, 600 mU/mg, 700 mU/mg, 800 mU/mg, 900 mU/mg, 1000 mU/mg, 1100 mU/mg, 1200 mU/mg, 1300 mU/mg, 1400 mU/mg, 5 U/mg, 10 U/mg, 50 U/mg, 100 U/mg, 200 U/mg, 300 U/mg, 400 U/mg, 500 U/mg, 600 U/mg, 700 U/mg, 800 U/mg, 900 U/mg, 1000 U/mg, for example 972 mU/mg, or for example 1256 mU/mg. In embodiments, the subject can be diagnosed with a gastrointestinal disease or at risk of a gastrointestinal disease if the iAP protein detection by anti-iAP antibody exceeds 4.8% of control via densitometry. In embodiments, the subject can be diagnosed with a gastrointestinal disease if the level of iAP protein is at least two standard deviations above the mean of the control sample. In embodiments, the control sample can comprise two or more control samples. In embodiments, the subject can comprise a mammal. In embodiments, the mammal can comprise a dog, cat, horse, cow, or human. In embodiments, the human can comprise an infant. In embodiments, the infant can comprise a preterm infant.

The present invention further provides for a disposable article, the disposable article comprising a biosensor, wherein the biosensor can comprise at least one bio-recognition element, and wherein the biosensor detects iAP in a sample.

In embodiments, the biosensor further detects iAP enzymatic activity, total fecal protein, iAP dimerization/dissociation, post-translationally modified iAP, or a combination thereof. In embodiments, the post-translational modification can comprise acetylation, acylation, alkylation, amidation, butyrylation, deamidation, formylation, glypiation, glycosylation, hydroxylation, iodination, ISGylation, lipoylation, malonylation, methylation, myristoylation, palmitoylation, phosphorylation, phosphopantetheinylation, prenylation, propionylation, ribosylation succinylation, sulfation, SUMOylation, or ubiquitination.

In embodiments, the sample can comprise a biological sample obtained from subject. For example, the biological sample can be a biological fluid, a biological solid, or a biological semi-solid. In embodiments, the sample can comprise fecal matter, meconium, vomit, peripheral blood, sera, plasma, or urine.

In embodiments, the biosensor is an immunosensor. In embodiments, the biosensor can comprise a detection signal. In embodiments, the detection signal can comprise a colorimetric signal, a fluorescent signal, or both. In embodiments, the bio-recognition element can comprise an anti-iAP antibody. In embodiments, the anti-iAP antibody can comprise a polyclonal or monoclonal antibody.

In an exemplary embodiment, the biosensor can comprise lateral flow immunoassays, also known as immunochromatography assay or a strip test. Lateral flow immunoassays comprise immunoassays adapted to operate along a single axis to suit the test strip format. A typical lateral flow test strip comprises a sample pad (an adsorbent pad onto which the test sample is applied), a conjugate or reagent pad (this contains binding agents, such as antibodies, specific to the target analyte conjugate to colored particles, such as colloidal gold nanoparticles or latex microspheres), reaction membrane (typically a nitrocellulose or cellulose acetate membrane onto which anti-target analyte binding agents, such as antibodies, are immobilized in a line that crosses the membrane to act as a capture zone or test line. A control zone will also be present, containing antibodies specific for the conjugate antibodies), and a wick or waste reservoir (a further absorbent pad designed to draw the sample across the reaction membrane by capillary action and collect it). The components of the strip are usually fixed to an inert backing material and may be presented in a simple dipstick format or within a plastic casing with a sample port and reaction window showing the capture and control zones.

In embodiments, the article can comprise a diaper to be worn by a subject, wipe for cleaning a subject, dipstick, spoon, scoopula, filter paper or swab.

In embodiments, the subject can comprise a mammal. In embodiments, the mammal can comprise a dog, cat, horse, cow, or human. In embodiments, the human can comprise an infant. In embodiments, the infant can comprise a preterm infant.

The present invention further provides for a kit for diagnosing a subject with a gastrointestinal disease. In embodiments, the kit can comprise a disposable article as described herein. In embodiments, the gastrointestinal disease can comprise colitis, inflammatory bowel disease (IBD), or a combination thereof. In embodiments, colitis can comprise necrotizing enterocolitis, adult necrotizing enterocolitis (ANEC), pseudomembranous enterocolitis, infectious colitis, ulcerative colitis, Crohn's disease, ischemic colitis, radiation colitis.

In embodiments, the kit can comprise an iAP bio-recognition element immobilized to a solid support and instructions for use of same.

In embodiments, the gastrointestinal disease can comprise colitis, inflammatory bowel disease, or a combination thereof. In embodiments, colitis can comprise necrotizing enterocolitis, adult necrotizing enterocolitis (ANEC), pseudomembranous enterocolitis, infectious colitis, ulcerative colitis, Crohn's disease, ischemic colitis, radiation colitis.

In embodiments, the bio-recognition element can comprise an antibody directed to iAP or an oligonucleotide directed to iAP, for example, that is affixed directly or indirectly to a solid support. Embodiments can also comprise a fluorescent substrate or inhibitor with high binding affinity to iAP attached to the solid support.

In embodiments, the solid support can comprise plastic, cardboard, or glass. In embodiments, the solid support can comprise a dip stick.

In embodiments, the subject can comprise a mammal. In embodiments, the mammal can comprise a dog, cat, horse, cow, or human. In embodiments, the human can comprise an infant. In embodiments, the infant can comprise a preterm infant.

The present invention further provides a diagnostic kit of molecular biomarkers for identifying a subject exhibiting or having a predisposition to develop a gastrointestinal disease. In embodiments, the kit can comprise at least one of a means for determining total fecal protein concentration, a means for determining intestinal alkaline phosphatase (iAP) activity, and an iAP bio-recognition element, wherein together represent a molecular signature that is indicative of the presence of or a predisposition to development of a gastrointestinal disease in a human subject. In embodiments, the gastrointestinal disease can comprise colitis, inflammatory bowel disease (IBD), or a combination thereof. In embodiments, colitis can comprise necrotizing enterocolitis, adult necrotizing enterocolitis (ANEC), pseudomembranous enterocolitis, infectious colitis, ulcerative colitis, Crohn's disease, ischemic colitis, radiation colitis.

In embodiments, the signature can comprise total protein concentration at least two standard deviations above the mean of a control sample, intestinal alkaline phosphatase protein concentration at least two standard deviations above the mean of a control sample, or intestinal alkaline phosphatase activity at least two standard deviations below the mean of a control sample. In embodiments, the control sample can comprise two or more control samples.

In embodiments, the signature can be selected from at least two of the group comprising total protein concentration at least two standard deviations above the mean of a control sample, intestinal alkaline phosphatase protein concentration at least two standard deviations above the mean of a control sample, and intestinal alkaline phosphatase activity at least two standard deviations below the mean of a control sample. In embodiments, the control sample can comprise two or more control samples.

In embodiments, the subject can comprise a mammal. In embodiments, the mammal can comprise a dog, cat, horse, cow, or human. In embodiments, the human can comprise an infant. In embodiments, the infant can comprise a preterm infant.

Aspects of the invention are further directed towards treating an NEC-afflicted subject by altering a feeding regimen. In one embodiment, the invention provides for a method for treating an NEC-afflicted subject. In some embodiments, the method comprises measuring, in a sample obtained from the subject according to the methods described herein, the amount or activity of iAP-bound agent, wherein the iAP-bound agent is at least one GI disease biomarker comprising iAP enzymatic activity, AP enzymatic activity, iAP protein level, AP protein level, iAP dimerization/dissociation, post-translationally modified iAP, total fecal protein, or a combination thereof; determining the post-partum developmental age of the subject; and withholding enteral feeding for a period of time sufficient to resolve gastrointestinal inflammatory processes or signs of feeding intolerance. In some embodiments, the method further comprises administering an antibiotic or an antifungal, either alone or in combination. In some embodiments, the method further comprises administering a probiotic, other biologic (such as stem cells or transcription factors), or therapeutic (such as TLR4 small molecules, alkaline phosphatase inhibitors or activators), antibiotics, intravenous fluids, an iAP replacement composition (such as that provide exogenously), a small molecule activator and/or effector of catalytic activity, an anti-inflammatory, parenteral (or intravenous) nutrition, either alone or in a combination thereof. In some embodiments, the post-partum developmental age of a subject can be 'post-menstrual age' or a 'post-menstrual developmental age'.

For example, oral feeding can be withheld for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

Non-limiting examples of biologics comprise stem cells and transcription factors. The small intestine epithelium is in a constant dynamic state of flux and replaces itself every 3-6 days. This continuous renewal is necessary for maintenance of normal gut structure and function. Further, non-limiting examples of transcription factors include those that can be expressed and used for enterocyte differentiation, such as the Kruppel-like factor (GKLF or KLF4) family.

In embodiments, the feeding regiment can comprise an intermittent feeding regiment. For example, during an extended period of withholding oral feeding, there may be one or more days of feed. For example, feeding can be withheld for about 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days, during which time there may be one or more days of oral feeding. For example, a doctor may suspect NEC and withhold feeding for a short period of time, such as one day or two days, until lab tests/examinations suggest that the baby does not have NEC, at which time they would resume feeding again. Several hours or days later, there may be another NEC scare and food would be withheld from the baby again for a period of time. Intermittent feed can occur one or more times throughout a subjects stay in the hospital. Such intermittent feeding may allow the clinician to determine the tolerability to feeding of the subject. In other embodiments, intermittent feeding may be recommended for a subject at risk of developing a gastrointestinal disorder. Other objects and advantages of this invention will become readily apparent from the ensuing description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4 shows demographic information of the study subjects. Averages and standard deviations are shown for gestational age and birth weight. Distribution of gestational age, gender, and Bell stage is also reported.

FIG. 6 shows demographics of patient enrollment in study.

FIG. 13 shows stool samples can be heterogeneous. There were two identifiable consistency compartments in a stool sample from a NEC patient. The stool compartments were separated and western blots were run on each compartment separately with differing results.

For this analysis, the term 'suspected NEC' is stage I and the 'proven NEC' is stage II and more severe stages; the term 'perforated NEC' was used only to describe stage IIIB. Information from chart review was used to diagnose stage I. Radiographic determination of stage II required a record of pneumotosis intestinalis.

Figure 15:

FIG. 15 shows immunohistochemical staining of intestinal tissue.

Figure 16:
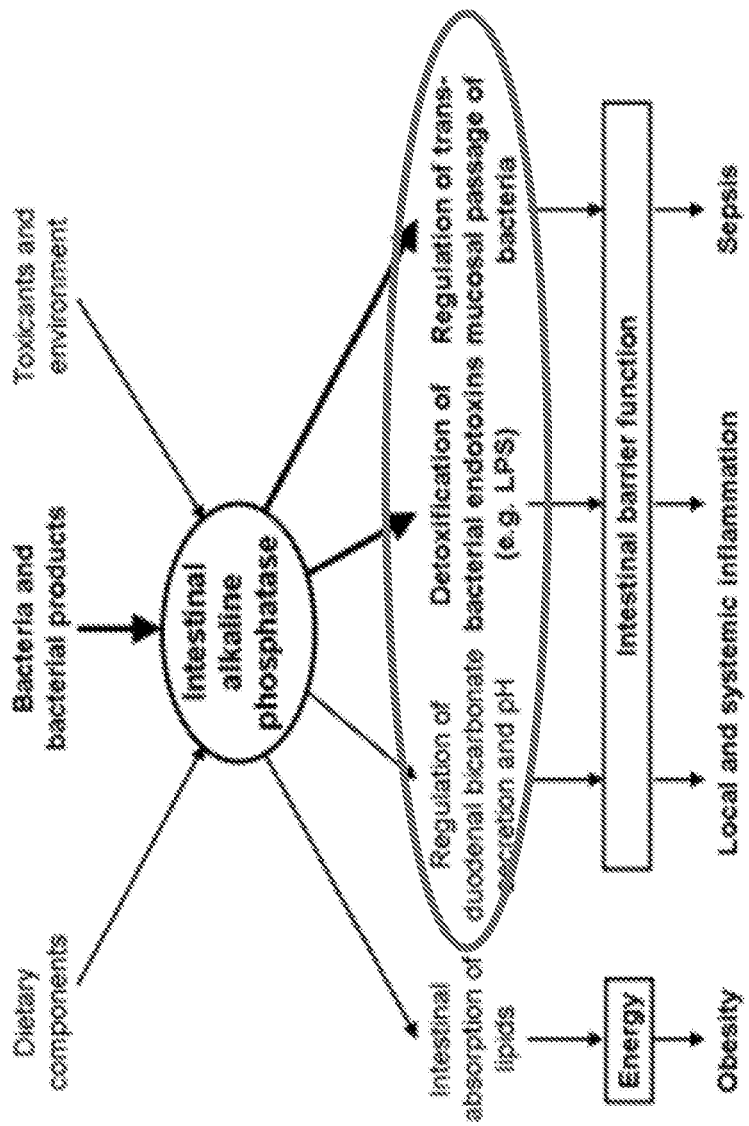

FIG. 16 shows schematic showing the many functions of iAP.

Figure 17:
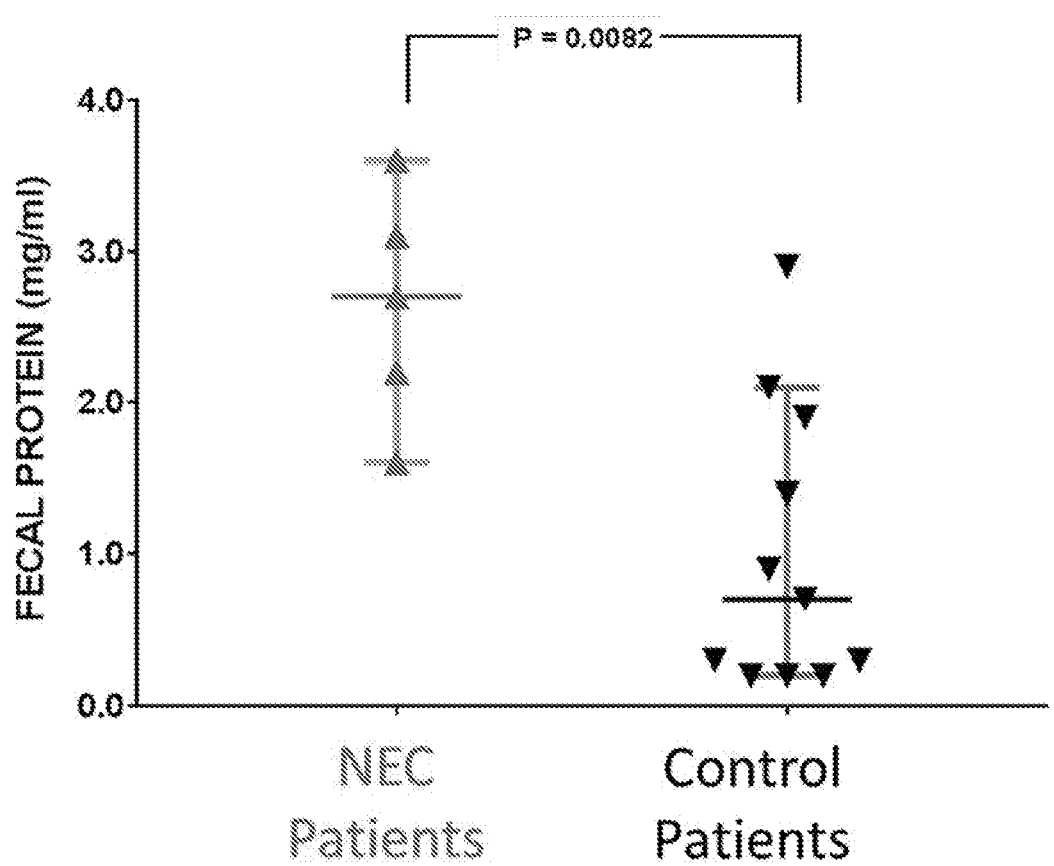

FIG. 17 shows fecal total protein content was higher in NEC patients than in control infants.

Figure 18:
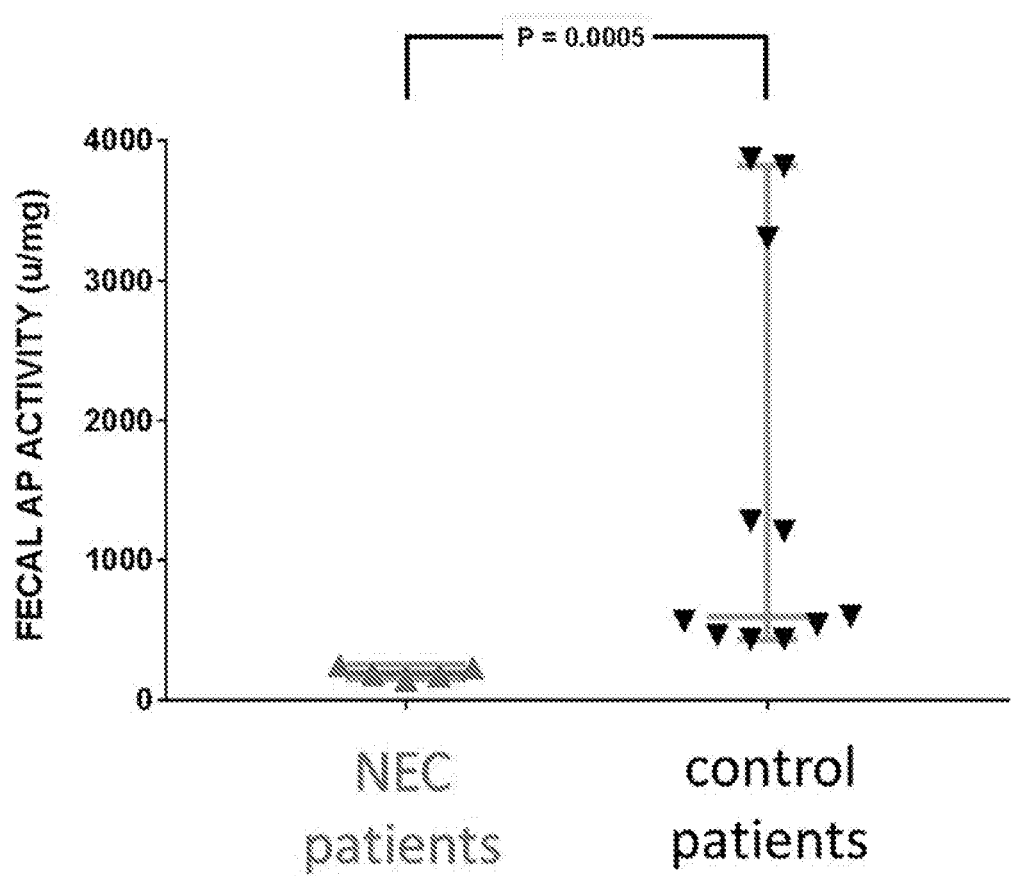

FIG. 18 shows fecal AP catalytic activity was consistently lower in NEC population.

Figure 19:
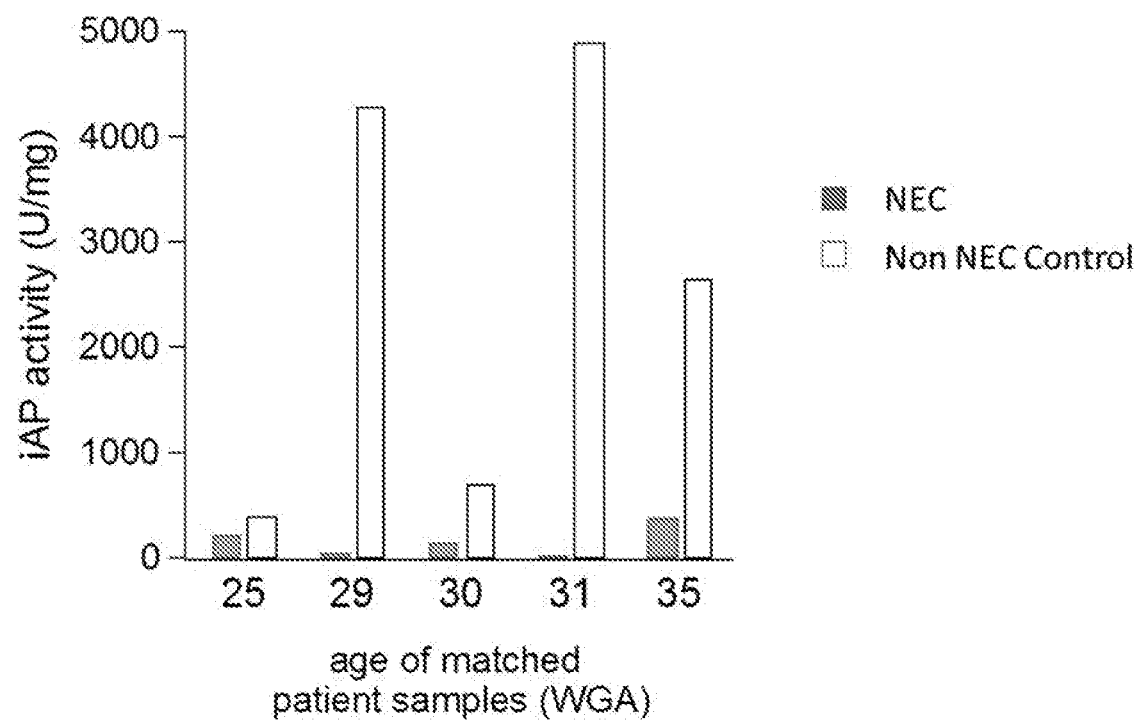

FIG. 19 shows AP enzyme activity at time of NEC diagnosis was always lower in matched patient samples.

Figure 20:
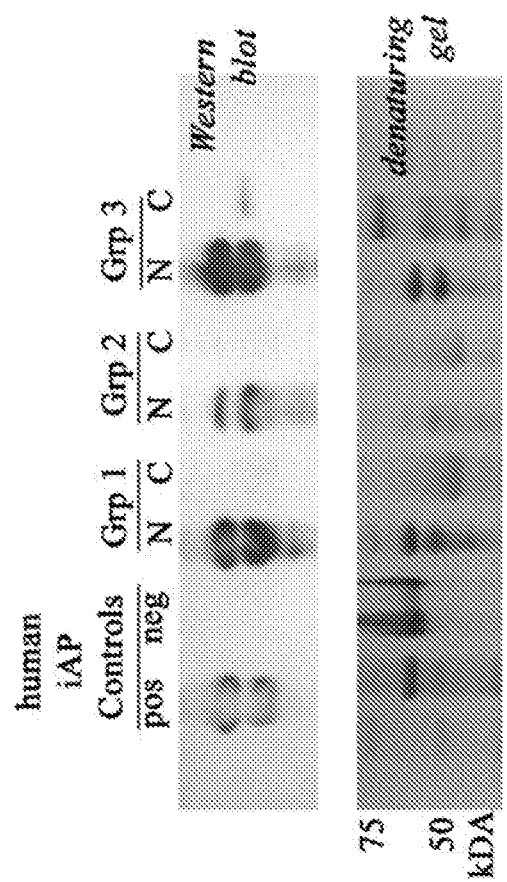

FIG. 20 shows high levels of iAP protein are detected in association with NEC.

Figure 21:
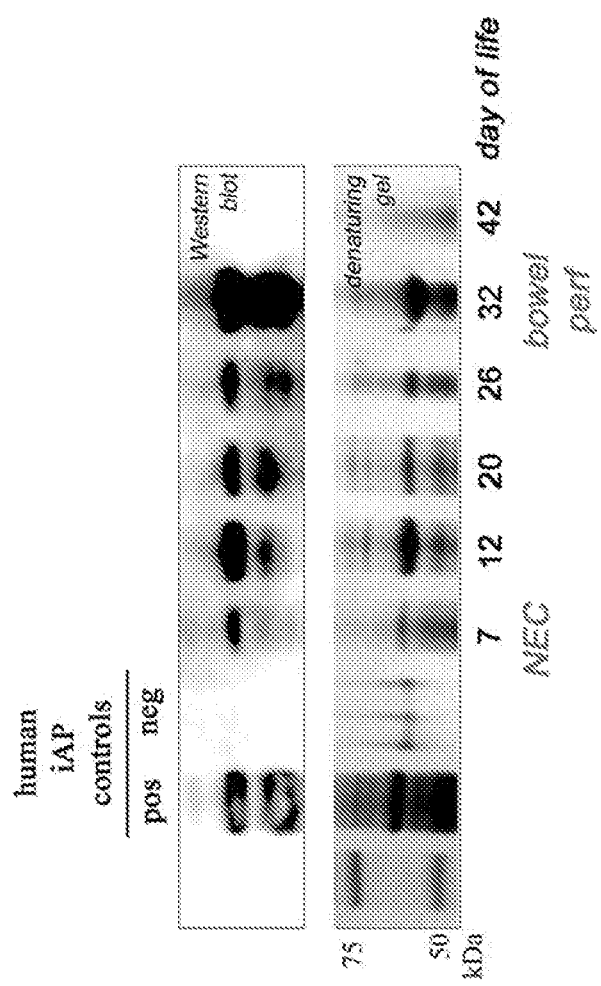

FIG. 21 shows increased fecal iAP protein levels in NEC episodes.

Figure 22:
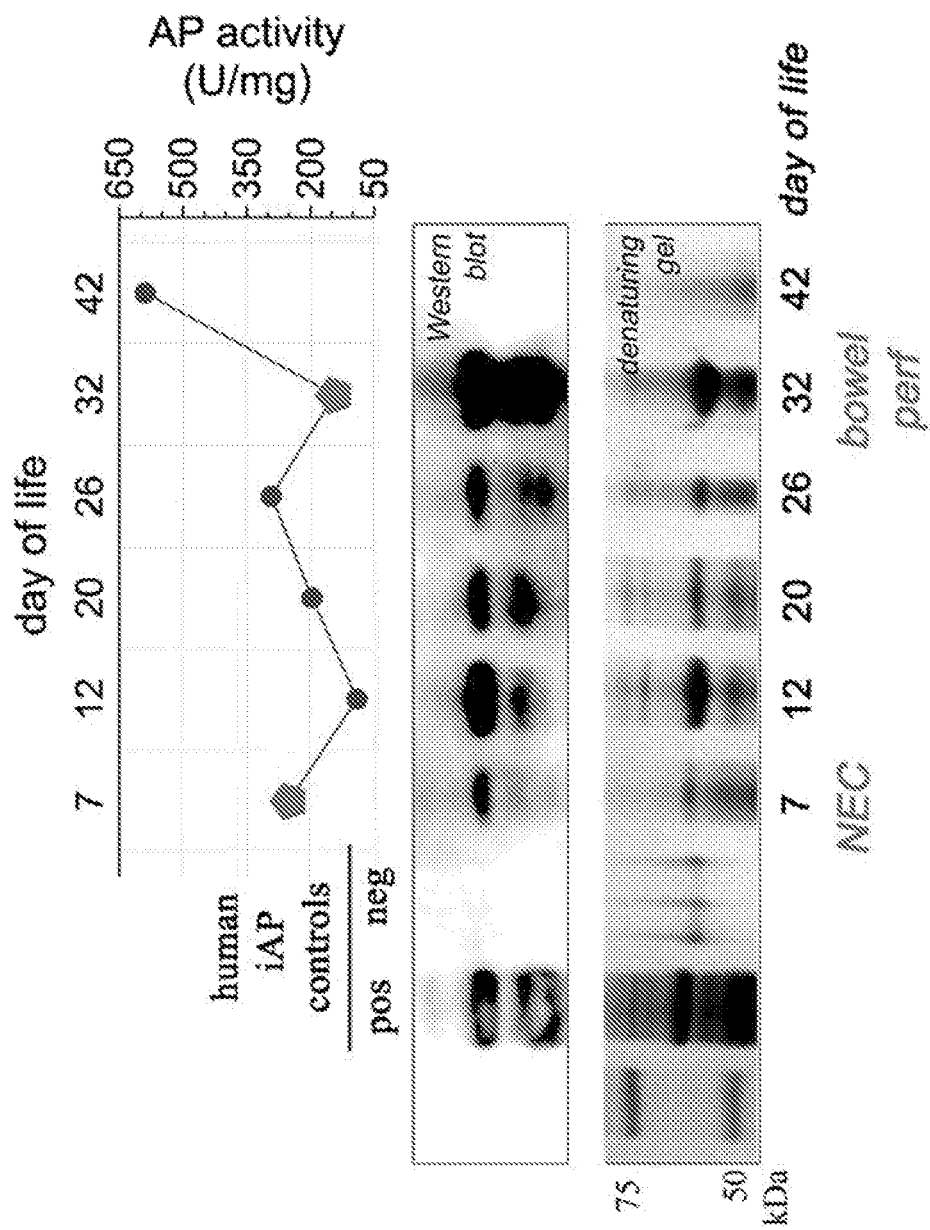

FIG. 22 shows increased iAP protein levels and decreased iAP enzyme activity in NEC episodes.

FIG. 23 shows a schematic for testing for non-specific binding of secondary antibody. Without being bound by theory, the enzyme assay can be conducted with just a secondary antibody conjugated with AP.

Figure 24:
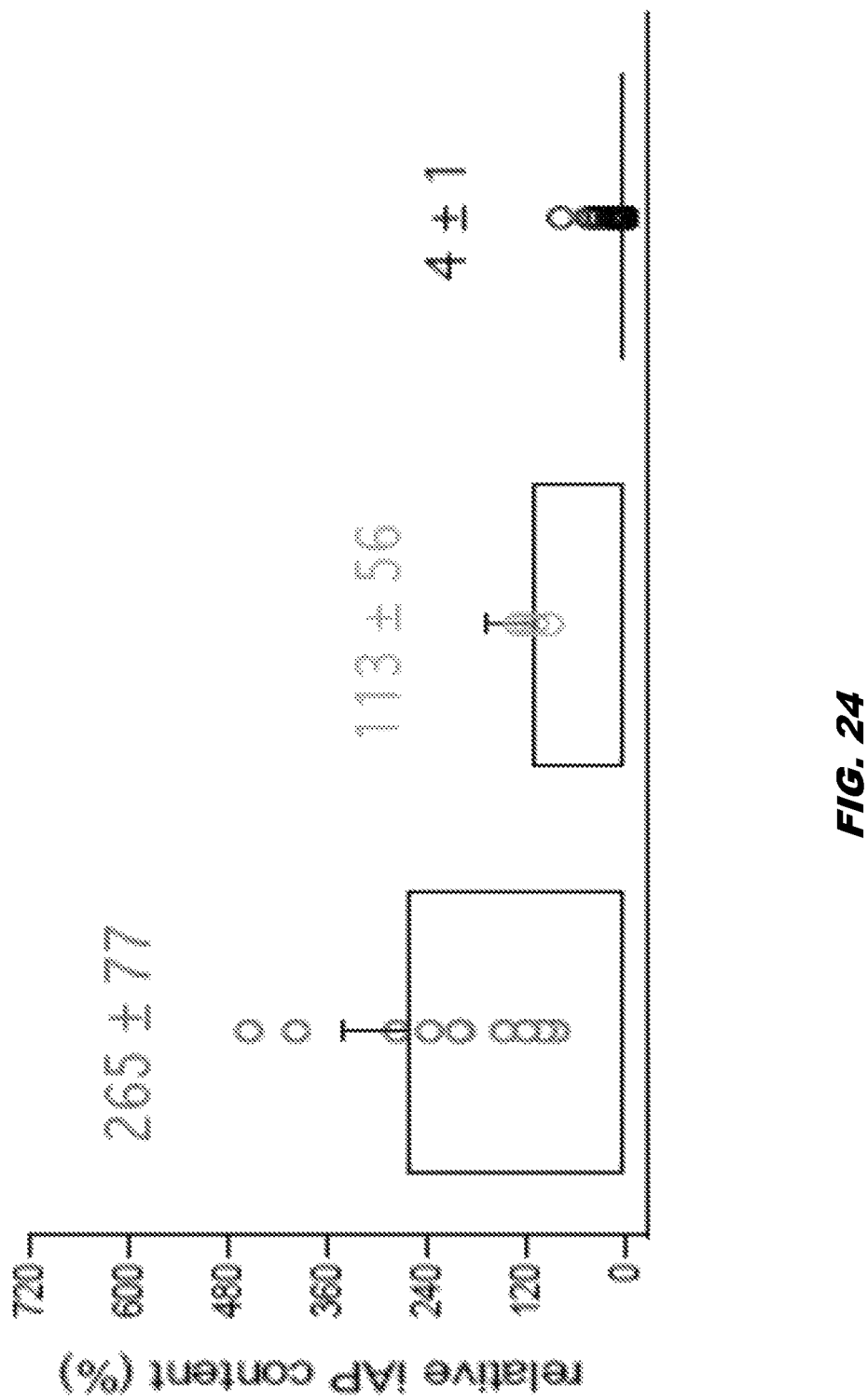

FIG. 24 shows clinical data that separates NEC diagnosis that matches X-ray and NEC suspicion (defined by neonatologists) and controls, demonstrating that the biomarker(s) can molecularly define NEC earlier.

Figure 25:
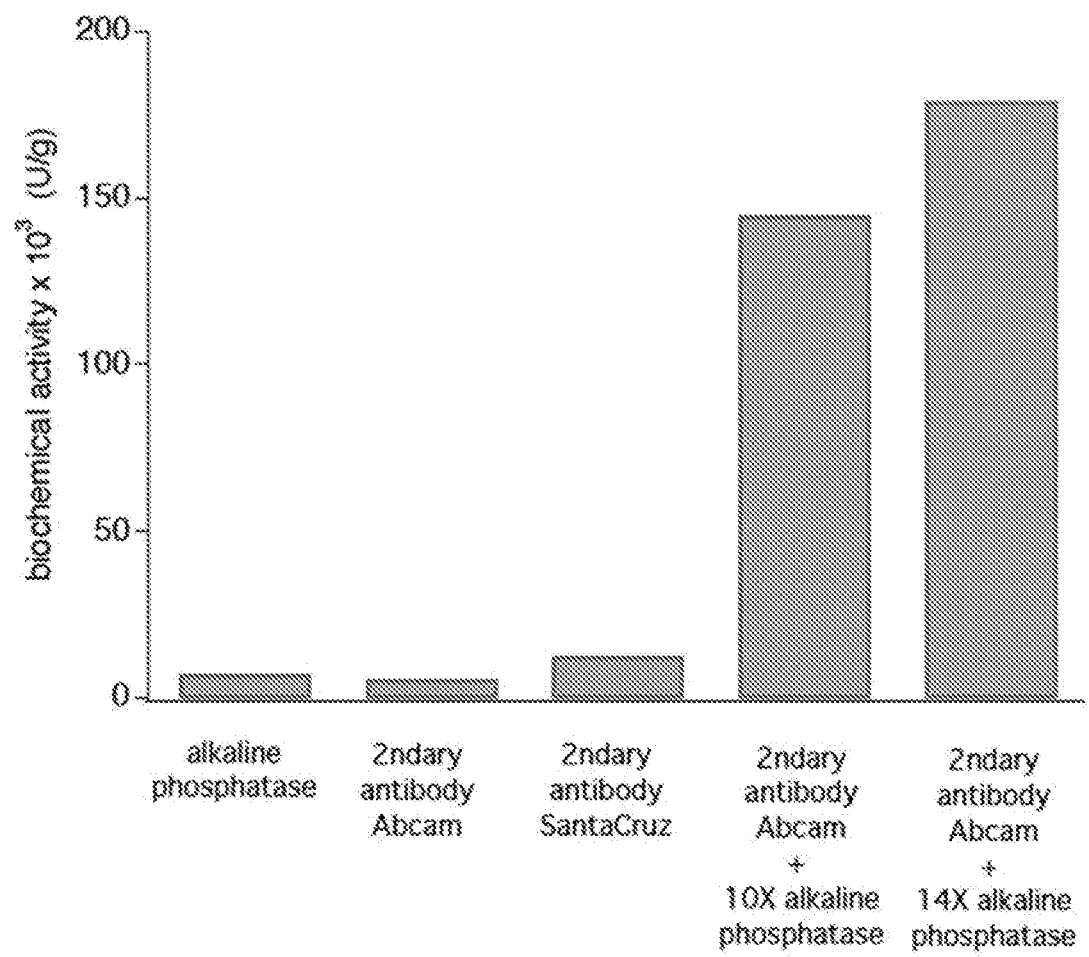

FIG. 25 is a bar graph showing that measurement of alkaline phosphatase can be confounded by signal from secondary antibodies. Isolated alkaline phosphatase can catalytically hydrolyze MUP to form the fluorescent product MU. Secondary antibodies, conjugated to AP, from two different commercial manufacturers can also hydrolyze MUP to form fluorescent product. When both alkaline phosphatase protein and the secondary antibody are in the same measurement, there is an increased level of catalytic activity observed. This can be monitored by both standard spectrophotometric readings of biochemical activity and by Western blot.

Figure 26:
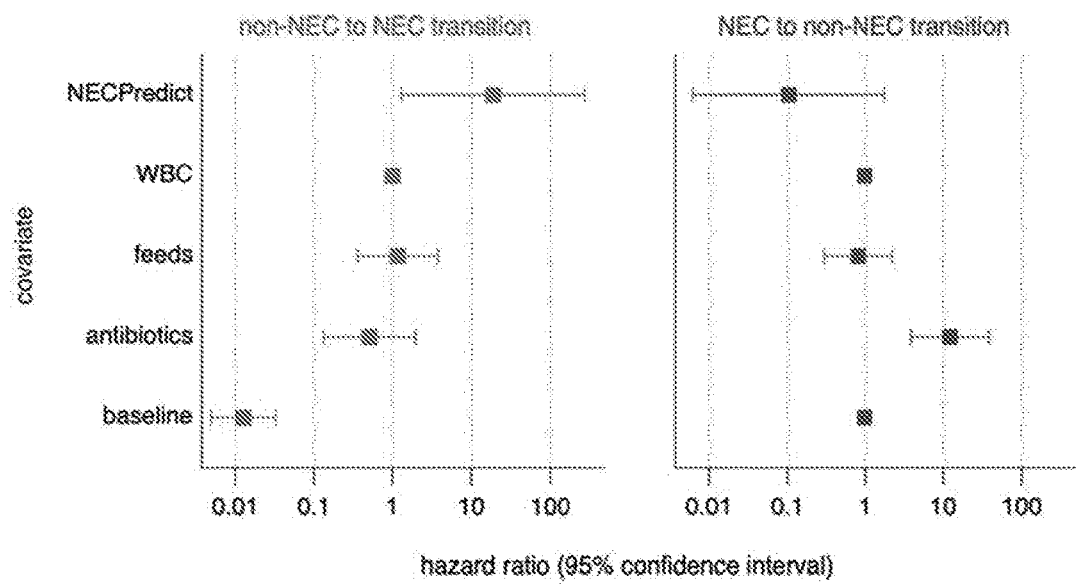

FIG. 26 shows the risk of non-NEC to NEC transition and NEC to non-NEC transition.

Figure 27:
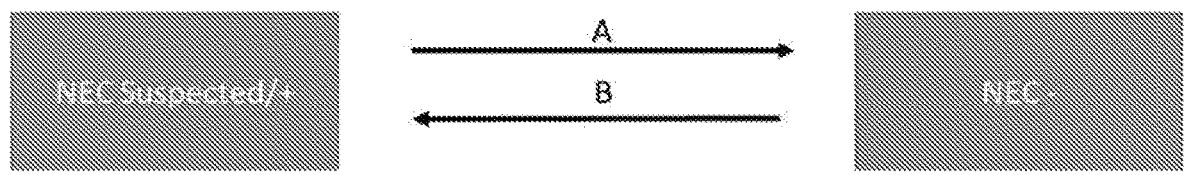

FIG. 27 shows a schematic of a Transition Model.

Figure 28:
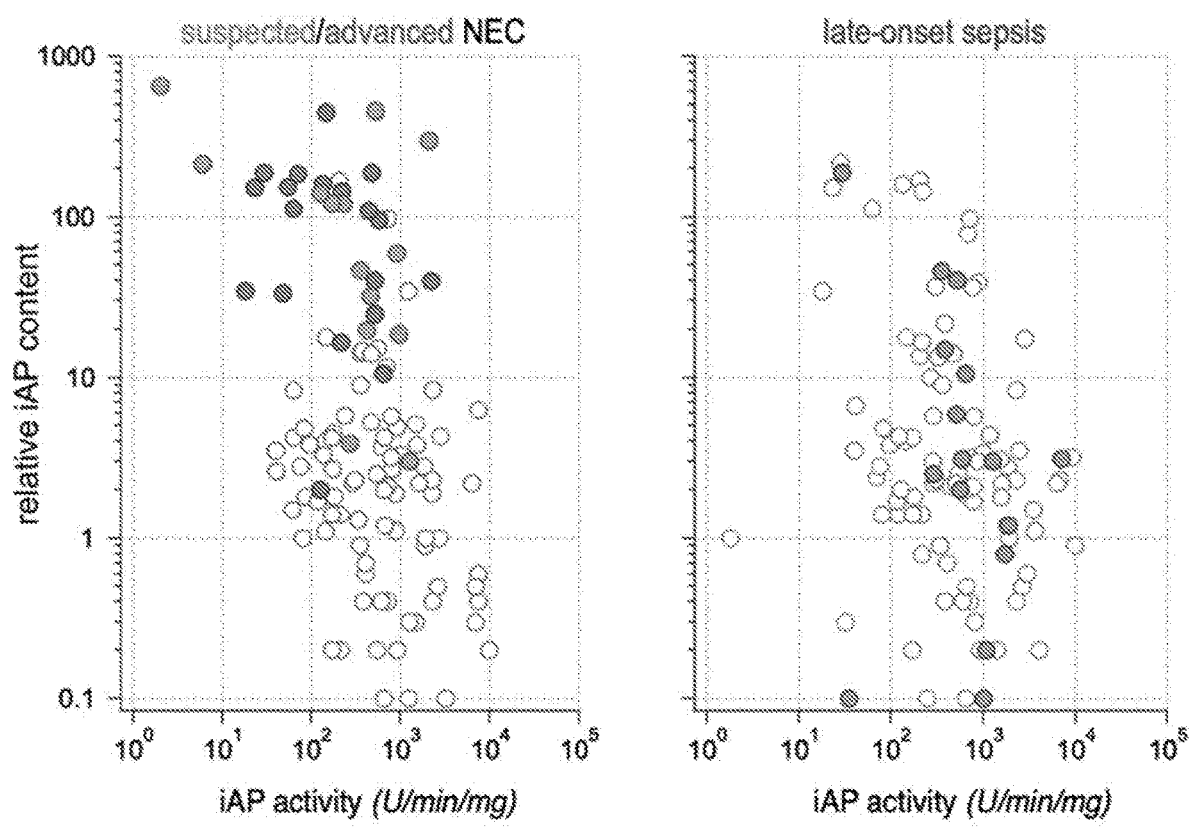
Figure 29:
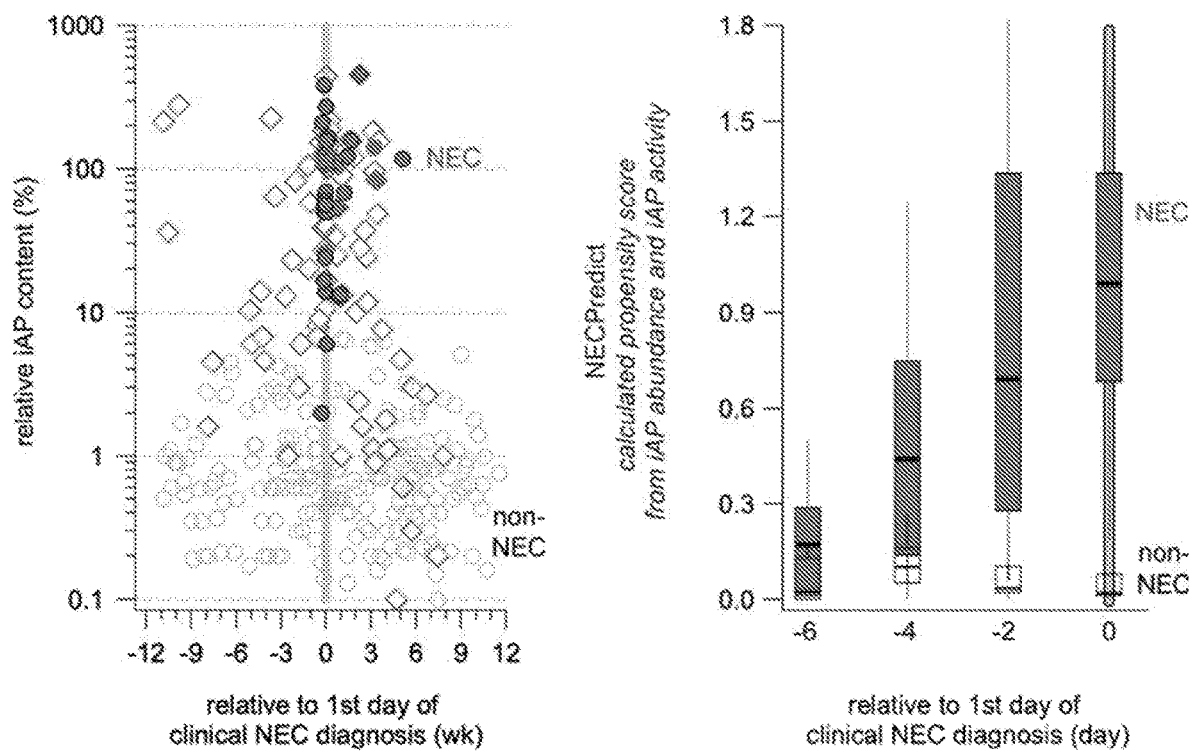

FIG. 28 shows bivariate analysis of abundance and catalytic ability of intestinal alkaline phosphatase found in preterm infant stool. Biospecimens sampled at the time of disease are shown in colored circles; suspected necrotizing enterocolitis is in pink, severe necrotizing enterocolitis is in red, late-onset sepsis is in blue. Complementary control groups are shown in open grey circles FIG. 29 shows analyses of intestinal alkaline phosphatase, found in preterm infant stool, relative to radiographic clinical evidence of diagnosis. Abundance of iAP in infant stool samples, relatively to human small intestinal lysate, is shown in the left panel. Biospecimens sampled at the time of clinical determination of disease (vertical blue bar) are shown in colored circles; samples collected prior and post-disease, from infants who did have NEC, are shown in open red diamonds; samples collected from non-NEC patients are shown in grey. Normalized iAP abundance and normalized iAP catalytic activity of iAP were multiplied to yield a propensity score (NECPredict) and these scores are shown on the right panel. The box plots shown the median values of NECPredict at the time of clinical diagnosis (red box on x-axis day zero), as well as two, four, and six days prior to radiological determination of disease. Also shown are the box plots for NECPredict values obtained from non-NEC infant samples. Whisker method is adjacent data points and quartile method is Tukey.

Figure 30:
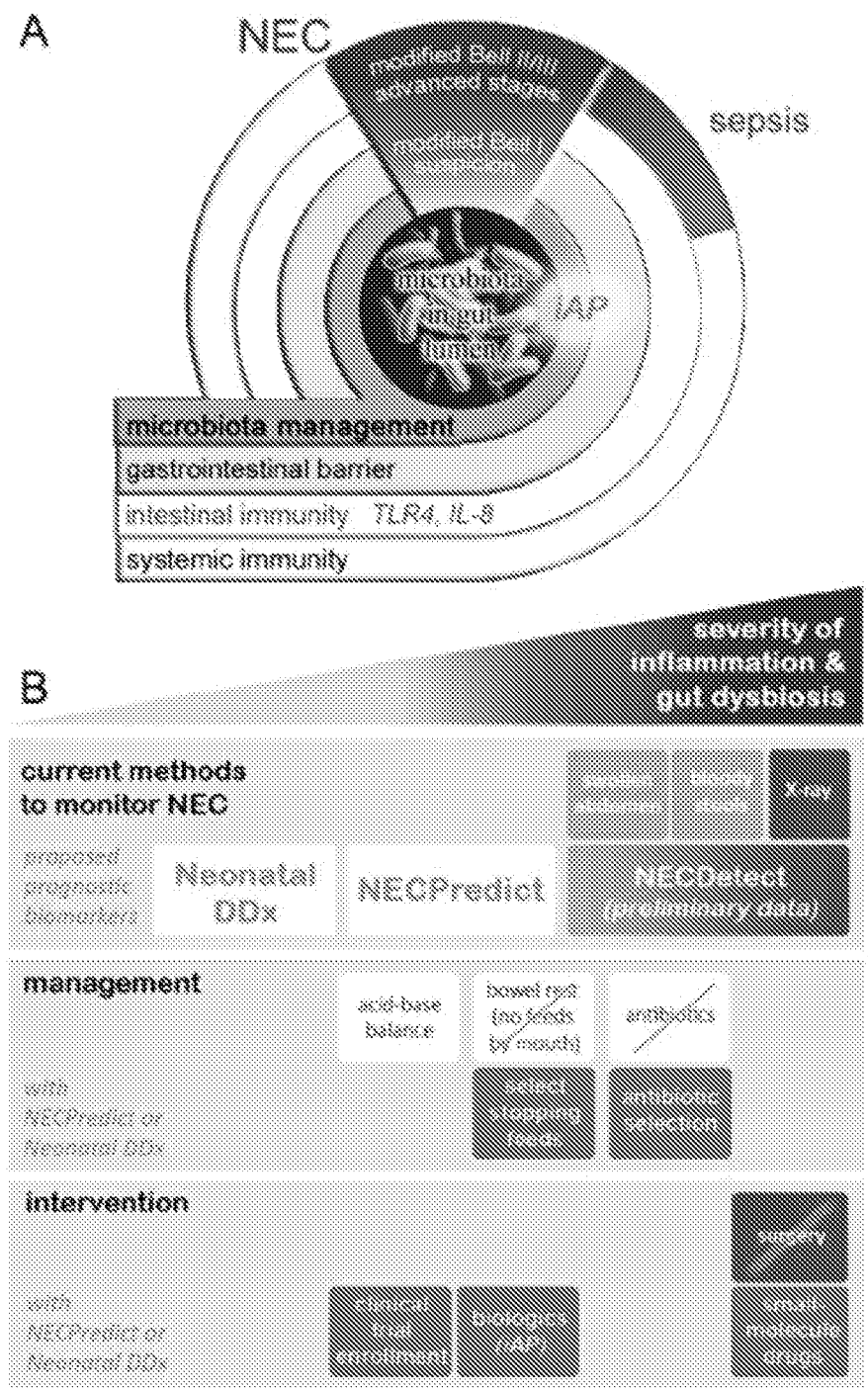

FIG. 30 shows (A) relationship between NEC, sepsis and gut defense mechanisms. Microbiota create distinct ecosystems in the gut lumen and mucosa. Various mucosal microbiota, both commensal and pathogenic, regulate intestinal immune function of the infant host. Activation of innate & adaptive immune systems by the microbiota in turn regulates systemic immune responses. In sepsis, immune responses in distant organ are triggered due to extreme signaling. Host proteins iAP (green), TLR4 and IL-8 (blue) are proteins involved in microbiota responses at early and later stages of inflammation. (B) Preemie standard of care requires new methods to monitor NEC disease. Gold standard for diagnosis is x-ray (blue box) and identifies only 44% of advanced NEC cases; other diagnostic methods (light blue boxes) are bedside observable states, but not molecular definitions Current management choices in NEC (white boxes) are contrasted with potential clinical outcomes (red boxes) from use of proposed biomarkers (green).

Figure 31:
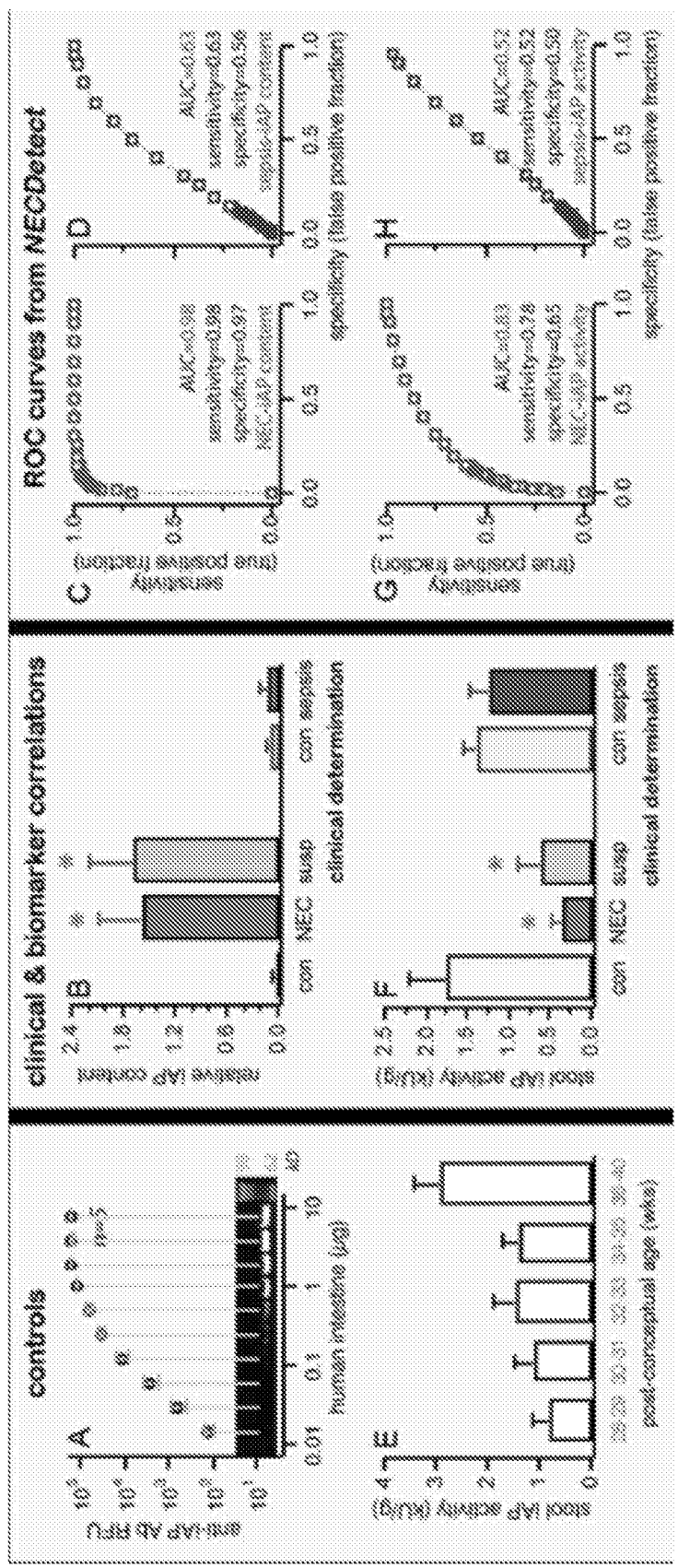

FIG. 31 shows amount of iAP protein and its catalytic activity were measured in stool samples. (A) Immunoblot-analysis showed that relative iAP content detected in a serial dilution of human small intestinal lysate had a linear relationship, if calibrator is ≤1 µg. Immunoblot bands are white against a black background. Log-log plot of signal versus calibrator is superimposed; averages and SEM of 5 replicates are shown. (B) Average±SEM of iAP content for samples free of disease (white), diagnosed with NEC (red), suspected of having NEC (pink) and diagnosed with sepsis (blue) are shown. Quantitation of iAP in each sample was determined using human intestine as the maximum positive control in linear range (100% iAP content) and calf iAP as the negative control (0% iAP content). Asterisks denote p-values<0.001 and significant differences between medians in disease-state versus control, using Mann-Whitney U-test. Immunoblot efficacy was assessed via sensitivity/specificity calculation for NEC diagnosis (C) and sepsis (D), using a simple threshold-based classifier. (E) There is direct correlation between stool iAP activity and post-conceptual age (PCA). Shown are averages and standard errors, binned by PCA. N=14-33 samples per control PCA bin. (F) Average±SEM of enzyme activity for samples free of disease (white), diagnosed with NEC (red), suspected of having NEC (pink) and diagnosed with sepsis (blue) are shown. Asterisks denote p-values<0.05. Sensitivity/specificity of iAP activity biomarker was assessed for samples at time of NEC diagnosis (G) and sepsis (H).

FIG. 32 shows stimulation scenarios considered for sample size justification.

FIG. 33 shows power analysis results for different effect sizes.

Figure 34:
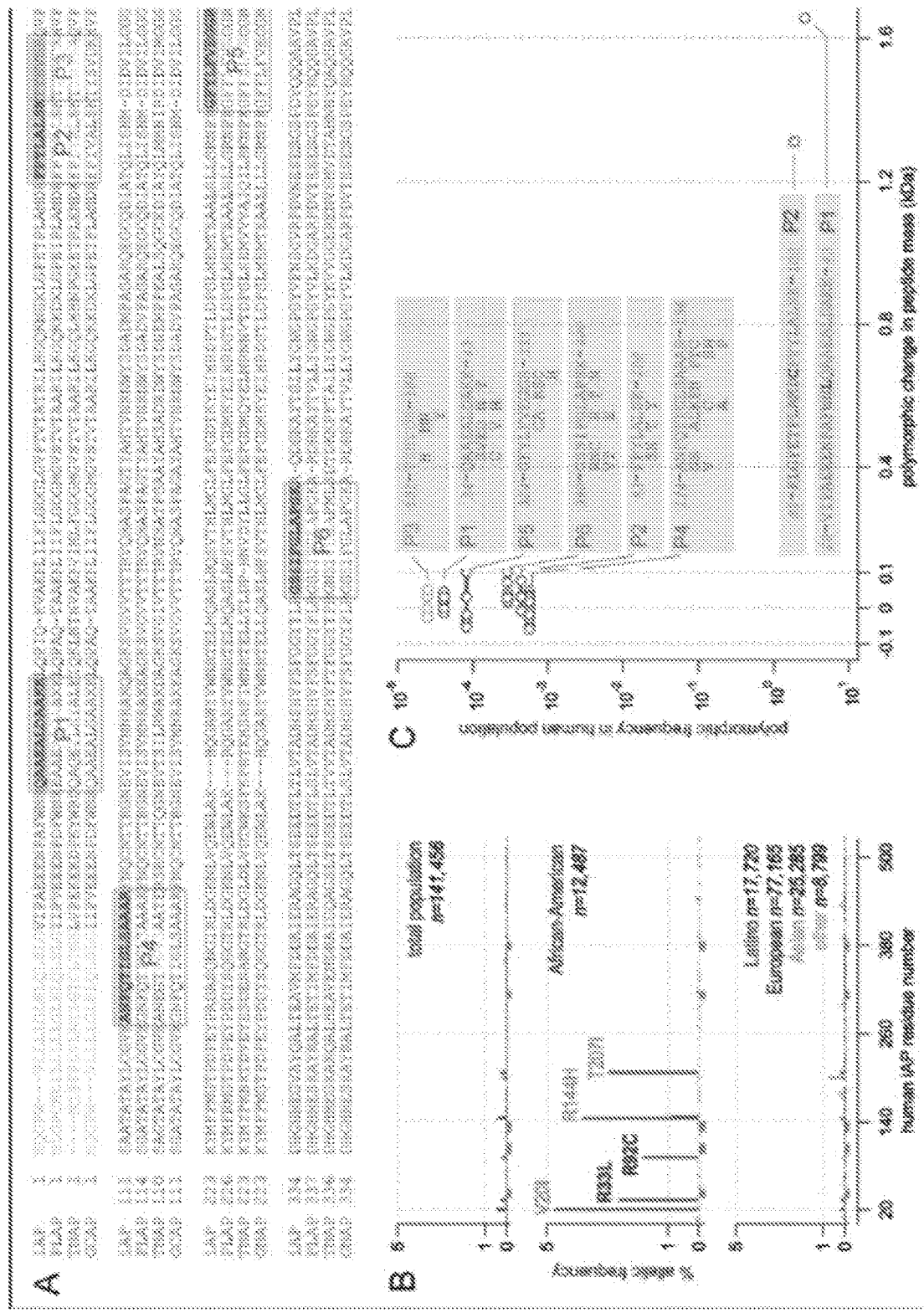

FIG. 34 shows iAP peptides that can be used as calibrators for mass spectral quantification. (A) Amino acid sequence alignment of human alkaline phosphatases: intestinal alkaline phosphatase (iAP; P09923), placental-like alkaline phosphatase (PLAP; P05187), tissue nonspecific alkaline phosphatase (TNAP; P05186), and germ-cell alkaline phosphatase (GCAP; P10696). Boxes P1-P6 feature 6 peptides which have unique mass spectral signatures that discriminate between the four human AP proteins. (B) Allelic frequency of missense, single nucleotide polymorphism catalogues in the human population. (C) Sequences of the six iAP peptides amenable for mass spectral quantification of protein abundance and single nucleotide missense polymorphisms identified for each residue position. Peptide with smallest deviation from zero on the x-axis and lowest polymorphic frequency on y-axis is best candidate for MS reference standards.

Figure 35:
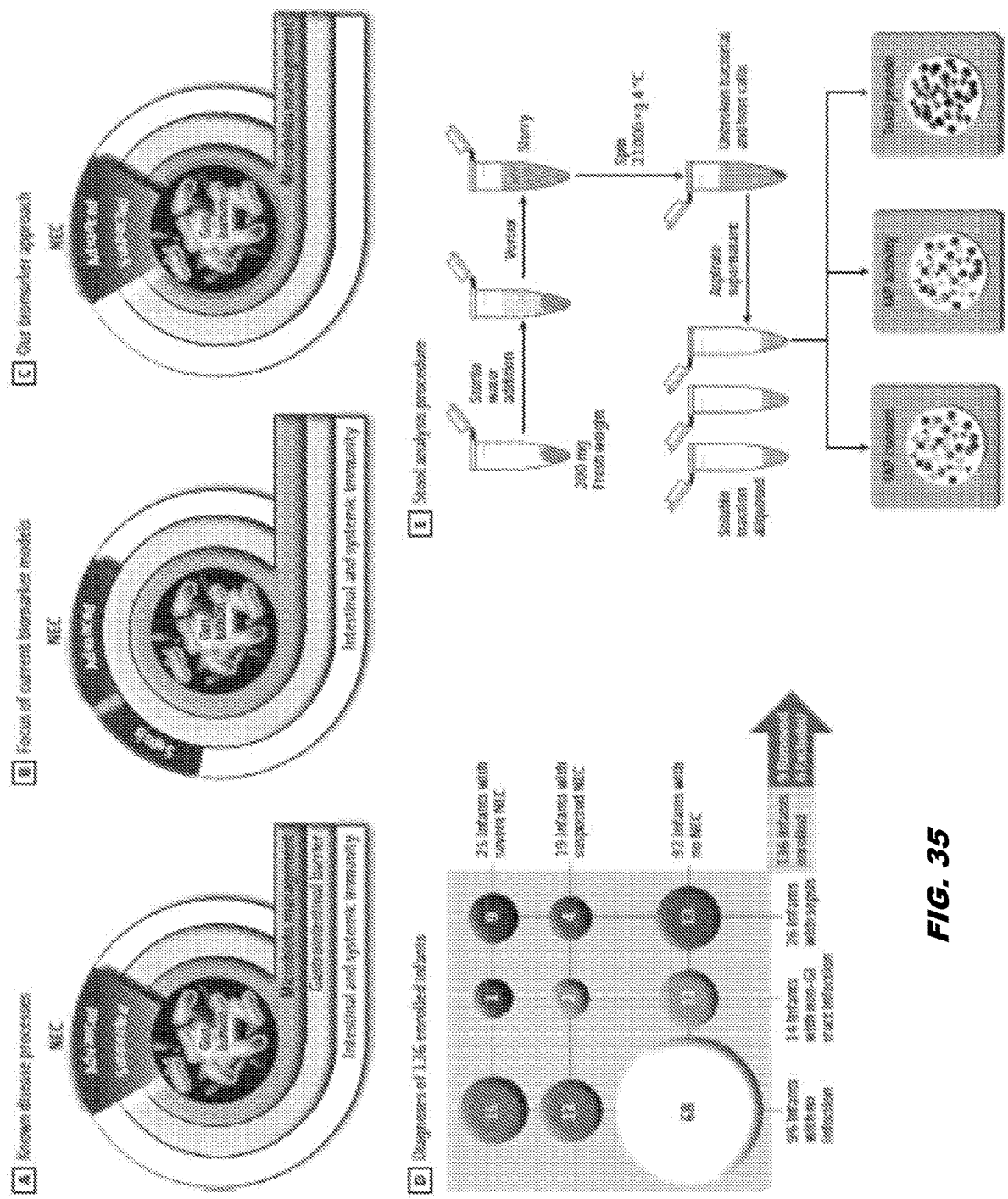

FIG. 35 shows association of Necrotizing Enterocolitis (NEC) and Late-Onset Sepsis with Gut Defense Mechanisms. A-C, Physiological and structural changes in the gut, associated with NEC, are overlaid in the cross-sectional view of the small intestine. Research efforts to develop an NEC biomarker has focused on proteins in immunity cascades and in dysbiosis of the microbiome. Our approach focused on host proteins involved in microbiota management. D, Prospective enrollment of premature infants with NEC and other confirmed infections. E, Workflow of stool sample preparation was optimized for assay reproducibility and standardization. GI indicates gastrointestinal; IAP, intestinal alkaline phosphatase.

Figure 36:
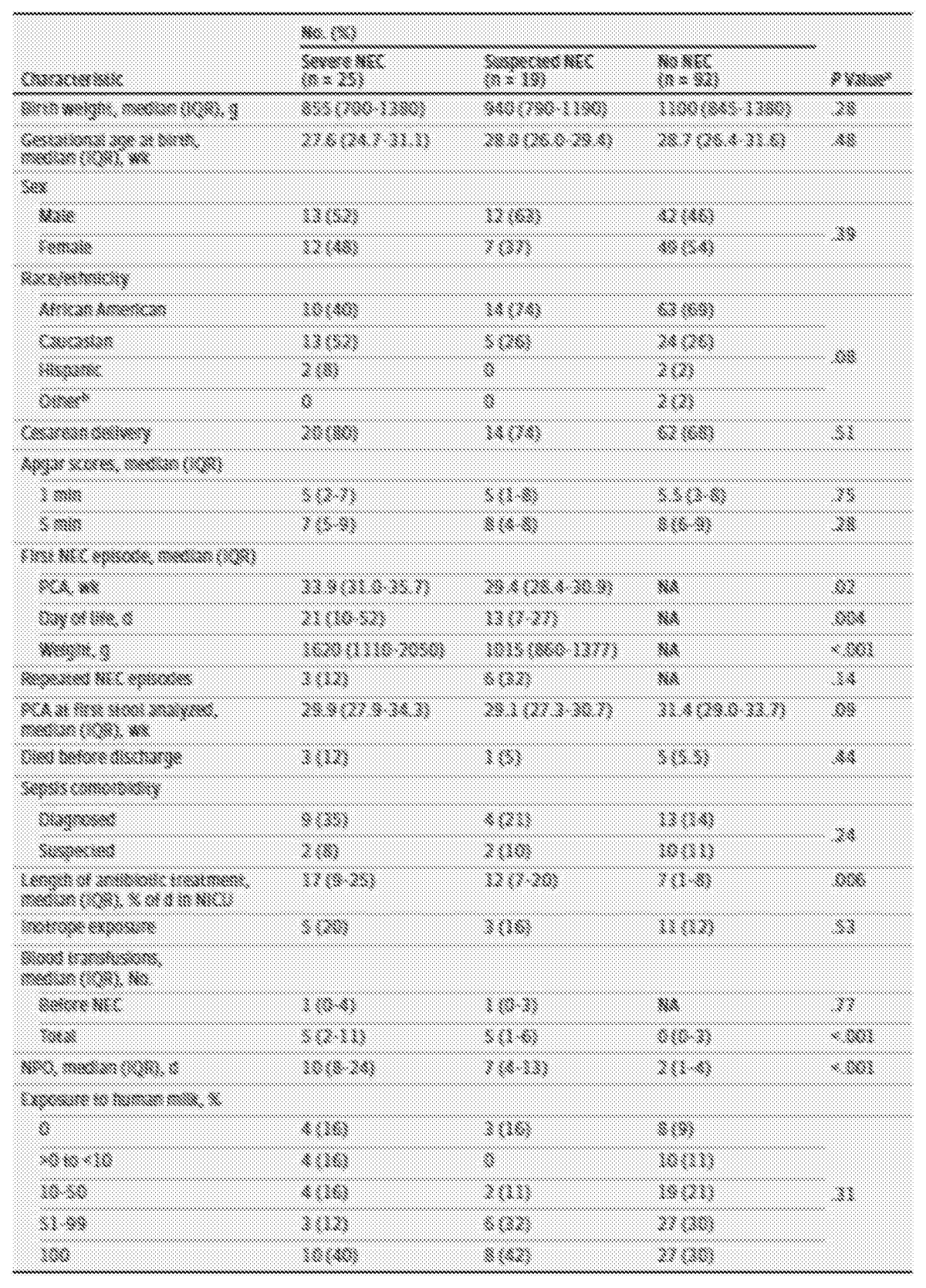

FIG. 36 shows clinical characteristics of patients with severe NEC, suspected NEC, or no NEC. Abbreviations: IQR, interquartile range; NA, not applicable; NEC, necrotizing enterocolitis; NICU, neonatal intensive care unit; NPO, nil per os; PCA, postconceptual age. (a) Using the appropriate method (analysis of variance, Kruskal-Wallis, or Fisher exact test) to compare differences among groups, P<0.05 indicated that there were statistically significant differences among the 3 infant populations. (b) Identified as more than 1 race by parents.

Figure 37:
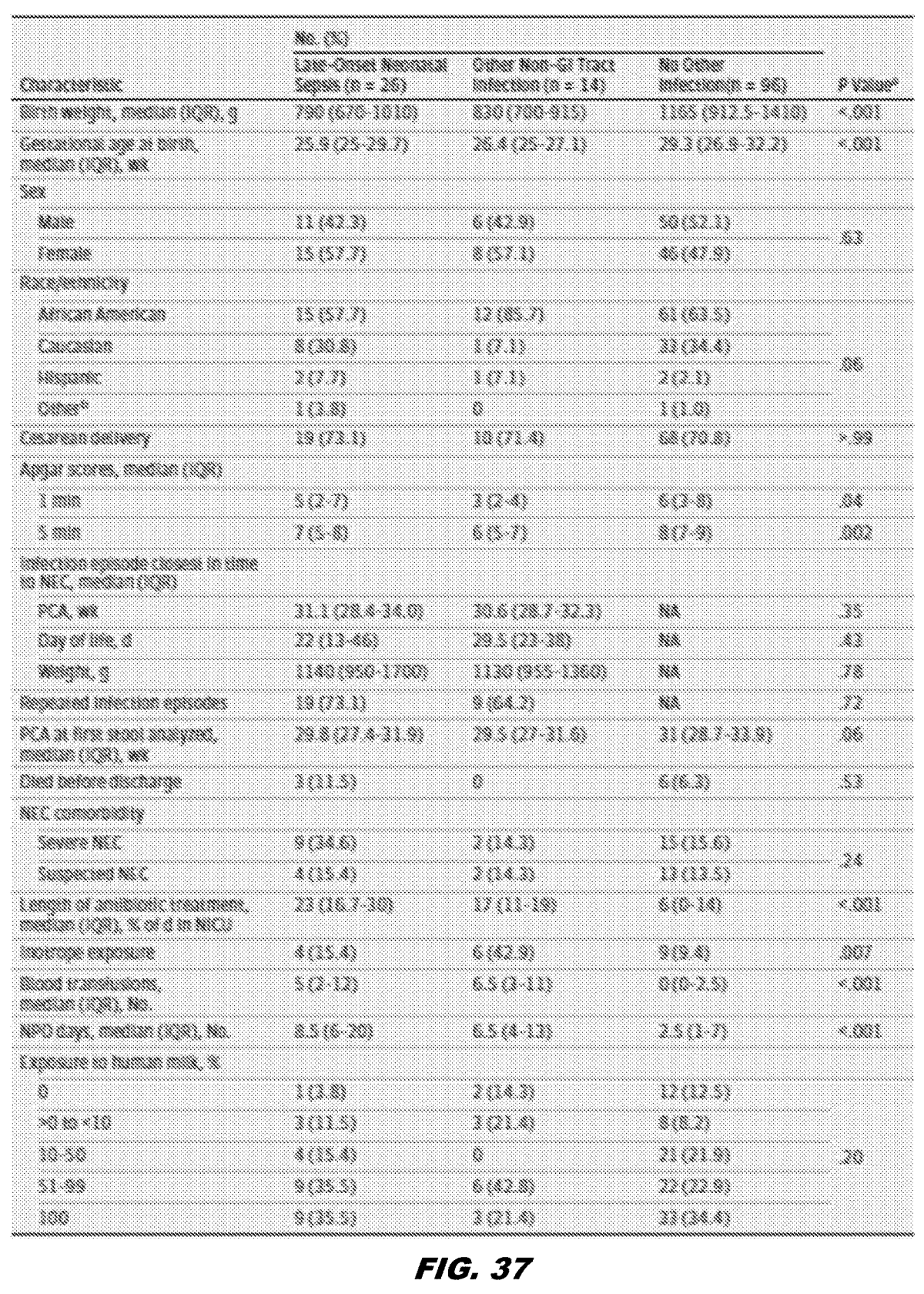

FIG. 37 shows clinical characteristics of patients with other confirmed infections. Abbreviations: GI, gastrointestinal; IQR, interquartile range; NA, not applicable; NEC, necrotizing enterocolitis; NICU, neonatal intensive care unit; NPO, nil per os; PCA, postconceptual age. (a) Using the appropriate method (analysis of variance, Kruskal-Wallis, or Fisher exact test) to compare differences among groups, P<0.05 indicated that there were statistically significant differences among the 3 infant populations. (b) Identified as more than 1 race by parents.

Figure 38:
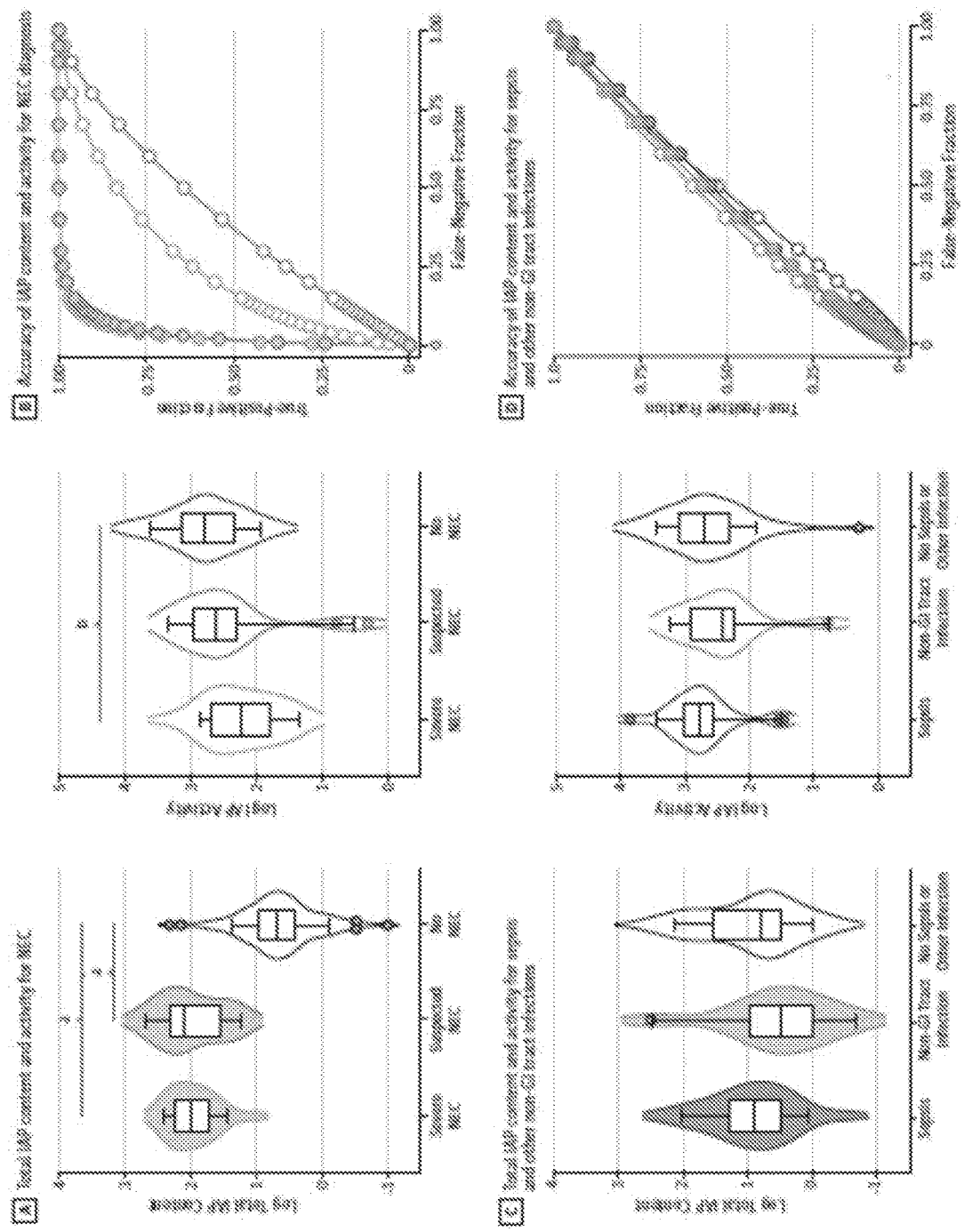

FIG. 38 shows association of Fecal Intestinal Alkaline Phosphatase (IAP) content and activity with necrotizing enterocolitis (NEC) and other confirmed infections. A, Box and violin plots of fecal abundance and activity of IAP are shown for samples collected at the time of severe (n=20) and suspected NEC (n=15). Samples from patients with no NEC (n=86), age-matched at the time of sample collection for NEC, are also shown. Box plot whiskers mark 9th and 91st percentiles. B, Receiver operating characteristic curves for IAP abundance (filled circles) and activity (open circles) in samples collected during severe (orange) or suspected (brown) NEC. C, Box and violin plots of fecal abundance and activity of IAP are shown for samples collected during sepsis (n=18), other non-gastrointestinal (GI) tract infection (n=10), and age-matched control patients (n=91). Box plot whiskers mark 9th and 91st percentiles. D, Receiver operating characteristic curves of IAP abundance (filled circles) and activity (open circles) in samples collected during sepsis (dark blue) and other non-GI tract infections (light blue). (a) P<0.001; (b) P=0.005

Figure 39:
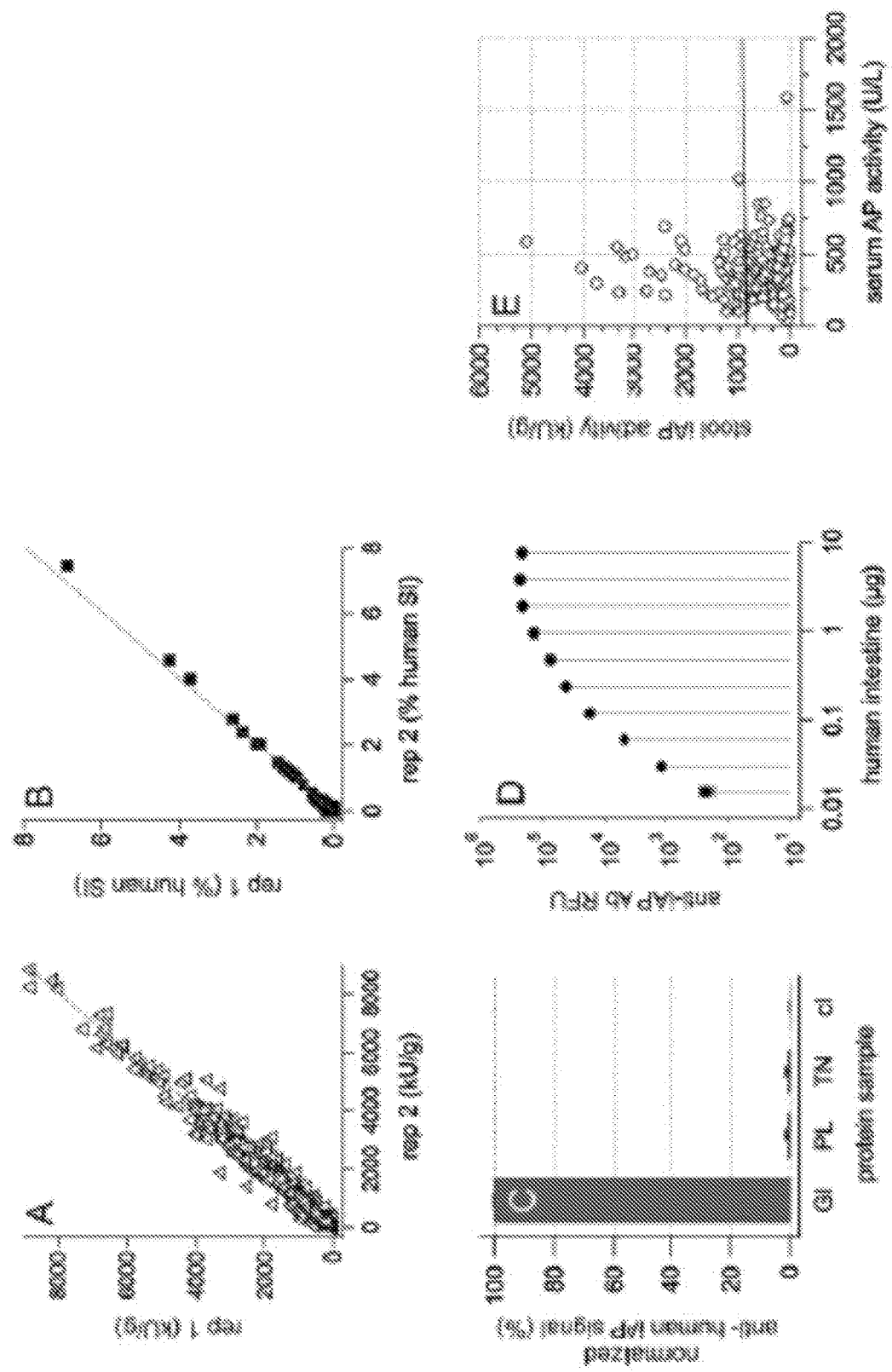

FIG. 39 shows control experiments demonstrated operator reproducibility, antibody reagent specificity, and biospecimen specifity. Five different operators performed (A) activity assay measurements and (B) iAP content determinations in the patient stool samples; dotted line marks the 1:1 correspondence between replicate 1 and replicate 2. (C) The anti-human iAP antibody used in this study was tested against human small intestine lysate (GI), purified human placental alkaline phosphatase (PL), purified human tissue nonspecific alkaline phosphatase (TN), and bovine intestinal alkaline phosphatase (cI). Quantitation from densitometry for the total amount of AP is listed as the average and SE: 100.0±0.1% (GI); 1.0±0.4% (PL); 0.9±0.5% (TN); 0.3±0.1% (cI); N=5. (D) Quantitation of immunoblot method used had a linear response to the amount of human intestinal alkaline phosphatase.5-7 The mean relative fluorescence units and standard error for the total iAP (open triangles) 216,692±14,533 for 7.5 µg; 233,533±20,264 for 3.75 µg; 211,176±132,267 for 1.875 µg; 142,834±13,019 for 0.938 µg; 75,727±7,637 for 0.469 µg; 44,101±1,410 for 0.234 µg; 18,234±450 for 0.117 µg; 4,918±549 for 0.059 µg; 1,164±79 for 0.029 µg; and 227±57 for 0.015 µg. (E) Comparison of serum AP activity and stool iAP activity, if serum clinical test and stool sample were collected on the sample day. No relationship was observed between serum AP activity and stool iAP activity measurements. N=148; solid line is best linear fit between stool iAP activity and serum AP activity.

Figure 40:
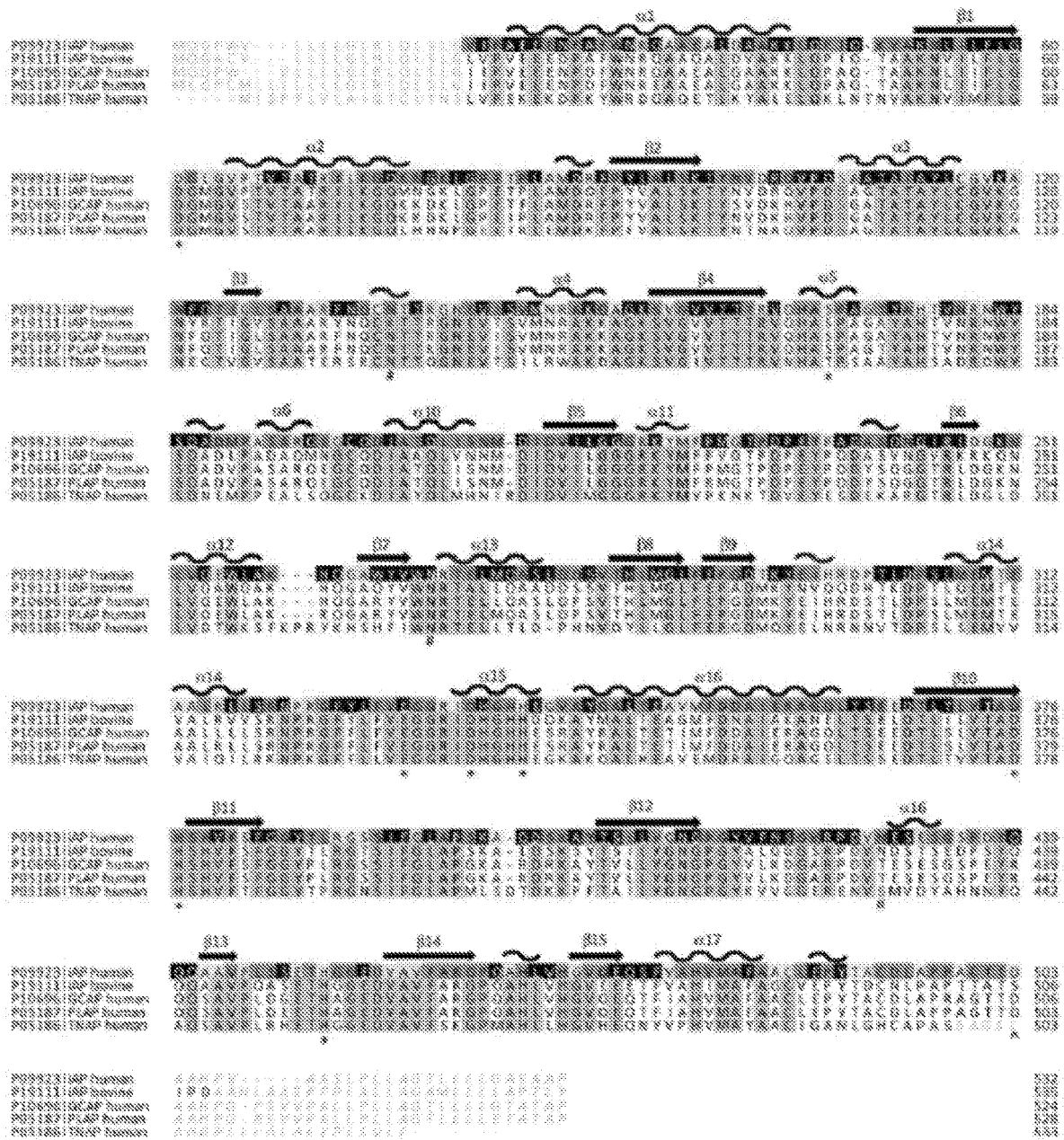

FIG. 40 shows sequence alignment of 4 human Alkaline Phosphatases and Calf Intestinal Alkaline Phosphatases. Sequences were shown are human intestinal alkaline phosphatase (iAP human; P09923 Uniprot ID), calf intestinal alkaline phosphatase (iAP bovine; P19111), germ cell alkaline phosphatase (GCAP human; P10696), placenta-like alkaline phosphatase (PLAP human, P05187), and tissue-nonspecific alkaline phosphatase (TNAP human, P05186). Signal peptide is in grey at the N-terminus of the sequences. Propeptide is in grey italics at the C-terminus of the sequences. Residues involved in metal binding are annotated with an asterisk; candidate glycosylation sites have a #symbol. Secondary structure motifs are shown from the human placenta alkaline phosphatase crystals (PDB ID 1EW2). Color heat map of number of polymorphisms found in the human population are overlaid on the IAP human sequence.

DETAILED DESCRIPTION OF THE INVENTION

Abbreviations and Definitions

Detailed descriptions of one or more preferred embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like is used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The present invention is directed to compositions and methods to detect and treat gastrointestinal diseases.

Gastrointestinal Diseases

Gastrointestinal diseases refer to diseases involving the gastrointestinal tracts. For example, necrotizing enterocolitis (NEC) is an acquired gastrointestinal disease often seen in pre-term infants. In NEC, bacteria invade the wall of the intestine, causing local infection and inflammation. NEC is characterized by high mortality and long-term morbidity, including short gut syndrome, recurrent infection, nutritional deficiency and neurodevelopmental delay. Despite an overall net decrease in mortality for premature infants, there has been an increase in NEC-associated deaths. NEC is often difficult to diagnose and manage, due to initial nonspecific symptomatology and rapid deterioration.

In addition to necrotizing enterocolitis seen in neonates and preterm neonates, necrotizing enterocolitis can also affect non-neonates. For example, necrotizing enterocolitis in non-neonates, such as adults, can result from inflammatory mediators; nutritional disorders, such as anorexia or significant weight loss; gastrointestinal dysfunction; alcoholism; malabsorption; agents that block intestinal proteases; smoking; circulatory disturbances, such as reduced mesenteric blood flow, bowel ischemia, atherosclerosis of the bowel arteries; cholelithiasis; administration of drugs; immunological deficiencies, such as of the IgA secretory component or intestinal T-lymphocytes coupled with poor antibody response; fecal impaction or constipation; or infectious agents, such as bacterial infections, food borne infections and food borne illnesses.

Non-limiting examples of such drugs include those with anticholinergic properties, such as neuroleptics or phenothiazine-based neuroleptics, narcotics, inflammatory mediators, antidepressants, iron pills, laxatives, or antacids.

Non-limiting examples of such infectious agents comprise bacteria like *Klebsiella, E. coli, Enterobacter, Pseudomonas*, Clostridia and *Staphylococcus epidermidis*, viruses like Corona virus, Rota virus and Entero virus and rarely, fungi like *Candida albicans*. Enteropathogenic viruses are believed to infect epithelial cells resulting in cell destruction, necrosis and intestinal perforation.

Constipation or fecal impact can have many different causes known to art, non-limiting examples of which include antacid medicines containing calcium or aluminum, changes in diet or activities, colon cancer, dairy products, eating disorders, neurological conditions, inactivity, dehydration, consuming fiber, overuse of laxatives, pregnancy, digestive disorders, resisting the urge to have a bowel movement, medications, stress, or hypothyroidism.

Aspects of the invention pertain to gastrointestinal diseases. Gastrointestinal diseases refer to diseases involving the gastrointestinal tract, namely the esophagus, stomach, small intestine, large intestine and rectum, and the accessory organs of digestion, the liver, gallbladder, and pancreas. For example, such diseases can result from infectious, autoimmune, and physiological states. Non-limiting examples of gastrointestinal diseases include colitis, inflammatory bowel disease (IBD), gastritis, gastroenteritis, pyloric stenosis, gastric cancer, infectious diarrhea, fecal impaction, constipation, intestinal obstruction and pseudo-obstruction, or malabsorption. In addition to necrotizing enterocolitis (NEC), non-limiting examples of types of colitis comprise adult necrotizing enterocolitis (ANEC), pseudomembranous enterocolitis, infectious colitis, ulcerative colitis, Crohn's disease, ischemic colitis, radiation colitis.

Intestinal Alkaline Phosphatase (iAP)

Using a single 100-150 mg stool sample from three healthy human donors, 234 human proteins, secreted from the gastrointestinal tract, were identified. Of these, a core proteome of 57 proteins, common between these three human individuals, was identified. Despite the reproducible presence of this core proteome, the relative abundance of most shared proteins varied between the three human subjects, suggestive that the core proteome can be used for identification of host-specific proteomic signatures.

Intestinal alkaline phosphatase (iAP) is expressed in small intestinal enterocytes, co-secreted into the intestinal lumen and systemic circulation and plays an integral role in maintaining gut barrier function by detoxifying bacterial lipopolysaccharides and maintaining microbial homeostasis. As the primary alkaline phosphatase in stool, iAP has been identified as one of the 57 proteins in the core human stool proteome.

Aspects of the invention pertain to methods for diagnosing a gastrointestinal disease in a subject. For example, the method comprises the steps of obtaining a sample from the subject; detecting the presence of at least one GI disease biomarker in the sample, wherein the GI disease biomarker comprises intestinal alkaline phosphatase (iAP) protein; comparing the GI disease biomarker profile to that of a profile obtained from a control sample; and treating the subject. Embodiments can also be directed towards preventing the progression of a gastrointestinal disease in a subject in need thereof, and ameliorating the symptoms associated with a gastrointestinal disease in a subject in need thereof. In embodiments, the control sample can comprise a two or more control samples.

As used herein, "changed as compared to a control" sample or subject is understood as having a level of the analyte or diagnostic or therapeutic indicator (e.g., marker such as iAP) to be detected at a level that is statistically different than a sample from a normal, untreated, or abnormal state control sample. Determination of statistical significance is within the ability of those skilled in the art, e.g., the number of standard deviations from the mean that constitute a positive or negative result and the statistical analyses to arrive at these intervals.

If a subject is diagnosed with a GI disease, embodiments of the invention comprise treating the subject. For example, treating the subject can comprise administering to the subject an effective amount of antibiotics, probiotics, intravenous fluids, an iAP replacement composition, parenteral (or intravenous) nutrition, or a combination thereof. An additional therapeutic approach can be withholding food from the subject. Non-limiting examples of an iAP replacement composition comprise gene or protein replacement compositions.

The term "administration" or "administering" can refer to introducing a substance, such as iAP protein or an antibiotic and/or an antifungal, into a subject. In general, any route of administration can be utilized including, for example, intracoronarilly, intramyocardially, intravenously, intraarterially, or any combination thereof. For example, the iAP can be administered to the subject prior to, concurrent with, or subsequent to diagnosis of a GI disease such as NEC.

Protein therapy can be accomplished by any method that effectively introduces iAP protein or a fragment thereof into the subject to restore or enhance iAP activity. An effective amount of an iAP protein (for example an amount sufficient to reduce or eliminate the symptoms associated with gastrointestinal diseases) can be administered alone or in association with an agent that facilitates the administration or activity of the protein. The "effective amount" can be determined by one of skill in the art based on such factors as the type and severity of symptoms being treated, the weight and/or age of the subject, the previous medical history of the subject, and the selected route for administration of the agent.

In embodiments, iAP protein can be associated with lipids, such as detergents or other amphipathic molecule micelles, membrane vesicles, liposomes, virosomes, or microsomes. Lipid compositions that are naturally fusogenic or can be engineered to become fusogenic (e.g. by incorporating a fusion protein into the lipid) are especially preferred. Fusion proteins can be obtained from viruses such as parainfluenza viruses 1-3, respiratory syncytial virus (RSV), influenza A, Sendai virus, and togavirus fusion protein. Nonviral fusion proteins include normal cellular proteins that mediate cell-cell fusion. Other nonviral fusion proteins include the sperm protein PH-30 which is an integral membrane protein located on the surface of sperm cells that is believed to mediate fusion between the sperm and the egg. Still other nonviral fusion proteins include chimeric PH-30 proteins such as PH-30 and the binding component of hemaglutinin from influenza virus and PH-30 and a disintegrin (e.g. bitistatin, barbourin, kistrin, and echistatin). In addition, lipid membranes can be fused using traditional chemical fusogens such as polyethylene glycol (PEG).

In embodiments, a subject can be treated by administration of an effective amount of iAP protein, optionally in a pharmaceutically acceptable carrier or diluent. An effective amount of iAP protein can be an amount sufficient to alleviate the symptoms of a gastrointestinal disease. iAP can be administered subcutaneously, intravenously, intraperitoneally, intramuscularly, parenterally, orally, submucosally, by inhalation (for example of an aerosolized pharmaceutical composition), or other appropriate route of administration in an effective dosage range. If necessitated by a particular mode of administration, iAP can be encapsulated within a material that protects it from enzymatic degradation. In addition, prior to administration, it can be useful to administer agents to clear bacterial infection.

Alternatively, a preparation of the gene encoding iAP or a fragment thereof can be incorporated into a suitable vector for delivering the gene into a subject's cells. In embodiments, the iAP gene therapy can be transient and require repeated delivery to the subject. In other embodiments, gene therapy can offer a cure for the gastrointestinal disease. For example, if genetic material encoding iAP is incorporated into stem cells of a subject, all subsequent generations of such cells can make authentic iAP from the integrated sequences and would correct the defect. Non-limiting examples of approaches and vectors that can be useful for performing iAP gene therapy include retroviruses, adeno-associated viruses, naked DNA, DNA-lipid complexes, receptor mediated entry, or adenovirus.

Non-limiting modes of administration of treatment comprise intravenous (IV); intramucosal; intramuscular; subcutaneously, and non-invasive modes of administration, such as oral, intranasal, buccal, intrapulmonary, intrabronchial, and transdermal.

Aspects of the invention further pertain to methods for screening for the presence of a signature in a subject at risk of developing a gastrointestinal disease or a subject with a non-symptomatic gastrointestinal disease. For example, steps of the method comprise obtaining a sample from the subject; measuring at least one GI disease biomarker in the sample, wherein the GI disease biomarker comprises intestinal alkaline phosphatase (iAP) protein; comparing the GI disease biomarker profile to that of a profile obtained from a control sample; and treating the subject. Similarly, aspects can also be directed towards methods for identifying a subject at risk for a gastrointestinal disease or a subject with a non-symptomatic gastrointestinal disease. In embodiments, the control sample can comprise two or more control samples.

Aspects of the invention comprise measuring total protein concentration in a sample, intestinal alkaline phosphatase protein concentration in a sample, intestinal alkaline phosphatase enzyme activity in a sample, or a combination thereof. Samples used in such methods, and assays used to collect such measurements are described herein. For example, a subject can be diagnosed as having a GI disease if the protein concentration in the sample is greater than about 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml. As another example, a subject can be diagnosed as having a GI disease if the iAP activity is lower than about 10 mU/mg, 20 mU/mg, 30 mU/mg, 40 mU/mg, 50 mU/mg, 60 mU/mg, 70 mU/mg, 80 mU/mg, 90 mU/mg, 100 mU/mg, 200 mU/mg, 300 mU/mg, 400 mU/mg, 500 mU/mg, 600 mU/mg, 700 mU/mg, 800 mU/mg, 900 mU/mg, 1000 mU/mg, 1100 mU/mg, 1200 mU/mg, 1300 mU/mg, 1400 mU/mg, 5 U/mg, 10 U/mg, 50 U/mg, 100 U/mg, 200 U/mg, 300 U/mg, 400 U/mg, 500 U/mg, 600 U/mg, 700 U/mg, 800 U/mg, 900 U/mg, 1000 U/mg. For example, a subject can be diagnosed with a gastrointestinal disease if the protein concentration in fecal sample is greater than about 1.6 mg/ml, or greater than about 1.8 mg/ml; if the iAP activity is lower than about 979 mU/m, or lower than about 1256 mU/mg; or if the level of iAP protein is at least two standard deviations above the mean of the control sample. As another example, a subject can be diagnosed as having a GI disease if the level of iAP protein is greater than about 0.05%, 1%, 2%, 3%, 4%, 5%, 6%, 7%, 8%, 9%, 10%, 20%, 30%, 40%, 50%, 60%, 70%, 80%, 90%, 100%, 125%, 150%, 175%, 200%, 225%, 250%, 275% of a control sample. For example, the subject can be diagnosed with a gastrointestinal disease if the iAP protein detection by anti-iAP antibody exceeds 10.7 of control via densitometry, or in excess of 4.8% of control via densitometry. In other embodiments, a subject can be diagnosed with a gastrointestinal disease if two of the thresholds are met, or if all three thresholds are met. In embodiments, the control sample can comprise a two or more control samples.

The term "threshold", for example a threshold indicative of NEC, refers to a value derived from a plurality of biological samples, such as donor stool samples, for a biomarker, such as iAP protein levels, iAP catalytic activity, or total fecal protein levels, above which threshold is associated with an increased likelihood of having and/or developing a gastrointestinal disease such as NEC.

Embodiments of the invention comprise diagnosing the subject with a gastrointestinal disease if the protein level of iAP in the sample, the level of iAP enzyme activity in the sample, or the fecal protein level is at least 0.5, 1, 1.5, 2, 2.5, 3, 3.5, 4, 4.5, 5, or 10 standard deviations above the mean level of the control sample. In other embodiments, a subject can be diagnosed with a gastrointestinal disease if two of the thresholds are met, or if all three thresholds are met. In embodiments, the control sample can comprise two or more control samples.

Embodiments of the invention comprise machine learning techniques or applications to determine appropriate clinical thresholds. For example, such techniques comprise those known to the field, including Naïve Bayes classifiers (NBC), linear discriminant analysis (LDA), or support vector machines (SVM). and support vector machine options. One of skill in the art readily understands that such a threshold value can vary depending on the sample size analyzed and the statistical analyses employed.

Aspects of the invention further comprise identifying and/or diagnosing both early stages of gastrointestinal disease and advanced stages of gastrointestinal disease. Certain embodiments can distinguish between early stage and late stage gastrointestinal disease. For example, embodiments as described herein can diagnose advanced states of inflammation, such as that identified by radiological findings of pneumatosis intestinalis (portal vein or biliary gas). As another example, embodiments can identify early stages of the disease before rampant inflammation of the gut is physiologically evident. Physicians currently suspect gastrointestinal disease from a range of physical signs, such as abdominal distension, abdominal tenderness, decreased bowel sounds, blood in stools, increased apnea, temperature instability, bilious aspirates, and feeding intolerance. Clinical signs for suspecting disease are dilated intestinal loops and thickened bowel walls from radiology. Laboratory findings for suspecting disease are decreased platelets, decreased or increased white blood cell count, increased band count, and metabolic acidosis. Embodiments can match identification of radiological findings of pneumatosis intestinalis (portal vein or biliary gas) in advanced stages of inflammation. The method also identifies early stages of the disease before rampant inflammation of the gut is physiologically evident.

Samples

Aspects of the invention comprise measuring or detecting biomarkers of gastrointestinal diseases in biological samples. Biomarkers of the invention can be measured in different types of biological samples. Non-limiting examples of biological samples that can be used in methods of the invention, although not intended to be limiting, include stool, plasma, cord blood, neonatal blood, cerebral spinal fluid, tears, vomit, saliva, urine, feces, and meconium. If desired, a sample can be prepared to enhance detectability of the biomarkers. For example, a sample from the subject can be fractionated. Any method that enriches for a biomarker polypeptide of interest can be used. Sample preparations, such as prefractionation protocols, are optional and may or may not be necessary to enhance detectability of biomarkers depending on the methods of detection used. For example, sample preparation can be unnecessary if an antibody that specifically binds a biomarker is used to detect the presence of the biomarker in a sample. Sample preparation can involve fractionation of a sample and collection of fractions determined to contain the biomarkers. Methods of prefractionation include, for example, size exclusion chromatography, ion exchange chromatography, heparin chromatography, affinity chromatography, sequential extraction, gel electrophoresis, mass spectrometry, and liquid chromatography.

The methods described herein can involve obtaining a biological sample from the subject, such as an infant. As used herein, the phrase "obtaining a biological sample" refers to any process for directly or indirectly acquiring a biological sample from a subject. For example, a biological sample can be obtained (e.g., at a point-of-care facility, such as a physician's office, a hospital, laboratory facility) by procuring a tissue or fluid sample (e.g., blood draw, marrow sample, spinal tap) from a subject. Alternatively, a biological sample can be obtained by receiving the biological sample (e.g., at a laboratory facility) from one or more persons who procured the sample directly from the subject. The biological sample can be, for example, feces, such as stool, a tissue (e.g., blood), cell (e.g., hematopoietic cell such as hematopoietic stem cell, leukocyte, or reticulocyte, stem cell, or plasma cell), vesicle, biomolecular aggregate or platelet from the subject.

Assays and Antibodies

Aspects of the invention comprise biomarkers of GI disease. For example, aspects comprise biomarkers of necrotizing enterocolitis. For example, biomarkers of GI disease comprise iAP enzymatic activity, iAP protein level, iAP dimerization/dissociation, post-translationally modified iAP, total fecal protein, or a combination thereof.

Aspects of the invention comprise an assay that measures iAP enzymatic activity. Aspects of the invention comprise an assay that measures iAP protein level. Aspects of the invention comprise an assay that measures iAP dimerization/dissociation. Aspects of the invention comprise an assay that measures post-translationally modified iAP. Aspects of the invention comprise an assay that measures total fecal protein.

Non-limiting examples of post-translational modifications comprises acetylation, acylation, alkylation, amidation, butyrylation, deamidation, formylation, glypiation, glycosylation, hydroxylation, iodination, ISGylation, lipoylation, malonylation, methylation, myristoylation, palmitoylation, phosphorylation, phosphopantetheinylation, prenylation, propionylation, ribosylation succinylation, sulfation, SUMOylation, or ubiquitination.

iAP is a homodimer; each protomer binds 4 divalent ($Zn^{2+}$ and $Mg^{2+}$) ions, which are essential in maintaining the structural integrity and catalytic activity of the enzymes. iAP is one of four different alkaline phosphatases found in human tissue that has been correlated with physiological function. Although it is found in high concentrations within luminal vesicles secreted by enterocytes on the microvilli brush border, small levels of iAP are released into the blood as well as the gut lumen, where in the latter travel throughout the intestinal tract.

Embodiments of the invention comprise measuring or detecting such biomarkers using assays known to the art. Non-limiting examples of assays include an immunoassay, a colorimetric assay, fluorimetric assay or a combination thereof. Non-limiting examples of immunoassays comprise a western blot assay, an enzyme-linked immunosorbent assay (ELISA), immunoprecipitation or a combination thereof. For example, a biological sample collected from a subject can be incubated together with a biomarker specific antibody, such as an anti-iAP antibody or fragment thereof, and the binding of the antibody to the biomarker in the sample is detected or measured.

In embodiments, the antibody or fragment thereof can be specific for iAP (anti-iAP). The antibody can be a polyclonal antibody or a monoclonal antibody. The antibody or fragment thereof can be attached to a molecule that is capable of identification, visualization, or localization using known methods. Suitable detectable labels include radioisotopic labels, enzyme labels, non-radioactive isotopic labels, fluorescent labels, toxin labels, affinity labels, and chemiluminescent labels.

Examples of assays that can be used in methods of the invention, although not intended to be limiting, comprise a Bradford assay, a bicinchoninic acid (BCA) assay, a Lowry assay, a pyrogallol red protein dye-binding assay, a Coomassie blue dye-binding assay, an endpoint assay, a kinetic assay, such as a kinetic assay using a fluorometric substrate such as 4-methyllumbelliferyl phosphate, chemiluminescent substrates such as CSPD and CDP-Star, DynaLight Substrate with RapidGlow enhancer, or colorimetric 4-nitrophenyl phosphate, an assay to detect phosphatase reactions, an assay to detect ATP hydrolysis, or a combination thereof. In embodiments, the assays can be provided in a multi-well format, such as a 6-, 12-, 24-, 48-, or 96-well plate. In embodiments, the assays can be provided in a standard cuvette, such as a 1 ml cuvette.

Total protein, such as total fecal protein, can be measured by assays known to one skilled in the art (see page 7, 27 and 85, for example, of Cardinal Health catalogue, Dublin, Ohio, 2013, which is incorporated by reference herein in its entirety, see Roche Total Protein/TP2, Cobas c502 TPUC3, or Abbott's Total Protein kit). For example, Pyrogallol Red Molybdate dye binding method provides a colorimetric method for total protein quantitation with greater linearity, using microliter volumes of biological samples in manual or automated systems. As described herein, pyrogallol red can be provided in a kit comprising reagent, controls, and reagent standards, such as 25 mg/dL, 50 mg/dL, 100 mg/dL, and 200 mg/dL.

The enzyme employed in embodiments herein, for example to detect protein levels or enzymatic activity, can be, for example, alkaline phosphatase, horseradish peroxidase, β-galactosidase and/or glucose oxidase; and the substrate can respectively be an alkaline phosphatase, horseradish peroxidase, β-galactosidase or glucose oxidase substrate (see *Molecular Probes Handbook-A Guide to Fluorescent Probes and Labeling Technologies,* 11th Edition (2010), Invitrogen, which is incorporated by reference herein in its entirety).

In embodiments, the enzyme, such as alkaline phosphatase or horseradish peroxidase, can be attached to a secondary antibody. Without being bound by theory, measurement of alkaline phosphatase can be confounded by signal from secondary antibodies. Isolated alkaline phosphatase can catalytically hydrolyze MUP to form the fluorescent product MU. Secondary antibodies, conjugated to AP, from two different commercial manufacturers, for example, can also hydrolyze MUP to form fluorescent product. When both alkaline phosphatase protein and the secondary antibody are in the same measurement, there is an increased level of catalytic activity observed. This activity can be monitored by both standard spectrophotometric readings of biochemical activity and by Western blot.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Horseradish Peroxidase (HRP, sometimes abbreviated PO) substrates include, but are not limited to, 2,2' Azino-di-3-ethylbenz-thiazoline sulfonate (ABTS, green, water soluble), aminoethyl carbazole, 3-amino, 9-ethylcarbazole AEC (3A9EC, red). Alpha-naphthol pyronin (red), 4-chloro-1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5' Tetramethylbenzidine (TMB, green or green/blue), TRUE BLUE™ (blue), VECTOR™ VIP (purple), VECTOR™ SG (smoky blue-gray), and Zymed Blue HRP substrate (vivid blue).

Glucose Oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitorphenyl)-3-phenyltetrazolium chloride (INT, red or orange precipitate), Tetrazolium blue (blue), Nitrotetrazolium violet (violet), and 344,5-dimethylthiazol-2-yl)-2,5-diphenyltetrazolium bromide (MTT, purple). All tetrazolium substrates require glucose as a co-substrate. The glucose gets oxidized and the tetrazolium salt gets reduced and forms an insoluble formazan which forms the color precipitate.

Beta-Galactosidase substrates, include, but are not limited to, 5-bromo-4-chloro-3-indoyl beta-D-galactopyranoside (X-gal, blue precipitate).

Other examples of alkaline and acid phosphatase substrates comprise 9H-(1,3-dichloro-9,9-dimethylacridin-2-one-7-yl) phosphate, diammonium salt (DDAO phosphate), 6,8-difluoro-4-methylumbelliferyl phosphate (DiFMUP), fluorescein diphosphate, tetraammonium salt (FDP), 4-methylumbelliferyl phosphate, free acid (MUP), and 4-methylumbelliferyl phosphate, dicyclohexylammonium salt, trihydrate (MUP DCA salt).

Alkaline phosphatase activity, such as intestinal alkaline phosphatase activity, can be detected and/or measured with use of chromogenic substrates and/or fluorogenic substrates of alkaline phosphatases. For example, 4-methylumbelliferyl phosphate (MUP) is a fluorogenic substrate for alkaline phosphatases, and alkaline phosphatase mediated hydrolysis of its phosphate substituent yields the blue-fluorescent 4-methylumbelliferyl (excitation/emission 386/448 nm). In embodiments, the alkaline phosphatase substrate can be directly admixed with the biological sample, such as stool, allowing for the direct dectection of the presence of alkaline phosphatase or the measurement of its activity.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Other substrates known in the art, including those described herein, can be used with embodiments of the invention (see *Molecular Probes Handbook-A Guide to Fluorescent Probes and Labeling Technologies,* 11th Edition (2010), Invitrogen, which is incorporated by reference herein in its entirety). Further, as desired, various fluorophores known in the art can be covalently attached to the substrate, such as MUP.

Enzyme reactions can provide a highly specific, rapid and sensitive assay for detection of specific proteins in a sample, such as iAP in stool. Examples of suitable fluorogenic substrates which can be utilized within the present invention comprise Fluorescein diacetate, 4-Methylumbelliferyl acetate, 4-Methylumbelliferyl casein, 4-Methylumbelliferyl-α-L-arabinopyranoside, 4-Methylumbelliferyl-β-D-fucopyranoside, 4-Methylumbelliferyl-α-L-fucopyranoside, 4-Methylumbelliferyl-β-L-fucopyranoside, 4-Methylumbelliferyl-α-D-galactopyranoside, 4-Methylumbelliferyl-β-D-galactopyranoside, 4-Methylumbelliferyl-α-D-glucopyranoside, 4-Methylumbelliferyl-β-D-glucopyranoside, 4-Methylumbelliferyl-β-D-glucuronide, 4-Methylumbelliferyl nonanoate, 4-Methylumbelliferyl oleate, 4-Methylumbelliferyl phosphate, bis(4-Methylumbelliferyl)phosphate, 4-Methylumbelliferyl pyrophosphate diester, 4-Methylumbelliferyl-β-D-xylopyranoside.

Non-limiting examples of suitable chromogenic substrates for use within the present invention comprise o-Nitrophenyl-β-D-galactopyranoside, p-Nitrophenyl-β-D-galactopyranoside, o-Nitrophenyl-β-D-glucopyranoside, p-Nitrophenyl-α-D-glucopyranoside, p-Nitrophenyl-β-D-glucopyranoside, p-Nitrophenyl-β-D-glucuronide, p-Nitrophenyl phosphate, o-Nitrophenyl-β-D-xylopyranoside, p-Nitrophenyl-α-D-xylopyranoside, p-Nitrophenyl-β-D-xylopyranoside, and Phenolphthalein-β-D-glucuronide.

Subjects

As described herein, embodiments of the invention comprise measuring or detecting a gastrointestinal biomarker in a subject. The term "subject" or "patient" can refer to any organism to which aspects of the invention can be administered, e.g., for experimental, diagnostic, prophylactic, and/or therapeutic purposes. Typical subjects to which compounds of the present disclosure can be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

In embodiments herein, a subject comprises a mammal, such as a human or vertebrate animal. Examples of such include but are not limited to a dog, cat, horse, cow, pig, sheep, goat, chicken, primate, e.g., monkey, fish (aquaculture species), e.g. salmon, rat, and mouse. A human comprises a preterm neonate, an infant, a child, an adolescent, an adult, or an elderly individual.

Although aspects of the invention as described herein relate to human gastrointestinal disorders, aspects of the invention are also applicable to other nonhuman vertebrates. Aspects of the invention are applicable for veterinary use, such as with domestic animals. In general, aspects will vary according to the type of use and mode of administration, as well as the particularized requirements of individual subjects.

In embodiments, the subject can be on an antibiotic regimen. The term "antibiotic regimen" refers to the treatment or prevention of a disease, such as an infection, or method for achieving a desired change, such as the reducing or prevention of an infection, wherein said treatment comprises administering to a subject an antibiotic to effectively treat the disease or produce the physiological change. An antibiotic regimen can comprise variations known to those skilled in the art, such as antibiotic choice (for example, comprises correct medication choice, route of administration and dosing schedule), timing of administration, and duration. Non-limiting examples of such antibiotics comprise Vancomycin, Ampicillin, Zosyn (combination of piperacillin and tazobactam), Gentamycin, Flagyl (metrodniazole generic), Meropenem, Metronidazole, Cefotaxime, Clindamycin, or any combination thereof. In some embodiments, an antifungal agent can further be administered. In other embodiments, the antifungal agent can be Fluconazole, Terconazole, Voriconazole, Posaconazole, Pentamidine, Itraconazole, Ketoconazole. In embodiments, methods as disclosed herein can further comprise treating the subject. In embodiments, treating can comprise administering to the subject diagnosed with a gastrointestinal disease an effective amount of antibiotics, probiotics, intravenous fluids, withholding oral feeding, an iAP replacement composition, parenteral (or intravenous) nutrition, or a combination thereof.

In an embodiment, such as a subject afflicted with NEC, antibiotics can be administered to a subject for a sufficient period of time, such as 10-14 days where antibiotics are administrated to the infant. For other embodiments, such as a subject with sepsis, 7 days of antibiotics can be administered to the patient. For example, antibiotic administration and/or prescription can be for broad spectrum coverage, such as for (i) gram-positive bacteria, (ii) gram-negative bacteria, and (iii) anaerobic bacteria. Non-limiting examples of such regimens comprise Vancomycin (gram-positive including MRSA), ceftazadime (third generation cephalosporins—gram negative, some grant positive, and *pseudomonas*), metronidazole (anaerobic coverage), oxacillin (gram positive). Non-limiting examples of general antibiotics regimes comprise ampicillin+gentamicin for possible vertically acquired infection from mother, and vancomycin+ cetazidime for possible hospital acquired infections. From 46 neonatologist responses at the NEC symposium in April 2017, commonly used antibiotics/antifungals for NEC treatment are Gentamycin (32%), Vancomycin (28%), Ampicillin (25%), Zosyn (combination of piperacillin and tazobactam; 15%), Flagyl (metrodniazole generic; 19%), Clindamycin (6%), Meropenem (4%), Fluconazole (antifungal agent, 7%), and other (1%).

In some embodiments, probiotics also can be administered to the subject. As used herein, probiotics refers to mono- or mixed cultures of live microorganisms that can help reestablish normal flora in the GI tract. Probiotics can enhance the immune response, elicit production of enzymes that degrade toxins and/or block attachment sites to the colon. See, See McFarland, *J. Medic. Microbiol.* 2005, 54:101-111. Non-limiting examples of probiotic organisms include those in the genera Bifidobacteria, *Lactobacillus, Lactococcus,* and *Pediococcus, Saccharomyces boulardii,* and related bacteria and yeast.

In some embodiments, intravenous fluids or intravenous therapy can be administered to the subject. Intravenous therapy can refer to the infusion of liquid substances directly into the vein of a subject. Non-limiting examples of such fluids comprise saline (such as 0.9% NaCl in water or 0.45% saline in water), Lactated Ringer's (0.9% NaCl with electrolytes and buffer), $D_5W$ (5% dextrose in water), $D_5NS$ (5% dextrose in 0.9% saline), $D_5$ 1/2 NS (5% dextrose in 0.45% saline), $D_5LR$ (5% dextrose in Lactated Ringer's), or Normosol-R. In embodiments, the solution can be isotonic. In other embodiments, the solution can be hypotonic.

In some embodiments, parenteral (or intravenous) nutrition can be administered to the subject. Non-limiting examples of parenteral (or intravenous) nutrition comprise intravenous dextrose solutions, intravenous amino acid solutions, intravenous fat emulsions, intravenous vitamin and mineral supplements, or a combination thereof.

In embodiments, feeding, such as oral feeding, can be withheld from the subject until feeding tolerance can be demonstrated. For example, feeding tolerance can be demonstrated when the preterm infant is capable of safely ingesting and digesting the prescribed enteral (via mouth) feeding without complications associated with gastrointestinal dysfunction or infection. Clinical evidence of feeding tolerance in very low birth weight preterm infant can include the number of days required to reach full-feeding volumes (reported ranged from 100-160 mL per kg per day), the number of episodes of feeding intolerance, the number of days feeds are withheld due to feeding intolerance symptoms, time to regain birth weight, lower leg growth, increase in weight gain, occipital-frontal head circumference, and length.

In embodiments, feeding refers to the intake of infant formula, such as EleCare (Abbott Nutrition), Neosure (Similac), EnfaCare (Enfamil), Pregestimil (Enfamil), Similac Special Care or SSC (Similac), Gentlease (Enfamil). Feeding can also refer to the intake of supplements, such as Microlipid (Nestle Health Science).

In embodiments, iAP replacement therapy can refer to protein replacement therapy. The term "protein replacement" can refer to the introduction of a non-native, purified protein, such as iAP, into an individual having a deficiency in such protein. The administered protein can be obtained from natural sources or by recombinant expression. The term also refers to the introduction of a purified protein in an individual otherwise requiring or benefiting from administration of a purified protein, e.g., suffering from protein insufficiency. The introduced protein can be a purified, recombinant protein produced in vitro, or protein purified from isolated tissue or fluid, such as, e.g, placenta or animal milk, or from plants. For example, Bifidobacteria, *Klebsiella,* and *E. Coli* alkaline phosphatases are also detected in human stool from preterm infants (Swittink et al. 2017. Metaproteomics reveals functional differences in intestinal microbiota development of preterm infants. Molecular & Cellular Proteomics. DOI: 10.1074/mcp.RA117.000102 (in press)), and can thus be sources of iAP protein for protein replacement therapy. Thus, in embodiments, increased AP activity can be a result of bacterial flora, and not from human iAP only.

Disposable Article

Aspects of the invention comprise a disposable article for detecting or measuring biomarkers of gastrointestinal diseases. The disposable article can comprise a biosensor, and can optionally comprise other components known to the art. In embodiments, the biosensor can comprise at least one bio-recognition element.

In embodiments, the biosensor can detect or measure iAP in a sample. In other embodiments, the biosensor can detect or measure iAP enzymatic activity, total fecal protein, iAP dimerization/dissociation, post-translationally modified iAP, or a combination thereof. Non-limiting examples of post-translational modifications and samples are described herein.

In embodiments, the biosensor can be an immunosensor, and can further comprise a detection signal. Non-limiting examples of detection signals comprise a radioactive signal, colorimetric signal, a fluorescent signal, chemiluminescent signal, or a combination thereof. For example, the biosensor can produce a new color or change in spectral absorption. In embodiments, the biosensor of the present invention comprises a bio-recognition element, or molecular recognition element, that provides the highly specific binding or detection selectivity for a particular analyte, such as iAP. The bio-recognition element, or system, can be a biologically derived material such as an enzyme or sequence of enzymes; an antibody or fragment thereof; a membrane receptor protein; DNA; an organelle, a natural or synthetic cell membrane; an intact or partial viable or nonviable bacterial, plant or animal cell; or a piece of plant or mammalian tissues, and generally functions to interact specifically with a target biological analyte. The bio-recognition element is responsible for the selective recognition of the analyte and the physico-chemical signal that provides the basis for the output signal. The physico-chemical signal generated by the bio-recognition element or elements can be communicated visually to the wearer or caretaker (i.e., via a color change visible to the human eye). Other embodiments can produce optical signals, which can require other instrumentation to enhance the signal. These include fluorescence, bioluminescence, total internal reflectance resonance, surface plasmon resonance, Raman methods and other laser-based methods.

Alternatively, the signal can be processed via an associated transducer which, for example, can produce an electrical signal (e.g., current, potential, inductance, or impedance) that can be displayed (e.g., on a readout such as an LED or LCD display) or which triggers an audible or tactile (e.g., vibration) signal or which can trigger an actuator, as described herein. The signal can be qualitative (e.g., indicating the presence of the target biological analyte) or quantitative (i.e., a measurement of the amount or concentration of the target biological analyte). In such embodiments, the transducer can optionally produce an optical, thermal or acoustic signal.

In any case, the signal can also be durable (i.e., stable and readable over a length of time typically at least of the same magnitude as the usage life of the article) or transient (i.e., registering a real-time measurement). Additionally, the signal can be transmitted to a remote indicator site (e.g., via a wire, or transmitter, such as an infrared or rf transmitter) including other locations within or on the article or remote devices. Further, the biosensor 60, or any of its components, can be adapted to detect and/or signal only concentrations of the target biological analyte above a predefined threshold level (e.g., in cases wherein the target biological analyte is normally present in the bodily waste or when the concentration of the analyte is below a known "danger" level).

In an embodiment, the disposable article can be a diaper to be worn by a subject. Non-limiting examples of additional disposable articles include wipe for cleaning a subject, dipstick, spoon, scoopula, filter paper, or swab.

In aspects of the invention, the disposable article as described herein can be a component of a kit useful for diagnosing a subject with a gastrointestinal disease. Additional components of kits of the invention can comprise a bio-recognition element, a support structure, and instructions for use thereof. For example, an iAP bio-recognition element, such as an antibody as described herein, can be immobilized to a solid support structure.

Non-limiting examples of the composition of the solid support structure comprise plastic, cardboard, glass, plexiglass, tin, paper, or a combination thereof. The solid support can also comprise a dip stick, spoon, scoopula, filter paper or swab.

Aspects of the invention are further directed to a diagnostic kit of molecular biomarkers for identifying a subject exhibiting or having a predisposition to develop a gastrointestinal disease. In embodiments, the kit comprises at least one of a means for determining total fecal protein concentration, a means for determining intestinal alkaline phosphatase (iAP) activity, and an iAP bio-recognition element, wherein together represent a molecular signature that is indicative of the presence of or a predisposition to development of a gastrointestinal disease in a human subject. In embodiments, the signature comprises total protein concentration at least two standard deviations above the mean of a control sample, intestinal alkaline phosphatase protein concentration at least two standard deviations above the mean of a control sample, or intestinal alkaline phosphatase activity at least two standard deviations below the mean of a control sample. In still other embodiments, the signature is selected from at least two of the group comprising total protein concentration at least two standard deviations above the mean of a control sample, intestinal alkaline phosphatase protein concentration at least two standard deviations above the mean of a control sample, and intestinal alkaline phosphatase activity at least two standard deviations below the mean of a control sample. In embodiments, the control sample can comprise two or more control samples.

In one embodiment, the kit includes (a) a container that contains components and support structures as described herein, and optionally (b) informational material. The informational material can be descriptive, instructional, marketing or other material that relates to the methods described herein and/or the use of the agents for diagnostic purposes. In an embodiment, the kit includes also includes a therapeutics, such as antibiotics, probiotics, or an iAP replacement composition.

The informational material of the kits is not limited in its form. In one embodiment, the informational material can include information about production of the components of the kit, such as molecular weight, concentration, date of expiration, batch or production site information, and so forth. In one embodiment, the informational material relates to methods of using the components of the kit, (e.g., to diagnose a subject with a GI disorder). The information can be provided in a variety of formats, include printed text, computer readable material, video recording, or audio recording, or information that provides a link or address to substantive material.

The kit can include other ingredients, such as solvents or buffers, a stabilizer, or a preservative. Optionally, the kit can comprise therapeutic agents, such as iAP replacement compositions or antibiotics, that can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Described herein are methods for diagnosis of a common, acquired gastrointestinal emergency in pre-term infants. This disease (necrotizing enterocolitis or NEC) occurs in 12% of pre-term infants; 30% of NEC patients do not survive. In total, ~5000 infants in the United States have NEC per year. The medical condition has delayed and poor diagnosis due to nonspecific symptoms. Biomarkers for reliable diagnosis are required. Using infant stool samples, three biomarker measurements are performed; classifier analysis of the three biomarkers together showed that NEC can be diagnosed with high total protein concentration, low intestinal alkaline (iAP) phosphatase activity, and high levels of intestinal alkaline phosphatase protein. The detection of intestinal alkaline phosphatase protein by western blot alone is strongly correlated with NEC diagnosis and can be used in ELISA format.

Current diagnostic methods in the clinic rely in imaging: x-ray, CT, and ultrasound. Radiography has a diagnostic success rate of only 48% at best. Embodiments as described herein have a 93% true positive rate and 95% true negative rate for disease diagnosis. Embodiments as described herein can have the potential for risk assessment and surveillance of the disease.

The method is relatively fast and inexpensive in comparison to proteomic efforts and mass spectrometry. In addition, other patent applications use serum or urine; serum is invasive and requires extraction of fluids from very fragile patients, whereas urine analysis does not provide a direct readout of the gastrointestinal distress.

Example 2

Abbreviations: AP, alkaline phosphatase; DOL, day of life; iAP, intestinal alkaline phosphatase; MUP, 4-methylumbelliferyl phosphate; NBC, Naïve Bayes classifier; NEC, necrotizing enterocolitis; WB, western blot Abstract Objective: Necrotizing enterocolitis (NEC) is the most common gastrointestinal emergency in premature infants and has high mortality and morbidity rates. Diagnosis and management can be difficult because of nonspecific symptomatology, inconsistent radiological findings and rapid deterioration. This investigation was undertaken to test whether fecal intestinal alkaline phosphatase (iAP) is a specific biomarker for NEC.

Study design: In a prospective, longitudinal, case control study, serial stool samples were collected from 6 NEC patients and 12 control infants for the measurement of total fecal protein, iAP activity and iAP protein detection by western blot. Data were evaluated by longitudinal assessment of individual patients, intergroup comparison and sensitivity/specificity evaluation in a classifier-based analysis.

Results: There were no significant differences in gestational age or birthweight between the 2 groups. In 2 patients followed longitudinally, fecal protein increased, iAP activity decreased, and iAP protein was detected on western blot after development of NEC. Mean fecal protein content was higher (p=0.005), iAP activity was lower (p<0.0001) and specific iAP protein band intensity on western blot was higher (p=0.002) in NEC patients at time of diagnosis compared with controls. A 3-feature Naïve Bayes Classifier distinguished NEC from control samples with 93% sensitivity and 95% specificity.

Conclusions: Despite a limited number of subjects and samples, the findings suggest that fecal protein, iAP activity and iAP western blot intensity undergo specific changes during NEC. Preliminary sensitivity and specificity studies suggest potential for the three-component biomarker as a non-invasive diagnostic and monitoring tool for NEC.

Introduction

Necrotizing enterocolitis (NEC) is a serious inflammatory disease of the gastrointestinal tract that affects >5000 very low birth weight (≤1500 g) infants each year.[1,2] It is characterized by high mortality (up to 30%) and long-term morbidity, including short gut syndrome, recurrent infection, nutritional deficiency and neurodevelopmental delay.[3,4] Despite an overall net decrease in mortality for premature infants, there has been an increase in NEC-associated deaths. 5 The disease is often difficult to diagnose and manage, due to initial nonspecific symptomatology and rapid deterioration. Clinicians rely on radiographic evidence, such as *pneumatosis intestinalis*, to make the diagnosis, but sensitivity of this finding has been reported to be as low as 44%.[6] Although many NEC biomarkers are under investigation,[7] currently none are widely utilized in clinical practice.

Without being bound by theory, intestinal alkaline phosphatase (iAP), measured in stool, offers diagnostic value as a marker for intestinal pathology. This protein is expressed in small intestinal enterocytes, co-secreted into the intestinal lumen and systemic circulation[8] and plays an integral role in maintaining gut barrier function by detoxifying bacterial lipopolysaccharides and maintaining microbial homeostasis.[9,10] As the primary alkaline phosphatase in stool,[3,4] iAP has been identified as one of the 57 proteins in the core human stool proteome.[11] Because of its protective effects, it has been investigated in animal models as a potential treatment for NEC.[12-15] However, most studies have not evaluated iAP as a diagnostic tool and only a few have examined iAP in humans. In this investigation, we examined fecal iAP as a potential biomarker for non-invasive monitoring NEC development in neonates. To our knowledge, this study is the first to investigate fecal iAP levels in human premature infants in order to establish its relationship to NEC.

Methods

Study Design and Participants. This prospective, longitudinal case control study was approved by the institutional review board of the Louisiana State University School of Medicine. It has been carried out according to the Code of Ethics of the World Medical Association (Declaration of Helsinki). After obtaining written parental informed consent, 18 premature infants from 23-37 weeks of gestational age were enrolled at Children's Hospital of New Orleans and Touro Infirmary Hospital. Demographic data of 6 NEC patients and 12 control infants are shown in Table 1. All patient samples were de-identified prior to analysis. Patient records were retrospectively evaluated to determine clinical correlatives. No patients in this study had known chromosomal abnormalities or congenital anomalies that precluded enteral feeding.

Sample Collection/Preparation: Stool samples were collected serially from diapers of study subjects after spontaneous stooling. Stool was stored briefly in hospital specimen refrigerators, until transport to the lab in cooler boxes. In the initial processing step, about 200 mg of stool was measured, and sterile, molecular grade water (Sigma Aldrich) was added to make a desired concentration of 200 mg/ml. The mixture was vigorously vortexed for 30-60 s, or until a well-mixed slurry was evident. The mixture was then centrifuged at 22,000×g for 30 min at 4° C. The supernatant was collected and was stored at −20° C. until assays were performed.

Protein concentration: The concentration of total protein in the stool supernatant was determined by Bradford assay (Coomassie Plus Protein Assay Reagent, Thermo-Scientific), using bovine serum albumin as the standard.

Denaturing gel electrophoresis and western blot: Supernatants of stool samples were mixed with 6X gel loading buffer (375 mM Tris pH 6.8, 50% (w/v) glycerol, 600 mM dithiothreitol, 420 mM sodium dodecyl sulfate) and boiled for 5 mins. A total of 10 μg of total protein was loaded per lane of a denaturing 4-12% Bis-Tris gel (Novex, Life Technologies). The positive control was small intestinal tissue lysate (Abcam). Purified bovine alkaline phosphatase from intestinal mucosa (Sigma Aldrich) was used as a negative control. Duplicate gels were run: one was Coomassie-stained to visualize all proteins in each lane and proteins in the second were transferred onto a PVDF membrane for immunoblotting detection of intestinal alkaline phosphatase. The membrane was serially blocked in 5% (w/v) nonfat dry milk in 50 mM Tris-HCl pH 7.5, 150 mM NaCl, and 0.1% Tween, incubated with primary rabbit polyclonal antibodies against human iAP (Abcam, ab7322 or ab198101), washed, and incubated with horseradish peroxidase-conjugated goat anti-rabbit secondary antibodies (Abcam, ab6721) at room temperature. Chemiluminescent signal was initiated using Pierce ECL western blotting substrate (ThermoScientific) and captured on developed photographic film (AFP Imaging). Western blot densitometry was performed on scanned films (Biorad GelDoc XR) using Image J. In the digitized western blots, the 60 kDa band, which corresponded to iAP, was manually identified. Equivalent areas were quantitated for each lane of each western blot. The negative control was subtracted from each patient sample and the difference was calculated as a percentage of the positive control standard.

Fecal iAP catalytic activity: Alkaline phosphatase activity was measured with use of 4-methylumbelliferyl phosphate (MUP) as a fluorescent substrate (Abcam, ab83371) in the presence and absence of L-phenylalanine, an inhibitor of iAP. Relative fluorescence units (RFUs) at 360/440 nm were measured using a Spectra Max M2e spectrophotometer (Molecular Devices, Sunnyvale, CA). Ninety-six-well black optical bottom plates were used. Standards and negative controls were prepared for each plate run. Total AP activity was determined as: AP activity (mU/mL)=(B×dilution factor)/(T×V), in which B is nmol of product; V is volume of sample added to the well; T is reaction time; and U is the amount of enzyme causing hydrolysis of 1 μmol of MUP per minute at pH 10.0 and 25° C. A 100 mM stock of L-phenylalanine (purity>98%; Sigma Aldrich) was freshly prepared in molecular grade water each day of use. A final assay concentration of 10 mM Phe was used to assess inhibition of iAP-specific activity.

Statistical and computational analyses for iAP biomarker classification: Differences in means between the NEC and control groups for total fecal protein, iAP activity and intensity of 60 kDa iAP band on western blots were tested using the nonparametric Mann-Whitney U-test; p-values<0.05 were considered significant. Potential biomarker efficacy was assessed via sensitivity (true positive rate) and specificity (true negative rate) calculation. Of the 49 unique fecal samples under analysis, 13 were obtained from NEC patients at the time of clinical diagnosis. Thirty-six samples are labeled as controls, of which 27 were from control subjects and 9 were from NEC patients during healthy intervals. For each variable of interest, specificity and sensitivity was initially obtained using a simple threshold-based classifier. Subsequently, using the scikit-learn package in Python,[16] multi-variable classifier performance was executed by training Naïve Bayes Classifiers (NBC). An NBC assumes each feature is statistically independent; however, it can perform well on multi-feature classification problems, even when the assumption of statistically independent features does not hold.[17] For each classifier, we computed standard error for our sensitivity and specificity estimations by performing five rounds of stratified jackknife resampling, in which 20% of the data was excluded for each round of resampling. We used a 5-fold stratified cross-validation scheme where, for each fold, the NBC was trained on 80% of the data, and the resulting classifier was tested for sensitivity and specificity on the remaining 20% of the data.

Results

Longitudinal Studies: To explore whether the 3 stool parameters correlated with NEC, two preterm infants were observed over time and their stool samples were monitored repeatedly.

Patient 1 (FIG. 1A) was diagnosed with NEC on day of life (DOL) 7. After 14 days of medical treatment, including bowel rest and antibiotics, clinical symptoms and *pneumatosis intestinalis* resolved. Enteral feeding was restarted with variable success until the baby experienced recurrent NEC and subsequent intestinal perforation on DOL 31. Three fecal analyses were performed: soluble protein concentration, catalytic activity of iAP, and immunoblot detection of iAP. Two stool samples were obtained on DOL 7: before NEC diagnosis (7A, FIG. 1A) and the bloody stool later in the day (7B, FIG. 1A). Data from five other stool samples (DOL 13, 20, 29, 32, and 42) also are presented.

Figure 1:
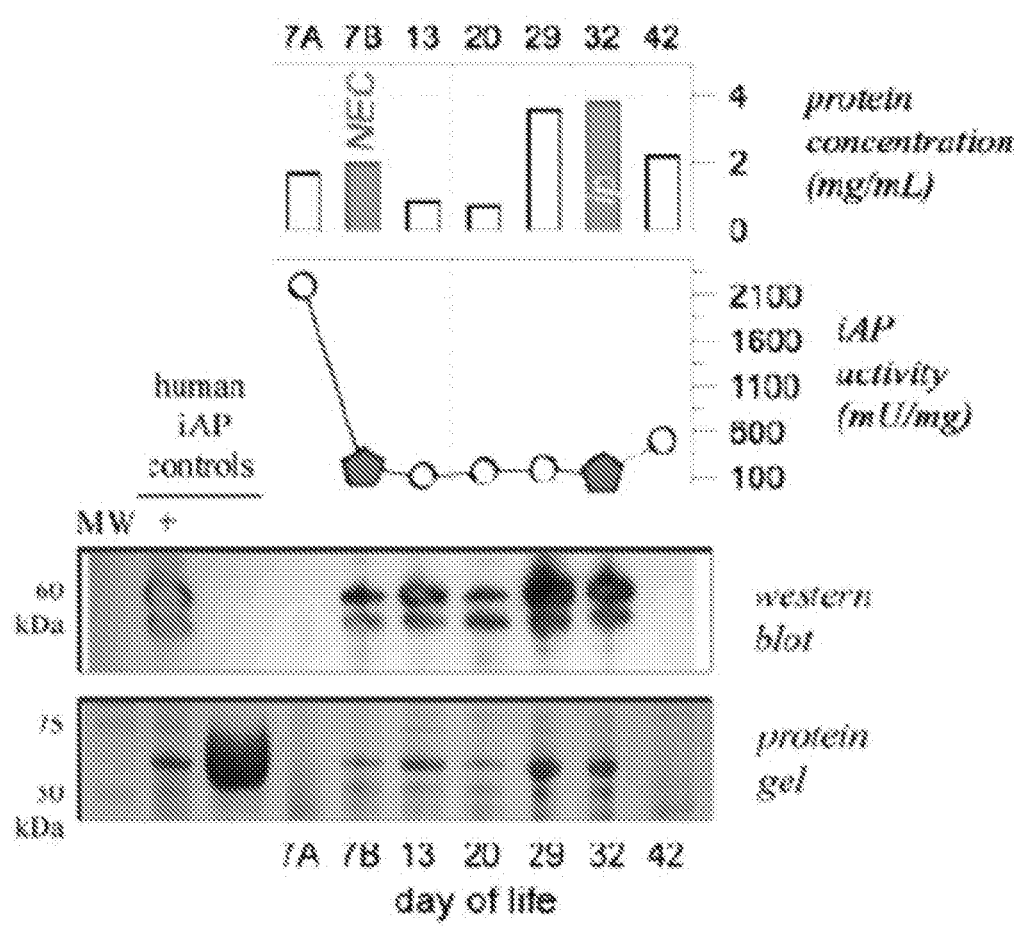
FIG. 1 shows the longitudinal measurements of total fecal protein, iAP enzymatic activity, and immunoblot detection of iAP protein is depicted for two pre-term infants. (A) Patient 1 was born at 30 weeks of gestation, developed NEC at 7 days of life, was treated medically and subsequently had recurrent NEC and an intestinal perforation on day of life 31. Infant recovered after placement of an intraperitoneal drain and 10 additional days of bowel rest and antibiotics. Red symbols and columns represent NEC episodes. 7A and 7B refer to 2 separate stool samples collected on day of life 7, one prior to and one following the diagnosis of NEC. (B) Patient 2 was born at 25 weeks of gestation, developed abdominal distension, suspicious for NEC, on DOL 19 (green symbol and column). Infant responded quickly to medical management and enteral feedings were soon resumed. Patient developed definite NEC (red symbol and column) on DOL 32, requiring assisted ventilation and aggressive medical management, but recovered fully by DOL 48. The tables below each figure illustrate which fecal assays met the criteria for NEC (+) and which did not (−). These criteria were defined by values outside the 95% confidence interval for control values. Risk for NEC was considered increased if: protein concentration exceeded 1.8 mg/ml; iAP activity was less than 979 mU/mg; or iAP protein detection by western blot exceeded 10.7% of control. Abbreviations: ip, intestinal perforation; ad, abdominal distension; MW, molecular weight ladder; and kDa, kilodalton.

Longitudinal monitoring of patient 1 showed that the 3 candidate biomarkers had diagnostic value (FIG. 1A). The DOL 7A stool sample had a protein concentration of 1.85 mg/mL, catalytic activity of 2218 U/g, and no detectable signal at 60 kDa in the western blot. The DOL 7B stool sample, collected several hours later, had a protein concentration of 2.1 mg/mL, catalytic activity of 250 U/g, and clear immunodetection of iAP. Comparison of the two stool samples from the same patient immediately before and after the onset of NEC indicated that a precipitous drop in iAP activity and an increase of iAP protein are characteristic of NEC.

These biomarkers also exhibited surveillance value. After initial NEC diagnosis on DOL 7, low iAP enzymatic activity and immunodetection of high iAP protein levels persisted in stool samples collected during the period of medical treatment, apparent "recovery", and reinstitution of enteral feeding. The infant subsequently experienced a reoccurrence of NEC with intestinal perforation on day of life 31. In combination, increased fecal protein, low iAP enzymatic activity and high levels of iAP protein in western blots heralded the perforation. After 10 days of treatment that included peritoneal drainage, bowel rest and antimicrobial therapy, the stool collected on DOL 42 had assay values that approximated those prior to the diagnosis of NEC.

Longitudinal monitoring also suggested the prognostic potential of the three candidate biomarkers. Patient 2 (FIG. 1B) was diagnosed with suspected NEC on DOL 19, kept on "NEC watch" (NEC surveillance, bowel rest, antibiotics) for several days before resumption of enteral feedings. Although a definite diagnosis of NEC was not made until DOL 32, stool samples on DOL 13 and 19 had two out of three biomarkers in the positive range for NEC association, potentially forecasting NEC.

Figure 2:
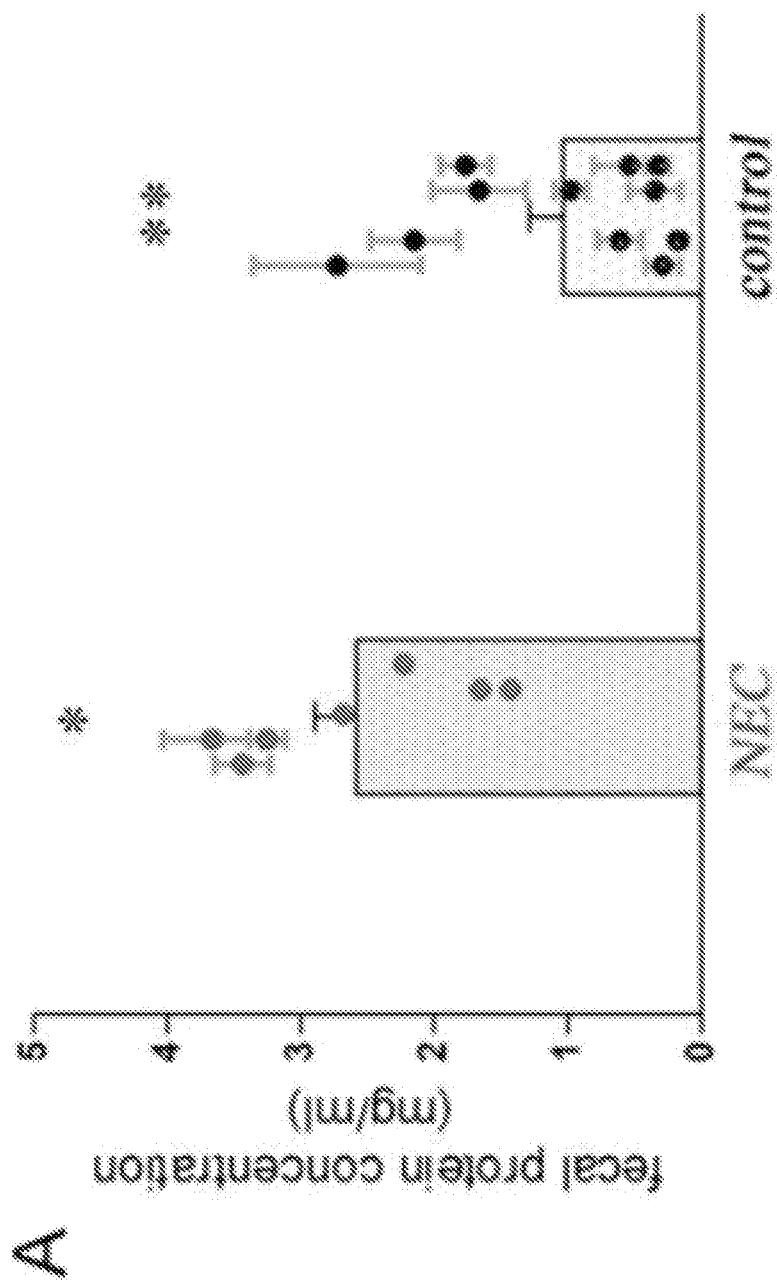
FIG. 2 shows increased concentration of total fecal protein, decreased fecal iAP enzymatic activity, and increased iAP detection on western blot at the time of NEC diagnosis. In the following panels, red circles represent individual stool samples collected during 7 distinct NEC events from 6 patients; black circles represent a composite average±standard error of 2-17 stool samples from 12 control patients. Red and grey columns represent the mean±standard error of all samples collected in NEC events and of all samples from control subjects, respectively. (A) Protein concentrations were higher in stool samples from patients at the time of NEC diagnosis compared with control samples (p-value=0.005). (B) iAP activity was lower in stool samples from patients at time of NEC diagnosis compared with control samples (p-value<0.0001). (C) Amount of iAP protein in stool, quantified by comparison with a positive control standard, was higher in patients at the time of NEC diagnosis compared with control samples (p-value=0.002). Statistical test: Mann-Whitney.

Cross-sectional Studies: In surveys of fecal material collected from 6 NEC and 12 control infants, there were marked differences for the 3 in vitro measurements between stool samples from patients with active NEC and those of controls (FIG. 2). The mean±SEM protein concentration of 2.62±0.33 mg/mL in stool samples from patients at the time of NEC diagnosis differed significantly from the level of 0.98±0.25 mg/mL found in fecal samples from control patients matched for post-conceptual age (p=0.005, FIG. 2A). Furthermore, NEC patients had a more than ten-fold lower mean fecal iAP enzymatic activity at the time of diagnosis compared with controls matched for post-conceptual age (162±30 mU/mg vs. 1826±376 mU/mg, NEC vs. control, respectively, p<0.0001, FIG. 2B).

Finally, samples from the 2 patient populations differed significantly (p=0.002) in the relative amount of specific iAP protein, determined by densitometric analysis of immunoblots probed with anti-human iAP antibody and expressed as a percent of a standard positive control. We found nearly a 30-fold higher iAP protein in stool samples from NEC patients compared with samples from healthy premature subjects (215.0±47.6% vs. 7.2±2.3%, NEC vs. control, respectively, FIG. 2C). In summary, stool samples from infants with NEC have increased total protein, decreased iAP enzyme activity, and increased iAP protein at the time of diagnosis compared with healthy controls.

Sensitivity Specificity Studies: In a 3-dimensional scatterplot (FIG. 3A), biomarkers from NEC samples (red circle) cluster independently from controls (black circles), suggesting high sensitivity and specificity can be achieved with these biomarkers. Despite some overlap, the potential for distinguishing between NEC and control patient samples remained clear even when total fecal protein levels were removed as a variable (FIG. 3B). We evaluated sensitivity and specificity directly with both single variable threshold classifiers and a Naïve Bayes Classifier (NBC), which classified the samples based on integration of all 3 tests (FIG. 3C). Clearly, there is a tradeoff between sensitivity and specificity. If maximal sensitivity, or the true positive rate, is the dominant goal, the 3-feature NBC biomarker performs best with 100% sensitivity and 92% specificity. However, if the goal is to simultaneously maximize both sensitivity and specificity, then the 3-feature NBC showed performance of 93% sensitivity and 95% specificity. The iAP activity level considered alone also performs almost as well in this case by achieving both sensitivity and specificity levels of 92%, when using a threshold of 300 mU/mg iAP activity. Perhaps unsurprisingly, though, total fecal protein level alone is not as robust a biomarker for NEC. At 92% sensitivity, specificity falls to 67% using a protein threshold of 1.35 mg/mL. Consequently, fecal iAP activity level and 60 kDa western blot intensity levels hold promise individually as NEC biomarker candidates. However, total fecal protein activity level is only likely to have utility if considered as part of a multi-feature diagnostic evaluation.

Discussion

The diagnosis and management of NEC is complicated by our current inability to accurately identify the disease prior to the development of irreversible intestinal damage. Clinical parameters alone cannot accurately predict disease progression in the majority of patients.[18] Although radiography, the cornerstone of NEC diagnosis and staging,[19] is rapid and accessible in intensive care units, this measure of disease pathology provides qualitative, rather than quantitative, endpoints. There is well-documented variability in interpretation of observable radiological signs determining disease severity.[6,20,21] Disturbingly, the hallmark radiological finding, *pneumatosis intestinalis*, was reported in only 44% of pathology-confirmed NEC.[22]

Quantitative markers, measured as a ratio or on an interval scale, are still needed to achieve a better understanding of NEC, e.g., to distinguish between normal and pathological biological processes or monitor a response to clinical interventions. The clinical definition of NEC could be significantly improved with a shift from sole dependence on clinical impression and imaging findings to an expanded diagnostic palette including reliable molecular biomarkers. Identification of molecular NEC biomarkers amenable to adoption in clinical practice has the potential to reduce neonatal deaths, morbidity, and associated healthcare costs. Moreover, characterization of such parameters can provide insight into cellular integrity, protein expression, and changes in gastrointestinal metabolism. Obtained from serum, urine, feces, and buccal swabs, the discovery of candidate biomarkers for NEC is a focus of current research.[23-25]

Our study demonstrated a correlation between 3 in vitro fecal parameters and patient pathology that is compatible with findings from animal studies. The increased concentration of total fecal protein measured in NEC patients likely is associated with mucosal sloughing and disease-associated inflammatory products, such as serum amyloid A, anaphylatoxin, C-reactive protein, platelet-activating factor, calprotectin, and alpha-1 antitrypsin.[26-31] Of these inflammation-based biomarkers, the latter three have been measured directly in neonatal stool samples.[27, 28, 32-34] However, biomarkers associated with inflammation, while often associated with gastrointestinal pathology, are not specific for NEC diagnosis.

In our study, increased iAP detection via western blot was inversely correlated with lower intestinal AP enzymatic activity in the NEC patients' fecal samples at the time of diagnosis. Our findings are consistent with other reports in the literature. First, biopsied intestinal tissue from patients with inflammatory bowel disease displayed lower AP activity, based on enzyme histochemical analysis.[35] Second, serum iAP was shown to be increased in patients who would go on to develop NEC; however, AP levels were monitored only by gel electrophoresis, and no positive detection of intestinal alkaline phosphatase was detailed.[36] Third, in animal models of induced NEC, the terminal ileum tissue samples in rats showed a decrease in protein content, activity and immunofluorescence specific for alkaline phosphatase.[14,37] Lastly, decreased mucosal AP activity was also reported in animal models, following ischemia reperfusion.[38] Increased shedding of mucosal protein, including inactivated iAP, could account for our findings.

We had several criteria in evaluating the translational promise of our NEC biomarkers. First, the molecular signatures should be direct readouts of gastrointestinal disease and readily detectable. In this study, we evaluated three candidates: total fecal protein, specific iAP activity, and western blot band intensity for iAP. Monitoring total protein levels in stool has a pathophysiological justification, since high protein levels in stool are closely linked to poor mucosal integrity in the immature neonatal intestine that can be exaggerated by inflammation. The appeal of iAP as a biomarker lies in its tissue-specific expression in the small intestine and its secretion into the mucous layer and gut lumen.[39,40] It is also responsible for majority of AP enzymatic activity in stool[41,42] and has been used as a measure of toxic damage to the small intestine in animal models.[43,44] All three of our stool biomarker candidates showed significant mean differences between NEC patients at the time of diagnosis versus control subjects (FIG. 2).

Second, essential features for a clinically useful molecular biomarker are ease of patient sample handing and a rapid turn-around time of <3 hours. Fresh weight-to-volume standardization in sterile water is rapid, requires minimal reagents, and allows storage in small disposables that facilitate packing and transport. Measurement of protein concentration requires less than 30 minutes. In its current implementation, iAP enzymatic assays and western blots can be completed in one or two hours, respectively.

Our third criterion in the evaluation of our NEC biomarker is the potential to outperform radiographic diagnosis. As a reference, a 7-parameter analysis of clinical diagnostic criteria established by the WHO Integrated Management of Childhood Illness program reported that 85% sensitivity and 75% specificity was high.[45] The detection of *pneumatosis intestinalis* has a sensitivity of only 44%.[22] In contrast, performance data for our diagnostic approach, including specific iAP activity, immunoblot detection and the three-parameter NBC, were promising, as both sensitivity and specificity were greater than 90%. We also note that, in general, marker performance is more robust for a positive diagnostic readout, such as increased immunoblot detection and protein concentration, than for a negative diagnostic readout: the latter mode is more susceptible to false positive (and false negative) diagnoses. Although future studies that involve a larger patient population can alter our performance data, we conclude that this stool sample analysis has potential clinical utility for improving prognostic diagnosis and subsequent surveillance for NEC.

Challenges to adopting our fecal biomarker analysis as a diagnostic tool for NEC are the heterogeneous composition of some stool samples, the intermittent and variable stooling pattern of some neonates, and the lack of immediate, on-demand test results. However, our 3-feature fecal biomarker analysis has the advantages of requiring less time, no special training or expertise, and is inexpensive in comparison with proteomics or mass spectrometry techniques. Adaptation of the test to continuous, noninvasive surveillance of preterm infants in newborn intensive care units would provide objective measures to assess mucosal integrity, help assess risk associated with feeding regimens, and contribute to our understanding of NEC.

In future studies, our Naïve Bayes Classifier methodology can be extended to simultaneously analyze iAP enzymatic activity, western blot signal and other candidate NEC biomarkers, such as fecal calprotectin and platelet-activating factor.[7] These fecal biomarkers could be added to our classification scheme without the need for additional blood or urine samples from the neonatal patient. The classifier performance of protein biomarkers in urine samples to distinguish between NEC and sepsis patients has been analyzed, and indeed, the efficiency of distinguishing between NEC and sepsis patients was decreased compared with that distinguishing between NEC and normal patients. 46 If our proposed biomarker scheme can maintain high sensitivity and specificity on a larger population of patients with a more complex group of controls, then iAP measurement in conjunction with machine learning analysis of other biomarker candidates could lead to significant advances in NEC diagnosis and management.

REFERENCES CITED IN THIS EXAMPLE

[1] Fitzgibbons S C, Ching Y, Yu D, Carpenter J, Kenny M, Weldon C, Lillehei C, Valim C, Horbar J D, Jaksic T. Mortality of necrotizing enterocolitis expressed by birth weight categories. J Pediatr Surg. 2009; 44:1072-6.

[2] González-Rivera R, Culverhouse R C, Hamvas A, Tarr P I, Warner B B. The age of necrotizing enterocolitis onset: an application of Sartwell's incubation period model. J Perinat. 2011; 31:519-23.

[3] Yee W H, Soraisham A S, Shah V S, Aziz K, Yoon W, Lee S K, Canadian Neonatal Network. Incidence and timing of presentation of necrotizing enterocolitis in preterm infants. Pediatrics. 2012; 129:e298-304.

[4] Young C, Sharma R, Handfield M, Mai V, Neu J. Biomarkers for infants at risk for necrotizing enterocolitis: clues to prevention? Pediatr Res. 2009; 65:91R-7R.

[5] Patel R M, Kandefer S, Walsh M C, Bell E F, Carlo W A, Laptook A R, Sanchez P J, Shankaran S, Van Meurs K P, Ball M B, Hale E C, Newman N S, Das A, Higgins R D, Stoll B J, Eunice Kennedy Shriver National Institute of Child H, Human Development Neonatal Research Network. Causes and timing of death in extremely premature infants from 2000 through 2011. N Engl J Med. 2015; 372:331-40.

[6] Tam A L, Camberos A, Applebaum H. Surgical decision making in necrotizing enterocolitis and focal intestinal perforation: predictive value of radiologic findings. J Pediatr Surg. 2002; 37:1688-91.

[7] Chu A, Hageman J R, Caplan M S. Necrotizing enterocolitis: predictive markers and preventive strategies. NeoReviews. 2013; 14:e113-e20.

[8] Eliakim R, Mahmood A, Alpers D H. Rat intestinal alkaline phosphatase secretion into lumen and serum is coordinately regulated. Biochim Biophys Acta. 1991; 1091:1-8.

[9] Lalles J P. Intestinal alkaline phosphatase: multiple biological roles in maintenance of intestinal homeostasis and modulation by diet. Nutr Rev. 2010; 68:323-32.

[10] Lalles J P. Luminal ATP: the missing link between intestinal alkaline phosphatase, the gut microbiota, and inflammation? Am J Physiol Gastrointest Liver Physiol. 2014; 306:G824-5.

[11] Lichtman J S, Marcobal A, Sonnenburg J L, Elias J E. Host-centric proteomics of stool: a novel strategy focused on intestinal responses to the gut microbiota. Mol Cell Proteomics. 2013; 12:3310-8.

[12] Biesterveld B E, Koehler S M, Heinzerling N P, Rentea R M, Fredrich K, Welak S R, Gourlay D M. Intestinal alkaline phosphatase to treat necrotizing enterocolitis. J Surg Res. 2015; 196:235-40.

[13] Riggle K M, Rentea R M, Welak S R, Pritchard K A, Jr., Oldham K T, Gourlay D M. Intestinal alkaline phosphatase prevents the systemic inflammatory response associated with necrotizing enterocolitis. J Surg Res. 2013; 180:21-6.

[14] Rentea R M, Liedel J L, Welak S R, Cassidy L D, Mayer A N, Pritchard K A, Jr., Oldham K T, Gourlay D M. Intestinal alkaline phosphatase administration in newborns is protective of gut barrier function in a neonatal necrotizing enterocolitis rat model. J Pediatr Surg. 2012; 47:1135-42.

[15] Heinzerling N P, Liedel J L, Welak S R, Fredrich K, Biesterveld B E, Pritchard K A, Jr., Gourlay D M. Intestinal alkaline phosphatase is protective to the preterm rat pup intestine. J Pediatr Surg. 2014; 49:954-60.

[16] Pedregosa F, Varoquaux G, Gramfort A, Michel V, Thirion B, Grisel O, Blondel M, Prettenhofer P, Weiss R, Dubourg V. Scikit-learn: Machine learning in Python. J Machine Learning Research. 2011; 12:2825-30.

[17] Rish I. An empirical study of the naive Bayes classifier. IJCAI 2001 workshop on empirical methods in artificial intelligence: IBM New York; 2001. p. 41-6.

[18] Ji J, Ling X B, Zhao Y, Hu Z, Zheng X, Xu Z, Wen Q, Kastenberg Z J, Li P, Abdullah F, Brandt M L, Ehrenkranz R A, Harris M C, Lee T C, Simpson B J, Bowers C, Moss R L, Sylvester K G. A data-driven algorithm integrating clinical and laboratory features for the diagnosis and prognosis of necrotizing enterocolitis. PLoS One. 2014; 9:e89860.

[19] Bell M J, Ternberg J L, Feigin R D, Keating J P, Marshall R, Barton L, Brotherton T. Neonatal necrotizing enterocolitis. Therapeutic decisions based upon clinical staging. Ann Surg. 1978; 187:1-7.

[20] Kosloske A M, Musemeche C A, Ball W S, Jr., Ablin D S, Bhattacharyya N. Necrotizing enterocolitis: value of radiographic findings to predict outcome. A J R Am J Roentgenol. 1988; 151:771-4.

[21] Coursey C A, Hollingsworth C L, Wriston C, Beam C, Rice H, Bisset G, 3rd. Radiographic predictors of disease severity in neonates and infants with necrotizing enterocolitis. A J R Am J Roentgenol. 2009; 193:1408-13.

[22] Ballance W A, Dahms B B, Shenker N, Kliegman R M. Pathology of neonatal necrotizing enterocolitis: a ten-year experience. J Pediatr. 1990; 117:S6-13.

[23] Evennett N, Cerigioni E, Hall N J, Pierro A, Eaton S. Smooth muscle actin as a novel serologic marker of severe intestinal damage in rat intestinal ischemia-reperfusion and human necrotising enterocolitis. J Surg Res. 2014; 191:323-30.

[24] Ng P C, Ma T P, Lam H S. The use of laboratory biomarkers for surveillance, diagnosis and prediction of clinical outcomes in neonatal sepsis and necrotising enterocolitis. Arch Dis Child Fetal Neonatal Ed. 2015; 100:F448-52.

[25] Sylvester K G, Ling X B, Liu G Y, Kastenberg Z J, Ji J, Hu Z, Peng S, Lau K, Abdullah F, Brandt M L, Ehrenkranz R A, Harris M C, Lee T C, Simpson J, Bowers C, Moss R L. A novel urine peptide biomarker-based algorithm for the prognosis of necrotising enterocolitis in human infants. Gut. 2014; 63:1284-92.

[26] Pourcyrous M, Korones S B, Yang W, Boulden T F, Bada H S. C-reactive protein in the diagnosis, management, and prognosis of neonatal necrotizing enterocolitis. Pediatrics. 2005; 116:1064-9.

[27] Amer M D, Hedlund E, Rochester J, Caplan M S. Platelet-activating factor concentration in the stool of human newborns: effects of enteral feeding and neonatal necrotizing enterocolitis. Biol Neonate. 2004; 85:159-66.

[28] Yang Q, Smith P B, Goldberg R N, Cotten C M. Dynamic change of fecal calprotectin in very low birth weight infants during the first month of life. Neonatology. 2008; 94:267-71.

[29] Tayman C, Tonbul A, Kahveci H, Uysal S, Koseoglu B, Tatli M M, Dilmen U. C5a, a complement activation product, is a useful marker in predicting the severity of necrotizing enterocolitis. Tohoku J Exp Med. 2011; 224: 143-50.

[30] Cetinkaya M, Ozkan H, Koksal N, Akaci O, Ozgur T. Comparison of the efficacy of serum amyloid A, C-reactive protein, and procalcitonin in the diagnosis and follow-up of necrotizing enterocolitis in premature infants. J Pediatr Surg. 2011; 46:1482-9.

[31] Ng P C, Ang I L, Chiu R W, Li K, Lam H S, Wong R P, *Chui* K M, Cheung H M, Ng E W, Fok T F, Sung J J, Lo Y M, Poon T C. Host-response biomarkers for diagnosis of late-onset septicemia and necrotizing enterocolitis in preterm infants. J Clin Invest. 2010; 120:2989-3000.

[32] Rabinowitz S S, Dzakpasu P, Piecuch S, Leblanc P, Valencia G, Kornecki E. Platelet-activating factor in infants at risk for necrotizing enterocolitis. J Pediatr. 2001; 138:81-6.

[33] Moussa R, Khashana A, Kamel N, Elsharqawy S E. Fecal calprotectin levels in preterm infants with and without feeding intolerance. J Pediatr (Rio J). 2016.

[34] Shulman R J, Buffone G, Wise L. Enteric protein loss in necrotizing enterocolitis as measured by fecal alpha 1-antitrypsin excretion. J Pediatr. 1985; 107:287-9.

[35] Tuin A, Poelstra K, de Jager-Krikken A, Bok L, Raaben W, Velders M P, Dijkstra G. Role of alkaline phosphatase in colitis in man and rats. Gut. 2009; 58:379-87.

[36] Kampanatkosol R, Thomson T, Habeeb O, Glynn L, Dechristopher P J, Yong S, Jeske W, Maheshwari A, Muraskas J. The relationship between reticulated platelets, intestinal alkaline phosphatase, and necrotizing enterocolitis. J Pediatr Surg. 2014; 49:273-6.

[37] Whitehouse J S, Riggle K M, Purpi D P, Mayer A N, Pritchard K A, Jr., Oldham K T, Gourlay D M. The protective role of intestinal alkaline phosphatase in necrotizing enterocolitis. J Surg Res. 2010; 163:79-85.

[38] Sisley A C, Desai T R, Hynes K L, Gewertz B L, Dudeja P K. Decrease in mucosal alkaline phosphatase: a potential marker of intestinal reperfusion injury. J Lab Clin Med. 1999; 133:335-41.

[39] Goldberg R F, Austen W G, Jr., Zhang X, Munene G, Mostafa G, Biswas S, McCormack M, Eberlin K R, Nguyen J T, Tatlidede H S, Warren H S, Narisawa S, Millan J L, Hodin R A. Intestinal alkaline phosphatase is a gut mucosal defense factor maintained by enteral nutrition. Proc Natl Acad Sci USA. 2008; 105:3551-6.

[40] Shifrin D A, Jr., McConnell R E, Nambiar R, Higginbotham J N, Coffey R J, Tyska M J. Enterocyte microvillus-derived vesicles detoxify bacterial products and regulate epithelial-microbial interactions. Curr Biol. 2012; 22:627-31.

[41] Horrigan F D, Danovitch S H. The origin of human fecal alkaline phosphatase. Am J Dig Dis. 1974; 19:603-8.

[42] Malo M S. A high level of intestinal alkaline phosphatase is protective against type 2 diabetes mellitus irrespective of obesity. EBioMedicine. 2015; 2:2016-23.

[43] Lehmann F G, Hufnagel H, Lorenz-Meyer H. Fecal intestinal alkaline phosphatase: a parameter for toxic damage of the small intestinal mucosa. Digestion. 1981; 21:156-62.

[44] Thomas D W, Henton D H. The use of fecal alkaline phosphatase as an indicator of intestinal damage. Digestion. 1985; 31:82-8.

[45] Group YICSS. Clinical signs that predict severe illness in children under age 2 months: a multi-centre study. The Lancet. 2008; 371:135-42.

[46] Sylvester K G, Ling X B, Liu G Y, Kastenberg Z J, Ji J, Hu Z, Wu S, Peng S, Abdullah F, Brandt M L, Ehrenkranz R A, Harris M C, Lee T C, Simpson B J, Bowers C, Moss R L. Urine protein biomarkers for the diagnosis and prognosis of necrotizing enterocolitis in infants. J Pediatr. 2014; 164:607-12 e1-7.

Example 3

Introduction

Necrotizing enterocolitis (NEC) is an extremely serious inflammatory disease of the gastrointestinal tract that primarily affects premature infants. It occurs in up to 10% of very low birth weight infants (≤1500 g at birth) and is characterized by high mortality (up to 30%) and significant long term morbidity, including infantile short gut syndrome, recurrent infection, parenteral nutrition related cholestasis, nutritional deficiency and neurodevelopmental delay (1). Despite advances in the field of neonatology, NEC is responsible for increasing deaths in very premature infants (2). The exact cause of the disease is still not well understood, making diagnosis and management a challenge. The course of the disease often involves initial nonspecific symptomatology and rapid clinical deterioration. Although many biomarkers are currently under investigation as potential aides in diagnosing NEC, none are widely utilized to determine the true integrity of the challenged intestine (3).

Intestinal alkaline phosphatase (iAP) has become an enzyme of interest in the study of gastrointestinal disease. Produced and secreted by enterocytes in the proximal small intestine, iAP activity is found throughout the small and large intestin(4). It is the primary alkaline phosphatase (AP) detected in stool (5,6). It has a variety of functions such as cleaving of lipopolysaccharide (LPS) produced by gram-negative bacteria and interfering with activation of Toll-like receptors in the gut (7). It dephosphorylates ATP and has been shown to affect microbial homeostasis through this interaction (8).

With such broad functions involving gut homeostasis, one might expect iAP to be altered in NEC. In rats, Biesterveld et al. demonstrated decreased endogenous iAP catalytic activity during induced NEC and a subsequent increase during recovery from insult (9). Lehmann and Lorenz Meyer observed an increase in fecal iAP after induced toxic damage to the small intestine in rats, followed by a marked reduction in fecal iAP (10). They suggested that fecal iAP could be used as a parameter for toxic damage to the small intestine (10). Thomas and Henton later investigated the use of fecal iAP as a potential marker for intestinal damage but found wide variability (11). They suggested a longitudinal approach to determine clinical usefulness (11). Supplemental iAP has been shown to abate some of the systemic inflammatory responses associated with NEC (9, 12, 14). A recent study proposed serum iAP as a potential biomarker and found a tendency for high iAP levels in infants who later developed NEC (15). These observations suggested the hypothesis that iAP might be a useful biomarker for NEC.

The focus of our study was to establish whether fecal iAP could be used as diagnostic tool for NEC. Fecal iAP measurements are less invasive compared to serum measurements in premature neonates who are already subject to multiple serological examinations. To date, no studies have been published that have investigated fecal iAP in human neonates and its relationship to NEC. We hypothesized that fecal iAP can be used as an objective and specific biomarker for diagnosing NEC and for monitoring the course of NEC once disease is established.

Development of Methodology

In preparation for this study, I sought and obtained Institutional Board Review approval. I designed an informed consent and enrolled a total of 20 infants. I enlisted the help of NICU nurses to help with collection and came up with a system of labeling that would protect patient confidentiality. Stool samples were collected prospectively and charts were reviewed retrospectively to determine clinical correlatives. The literature on fecal iAP measurements is sparse. I found a reference describing how rat fecal matter was mixed with water then centrifuged to obtain a supernatant 16 and so I proceeded with a similar methodology for handling of human stool samples. We determined that 200 mg of measured stool was sufficient to allow for easy supernatant collection and protein quantification. The consistency of stool was highly variable, making wet weight an unreliable parameter. Fecal total protein content (determined by Bradford assay) was used to standardize iAP measurements.

To confirm the presence of IAP in stool we chose western blot (WB) as an initial assay. Surprisingly, positive detection of the protein in stool was extremely difficult in our healthy controls. In fact, there were over 10 samples analyzed that yielded negative results, with no band signal or signal at a much lower than expected position. Initially, we thought our negative results were from failures in handling and/or storage. However, even same-day measurement of freshly acquired stool samples did not yield evidence of protein recognition by anti-iAP antibodies on western blot. It was only upon analyzing a stool sample from our first NEC patient that we found evidence of the full length protein on western blot. When we enrolled a second NEC patient we again had positive results locating the iAP on WB.

Determination of the presence of iAP protein on WB in at least some experiments gave us confidence to move forward with our research. We then performed experiments to determine the ideal handling and storage techniques. We subjected some samples to several days in the refrigerator at 4° Celsius and after 5 days in the refrigerator there was no significant degradation of the protein. Western blots showed continued positive detection of iAP by anti-iAP. Enzymatic activity measurements showed minimal variance from day to day. We also froze our supernatants at −20° Celsius but determined that short periods of storage in the refrigerator at the hospital was acceptable.

We thought that 200 mg of stool would be needed to produce reliable results. In one case, although we collected only 10 mg of stool at the time of NEC diagnosis, we were still able to demonstrate a strong band for fecal iAP on western blot, indicating usefulness of the test even when small amounts of feces are available.

Figure 5:
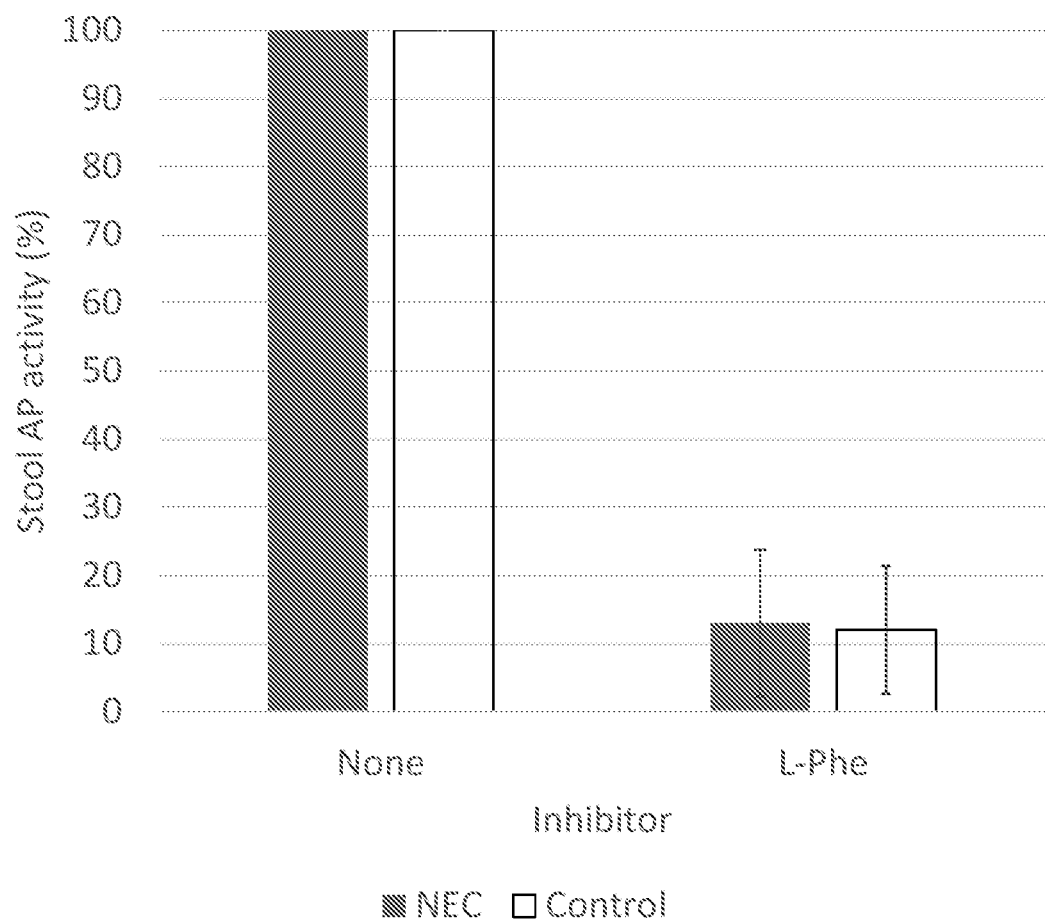
FIG. 5 shows Alkaline phosphatase activity was mostly due to intestinal alkaline phosphatase (iAP). Activity was inhibited by L-Phe which is a specific inhibitor of intestinal alkaline phosphatase activity. There was no observable difference in the degree of inhibition between NEC samples and control samples. NEC samples showed 90% inhibition with standard deviation +/−10. Control samples showed 91% inhibition with standard deviation of +/−9. This represents 12 samples from 6 NEC patients and 64 samples from control patients (n=18).

We chose fluorometric assays to measure activity, because of its sensitivity (detection sensitivity of ~1 µU) over colorimetric methods (17). We were surprised to find there was evidence of alkaline phosphatase activity even in the samples that did not yield a signal on WB. Since our fluorometric activity assays are not specific for intestinal alkaline phosphatase, other alkaline phosphatases in stool can have caused the discrepancy between WB and activity assays. Our next set of investigations were designed to measure the actual activity of iAP present by performing sample assays in the presence and absence of L-phenylalanine (L-Phe), a specific inhibitor of iAP (4, 18). L-Phe blocked 90%±10% (SD) of AP activity in samples from NEC patients and 91%±9% (SD) of AP activity in those from controls, indicating that iAP was the major contributor to alkaline phosphatase activity in the fecal samples studied (FIG. 5). This finding is in agreement with previous reports (3,4) confirming that iAP is the most common AP in stool.

Methods

Study Design and Participants—This was a prospective, case-control study. After obtaining parental informed consent, 20 premature infants from 23-37 weeks gestational age (WGA) were enrolled at Children's Hospital of New Orleans and Touro Infirmary Hospital. Six infants had NEC defined by Bell staging (19). Infants with known chromosomal abnormalities or congenital anomalies that would preclude them from feeding were excluded. Fecal samples from 2 subjects were excluded from statistical analysis due to dissimilar handling. Demographic data of the remaining 18 subjects (6 NEC patients and 12 controls) are shown in Table 1. Handling of Stool—Stool samples were collected serially from diapers of study subjects after spontaneous stooling. Stool was stored briefly at the hospital in specimen refrigerators. The samples were transported in cooler boxes to the lab for initial processing. About 200 mg of stool was measured out, when possible, and molecular grade water was added to make a desired concentration of 200 mg/ml. The mixture was vigorously vortexed for 30 secs to 1 min or until a well-mixed slurry was evident. The mixture was then centrifuged at 22,000×g for 30 min at 4° C. The supernatant was collected and was stored at −20° C. until assays were performed.

Determination of protein concentration—Total protein concentration in stool supernatant was determined by Bradford assay (Coomassie Plus Protein Assay Reagent, Thermo-Scientific), using bovine serum albumin as the standard.

Denaturing gel electrophoresis and western blot—Supernatants of stool samples were mixed with gel loading buffer (375 mM Tris pH 6.8, 50% (w/v) glycerol, 600 mM dithiothreitol, 420 mM sodium dodecyl sulfate) then boiled for 5 mins. A total of 10 micrograms of total protein was loaded per each lane of precast denaturing 4-12% Bis-Tris gel (Novex, Life Technologies). Duplicate gels were run. One gel was stained with Coomassie and the other gel electroblotted onto polyvinylidene difluoride membrane (PVDF) and blocked in 5% nonfat dry milk with Tris buffered Saline and Tween® 20 (50 mM Tris HCl, 150 mM NaCl, Tween® 20). The PVDF was incubated with primary antibodies to full length human iAP ab7322/ab198101 (Abcam) and horseradish peroxidase conjugated Goat anti-rabbit secondary antibodies ab6721 (Abeam). We used Pierce ECL western blotting substrate (Thermo-scientific) as the peroxidase substrate for chemoluminescence. A developer (AFP Imaging; Mount Kisco, NY) was used to produce films after WB and an imager (Biorad Gel-Doc XR; Hercules, CA) was used to scan western blots and gels. Densitometry was done to analyze digitized images of western blots. We manually identified bands at 60 kDa on the western blots, which corresponded to intestinal alkaline phosphatase. We then calculated the area relative to background for each 60 kDa band and then expressed this value as a percentage of the positive control. Positive controls were hepatocellular carcinoma whole cell lysate or small intestine tissue lysate (Abcam). Purified bovine alkaline phosphatase from intestinal mucosa (Sigma Aldrich) was used as a negative control.

Fecal iAP Activity—Alkaline phosphatase activity was ascertained with the use of 4-methylumbelliferyl phosphate as a fluorescent substrate ab83371 (Abcam). Substrate background controls and background controls were done to improve accuracy. Relative fluorescence units (RFUs) at 360/440 nm wavelengths were measured using a Spectra Max M2e spectrophotometer (Molecular Devices, Sunnyvale, CA). Ninety-six well black, optical bottom plates were used. Reaction wells for samples, standards and negative background controls were prepared each time the assay was performed and total alkaline phosphatase activity was determined using:

$$ALP \text{ activity } (mU/ml) = (B/T)/V \times \text{dilution factor}$$

in which B is nmol of 4-methylumbelliferone (4-MU), V is volume of sample added to the well, and T is reaction time. U is the amount of enzyme causing hydrolysis of 1 μmol of product per minute at pH 10.0 and 25° C. (glycine buffer). A 100 mM stock of L-phenylalanine (purity>98%; Sigma Aldrich) was freshly prepared in molecular grade water each day assays were performed. A final concentration of 10 mM of L-Phe was added to each well to inhibit iAP activity.

Computational and statistical analyses for iAP biomarker classification—We included 18 infants in our analysis of fecal protein and fecal iAP datasets due to uniformity in handling of the stool and similar gestational ages. Differences in means between the NEC and control groups for total fecal protein, iAP activity and intensity of iAP protein band on WB were tested using the nonparametric Mann-Whitney U-test (GraphPad Instat v. 3; La Jolla, CA). Linear regression analysis was used to determine correlations between days until full feeds and total fecal protein and between days until full feeds and iAP activity (GraphPad Prism v7; La Jolla, CA). P-values less than 0.05 were considered significant. Igor Pro (Lake Oswego, OR) was used to generate FIG. 10.

A separate subset of data was used for 51 fecal samples (from 6 NEC patients and 7 controls) for which we had available measurements of specific iAP activity, WB and fecal protein. For western blot band intensity, and total fecal protein levels, we analyzed the distributions of these measurements and investigated the sensitivity and specificity of these measurements when utilized as prognostic and diagnostic biomarkers. Sensitivity is equivalent to the true positive rate for a classifier, while specificity is 1—FPR (the false positive rate) for a classifier. For each of our three variables of interest, we first investigated the specificity and sensitivity obtained using a simple threshold based classifier. For each of these classifiers, we computed standard error for our sensitivity and specificity estimations by performing five rounds of jackknife resampling in which 20% of the data was excluded from the estimation of sensitivity and specificity for each round of resampling. Our data was stratified by class label during this resampling process, so that for each round of resampling 6-7 control samples and 3-4 NEC samples (20% of each class total) were excluded from the analysis.

After investigating single variable classifiers, we explored the utility of multi-variable classifiers by training Naïve Bayes Classifiers (NBC) using the scikit-learn package in Python (20). A Naïve Bayes Classifier assumes that each feature used in classification is statistically independent (21). This naïve assumption is untrue for our three features (iAP activity level, total protein, and WB intensity). However, prior work in the machine learning community has shown that NBCs can perform well on multi-feature classification problems even when the assumption of statistically independent features does not hold (21). To avoid overfitting of the multi-feature classifier, we used a 5-fold stratified cross-validation scheme where, for each fold, the NBC was trained on 80% of the data, and then the resulting classifier was tested on the remaining 20% of the data in order to estimate sensitivity and specificity.

Results

Figure 7:
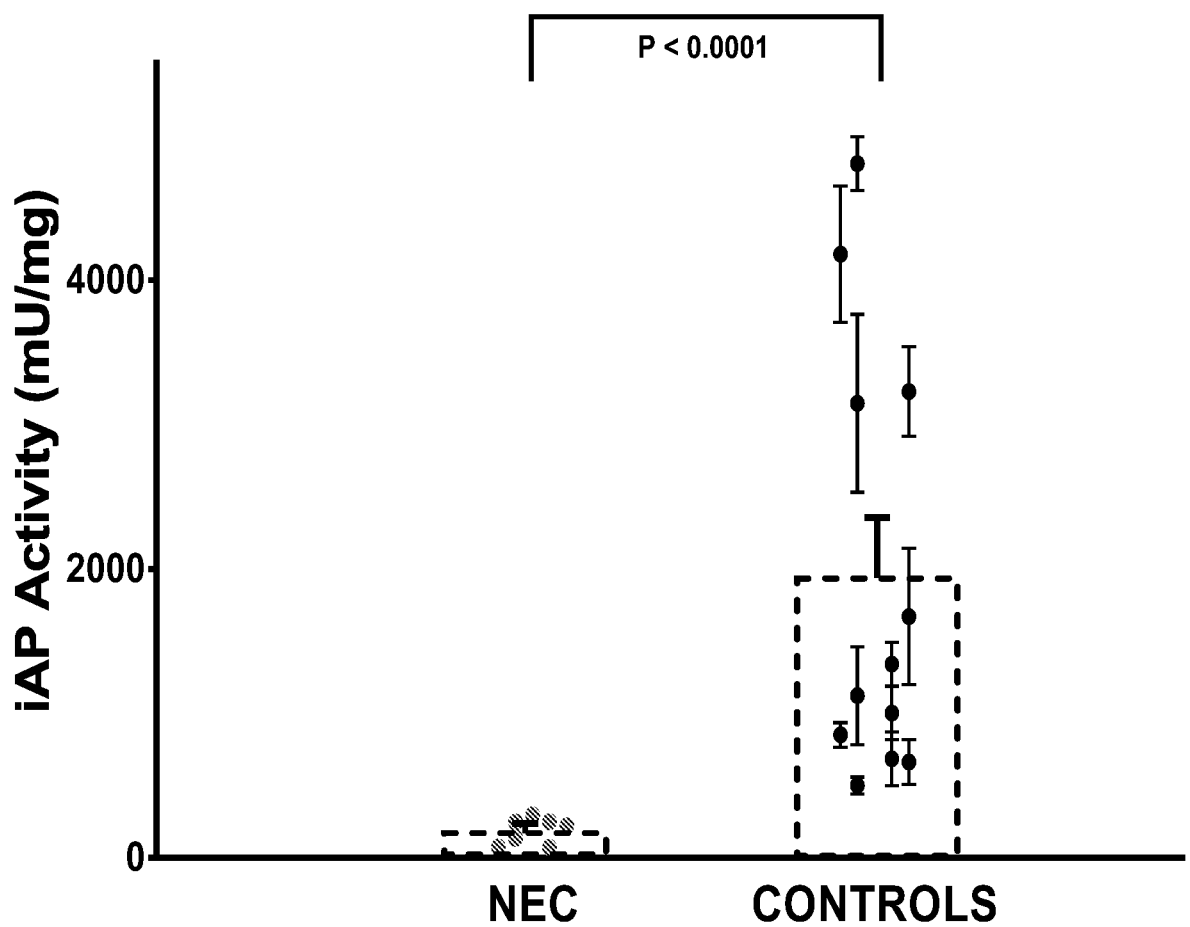
FIG. 7 shows iAP activity was lower in stool samples from patients at time of NEC diagnosis compared to control samples. The red circles represent iAP activity during 7 distinct NEC events of 6 patients (post conceptual age: 29-43 weeks). Each black circle represents a composite average +/− SEM of 2-8 stool samples from each of 12 controls (post-conceptual ages 29-45 weeks). Statistical significance analysis: Mann-Whitney Test, P<0.0001.
Figure 8:
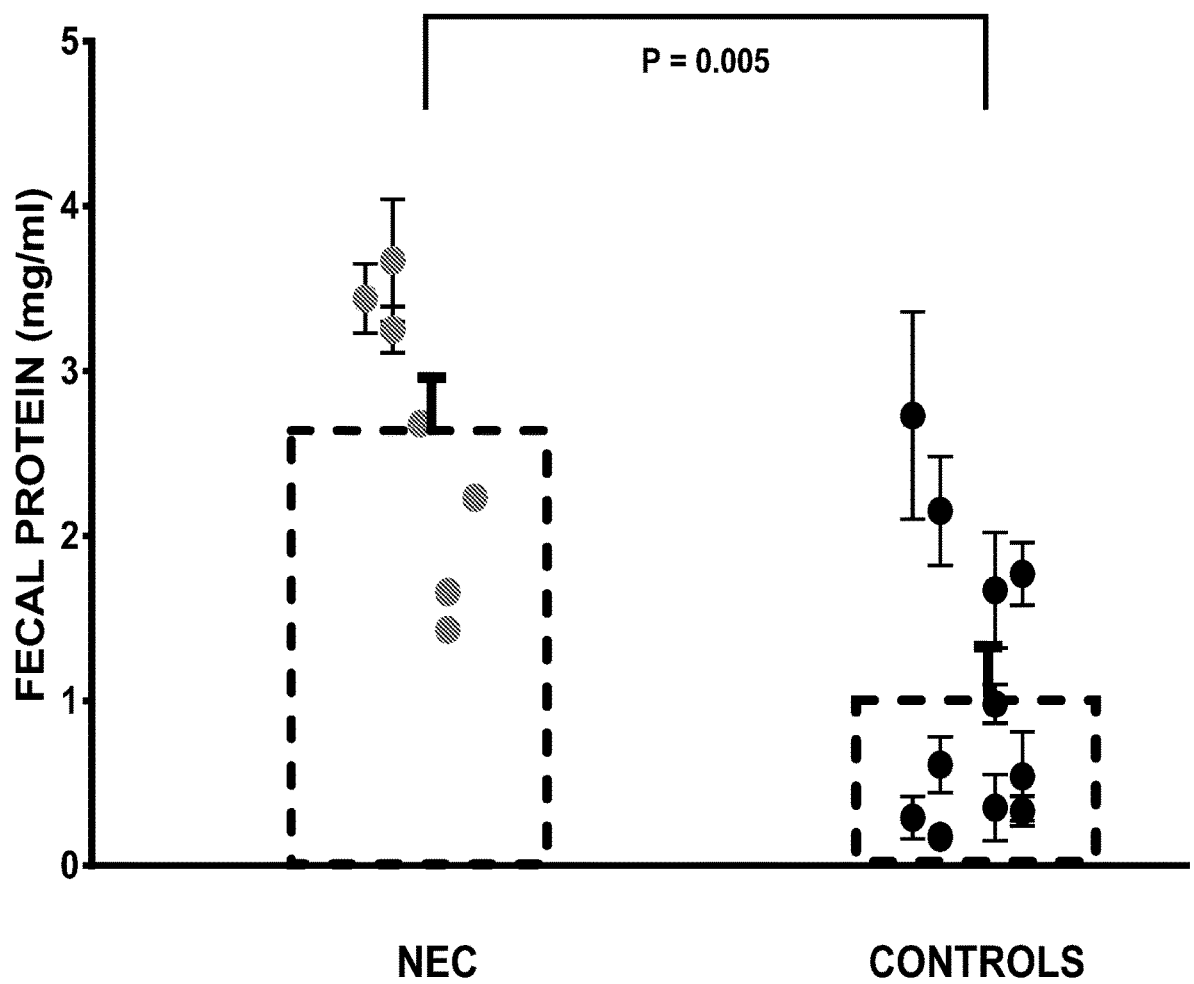
FIG. 8 shows total fecal protein was higher in stool samples from patients at the time of NEC diagnosis compared to control samples. The red circles represent total fecal protein levels during 7 distinct NEC events of 6 patients (post conceptual age: 29-43 weeks). Each black circle represents a composite average =/− SEM of 2-16 stool samples from 12 controls (post conceptual ages: 29-45 weeks). Statistical analysis: Mann-Whitney Test, P=0.005
Figure 9:
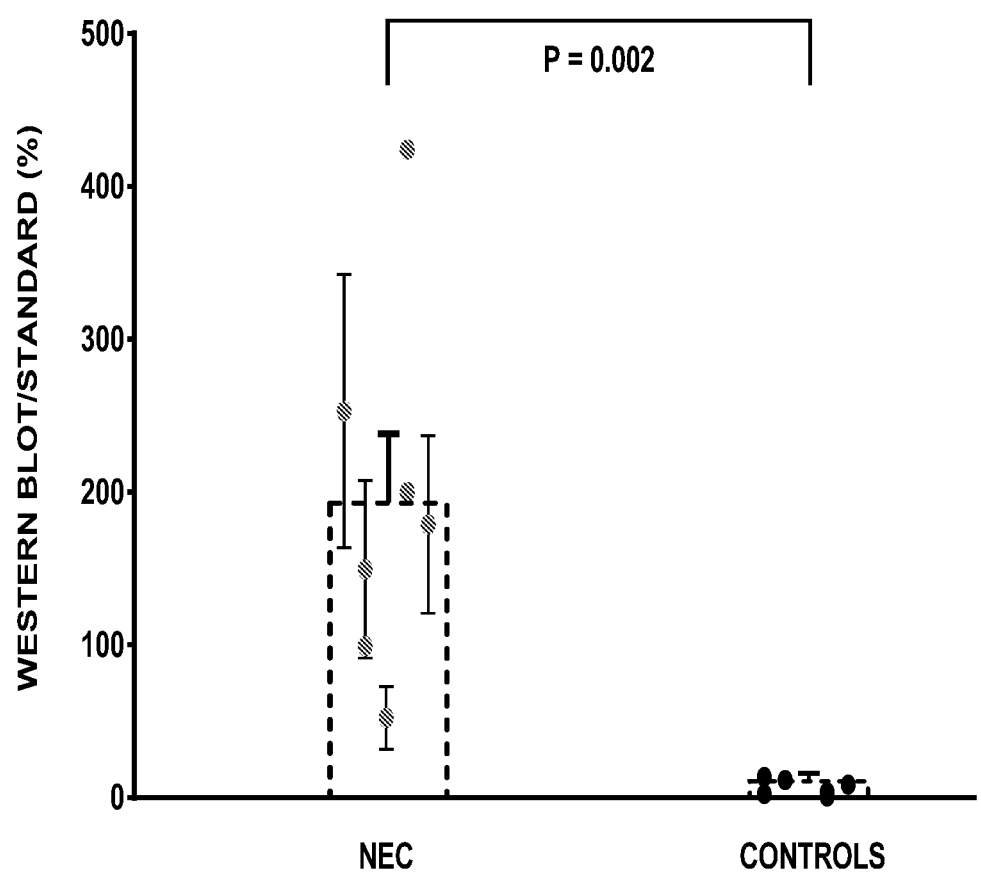
FIG. 9 shows the intensity of iAP protein signal quantified as a percentage of positive control signal was much higher in stool samples from patients at the time of NEC diagnosis compared to control samples. The red circles represent the intensity of iAP protein signal during 7 distinct NEC events of 6 patients (post conceptual age: 29-43) Each black circle represents at least 1 stool sample from 7 controls (post conceptual age 29-35 weeks). Statistical analysis: Mann-Whitney Test, P=0.002

Compared with multiple samples from the controls roughly matched for the gestational and chronological age, stools from NEC patients at the time of diagnosis had decreased iAP activity (FIG. 7), increased total fecal protein (FIG. 8) and increased detection of iAP protein (FIG. 9). Fecal iAP activity was low at the time of diagnosis of NEC compared to averaged controls. When the Mann-Whitney test was applied there was statistical significance between the groups. The mean values for fecal iAP activity was 184 mU/mg with a standard error of measurement (SEM) of 34 vs 1932 mU/mg in the control group with SEM of 433 (P<0.0001). This is illustrated in FIG. 2.

Figure 3:
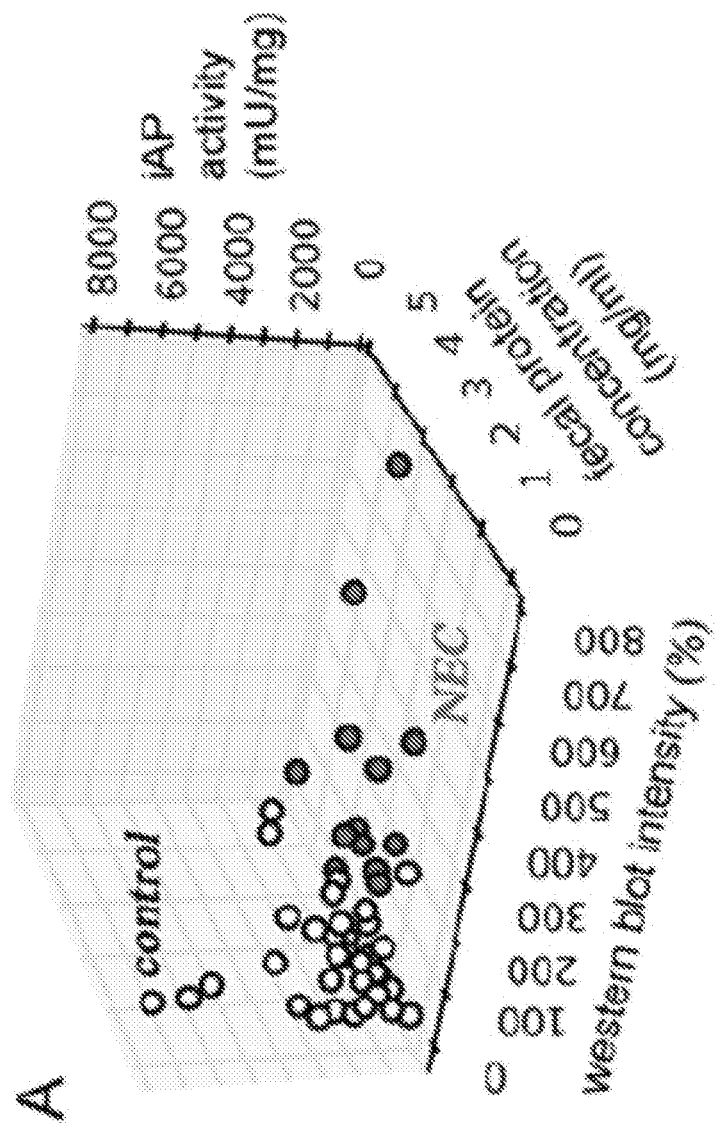
FIG. 3 shows fecal iAP-related measurements have high specificity and sensitivity. (A) 3-dimensional scatterplot of measurements for our biomarker candidates, where red diamonds represent NEC samples and black circles represent controls. (B) A 2-dimensional projection of the 3-dimensional scatterplot that relates exclusively to iAP activity and western blot intensity measurements. (C) Sensitivity and specificity curves for each biomarker candidate individually, as well as for a combined Naïve Bayes Classifier that considers all 3 features simultaneously. Analysis covers 49 samples with 13 NEC samples, 9 NEC patient-derived control samples, and 27 control patient-derived control samples. The Spearman correlation coefficient was 0.19 for comparison of western blot intensity and total protein content, −0.48 for total protein content and iAP activity, and −0.58 for iAP activity and western blot intensity.
Figure 3:
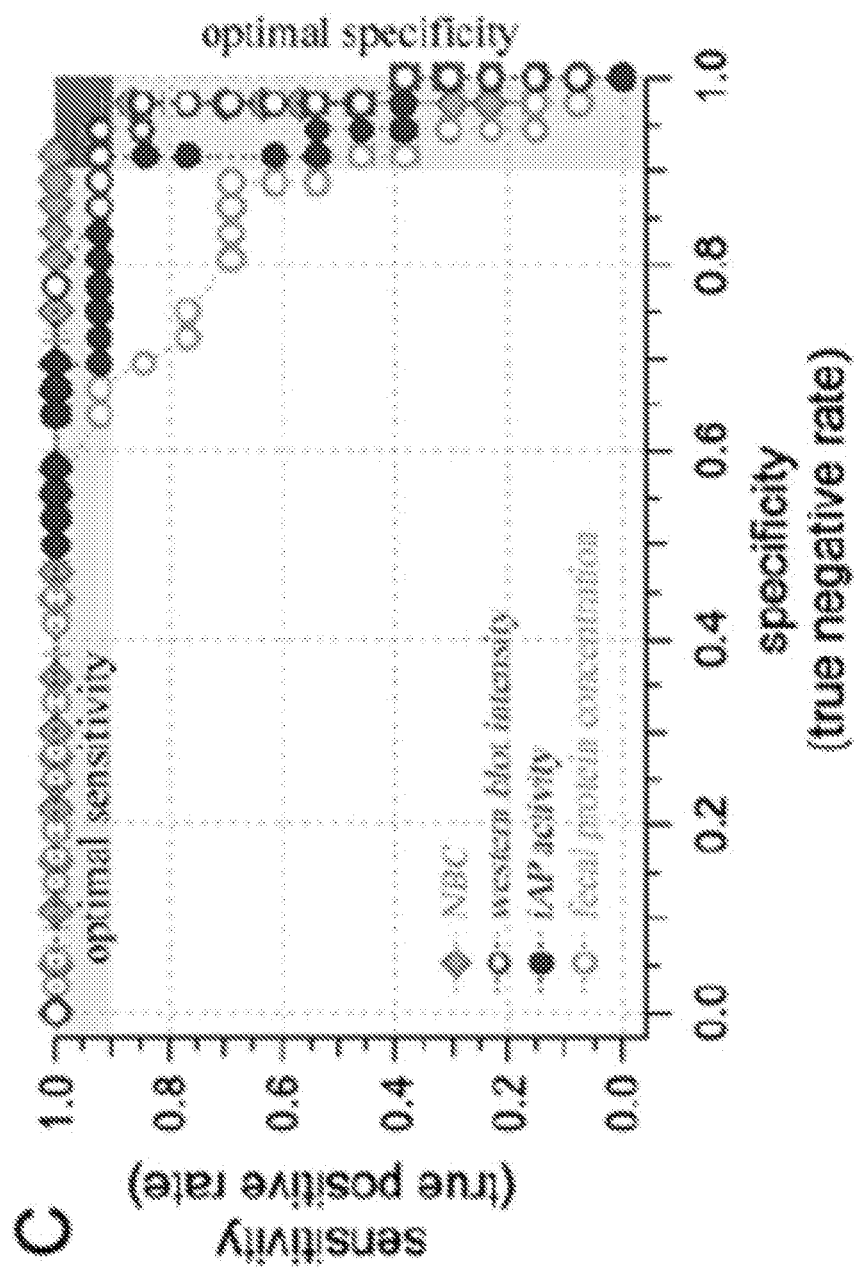

We found that NEC patients had significantly higher amounts of fecal protein at the time of diagnosis compared to matched controls for post conceptual age. We averaged protein amount from individual non-NEC patients between 29-43 PCA and compared this to the patient stool samples at the time of diagnosis of NEC totaling 7 events from 6 patients (FIG. 3). Nonparametric tests (Mann-Whitney) were used to compare the non-normally distributed data and there was a statistically significant difference (P=0.005) between the groups. Mean at time of diagnosis was 2.62 with SEM of 0.33 in NEC patient samples compared to a mean of 0.98 with SEM of 0.25 in averaged controls.

WB quantification by percentage of positive control was performed using 7 NEC events in 6 patients and 7 control patients. Mean WB percent in the NEC patient samples was 193% vs 6% in controls (P=0.0022). The standard error of measurement was 45 in NEC vs 1.9 in controls. (FIG. 4).

Figure 10:
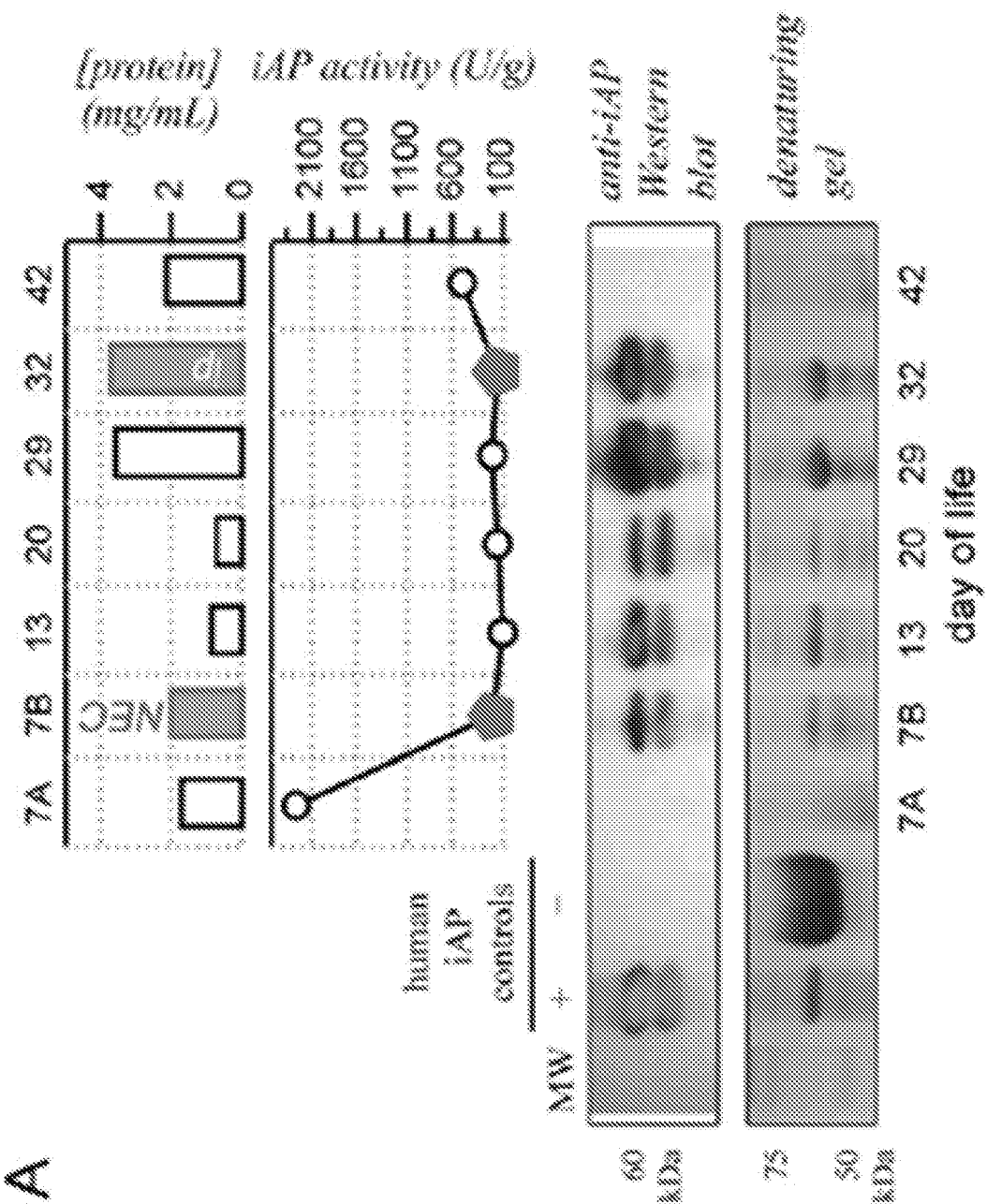
FIG. 10 shows there are decreased fecal iAP enzymatic activity, increased total fecal protein and increased iAP detection on WB at the time of NEC diagnosis. (A) Illustrates longitudinal measurements of iAP activity, total fecal protein and iAP enzymatic activity in a NEC patient who subsequently developed perforation. The red points and columns represent NEC episodes. There is a precipitous decrease in fecal iAP activity corresponding to time of diagnosis demonstrating fecal iAP activity as a diagnostic tool for NEC. There is emergence of intense iAP protein detection on western blot. The patient completes 14 days of treatment, but had an intestinal perforation (ip) on day of life 31. After 10 additional days of bowel rest there was no longer strong detection of iAP by the anti-iAP antibody and a trend towards higher iAP activity. (B) There is a similarly observed decreased fecal iAP activity and increased iAP amounts at the time of NEC diagnosis in a second patient. The green point represents an episode of bloody stool and corresponds to suspected NEC with bowel distension (bd). There was emergence of iAP detection during NEC surveillance that was no longer evident until NEC diagnosis on day of life 32. Again noted was a drop in activity surrounding the diagnosis of NEC (red dot and column) and trend towards higher activity and decreased iAP detection on WB after recovery. (C) NEC was associated with low fecal iAP activity, high fecal protein and high fecal iAP amounts (on WB). Three samples from 3 NEC patients (labeled N, red columns) at the time of NEC diagnosis were are matched with 3 samples from 3 control subjects (labeled C, white columns) with similar gestational and chronological age. The difference in group 3 is less striking and can have represented subclinical disease in a premature infant with feeding intolerance (D) This figure represents sequential stool sampling pre-diagnosis (labeled pre, white column) and at the time of diagnosis (labeled d, red column) in 4 NEC patients with corresponding iAP enzymatic activity, total fecal protein and iAP detection on western blot.

The antibody we chose for western blot analysis did not easily detect iAP in stool except in the cases of NEC. Longitudinal observations of 2 patients with NEC are shown in FIGS. 10A and 10B. Panel A highlights a premature infant with prolonged course of NEC followed by perforation. It shows a precipitous drop in iAP activity and appearance of iAP protein on WB at the time of initial NEC diagnosis, a persistently low iAP activity and evidence of iAP protein on WB during initial therapy until subsequent perforation. After Penrose drain placement and ten days of bowel rest, there was no longer evidence of high iAP protein on the WB, but there was an increase in fecal iAP activity. Panel B highlights a different infant with multiple NEC surveillance events (one event is represented by the green point) prior to NEC. The suspected NEC episode was associated with evidence of iAP protein on WB, but normal iAP activity. This resolved before the precipitous drop in the iAP activity and emergence of high iAP protein on WB at the time of NEC. After medical management and recovery from NEC, iAP activity increased and there was no longer iAP protein demonstrable on WB. FIG. 10 Panel C shows 3 groups of samples, each consisting of stool from a NEC patient at the time of diagnosis compared with that from a closely matched control. Groups 1 and 2 clearly show increased total fecal protein, decreased iAP activity, and evidence of iAP protein on WB. In group 3, there was no significant difference in iAP activity and total fecal protein, but the western blot clearly differentiates between the NEC and control samples. FIG. 5 Panel D shows stools taken prior to and at the time of diagnosis from 4 different NEC patients. Using each patient as his or her own control, the diagnosis of NEC was associated with decreased iAP activity, increased total fecal protein and the demonstration of iAP protein on WB.

Figure 11:
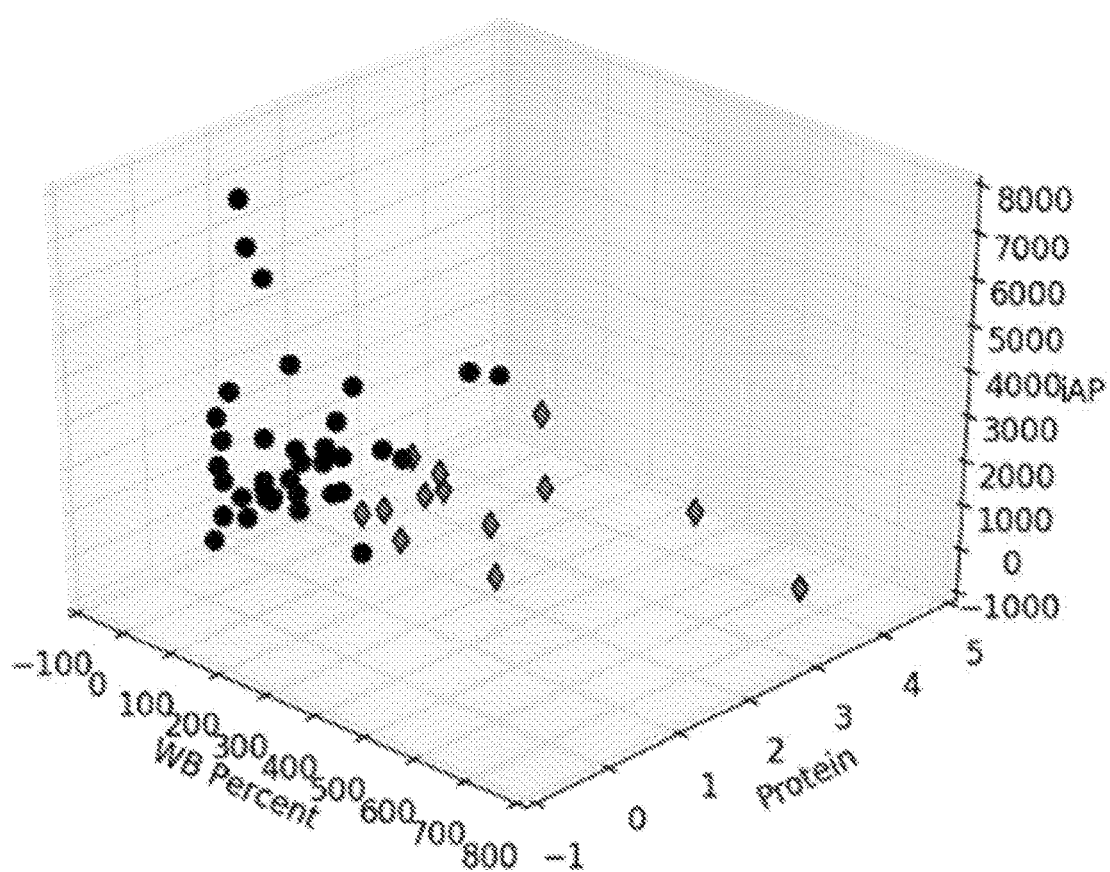
FIG. 11 shows that combining all 3 biomarkers has possible clinical utility and improvement in sensitivity and specificity. Figure Represents data points from 6 NEC patients and 7 controls with a total of 51 samples included. (A) illustrates a 3D scatterplot graph comparing WB data, fecal iAP activity and fecal protein The red diamonds represent averaged total fecal protein, iAP activity and WB percentage of fecal samples from NEC patients at the time of diagnosis. The black circles represent averaged total fecal protein, iAP activity and WB percentage of control points (inclusive of NEC patients in disease-free period) (B) Represents a 2D scatterplot graph that shows the relationship between fecal iAP activity and WB percentage. There is clustering of control samples (black circles) in lower WB percentage and tendency towards high activity. The opposite is demonstrated with NEC samples whereby there is higher WB percentage and low activity. (C) Schematic illustrating Naïve Bayes Classifier used to demonstrate sensitivity and specificity of all three biomarkers individually and in combination to improve performance.

FIG. 11 Panel A is a 3D scatterplot illustrating NEC samples and controls with fecal iAP activity, fecal protein and WB data points. NEC samples are labeled in red. Panel B depicts a 2D scatterplot showing iAP activity and WB percentage. There is high activity and low WB percentage in controls. Combining all 3 biochemical assays increased sensitivity and specificity observed despite low sample amounts and patient numbers. FIG. 6 panel C demonstrates the utility of examining multiple features simultaneously by depicting the trade-off between sensitivity and specificity for multiple threshold values and multiple feature selections. Western blot intensity considered alone performs best with 100% sensitivity at 70% specificity for a detection threshold of 10% positive control band intensity. However, if 100% sensitivity is not required and the goal is to simultaneously maximize both sensitivity and specificity, then the 3 feature Naïve Bayes Classifier performs best by reaching a sensitivity of 95% and a specificity of 93%. The iAP activity level considered alone performs almost as well in this case by achieving a sensitivity level of 95% and a specificity of 91% when using a threshold of 300 mU/mg iAP activity. When western blot intensity level is considered alone at 95% sensitivity, the specificity level is 88% using a 30% positive control band intensity threshold. However, perhaps unsurprisingly, total fecal protein level alone is not specific for NEC. In order for total fecal protein level to achieve 95% sensitivity, the specificity must drop to 44% using an interpolated threshold of 1.02 mg/mL. Consequently, fecal iAP activity level and 60 kDa western blot intensity levels hold promise individually as NEC biomarker candidates.

Figure 12:
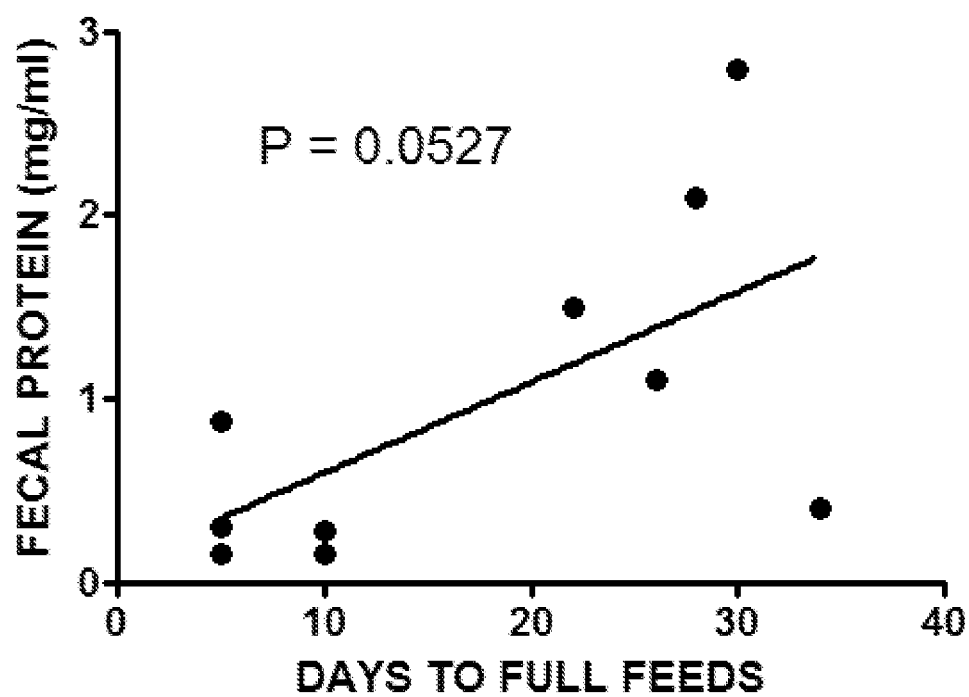
FIG. 12 shows there was an identifiable trend towards lower fecal protein (Panel A) and higher fecal iAP enzymatic activity (Panel B) in those infants who tolerated feeds well and advanced rapidly to full feeds without issue. Graph represents average total fecal protein and fecal iAP activity in stool from 10 control patients during the first month of life related to the duration of time until achievement of full enteral feeds.

There was a noted trend towards higher fecal protein in controls with feeding intolerance, as defined by the number of days needed to reach target enteral feeding volume (FIG. 12). The opposite trend is seen in iAP activity although the association is much less striking.

Heterogeneity of stool could interfere with the reliability of the test. In one particular inhomogeneous stool, the mucous-containing portion (FIG. 13A) resembled other NEC samples, whereas the more solid portion of the stool (FIG. 13B) was similar to control in terms of iAP protein on WB and iAP activity.

Discussion

In our study, we observed alterations in total fecal protein, iAP protein by WB and iAP activity in stools from NEC patients at the time of diagnosis. The high protein levels in stool of NEC patients at the time of diagnosis can reflect loss of mucosal integrity in an already immature intestine as well as inflammatory products associated with the disease. Shulman et al. demonstrated a similar trend with significantly increased alpha 1 antitrypsin in stool at the time of NEC diagnosis compared to controls (22).

Intestinal alkaline phosphatase is expressed primarily in the apical enterocytes of the small intestine, making it an ideal, relatively specific candidate biomarker for localizing gastrointestinal disorders such as NEC. It adheres closely to the membrane but is also shed into the lumen (4). iAP was recently demonstrated by Shifrin et al. to be distributed into the mucus layer and gut lumen via microvillar vesicle shedding (23). During inflammatory insult and bowel necrosis, disruption of the mucosal barrier and cell death, as well as shedding of the mucosal lining, would lead to an increased release of mucosal proteins such as iAP into the feces. The rarity of iAP signal on western blot, but high iAP activity in the stools of control subjects is still not well understood. Perhaps the normal shedding process changes free luminal iAP structure in a way that does not allow for recognition by our particular antibody. The immunogen for the antibody is full length native human iAP from small intestinal tissue and it can be more sensitive to the membrane bound full length protein. Alternatively, there are 2 known isoenzymes of iAP, the fetal and adult forms that undergo developmental changes (24,25). It can be that NEC inflammation is associated with production of an isoenzyme recognized by our antibody, whereas iAP produced under normal conditions is another isoenzyme that is not recognized. In any case, the difference in WB findings is highly suggestive of a conformational difference in fecal IAP between the healthy and diseased state.

The sudden decrease in overall fecal iAP activity that we found in fecal samples from NEC patients at the time of NEC diagnosis was similarly found in rat pups with induced NEC (13,26). Whitehouse et al. demonstrated via intestinal histology and tissue sampling of terminal ileum a decrease in tissue iAP protein and activity (26). The cellular loss, and presumed shedding into the intestinal lumen, that is used to explain decreased iAP protein and activity, at the tissue level, can also help explain increased iAP protein and decreased activity in the stool of patients with NEC. It is interesting to note that adult patients with inflammatory bowel disease were found to exhibit lower AP activity in biopsied intestinal tissue (27).

The mechanism for low iAP activity at the time of NEC does not appear to be due to an initial deficiency since we observed a rapid decline in activity from normal levels in some NEC patients. The loss of iAP enzymatic activity can reflect damage to the enzyme's catalytic site. In an animal model, Sisley et al. demonstrated decreased mucosal AP activity following ischemia reperfusion and suggested that the metal binding sites can be more susceptible to oxidative damage (28).

The drop in fecal iAP activity with a corresponding sudden appearance of fecal iAP protein on WB sometimes happens just hours prior to diagnosis. This observation indicates that the use of activity assays and western blot for iAP detection can offer diagnostic value with an initial event. An additional biomarker of this sort can offer little benefit in cases where NEC can be identified readily by traditional means (bloody stools, *pneumatosis intestinalis* etc.). However, use of fecal iAP would be most beneficial in establishing the diagnosis in those with subclinical disease or in those who lack clear radiographic evidence. Although thought to be pathognomonic for NEC, Ballance et al. showed that *pneumatosis intestinalis* was actually present in only 48% of pathologically confirmed in the NEC patient population (29). Fecal iAP could be also used during recovery from NEC to gauge the integrity of the bowel and guide feeding strategies in our most vulnerable patient population and to determine the length of time needed for recovery.

Without being bound by theory, the needs of some children can vary from 7-14 days of treatment that is considered standard management.

These biomarkers can even be useful in patients without NEC. We observed a tendency for control infants with feeding intolerance and delayed achievement of full enteral feeding to have higher total fecal protein and lower iAP activity. Control infants who tolerated feeds well exhibited low total fecal protein and very high iAP activity. We have no information yet concerning the presence or absence of iAP protein by WB as it relates to feeding intolerance. If this is confirmed by larger studies, it would provide more incentive to explore the potential benefit of iAP supplementation in these cases. More studies are needed to establish normal values for each parameter at all gestational and chronological ages, and to determine dietary and other factors that can influence them.

No method is without limitations. A potential confounding factor of fecal iAP testing is the heterogeneous nature of stool. We had one stool sample collected at the time of NEC diagnosis that had two distinct consistencies namely mucous and normal appearing stool. We separated the parts and the normal appearing stool had results similar to controls, whereas the mucous-containing portion had the expected low iAP activity and high iAP signal on western blot (FIG. 13). We did not include these data points in our analysis due the wide discrepancy of stool preparation. This was the only sample with this problem and the frequency of this occurrence is unknown. Another challenge we faced was the infrequent and sporadic stooling patterns associated with prematurity that did not allow for exact standardized collection times among subjects. In the clinical realm, depending solely on stool samples might lead to delayed diagnosis due to poor stooling. No biomarker will substitute for a good physical exam and clinical expertise. Probably the best use of fecal iAP as a biomarker would be as an adjunct in establishing the diagnosis of NEC, monitoring disease progression and in surveillance or monitoring of high risk groups.

In our examination of 3 potential NEC biomarkers related to intestinal alkaline phosphatase, we have demonstrated that stool sample analysis has potential clinical utility for improving diagnosis of necrotizing enterocolitis. We have shown that specific iAP activity levels and western blot band intensity can both be used to identify NEC patient fecal samples with high sensitivity and specificity when considered independently. We have also shown that multiple features can be combined using a Naïve Bayes Classifier in order to simultaneously achieve better levels of sensitivity and specificity. Moreover, in future work, our Naïve Bayes Classifier methodology can be extended to simultaneously analyze iAP activity, western blot band intensity, and multiple other candidate NEC biomarkers which were beyond the scope of this current study.

Conclusion

Fecal iAP protein on WB, and total fecal protein are increased, but fecal iAP activity is decreased in patients with NEC at the time of diagnosis. Measurements of iAP protein by WB, iAP activity and fecal protein amounts are useful biomarkers individually, but sensitivity and specificity of diagnosis can be improved by combining the 3 parameters. More studies are needed to determine sensitivity and specificity of each assay individually and in combination.

REFERENCES CITED IN THIS EXAMPLE

1 Neu, J. & Walker, W. A. Necrotizing enterocolitis. N Engl J Med 364, 255-264, doi:10.1056/NEJMra1005408 (2011).
2 Patel, R. M. et al. Causes and timing of death in extremely premature infants from 2000 through 2011. N Engl J Med 372, 331-340, doi:10.1056/NEJMoa1403489 (2015).
3 Ng, P. C., Chan, K. Y. & Poon, T. C. Biomarkers for prediction and diagnosis of necrotizing enterocolitis. Clin Perinatol 40, 149-159, doi:10.1016/j.clp.2012.12.005 (2013).
4 Goldberg, R. F. et al. Intestinal alkaline phosphatase is a gut mucosal defense factor maintained by enteral nutrition. Proc Natl Acad Sci USA 105, 3551-3556, doi: 10.1073/pnas.0712140105 (2008).
5 Horrigan, F. D. & Danovitch, S. H. The origin of human fecal alkaline phosphatase. Am J Dig Dis 19, 603-608 (1974).
6 Malo, M. S. A High Level of Intestinal Alkaline Phosphatase Is Protective Against Type 2 Diabetes Mellitus Irrespective of Obesity. EBioMedicine 2, 2016-2023, doi:10.1016/j.ebiom.2015.11.027 (2015).
7 Fawley, J. & Gourlay, D. M. Intestinal alkaline phosphatase: a summary of its role in clinical disease. J Surg Res 202, 225-234, doi:10.1016/j.jss.2015.12.008 (2016).
8 Malo, M. S. et al. Intestinal alkaline phosphatase promotes gut bacterial growth by reducing the concentration of luminal nucleotide triphosphates. Am J Physiol Gastrointest Liver Physiol 306, G826-838, doi:10.1152/ajpgi.00357.2013 (2014).
9 Biesterveld, B. E. et al. Intestinal alkaline phosphatase to treat necrotizing enterocolitis. J Surg Res 196, 235-240, doi:10.1016/j.jss.2015.02.030 (2015).
10 Lehmann, F. G., Hufnagel, H. & Lorenz-Meyer, H. Fecal intestinal alkaline phosphatase: a parameter for toxic damage of the small intestinal mucosa. Digestion 21, 156-162 (1981).
11 Thomas, D. W. & Henton, D. H. The use of fecal alkaline phosphatase as an indicator of intestinal damage. Digestion 31, 82-88 (1985).
12 Riggle, K. M. et al. Intestinal alkaline phosphatase prevents the systemic inflammatory response associated with necrotizing enterocolitis. J Surg Res 180, 21-26, doi:10.1016/j.jss.2012.10.042 (2013).
13 Rentea, R. M. et al. Intestinal alkaline phosphatase administration in newborns is protective of gut barrier function in a neonatal necrotizing enterocolitis rat model. J Pediatr Surg 47, 1135-1142, doi:10.1016/j.jpedsurg.2012.03.018 (2012).
14 Heinzerling, N. P. et al. Intestinal alkaline phosphatase is protective to the preterm rat pup intestine. J Pediatr Surg 49, 954-960; discussion 960, doi:10.1016/j.jpedsurg.2014.01.031 (2014).
15 Kampanatkosol, R. et al. The relationship between reticulated platelets, intestinal alkaline phosphatase, and necrotizing enterocolitis. J Pediatr Surg 49, 273-276, doi: 10.1016/j.jpedsurg.2013.11.037 (2014).
16 Malo, M. S. et al. Intestinal alkaline phosphatase preserves the normal homeostasis of gut microbiota. Gut 59, 1476-1484, doi:10.1136/gut.2010.211706 (2010).
17 Porstmann, B., Porstmann, T., Nugel, E. & Evers, U. Which of the commonly used marker enzymes gives the best results in colorimetric and fluorimetric enzyme immunoassays: horseradish peroxidase, alkaline phosphatase or beta-galactosidase? J Immunol Methods 79, 27-37 (1985).
18 McLachlan, R., Coakley, J., Murton, L. & Campbell, N. Plasma intestinal alkaline phosphatase isoenzymes in neonates with bowel necrosis. J Clin Pathol 46, 654-659 (1993).

19 Uauy, R. D. et al. Necrotizing enterocolitis in very low birth weight infants: biodemographic and clinical correlates. National Institute of Child Health and Human Development Neonatal Research Network. J Pediatr 119, 630-638 (1991).
20 Pedregosa, F. V. G., Gramfort A, et al. Scikit-learn: Machine learning in {P}ython. J Mach Learn Res 12, 2825-2830 (2011).
21 Rish, I. An empirical study of the Naive Bayes Classifier IJCAI 2001 Work Empir Methods Artif Intell 22230, 41-46 (2001).
22 Shulman, R. J., Buffone, G. & Wise, L. Enteric protein loss in necrotizing enterocolitis as measured by fecal alpha 1-antitrypsin excretion. J Pediatr 107, 287-289 (1985).
23 Shifrin, D. A., Jr. et al. Enterocyte microvillus-derived vesicles detoxify bacterial products and regulate epithelial-microbial interactions. Curr Biol 22, 627-631, doi: 10.1016/j.cub.2012.02.022 (2012).
24 Mulivor, R. A., Hannig, V. L. & Harris, H. Developmental change in human intestinal alkaline phosphatase. Proc Natl Acad Sci USA 75, 3909-3912 (1978).
25 Vockley, J., Meyer, L. J. & Harris, H. Differentiation of human adult and fetal intestinal alkaline phosphatases with monoclonal antibodies. Am J Hum Genet 36, 987-1000 (1984).
26 Whitehouse, J. S. et al. The protective role of intestinal alkaline phosphatase in necrotizing enterocolitis. J Surg Res 163, 79-85, doi:10.1016/j.jss.2010.04.048 (2010).
27 Tuin, A. et al. Role of alkaline phosphatase in colitis in man and rats. Gut 58, 379-387, doi:10.1136/gut.2007.128868 (2009).
28 Sisley, A. C., Desai, T. R., Hynes, K. L., Gewertz, B. L. & Dudeja, P. K. Decrease in mucosal alkaline phosphatase: a potential marker of intestinal reperfusion injury. J Lab Clin Med 133, 335-341 (1999).
29 Ballance, W. A., Dahms, B. B., Shenker, N. & Kliegman, R. M. Pathology of neonatal necrotizing enterocolitis: a ten-year experience. J Pediatr 117, S6-13 (1990).

Example 4

Summary:

Results from three different biochemical tests, performed on preterm infant stool, were grouped by post-conceptual age, which permits comparison of gut development of preterm infants through term infants. Measurement of relative iAP content in stool is a biomarker for bowel infection. Measurement of iAP activity is a biomarker for maturation of intestine in preterm infants. Measurement of fecal protein concentration is correlated with an intestinal inflammation response or diseased state.

Overview and Results:

Necrotizing enterocolitis (NEC) is a multi-factorial disease that predominately affects premature infants and is the leading cause of late mortality and morbidity in very preterm infants (Caplan, 2008; Christensen et al, 2010). Although the etiology of NEC Is not clearly defined (Dominguez and Moss, 2012; Gephart et al., 2012), NEC is believed to represent a severe inflammatory disorder in the intestine (Balance et al., 1990; Zhang et al., 2011). Excessive inflammatory responses to environmental insults in the immature intestine are a hallmark of NEC (Chan et al., 2009). Specifically, increased levels of LPS/TLR4 signaling have been suggested to contribute to the pathogenesis of NEC (Chan et al., 2009; Fusunyan et al., 2001; Leaphart et al, 2007; Nanthakumar et al., 2011). Inhibition of LPS/TLR4 signaling attenuates intestinal inflammation and mitigates NEC pathology in animal models (Chan et al., 2009; Gribar et al., 2009).

Intestinal alkaline phosphatase (iAP) is a critical component of innate intestinal immunity. The enzyme, typically anchored to the intestinal brush border, cleaves phosphate groups, and as such can dephosphorylate lipopolysaccharides (LPS). LPS dephosphorylation inhibits a potent signaling pathway; thus, proinflammatory cytokines release and immune responses by LPS-activation of TLR4 (toll-like receptor 4; Lalles, 2010) are blocked by iAP. In addition, iAP is concentrated in specialized membrane vesicles, which are released from distal tips of enterocyte microvilli into the intestinal lumen (McConnell et al., 2009; Shilfrin et al., 2012). These released vesicles interact with and limit the pro-inflammatory potential of both bacteria and bacterial products.

Thus, we would expect that iAP would be measureable in human stool samples; this is confirmed from iAP being one of the core proteins in the human stool proteome. A steady state baseline of iAP would be detected from intestinal epithelial cells shed in the lumen and detected in stool. iAP content in stool would increase from released membrane vesicles loaded with iAP, if there was risk of bacteria-induced inflammation. Samples from non-NEC infants that were grouped by post-conceptual age (grey bars, FIG. 14A) showed the premature infants have low amounts of iAP, relative to a positive control from human small intestine tissue lysate. Our data also show that infants who have NEC have a high relative content of iAP (120-320% of positive control) in their stool samples at the time of clinical diagnosis.

Second, a dynamic transition of iAP isozyme forms is associated with the maturation of fetal intestine (Mulivor et al., 1978; Suriura et al., 1981). The fetal isoform of intestinal AP has a low biochemical activity, whereas the adult iAP has a high biochemical activity. We hypothesized that iAP activity would change with fetal development, i.e. preterm infants would have lower iAP activity than full-term infants. We reasoned that the limited iAP biochemical activity in neonates could lead to overactive LPS/TLR4 signaling. We tested this hypothesis by comparing stool iAP activities from infants of different gestational ages. Stool thus provides an accurate measurement of iAP activity in the neonatal intestine.

Figure 14:
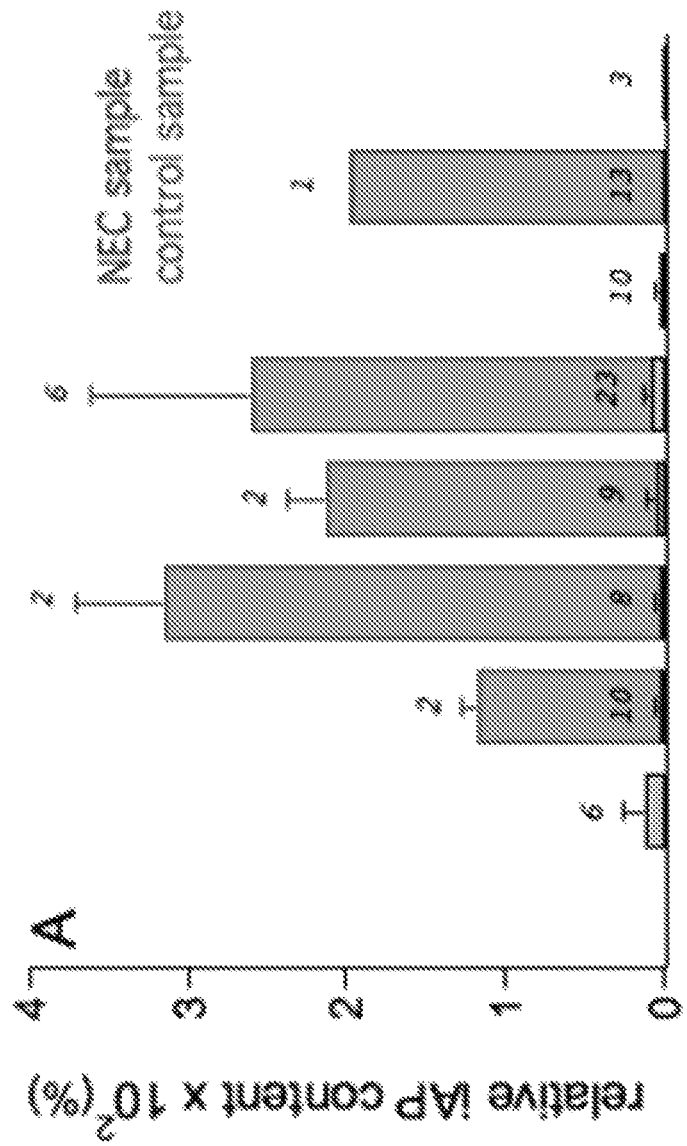
FIG. 14 shows relative iAP content, iAP activity, and protein concentration. NEC was classified according to the criteria of Bell et al. and modified by Walsh and Kliegman.

Our data indicate the premature infants have reduced iAP activity as compared to full-term infants. FIG. 14B shows average iAP activities, normalized to protein concentrations, of stool samples that are grouped by post-conceptual age (grey bars). There is a strong positive correlation between iAP activity and post-conceptual age. When comparing iAP activities spanning 24-41 weeks post-conceptual age, a one-way ANOVA and Tukey's multiple comparison test was performed and showed that the samples were statistically separated into two groups: the preterm group (post-conceptual age ≤35 weeks) and the full-term group (post-conceptual age ≥36 weeks). Comparison of all stool samples from full-term infants (post-conceptual age ≥36 weeks, n=28) with all samples from premature infants (post-conceptual age ≤35 weeks, n=79) revealed the latter group to have significantly lower iAP activities (p<0.0001; one-tailed t-test).

In comparison, infant stool collected on the same day of clinical NEC diagnosis (red bars) had much lower iAP activity, when compared to age-matched controls. Therefore, extremely low activity of iAP is correlated with NEC. Stool samples that have iAP activity below 240 U/mg can be used as a biomarker to identify infants at greatest risk for NEC. The sensitivity of this univariate biomarker is 100% with a 95% CI of 66-100%. The specificity is 100% with a 95% CI of 97-100%. For this sample set the disease prevalence is 7.8%, the positive predictive value is 100%, and the negative predictive value is 100%.

Without wishing to be bound by theory, the reduced capacity of preterm infant intestines to dephosphorylate proinflammatory LPS can increase the risk of excessive inflammatory responses to bacterial colonization and NEC development. Furthermore, based on these findings and without wishing to be bound by theory, prophylactic iAP supplementation to premature infants can warrant further study as a strategy for decreasing the risk of NEC. Our data also show that infants who have NEC have a high relative content of iAP and of protein in their stool samples at the time of clinical diagnosis.

Example 5

Feeding tolerance is demonstrated when the preterm infant is capable of safely ingesting and digesting the prescribed enteral (via mouth) feeding without complications associated with gastrointestinal dysfunction or infection. Clinical evidence of feeding tolerance in very low birth weight preterm infant is most often described in the literature as the number of days required to reach full-feeding volumes (reported ranged from 100-160 mL per kg per day), the number of episodes of feeding intolerance, the number of days feeds are withheld due to feeding intolerance symptoms, time to regain birth weight, lower leg growth, increase in weight gain, occipital-frontal head circumference, and length. None of the infants studied had reached full-feeding volumes.

Types of formula include, but are not limited to: EleCare (Abbott Nutrition), Neosure (Similac), EnfaCare (Enfamil), Pregestimil (Enfamil), Similac Special Care or SSC (Similac), and Gentlease (Enfamil).

Supplements can include without limitation Microlipid (Nestle Health Science).

Non-limiting examples of parenteral (or intravenous) nutrition comprise intravenous dextrose solutions, intravenous amino acid solutions, intravenous fat emulsions, intravenous vitamin and mineral supplements, or a combination thereof.

Example 6

NEC is a devastating GI disease that primarily affects premature infants (Incidence: 4-14%; Mortality: 15-30% (up to 50%); Morbidity: up to 50% of survivors). Clinical manifestations of NEC comprise abdominal distension, poor gastrointestinal motility, and bloody stools. X-ray findings comprise *pneumatosis intestinalis* and perforation.

Diagnosis of NEC is difficult because early manifestations are non-specific, the presence of *pneumatosis intestinalis* is inconsistent, and there is rapid clinical deterioration despite aggressive management. Pneumatosis, for example, is seen in only 48% of pathological confirmed necrotizing enterocolitis. There are currently no biochemical measures to identify those infants most at risk and to enable early diagnosis.

As described herein, intestinal alkaline phosphatase (iAP) can serve as a biomarker for NEC, and that deficiency of iAP is correlated with a predisposition to NEC.

iAP is produced by apical enterocytes and secreted into luminal brush border and catalyzes hydrolysis of phosphomonoesters. iAP is active as a homodimer and requires $Zn^{2+}$ and $Mg^{2+}$ ions in the active site. Substrates of iAP include LPS and nucleotide triphosphates. iAP has multiple roles affecting gut barrier function and inflammation. iAP is shed in stool. iAP is tissue specific AP, meaning made mostly in intestine, as demonstrated by immunohistochemical staining of intestinal tissue (FIG. 15).

iAP maintains gut barrier function (FIG. 16).

This study investigated whether fecal iAP is a diagnostic tool for NEC. Serial patient stool samples collected and processed within 4 days. Slurry of 200 mg stool/1 ml molecular grade water, Centrifugation at 14000 rpm at 4 degrees Celsius. Supernatants stored at −20 degrees Celsius until analysis. Biochemical Assays performed comprise concentration of total protein in stool, enzymatic activity of alkaline phosphatase, and western blot with human iAP. 16 infants from Touro Infirmary and Children's Hospital of New Orleans provided samples (NEC: 5 patients (25-35WGA); Non NEC: 11 Patients (23-34 WGA)). Over 100 stool samples processed and analyzed.

5 NEC patients at time of diagnosis were compared with 11 control patients, and the control patients fecal total protein between corrected gestational age 29-35 corresponding with the corrected gestational ages of the NEC patients was averaged. The results were statistically significant with median total fecal protein being 2.7 mg/ml in NEC patients and 0.7 mg/ml in Non NEC patients. Fecal total protein content was higher in NEC patients than in control infants (FIG. 17). The median (5%-95% CI) for Fecal Protein NEC 2.7 (1.6-3.6); Controls 0.7 (0.2-2.1).

The determination of fecal protein content requires ~1 hr of lab work. Measurement of fecal protein concentration above 2 mg/ml can serve as an early indicator of NEC onset.

Total fecal AP is predominantly intestinal isoform. There are other alkaline phosphatases in the intestine, such as bacterial and TNAP. We quantitated the proportion of intestinal AP catalytic activity from stool by using L-phenylalanine which specifically inhibits activity of only the intestinal type alkaline phosphatase. Specifically, we obtained AP activity with and without L-Phe added to determine specific iAP activity, and concluded that iAP is the main form of AP in stool. Fecal AP catalytic activity was consistently lower (statistically significant) in NEC population (FIG. 18).

TABLE 1

Median values 200 and 600. Statistically significant difference Summary of Data

| Parameter: | nec | controls |
| --- | --- | --- |
| Mean: | 199.00 | 1501.6 |
| # of points: | 5 | 11 |
| Std deviation: | 42.279 | 1426.7 |
| Std error: | 18.908 | 430.17 |
| Minimum: | 146.00 | 434.00 |
| Maximum: | 250.00 | 3872.0 |
| Median: | 189.00 | 598.00 |
| Lower 95% CI: | 146.51 | 543.22 |
| Upper 95% CI: | 251.49 | 2460.1 |

When NEC patients were matched with a specific control of similar age and gestational age, the AP enzymatic activity was lower (FIG. 19).

Measurement of low AP activity (<200 U/mg) is a potential biomarker of NEC. There is a uniform reduction of alkaline phosphatase activity in NEC patients compared to matched controls. Without wishing to be bound by theory, iAP silencing can be a component of gut mucosal barrier dysfunction in critically-ill NEC patients. Goldberg et al. Proc Natl Acad Sci 105, 3551.

Unexpectedly high levels of iAP protein are detected in association with NEC. A specific antibody for human iAP was used in western blot analyses and, surprisingly, detected appropriate signal only in the NEC samples (labeled N) and absent in control samples. Each group represents different NEC patients at the time of diagnosis and the controls which were age and gestational age matched. There are much higher iAP amounts present in stool of NEC patients at the time of diagnosis (FIG. 20).

NEC episodes demonstrate increased fecal iAP protein levels. One NEC patient serially was followed and found that the patient continued to have high iAP levels even after medical management. The patient subsequently had a perforation followed by surgical intervention. Stool 10 days following surgery no longer has high levels of iAP protein. There is no signal on day 42 (FIG. 21). Contrasted with AP activity, the patient maintained lower AP activity until surgical intervention. 10 days after surgery AP activity begins to increase. The presence of persistent high fecal iAP levels and low activity could have been an indication of compromised bowel leading up to perforation. (FIG. 22).

iAP is developmentally regulated, and its expression and activity in rat models has been shown to be decreased in premature pups. Data corroborate iAP activity is decreased in human NEC infants, but not its expression. Without wishing to be bound by theory, a third NEC biomarker can be western blot analysis or ELISA of iAP protein levels in preterm infants (Rentea et al. Eur J Pediatr Surg 23, 39; Heinzerling et al. J Pediatr Surg 49, 954; Biesterveld et al. J Surg Res 196, 235).

This study provides preliminary evidence that three lab tests on stool samples can serve as biomarkers of NEC. Technique, length of time, and required equipment varies between the three tests. Combining the three markers can increase diagnostic value over using a single biomarker. Subsequent studies will optimize specificity and sensitivity of each method.

There are differences between proximal and distal halves of intestine in suckling rats. Structural differences comprise majority of iAP is membrane-bound in the proximal half of the intestine; in the ileum, however, iAP is found in the supernatant fraction of intestinal homogenate; in adults, more than 95% of iAP is membrane-associated. Functional differences comprise during suckling period, total alkaline phosphatase activity higher in ileum; when rat matures, activity falls in ileum and becomes higher in proximal bowel. Yedlin et al. J Biol Chem 256, 5620.

Testing for non-specific binding of secondary antibody (FIG. 23).

Methods: fluorimetric assays. Alkaline Phosphatase cleaves the phosphate group of the non-fluorescent 4-Methylumbelliferyl phosphate disodium salt (MUP) substrate; Results in an increased fluorescent signal when dephosphorylated; Measured using a spectrophotometer.

Example 7

Antibiotics for Nec

For NEC, 10-14 days of antibiotics is administrated to the infant, but the prescription is variable between hospital practices. Ideally, prescription would be for broad spectrum coverage for (i) gram-positive bacteria, (ii) gram-negative bacteria, and (iii) anaerobic bacteria. For example, Vancomycin (gram-positive including MRSA), ceftazadime (third generation cephalosporins—gram negative, some grant positive, and *pseudomonas*), metronidazole (anaerobic coverage), oxacillin (gram positive).

Examples of general antibiotics regimes are: ampicillin+ gentamicin for possible vertically acquired infection from mother, and vancomycin+cetazidime for possible hospital acquired infections. Commonly used antibiotics are Gentamycin, Vancomycin, Ampicillin, Zosyn (combination of piperacillin and tazobactam), Flagyl (metrodniazole generic), Clindamycin, Meropenem, Fluconazole (antifungal agent).

For sepsis, 7 days of antibiotics would be administered to the patient.

Feeding and Nutrition Regimens for Preterm Infants:

One of the challenging tasks for the neonatologist is to adequately and safely provide nutrition to very preterm infants. Enteral supply (feeding by mouth) is the most challenging balance of safety and nutrition. Signs for feed intolerance, or an inability to digest enteral feeds, is frequently encountered in preterm infants. Intolerance to enteral feeds can be a benign condition but there is overlap with necrotizing enterocolitis. Moreover, there are clear detrimental effects associated with fasting.

Complete parenteral nutrition (PN) solutions were provided on the first afternoon following birth. Infants receive stock solutions containing glucose (10 g/dL), amino acid (2.5 g/dL), and lipid s in the first 2 hours of life. Amino acid solutions contained AminosynPF10% (Hospira Inc) or TrophAmine 10% (B Braun Medical Inc). Intralipid 20% (Baxter) Liposyn III 20%, and Liposyn II 20% (Hospira Inc) provided parenteral lipids. Fluids typically provided 80 to 100 mL/kg per day at birth and increased by 20 mL/kg to 140-160 mL/kg per day in the first week of life. Acetate salts of sodium and potassium in PN solutions are buffers against metabolic acidosis.

PN solutions provided most of the nutrition in the first week of life. Enteral nutrition (EN) typically contributed only minimal energy until the end of the second week. The transition to exclusively EN was typically achieved before the end of the fourth week. When available, infants received their mother's breast milk. After tolerating breast milk at 150 mL/kg per day, infants received supplemental human milk fortifier (Mead-Johnson). When breast milk is not available, infants received formula specific for premature infants. The maximum caloric density of supplemented breast milk or formula was provided at 0.8 kcal/mL (80 kcal/dL; 24 kcal/oz).

Types of formula: Premature Enfamil Formula (Enfamil), EleCare (Abbott Nutrition), Neosure (Similac), EnfaCare (Enfamil), Pregestimil (Enfamil), Similac Special Care or SSC (Similac), Gentlease (Enfamil). Pregesternil and Elecare are hydrolyzed cow-based formulas, typically used for post-NEC babies or those with history of feeding intolerance. Enfacare and Neosure are discharge preterm formula. Premature Enfamily Formula and Similac Special Care are hospital premature formula.

Feeding tolerance is demonstrated when the preterm infant is capable of safely ingesting and digesting the prescribed enteral feeding without complications associated with gastrointestinal dysfunction or infection. Clinical evidence of feeding tolerance in very low birth weight preterm infant is most often described in the literature as the number of days required to reach full-feeding volumes (reported ranged from 100-160 mL per kg per day), the number of episodes of feeding intolerance, the number of days feeds are withheld due to feeding intolerance symptoms, time to regain birth weight, lower leg growth, increase in weight gain, occipital-frontal head circumference, and length.

Proposed prevention/treatment strategies for feeding intolerance in preterm infants include:

TABLE 2

Proposed prevention/treatment strategies for feeding intolerance in preterm infants.

| Altered/immature function | Prevention/treatment strategy |
|---|---|
| 1. Motility | |
| a. Sucking-swallowing coordination | Non nutritive sucking Tube Feeding:    I. Gastric vs transpyloric    II. Continuous vs intermittent bolus |
| b. Gastro-esophageal reflux | Infant positioning Prevention/treatment of apnoeic episodes Drugs:    I. Acid suppressors    II. prokinetics |
| c. Gastric emptying | Low fat content Osmolality (?) Prokinetic drugs |
| d. Intestinal motility | Prokinetic drugs Osmotic solutions Enemas Abdominal massage (?) |
| 2. Digestion | |
| a. Lactose | Lactose free formula Lactase-treated formula |
| b. Protein | Hydrolysed protein formula Amino acid-based formula |
| c. Fat | MCT/LcPUFA content |
| 3. "Intestinal millieu" | |
| a. Microflora | Probiotics Prebiotics Lactoferrin |
| b. Intestinal barrier | Glutamine Probiotics Lactoferrin |

REFERENCES CITED IN THIS EXAMPLE

Herrmann and Herrman. 2010. Nutrition in Clinical Practice 25, 69-75

Fanaro. 2013. Early Human Development 89, S13-S20

Example 8

PROP=propensity of getting NEC=(1-activity)*WB

1. The Markov transition model was fitted with PROP, white blood cell count, antibiotic (Yes/No), and whether or not a baby had some volume of food (>0).

TABLE 3

| | Coefficient + Confidence Interval | |
|---|---|---|
| Variable | Transition to NEC | Transition to Non-NEC |
| PROP | 18.7845 (1.302252, 270.9) | 0.1038 (0.006116, 1.76) |
| White Blood Cell Count | 0.9975 (0.9777, 1.018) | 0.9726 (0.9246, 1.023) |
| Antibiotics | 0.5051 (0.1323, 1.928) | 11.9612 (3.8391, 37.267) |
| Volume Given >0 | 1.1571 (0.3602, 3.717) | 0.8028 (0.2958, 2.179) |

Volume given=0

Without being bound by theory, increased PROP significantly increases the risk of transitioning to NEC. Without wishing to be bound by theory, using Antibiotics increases the probability of transitioning to non-NEC from NEC status.

Without wishing to be bound by theory, when the data from the table are plotted, there is a symmetry relationship between the state 1 to 2 and the state 2 to 1 ratios.

For example, using the data set without the extra assay data from 2019, the coefficient for PROP was around 11 or 12.

The result printouts are below:

Maximum likelihood estimates
Baselines are with covariates set to their means
Transition intensities with hazard ratios for each covariate

| | Baseline | PROP |
|---|---|---|
| State 1 - State 1 | −0.01257 (−0.03220, −0.00491) | |
| State 1 - State 2 | 0.01257 (0.00491, 0.03220) | 18.7845 (1.302252, 270.96) |
| State 2 - State 1 | 1.22270 (0.43181, 3.46219) | 0.1038 (0.006116, 1.76) |
| State 2 - State 2 | −1.22270 (−3.46219, −0.43181) | |

ANTIBIOTICS

| | | |
|---|---|---|
| State 1 - State 1 | | |
| State 1 - State 2 | 0.9975 (0.9777, 1.018) | 0.5051 (0.1323, 1.928) |
| State 2 - State 1 | 0.9726 (0.9246, 1.023) | 11.9612 (3.8391, 37.267) |
| State 2 - State 2 | | |

VOL1TRUE

| | | |
|---|---|---|
| State 1 - State 1 | | |
| State 1 - State 2 | | 1.1571 (0.3602, 3.717) |
| State 2 - State 1 | | 0.8028 (0.2958, 2.179) |
| State 2 - State 2 | | |

Using additional variables (IT ratio, Platelet count, Time) resulted in models that did not converge. Without wishing to be bound by theory, this may be due to the fact that observations are carried forth to days where we have missing values. For example, if it is known on Tuesday that a baby has a PROP score of 0.05 on a Monday, and another PROP value is not obtained until Thursday, the baby's PROP values on Tuesday and Wednesday are 0.05.

2. In embodiments, certain variables can be removed, for example if the model is complicated and the preliminary data is limiting. When it comes to predicting a transition into NEC status, a significant variable is PROP (since the confidence interval doesn't contain 1). Without wishing to be bound by theory, if a model is fitted with only this term, the table is as follows:

TABLE 4

| Variable | Coefficient + Confidence Interval | |
|---|---|---|
| | Transition to NEC | Transition to Non-NEC |
| PROP | 52.5438 (5.51, 500.99) | 0.2727 (0.012, 6.01) |

In another embodiment, antibiotics is left in the analysis, which seem to be significantly related with a switch from NEC to non-NEC status. Without wishing to be bound by theory, in this case, the table is as follows:

| Variable | Coefficient + Confidence Interval | |
|---|---|---|
| | Transition to NEC | Transition to Non-NEC |
| PROP | 24.12 (1.85, 313.85) | 0.137 (0.0079, 2.38) |
| Antibiotics | 0.3871 (0.126, 1.19) | 10.52 (3.59, 30.81) |

3. FIT of Linear Mixed Model for PROP Score

Next, a linear mixed model was run to predict PROP score as a function of ONLY the values currently in possession (i.e. we did not impute values of PROP by carrying one forward) over time. This resulted in 580 datapoints for 92 patients, with about 45 (7%) of these datapoints containing PROP values corresponding to patients with a NEC diagnosis at that time. This model was fit for only the covariates NEC, Antibiotics (YES/NO) and Volume fed >0 (NO/YES) since introducing more covariates dropped the complete cases to 78 datapoints. A linear and quadratic time effect was initially included, but, without being bound by theory, the likelihood ratio test showed that this was not necessary. The results of the reduced model without a time effect is below:

| | Coef | S.E. | t | Pr(>|t|) |
|---|---|---|---|---|
| Intercept | −0.0636 | 0.0178 | −3.57 | 0.0004 |
| NEC | 0.0733 | 0.0149 | 4.93 | <0.0001 |
| ANTI | 0.0074 | 0.0086 | 0.86 | 0.3876 |
| VOL1 | 0.0502 | 0.0128 | 3.92 | 0.0001 |

In additional embodiments, having the explicit mathematical terms may allow analysis of data from the linear mixed model.

Without wishing to be bound by theory, mixed models are used for analysis of correlated data, such as longitudinal data or information that may have multiple dependencies. A key feature of mixed models is that, by introducing random effects in addition to fixed effects, they allow for addressing multiple sources of variation, i.e. within- and between-subject variation, and interactions between combinations of discrete and continuous variables. In an embodiment, the 't' in the information in Example 8 can refer to an abbreviation for time. In this embodiment, NEC PROP may be able to predict disease 4.93 days prior to x-ray.

As described herein, if a patient is diagnosed with NEC on a given day, it can be predicted that they will have a significantly higher PROP score, as the NEC coefficient is positive (0.0733) and the p value is less than 0.0001. There is an interaction between NEC Prop and no feeds; the Vol 1 coefficient is 0.0502. This interaction is significant, as it has a p value of 0.0001. Without wishing to be bound by theory, such an interaction would be expected, since the medical staff halt feeds when NEC is diagnosed. Antibiotic use has no associative interaction with NEC propensity. This mixed model accounts for multiple observations on each interval over time.

Example 9

Without wishing to be bound by theory, PROP Score can be a function of iAP activity and WB value:

$$Prop_i = \left(1 - \frac{iAP_{Activity_i}}{\max(iAP_{Activity})}\right) \frac{WB_i}{\max(WB)}$$

Transition Model:

Does increased PROP increase (decrease) the rates of transition A and B?

A. PROP Only

In an embodiment, the analysis carried forth the patient's PROP score to days that did not have data. For example, if a patient had a PROP score from day 3 and 7, then their PROP score from days 4-6 are equal to that at day 3.

TABLE 5

| Variable | Coefficient + Confidence Interval | |
|---|---|---|
| | Transition to NEC | Transition to Non-NEC |
| PROP | 52.5 (5.51, 501) | 0.273 (0.01, 6.01) |

Increased PROP was associated with a significantly increased transition risk to NEC suspicion/(+).

B. PROP and Antibiotics

The same carry forward was done with the antibiotics, only considering whether or not the baby was on antibiotics, without considering what kind of antibiotics. for example.

TABLE 6

| Variable | Coefficient + Confidence Interval | |
|---|---|---|
| | Transition to NEC | Transition to Non-NEC |
| PROP | 24.1 (1.85, 314) | 0.14 (0.01, 2.38) |
| Antibiotics | 0.39 (0.13, 1.19) | 10.52 (3.59, 30.8) |

Increased PROP was associated with an increased risk of transition to NEC. Antibiotics increased the probability of transitioning from NEC to NEC(−).

C. Full Model

TABLE 7

| Variable | Coefficient + Confidence Interval | |
|---|---|---|
| | Transition to NEC | Transition to Non-NEC |
| PROP | 18.8 (1.30, 271) | 0.10 (0.01, 1.76) |
| White Blood Cell Count | 1.00 (0.98, 1.02) | 0.97 (0.92, 1.02) |
| Antibiotics | 0.51 (0.13, 1.93) | 12.0 (3.84, 37.3) |
| Volume Given = 0 | 1.16 (0.36, 3.72) | 0.80 (0.30, 2.18) |

In the referenced embodiment, additional covariates could not be considered due to convergence issues.

White blood cell counts were carried forward, as was whether the patient had not received food.

After adjusting for white blood cell count and whether or not the patient received food, the results demonstrate that PROP and antibiotics are significant predictors of transition risks.

Data shows partial symmetry with that in FIG. 26.

Interval overlap with 1 infers no significant difference.

Linear Mixed Model for PROP Score

It is noted that we did not carry any points further; thus, without wishing to be bound by theory, we used observed 580 PROP datapoints on 92 patients Model Fits:

$$PROP_{ij} = \alpha_1 NEC_{ij} + \alpha_2 ANTI_{ij} + \alpha_3 VOLO_{ij} + \alpha_4 t_{ij} + \alpha_5 t_{ij}^2 + b_i$$

$PROP_{ij}$ is the prop score of patient i at the jth measurement.

$t_{ij}$ is the time (in PCA days) of the jth measurement for patient i.

Time and Time^2 were not needed in the regression model.

TABLE 8

| Variable | Coefficient | Test Statistic | P-value |
|---|---|---|---|
| Nec+ | .0733 | 4.93 | <.0001 |
| Antibiotics | .0074 | .086 | .3876 |
| Volume = 0 | .0502 | 3.92 | .0001 |

NEC associated with a significant increase in PROP score.

Without wishing to be bound by theory, being fed no food on a given day associated with a significant increase in PROP score.

Without wishing to be bound by theory, assumed normality for PROP.A beta regression had mixed effects modeling capabilities.

Using beta regression without mixed effects, the same results are obtained

Embodiments could use Bayesian methods to fit the beta-mixed regression if desired.

Example 10

Example 10, for example, refers to FIG. 28 and FIG. 29. We have been collecting stool samples from preterm infants and analyzing the abundance and enzyme ability of intestinal alkaline phosphatase (iAP). One of the original plots I generated (FIG. 28) highlights that these two biochemical properties segregate NEC disease from non-disease. When examining sepsis in this sample patient population, there is no segregation of this blood infection with non-blood infection.

Given that both of these biochemical properties of iAP could distinguish NEC disease, we were interested in developing a simple algebraic formula to incorporate equal contribution from both parameters. We crafted a formula in which the iAP abundance is multiplied by the magnitude of iAP enzyme dysfunction. This product can be referred to as a PROP score or as a 'NECPredict' score.

The first term in the formula is iAP abundance. iAP will be shed into the gut lumen, and thus found in stool, if there is an imbalance of bacteria that are not beneficial. The normalized percentage of iAP, relative to what is found in human small intestinal lysate samples, is high when there is a bacterial imbalance or at the time of NEC diagnosis (see Heath, Maya, et al. "Association of Intestinal Alkaline Phosphatase With Necrotizing Enterocolitis Among Premature Infants." JAMA network open 2.11 (2019): e1914996-e1914996, which is incorporated by reference herein in its entirety). I also knew that we were detecting the amount of iAP protein in stool samples well before clinical diagnosis (FIG. 29).

The second term in the NECPredict formula (also referred to as the PROP score) is iAP dysfunction. iAP, which is responsible for neutralizing signals that originate from gram-negative bacteria and trigger the human innate immune response. Humans with robust iAP function can prevent inappropriate pro-inflammatory signal cascades in the human gut and contribute to beneficial microbiota maturation. In infants with NEC, we have found at that iAP is not functional, compared to control infants, at any time during the clinical study. To provide a mathematical term for this dysfunction, the difference between the maximum iAP activity found in our patient population and any given stool reading was determined; normalization of this algebraic subtraction was needed to give equal weight between the protein abundance and protein function. The iAP abundance and iAP function terms are multipled to provide a propensity (NECPredict) score.

The median NECPredict score was nearly 1 (FIG. 29) at the time of clinical diagnosis and was clearly higher than that of controls. Even prior to clinical diagnosis, the NECPredict score in infants with disease was significantly different from the control infants. These data point out that there is a clear clinical-iAP biochemical relationship for NEC disease. Without wishing to be bound by theory, any NECPredict score above 0.5 could be used as an adjunct in the clinic for disease intervention, such as withholding feeds by mouth and prescription of antibiotics in the neonatal intensive care unit.

Example 11

The goal of this project is to obtain data for a prognostic biomarker that predicts necrotizing enterocolitis (NEC), the most frequent and lethal gastrointestinal disease in preterm infants. Such a tool, which is sensitive and specific for the disease, is essential to support the development of new medicines in this smallest and most fragile patient population. Moreover, this effort directly addresses critical decision points in current clinical practice: neonatologists in the area and patient advocacy groups have directly challenged us to find the window of disease reversibility. The team first developed a diagnostic test for NEC, NECDetect. From analysis of samples from 135 preterm infants at three hospitals, NECDetect identified >95% true positives and >95% true negatives at the time of disease; importantly, it was not correlated with neonatal late-onset sepsis. Without wishing to be bound by theory, NECDetect components can be used to assess the risk of NEC, prior to its severe onset. Our prospective, observational study will evaluate if NECPredict, a calculated probability based on biochemical data from infant, forecasts disease 36-48 hours before it is clinically evident and if Neonatal DDx, a genetic polymorphism screen, identifies infants at birth with a predisposition to develop NEC. Enrollment target is 150 preterm infants for 90% statistical power. Although the low number of preterm infants limits participants enlisted, this goal still exceeds the targets of most studies registered on ClinicalTrials.gov, 62 percent of which accrue fewer than 100 participants. This effort also is the first study involving the NEC Biorepository, a virtual biobank of 8 different academic center hospitals. Future clinical studies, backed by this consortium infrastructure, will have access to infant patient enrollment in the thousands, which would place it in the top 6% of clinical study enrollment targets. If successful, accurate, rapid, and inexpensive diagnostics can make personalized management of gut inflammation and therapeutic improvements accessible for infants.

Necrotizing enterocolitis is the most common gastrointestinal disease in preterm infants. With no diagnostics available, it is critical to better understand the pathogenesis of human-microbiome crosstalk in this disease. These studies will define the window of reversibility in which infants can be selected for proactive management and clinical trials for therapeutic interventions.

Specific AIMS

Necrotizing enterocolitis (NEC) in preterm infants is a devastating gastrointestinal disease, which has high mortality and morbidity rates. Initially described 200 years ago, there are still fundamental knowledge gaps regarding this rare disease. We do not know its cause, but it is correlated with infant development, feeding, and microbiome taxa shifts. Second, and more clinically urgent, no single factor or combination of known factors can explain the wide variability in NEC onset: we do not know who will get the disease and when. Such insight would open new avenues of care, such as earlier and more effective management of fragile preemies in the neonatal intensive care unit (NICU) and selection of infants for therapeutic clinical trials.

This proposal addresses the unmet need for prognostic biomarkers that foretell the onset of NEC in the neonate. To achieve this, the initial barrier is elucidating molecular characteristics, or biomarkers, that intersect with dysbiosis, human epithelial function, and NEC. Without wishing to be bound by theory, aberrant biochemical communication between the premature infant host and gut bacteria is a predictor of necrotizing enterocolitis. Our preliminary data highlight that biochemical assays measuring host response to gut bacteria are diagnostic biomarkers for NEC. When examining biospecimens from 135 very low birth weight infants at three different hospitals, the key feature of NEC-Detect is its improved identification of true positives at the time of disease. Another distinguishing characteristic of NECDetect is its usability; it is non-invasive, rapid, low cost and readily integrated into existing pathology workflows.

From this prerequisite effort that answered the question 'if', this application will determine whether the NECDetect components can be used as prognostic biomarkers that address the 'who' and 'when.' Our approach is to conduct a prospective, longitudinal study of preterm infants in NICUs in two different cities and collect biological samples at regular intervals. We will enroll 150 preterm and/or growth restricted infants (<34 weeks gestational age; <2.5 kg birth weight) from two clinical sites. This study analyzes specific biomarkers and temporal clinical correlations in NEC and non-NEC patients. For this application, we will focus on the following aims:

AIM 1: Are iAP polymorphisms predictive of NEC predisposition? Our hypothesis is that infants diagnosed with NEC will have mutations in the gene for intestinal alkaline phosphatase, ALPI, which lower their catalytic ability to detoxify harmful Gram-negative bacteria. Methods will involve Sanger sequencing of PCR products amplified from genomic DNA of infants diagnosed with NEC and of infants without NEC. DNA will be isolated from cheek swabs or from peripheral blood cells. The significance of this effort would be the first mechanistic definition between disease severity, biochemistry, and genetic polymorphism. If achieved, this NEC predisposition screen, termed Neonatal DDx, would be indispensable in identifying the earliest possible therapeutic option and to improving long-term outcome and life quality.

AIM 2: Are intestinal alkaline phosphatase (iAP) levels in stool a prognostic biomarker for NEC? This aim will determine if NEC onset can be determined at a molecular level before the most severe physical symptoms are observable at a clinical level. Without wishing to be bound by theory, increased release of iAP protein in the human gut lumen is a response to microbe-induced inflammation in NEC and measurable as a function of time. In total, over 2,000 patient samples will be longitudinally collected and analyzed for iAP protein content. In vitro results and corresponding clinical data will be used to validate associations between iAP as a biomarker and prediction of NEC diagnosis with a computational platform, NECPredict. Its significance is twofold. This effort will be the first study to test a continuous-time process in which patients move between clinical states during the disease process, rather than traditional binary distinctions between NEC event and no-NEC event. It also will determine the temporal window of reversibility for proactive, rather than reactive, medical management.

In net, these aims offer personalized prediction methods for handling human diversity, variability in infant gut development, and clinical care choices. To do so requires temporal granularity of patient samples and clinical information; such an effort can only be achieved due to the non-invasive nature of our biospecimen procurement. Embedded in this work is a platform to study the operational and feasibility issues in our clinical study protocol in obtaining and integrating large datasets of clinical and biochemical information between two large academic medical centers. Such study optimization and data harmonization across a wide array of clinical measures will justify a future multi-center study with a larger number of NICUs, coordinated through the nascent, national NEC Biorepository. Importantly, this proposal will validate an urgently needed biomarker that can predict and detect NEC. These studies are critical to advancing our understanding of gastrointestinal disease in the most vulnerable infants and can be extended to the adult population.

Research Strategy (a) Background and Significance

Our goal is to define mechanisms that alter homeostasis between human host and gut bacteria that give rise to gastrointestinal inflammation. Severe forms of GI inflammation, irrespective of age of onset, are debilitating and life-threatening. Its pathophysiology remains unclear; currently, both genetic and non-genetic factors are argued to be required for these complex diseases.

Case in point, necrotizing enterocolitis (NEC) in premature infants remains one of the most feared and costly neonatal diseases [1]: we do not know who will get it, when they will get it, or if they will survive it. NEC progresses rapidly from mild abdominal distension and feeding intolerance to shock, intestinal necrosis, and death. Its quick progression and imprecise clinical presentation engendered a Bell staging rubric, the most commonly used classification scheme based on broad bedside clinical and radiographic findings [2, 3]: early stages are termed Bell stage I, medical NEC is Bell stage II, and surgical NEC is Bell stage III (FIG. 30, panel A). However, Bell staging is not specific for NEC nor is it predictive of disease severity. Mortality rate is between 30-50% [4] and it usually presents with other lethal diseases, such as sepsis. Survivors may have short gut syndrome, poor neurodevelopmental outcomes, bronchopulmonary dysplasia, and intracranial hemorrhage [5-7].

Lack of reliable molecular biomarkers for gut inflammation frustrates clinicians and is an obstacle for biomedical advances. X-ray radiography (FIG. 30, panel B), the current gold standard, only detects NEC in life-threatening advanced stages (modified Bell stages II and III) and only identifies 44% of true positives [8]. Moreover, despite its frequent and consistent use, individual radiographic signs of NEC do not readily correlate with disease severity. More critical, missing in the medical toolbox is a biological marker for early, reversible stages of disease (modified Bell stage I). Instead, a combination of phenotypic and serologic information is used to guide clinical intuition.

Defining a prognostic biomarker for NEC is significant for both the scientific and medical communities. It would provide insights into key mechanisms, and be indispensable for establishing and monitoring intestinal homeostasis in premature infants. On a clinical level, an early stage biomarker would mitigate surgical resection of necrotic bowel and long-term chronic effects of this disease. We conducted a survey of 70 physicians, and we found that the minimum significant difference in time to identify NEC earlier than x-ray, which would allow for beneficial patient management, was 48 hours. Timely management decreases the need for surgery by half [9]: medical treatment typically consists of bowel rest, antibiotics, and supportive care (white boxes, FIG. 30, panel B). Second, prognostic biomarkers are necessary to demarcate the period of NEC reversibility. This is not trivial, as NEC has a compressed timeframe, with no medical equivalent in adult GI disease. Moreover, this early window for disease management is needed for drug development and enrollment in clinical trials for therapeutic agents.

(b) Innovation

Three unique aspects distinguish this proposal. The first innovation is to evaluate non-inflammatory proteins that precede the immune activation cascade as a biomarker for NEC. Without wishing to be bound by theory, intestinal alkaline phosphatase (iAP; [10]), an initial host regulator in microbial management (FIG. 30, panel A), is a biomarker for early NEC in premature infants. Development of gut inflammation depends on the degree to which bacteria symbiosis is accompanied by cellular signaling via innate immune mechanisms [11, 12]. Yet, to date, NEC biomarker research has focused predominantly on gene products that regulate intestinal immunity, mucosal injury that permits bacterial translocation, and host inflammation (FIG. 30, panel A). Unfortunately, such proteins, although correlated with advanced NEC stages, are not specific biomarkers for GI disease and importantly, they are also associated with non-GI infections as well as sepsis. As such, they cannot serve as prognostic biomarkers and are not promising targets for therapeutic intervention.

Encoded by the human ALPI gene, iAP has a crucial role in host-microbiota interactions via restraining downstream host inflammatory responses. It is a metalloenzyme with tissue-specific expression in the small intestine that is readily detectable in the mucous layer and gut lumen [14, 15]. Membrane-anchored in enterocytes, iAP only sheds into the gut lumen, and thus measurable in stool, to control bacterial colonization [15, 16]. It hydrolyses phosphate from lipopolysaccharides (LPS) and thereby reduces Toll-like receptor 4 (TLR4; FIG. 30, panel A) agonist activity. Notably, TLR4 has been implicated in the pathogenesis of NEC [17-20]. As such, iAP has been used as a measure of toxic damage to the small intestine in animal models [21]. In contrast, our proposal examines iAP in human biospecimens and evaluates it over the course of the infant's stay in the NICU.

Our second innovative direction is development of diagnostics specific for an infant disease, rather than utilizing a well-established adult biomarker and testing its applicability to children [22]. While clinical studies are conducted in all diseases, it is clear that trial portfolios do not match public health or community medical practice needs in terms of either urgency or magnitude. Children and adults differ in physiological capabilities, pharmacokinetic profile, and pharmaco-dynamic characteristics; metabolic pathways, organ functions, and metabolic rates differ widely as well [23-25]. In addition, age, growth, and development are coupled to severity of disease in neonates, infants and children [26, 27]. Despite clear recognition that children are not 'little adults,' the necessity for pediatric-specific healthcare solutions is frustrated by invasive and harmful biospecimen procurement methods and a relatively small number of available participants for clinical studies and trials [28]. Toward the former challenge, this research evaluates infant stool in disposed diapers, providing minimal risk to infants and a favorable factor in study enrollment. Toward the latter, the PI and consortium PI are part of the NEC Biorepository, for which 8 different academic center hospitals have agreed to share samples and clinical data from NEC infants [29]. If this first test collaboration is successful, other hospital partners in the NEC Biorepository are poised to accelerate larger-scale translational studies of NEC in the future.

Third, advanced testing of clinical workflow and assay systems position us to effectively handle increased number of infants in shorter study periods. Obstacles created from increasing scale are well understood in engineering, but still relatively new in biomedical research. The preliminary data below confirm our ability to collaborate in a multisite study. This effort also provided understanding of clinical site batch effects, such as systematic differences in practice, documentation, patient population, and others. We invested substantial time and effort to make analyses of biochemical and clinical data repeatable and reproducible. Data below had to overcome challenges in patient sample handling, biobanking, biospecimen quality, and data harmonization [30]. As such, we have firsthand knowledge of how to bring together data from multiple sources, ensure uniform and consistent processes, cleaning and applying quality control metrics to accepted and processed data alike.

(c) Preliminary Data

Our prospective study assessed the independent correlation of 2 stool biomarkers, which comprise NECDetect (FIG. 30, panel B), in 136 premature infants from neonatal intensive care units affiliated with LSU School of Medicine and Washington University School of Medicine (1.1±0.5 kg; 27.6±0.8 weeks gestational age; please see Inclusion Report). In summary, our data show that the presence of high amounts of iAP protein in stool and low iAP enzyme activity are biomarkers for NEC. In effect, NEC infants are 'shooting blanks' into the gut lumen to manage aberrant microbial development. iAP biomarkers do not correlate with sepsis or other non-GI infections.

Infants Suspected of NEC and Infants with Advanced NEC Disease Shed iAP Protein into Gut Lumen at Levels that Exceed the Amount Typically Found in Human Small Intestine.

Baseline evaluation of iAP detection using immunoblots. Immunoblotting can determine the relative expression of a protein within complex biological samples. Development of sensitive antibody labels with truly quantifiable linear ranges and greater limits of detection with digital image analysis allow proteins to be probed with higher resolution than previously achievable [31]. To account for sample prep, detection scheme, and normalization approach in our hands, a calibration curve of human intestinal lysate (FIG. 31, panel A), our positive control, showed that the linear portion of anti-human iAP signal detection and our working range overlapped [32]. Positive control and negative control (calf iAP) were from single lots and served as calibrators for our quantitation; both are loaded on every gel with patient samples. Equivalent total protein was loaded per lane.

High iAP protein levels are associated with NEC diagnosis and NEC suspicion, but not sepsis. We established baseline iAP levels, shed in the gut lumen and detected in stool, in non-diseased infants [33]. Control patient stools had very low amounts of iAP, compared to human small intestine lysate and calf iAP controls (<2%; FIG. 31, panel B). We conclude that very little iAP is shed into the gut lumen when no dysbiosis is imminent.

High amounts of fecal iAP protein are found at the time of clinical NEC diagnosis (red bar, Bell stage II and III; FIG. 31, panel B). iAP content in stool would increase from released membrane vesicles loaded with iAP, if there was a risk of bacteria-induced inflammation [15, 16]. Our data show that iAP shed into the gut lumen and stool, at levels equivalent or greater than what is found in a human intestinal lysate sample, is a molecular biomarker superior to clinical diagnosis (x-ray evidence of *pneumatosis intestinalis*). As a NEC biomarker, sensitivity and specificity of fecal iAP content is greater than 95% (FIG. 31, panel C).

NEC suspicion, or early NEC, also correlated with high levels of iAP in stool (pink bar, Bell stage I; FIG. 31, panel B). In stool samples with a clinical concern for advanced NEC, even if *pneumatosis intestinalis* was not detectable by x-ray, the amount of iAP protein was statistically different from controls (pink bar, FIG. 31, panel B). However, there was no difference between NEC suspicion (pink bar) and diagnosis mean values (red bar, FIG. 31, panel B). Fecal iAP levels had no measurable correlation with sepsis (blue bar, FIG. 31, panels B and D). Severely preterm infants (<32 weeks) have not only improperly formed intestines, but also an immature immune system. Their increased risk of sepsis [34, 35] can confound diagnosis of NEC, as it a common co-morbidity with limited diagnostic tools. Our preliminary data show that iAP protein levels are not statistically correlated with clinical diagnosis of sepsis.

Infants with Advanced NEC Disease have Extremely Low Enzyme Activity, Whereas Infants Suspected of NEC have Intermediate iAP Catalytic Activity.

Evaluation of iAP enzyme activity in non-NEC infants. Normalized to protein concentrations, we discovered that iAP activity in premature infant stool is reduced, compared to near full-term infants (36-40 wks postconceptual age or PCA). There is a strong positive correlation between iAP activity and post-conceptual age (FIG. 31, panel E). When comparing IAP activities spanning 28-40 wks PCA, a one-way ANOVA and Tukey's multiple comparison test was performed and showed that the samples were statistically separated into two groups: the preterm group (PCA ≤35 wks) and the full-term group (PCA≥36 wks). Comparison of all stool samples from full-term infants (n=28) with all samples from premature infants (n=79) revealed the latter group to have significantly lower iAP activities ($p<0.0001$; one-tailed t-test). This is consistent with a switch between the fetal and 'adult' iAP isoforms at this developmental time point: a dynamic transition of IAP isozyme forms is associated with the maturation of fetal intestine [36]. Fetal isoform of iAP has a low biochemical activity, whereas adult iAP has robust catalytic rates. Thus, iAP activity is a biomarker that is directly related to postconceptual age. Such normative data across different gestational ages is needed for appropriate design and analysis of biomarker studies.

Low iAP activity also is associated with NEC diagnosis and NEC suspicion, but not sepsis. We discovered that iAP activity of infant stool collected on the same day of clinical NEC diagnosis was much lower than age-matched controls (red bar, FIG. 31, panel F), indicating that extremely low activity of iAP correlates with NEC. There is evidence that the reduced capacity of preterm infant intestine to dephosphorylate proinflammatory LPS may increase the risk of excessive inflammatory responses to bacterial colonization and NEC development [37]. Consistent with the idea that biochemical measures of iAP are NEC biomarkers, iAP activity of suspected NEC stool samples (pink bar, FIG. 31, panel F) also exhibited low rates, potentially heralding NEC due to the inability to manage bacterial colonization. Lastly, measure of iAP activity had no correlation with sepsis (FIG. 31, panel F and H).

(d) Approach

SPECIFIC AIM 1: Are iAP polymorphisms predictive of NEC predisposition? Without wishing to be bound by theory, infants diagnosed with NEC will have single nucleotide polymorphisms (SNPs) in the gene for intestinal alkaline phosphatase, ALPI, which lower their catalytic ability to detoxify lipopolysaccharide-dependent signaling of harmful Gram-negative bacteria. Our preliminary data indicates that the enzymatic ability of a single gene product, iAP, is correlated with NEC disease development. In patients with extreme forms of NEC (Bell stage II and III), the enzymatic activity is nearly non-existent and therefore, these infants are not able to moderate TLR4-dependent IL-8 transcription (FIG. 30, panel A). In early stage NEC (Bell stage I), enzymatic activity of iAP is lower than non-NEC samples, but higher than those in Bell stage II and III infants (FIG. 31, panel F).

Rationale. Genetic variations in TLR signaling have been studied, since this receptor has been shown to play an important role in disease. Naturally occurring single base pair changes in the genome that can alter protein function and disease processes, SNPs in TLR2, TLR4, TLR5, IRAK1 and TIRAP genes did not appear to be associated with NEC [38-45]. Understanding mechanism and causality are indispensable in identifying the earliest possible therapeutic option and to improving long-term outcome and life quality. This effort would lay the groundwork for ALPI screening for monogenic diseases and ALPI-based treatment for NEC. Such ALPI polymorphisms found in NEC patients would be the basis for Neonatal DDx, a screening tool for infants at birth.

Study enrollment. In this prospective study, preterm infants (non-NEC and NEC) in the neonatal intensive care units (NICU) of LSU School of Medicine and Washington University School of Medicine will be enrolled; single IRB and IBC approvals, in which parental consent for biospecimen collection and genetic testing is requested, are already in hand. Recruitment and enrollment of low birth weight (LBW) preterm infants (<2,500 g birthweight and/or <34 wks gestational age) are processes restricted by the number of infants born in our hospitals. We will enroll at least 120 (LBW) infants in year one, or at least 5 infants per month per site (please see Human Subjects Inclusion Reports 1 and 2). We anticipate 25-30 will develop NEC Bell stage II/III and a nearly equivalent number will have NEC Bell stage I.

Clinical information. This study is observational, neither invention nor deviation from standard clinical care in the NICU will be requested. The following clinical data will be obtained: demographics, medical history, antibiotics/antifungals/medications, physical examinations, complete blood counts, blood cultures, abdominal radiographs, surgical consultation notes, and feeding history. The study will be conducted in compliance with institutional, local, state, and federal regulations regarding use of PHI as defined by the Health Insurance Portability and Accountability Act.

Specimen collection. DNA samples are collected non-invasively from cheek swabs or from residual blood draws.

Methods. Genomic DNA will be isolated from (i) saliva swabs from infant cheek using or (ii) either peripheral blood cells or whole blood with QIAamp DNA Blood Mini Kit. For genetic sequencing, ALPI variants will be identified by Sanger sequencing of PCR products amplified from genomic DNA. We regularly sequence mutations in human proteins (e.g., [46]) with Eurofins. PCR will be performed with AmpliTaq polymerase, using a GeneAmp PCR system. Primer pairs used for DNA amplification are: 5' GGACCTTCAGTGGTTCCAGG-3' (f) and 5'CCAAGGACCTGGTTCTGGTC-3' (r). A list of variants identified by sequencing will be subject of filtering procedures, such as excluding common variants in the human population, low quality variants and synonymous changes. Sequence data can be compared with various public databases (single nucleotide polymorphism database (dbSNP [47]); the 1000 Genomes Project [48]; and the Exome Variant Server [49, 50]). Comparisons will seek the rare variants occurring at a frequency of <1% in controls. Initially, both inherited variants and de novo variants in NEC patients will be catalogued as Neonatal DDx.

Alkaline phosphatase enzyme activity is measured with use of 4-methylumbelliferyl phosphate (MUP) as a fluorescent substrate in the presence and absence of 10 mM L-phenylalanine, an inhibitor of iAP [51, 52]. Relative fluorescence units at 360/440 nm will be measured in samples using 96-well black optical bottom plates. Total AP activity was determined in mU/mg, in which U is the amount of enzyme hydrolysing 1 μmol of MUP/minute at pH 10 and 25° C. Determination of total protein in the stool supernatant is determined using Bradford assays. Protein standards (bovine serum albumin) and patient samples will be prepared, using molecular grade water as the diluent. Standards are run each day of data collection and must have a r2 value greater than 0.99 for acceptance.

Results. Without wishing to be bound by theory, infants who develop NEC will have at least one allele with non-conservative polymorphisms that gives rise to a loss-of-function phenotype. Lack of stool iAP activity (<240 U/mg) will confirm that the ALPI mutation gives rise to a loss-of-function phenotype. DNA sequence will identify SNP in infant ALPI gene; its relative amino acid position can be identified using homology models of AP crystal structures [53-55]. A disease gene responsible for as low as 5% of the population can be identified by sequencing just 200 unrelated patients [56]. Without wishing to be bound by theory, mutations will occur at the active site and/or dimerization interface of iAP [54, 57].

Statistical strategies for identification of disease-causing polymorphisms are based on nature of the disease mutation [58]. For example, statistical analyses will be conducted using a dominant model, comparing wildtype homozygous to both heterozygous and homozygous rare allele groups combined. This assumes that carrying at least one copy of the variant allele confers increased risk of disease. Primary outcome measures include presence of NEC, severity of disease (Bell stage II/III versus Bell stage I) and NEC-related bowel perforation.

Hardy-Weinberg equilibrium will be determined using a chi-square test to compare the observed genotype frequencies to those expected under Hardy-Weinberg equilibrium. Ordinal logistic regression will be used to compare severity of disease. Significance level will be set at $p<0.05$.

Alternative approaches. Statistical evaluation of the sequence data may require using a recessive model [56,59]. If polymorphisms associated with NEC predisposition are uncovered, future studies will involve linkage mapping and candidate gene analysis [60]. For autosomal dominant disorders, associations with defined disease interval were identified with linkage analyses of a large pedigree (e.g., [61, 62]). De novo dominant mutations can be identified by analysis of parent-child trios (e.g., [63]) or intersection of heterozygous variants across unrelated probands with the same de novo autosomal dominant disorder (e.g.,[64]).

Although modest sample sizes for less common diseases in preterm infants may limit power to detect associations, such studies are critical as a preliminary step to provide a targeted treatment for children, discover important insights into factors related to disease risk, and identify networks involved in disease pathogenesis.

SPECIFIC AIM 2: Does intestinal alkaline phosphatase protein levels in stool serve as a prognostic biomarker for NEC? The neonatology field is hampered by the inability to detect NEC early in the disease process. Without wishing to be bound by theory, microbe-induced inflammation in NEC results in increasing iAP protein levels in the gut lumen and stool. If asymptomatic or only exhibiting nonspecific symptoms, infants with early NEC will have detectable amounts of iAP 36-48 hrs. prior to NEC diagnosis. Our data indicate that prognostication for NEC is feasible. Although our clinical focus was stool collection at time of disease diagnosis, 5 of 25 NEC Bell stage II/III patients and 9 of the 19 NEC Bell stage I infants had stool samples serendipitously collected prior to disease onset; 19 of 62 non-NEC patients had a median 4 samples collected before 31 weeks. We will collect stool samples in a longitudinal series from each infant, measure twice weekly samples for iAP content, and model the prognostic capability of a continuous biomarker, NECPredict.

Statistical considerations. Study enrollment and clinical information protocols detailed in aim 1 will be followed for this aim. We will need 150 subjects to achieve 90% power for aim 2. This is based on simulation results, as existing sample size calculations for prognostic biomarkers [65-67]

are only appropriate for differences between two groups [68]. We perform a simulation study with four different combinations of (a #, a %) and examine our probability of detecting a significant difference from 0 for these coefficients. For n=50, 100, 150, or 200, we achieve power values greater than 0.8, 0.8, 0.9, and 0.95. This power analysis suggests that a sample size of n>100 is needed and that n=150 can provide a significant benefit compared to n=100.

Specimen collection & preparation. Continuous surveillance with a novel protein biomarker requires collection of stool from time of study participation to discharge. There are no identifiable risks to the patient, as noninvasive sample collection from disposed diapers is painless and causes no harm to fragile patients. Stool specimens will be collected every 3-4 days until infant reaches 37 wks post-conceptual age or is discharged. Estimates of average length of hospital stay is 49 days for infants [70] to 54 days (see preliminary data); ~15 samples will be collected from diapers per infant. A stool sample is termed 'NEC' if collected during the period from the first day of a radiological finding for NEC (Bell stage II or III) to last day of NEC management (antibiotic administration and no feeding by mouth). Collected sample is termed 'suspicion' from first day of 2+ clinical signs to the last day of medical management. A sample is 'control' if obtained on a day in which no NEC diagnosis was made.

Stool is stored in a 4° C. specimen NICU refrigerator, until samples are delivered to the lab. Upon receipt of each de-identified patient sample, stool is homogenized and a 200 mg/mL slurry is made with molecular grade water in a sterile microfuge tube. Following vortexing and centrifugation, the supernatant is collected, aliquoted, and banked at −80° C. [71]. Safe handling (gloves, lab coats, goggles), use of absorbent bench paper, decontamination with EPA-registered hospital disinfectant, and proper disposal of biohazards are followed.

Determination of relative iAP protein content. Duplicate denaturing SDS-PAGE gels will be run on stool supernatants to visualize all proteins in each lane and for immunoblotting detection of iAP. iBlot and iBind will be used for protein transfer and Western blot, respectively. Bands are quantified with Amersham Imager 600; relative iAP protein in stool sample is the fraction of protein found in human intestinal lysate tissue.

Arguably, the biggest source of confusion in quantitative immunoblotting is the role of protein loading and loading controls [72]. Immunoblot samples are often prepared according to total protein [73-75], assuming that the average protein content per cell is constant across different conditions. However, in our analyses, stool samples are not fractionated to lyse cells: only the gut lumen content is being evaluated. Therefore, total cellular protein cannot be determined, and the input must be normalized to some estimate of protein loading. We use two loading controls as well as total protein [76-81].

In FIG. 31, panel A, control experiments assessed the immunoblot workflow for accuracy and precision. Such experiments minimize over- or under-estimates of true differences in protein abundance. A serial dilution of a positive control (small intestinal tissue lysate) and negative control (purified bovine iAP) show our dynamic range and quantitative accuracy. The 60 kDa iAP signal from patient samples is determined; this value is ratioed to the difference between the positive control and negative control measurements.

Results. Without wishing to be bound by theory, we will detect iAP levels of 0.14±0.10 (mean±SE) compared to human small intestinal lysate from samples collected up to 7 days prior to NEC. Our preliminary data provide thresholds for anticipated immunoblot values. In stool samples at NEC diagnosis, iAP content was 1.59±0.48 more than human small intestinal lysate. Stool from non-NEC patients had an iAP content of 0.02±0.01. As these protocols are established and have been performed by 3 different operators successfully, we do not foresee technical problems.

With NECPredict, we will model the probability that a patient has signs or has been diagnosed with NEC as a function of the iAP content in the stool samples collected 3-5 days and prior 6-8 days prior. In this testing of the prognostic capability of a continuous biomarker, differences in mean values between NEC and control samples for relative iAP protein content will be tested by modeling the link between the probability of NEC diagnosis at any given day and iAP content in the diaper 3-5 days prior along with the diaper before that (6-8 days prior).

Specifically, NECPredict will use a generalized linear mixed effects model with NEC diagnosis as the response, iAP content of the last two collected samples as the predictors (fixed effect), and patient level error terms. We model whether a patient has signs of or has a diagnosis of NEC as: $\text{logit}\{P[NEC_{t,i}=1]\}=\alpha_1 D_{t-1,i}+\alpha_2 D_{t-2,i}+\beta+\varepsilon_i$, where $NEC_{t,i}=0$ if patient i is NEC negative at diaper collection time t and 1 if the patient has NEC diagnosis or NEC signs/diagnosis (separate analyses). $D_{t-1,I}$ and $D_{t-2,I}$ are the iAP contents of the last two collected diapers. $\varepsilon_i$ is a subject specific error term, that incorporates the dependence on time and individual for NEC diagnosis and diaper content. We use the lme4 package in R [83] to analyze this model. Significant positive estimated values of al indicate that high iAP content from the last collected diaper (about 3 days before) predicted future NEC diagnosis and $\alpha_2>0$ indicates that high iAP from the week prior predicts future NEC diagnosis. This information indicates iAP can be established as a prognostic biomarker for NEC.

In conclusion, in vitro results and clinical data will identify associations with these markers and NEC risk. Without wishing to be bound by theory, ALPI polymorphisms give rise to low iAP activity and Neonatal DDx can be used as a biomarker to identify infants at greatest risk for NEC. Second, the presence of iAP protein with NECPredict will have the strongest prognostic value and will identify NEC development prior to symptoms. These studies will be the first biochemical and physiological markers that links two NEC triggers: alterations in the microbiome with gut development. Another important outcome is that indiscriminate withholding of feeds and broad-spectrum prophylactic antibiotics can be minimized. Thus, these studies provide the first lab test that personalizes treatment in the NICU. Future directions may include iAP supplementation as a preventative strategy for NEC, as enzyme replacement therapy is an low-cost, low-risk approach for rare diseases that is often successful [84]. Lastly, these personalized biomarker approaches are not limited to children; iAP as a biomarker for infant gut inflammation has parallels to adult diseases, such as IBD.

REFERENCES CITED IN THIS EXAMPLE

1. Hackam, D. and M. Caplan, *Necrotizing enterocolitis: pathophysiology from a historical context*. Semin Pediatr Surg, 2018. 27(1): p. 11-18.
2. Bell, M. J., *Neonatal necrotizing enterocolitis*. N Engl J Med, 1978. 298(5): p. 281-2.

3. Kliegman, R. M. and M. C. Walsh, *Neonatal necrotizing enterocolitis: pathogenesis, classification, and spectrum of illness*. Curr Probl Pediatr, 1987. 17(4): p. 213-88.
4. Lin, P. W., T. R. Nasr, and B. J. Stoll, *Necrotizing enterocolitis: recent scientific advances in pathophysiology and prevention*. Semin Perinatol, 2008. 32(2): p. 70-82.
5. Hunter, C. J., et al., *Understanding the susceptibility of the premature infant to necrotizing enterocolitis (NEC)*. Pediatr Res, 2008. 63(2): p. 117-123.
6. Neu, J. and W. A. Walker, *Necrotizing enterocolitis*. New England Journal of Medicine, 2011. 364(3): p. 255-264.
7. Patel, J. C., et al., *Neonatal necrotizing enterocolitis: The long-term perspective/discussion*. Amer Surgeon, 1998. 64(6): p. 575.
8. Tam, A. L., A. Camberos, and H. Applebaum, *Surgical decision making in necrotizing enterocolitis and focal intestinal perforation: predictive value of radiologic findings*. J Pediatr Surg, 2002. 37(12): p. 1688-91.
9. Lin, P. W. and B. J. Stoll, *Necrotising enterocolitis*. Lancet, 2006. 368(9543): p. 1271-83.
10. Fawley, J. and D. M. Gourlay, *Intestinal alkaline phosphatase: a summary of its role in clinical disease*. J Surg Res, 2016. 202(1): p. 225-34.
11. Stewart, C. J., et al., *Preterm gut microbiota and metabolome following discharge from intensive care*. Sci Rep, 2015. 5: p. 17141.
12. Stewart, C. J., et al., *The preterm gut microbiota: changes associated with necrotizing enterocolitis and infection*. Acta Paediatr, 2012. 101(11): p. 1121-7.
13. Rusconi, B., M. Good, and B. B. Warner, *The microbiome and biomarkers for necrotizing enterocolitis: are we any closer to prediction?* J Pediatr, 2017. 189: p. 40-47 e2.
14. Goldberg, R. F., et al., *Intestinal alkaline phosphatase is a gut mucosal defense factor maintained by enteral nutrition*. Proc Natl Acad Sci USA, 2008. 105(9): p. 3551-6.
15. Shifrin, D. A., Jr., et al., *Enterocyte microvillus-derived vesicles detoxify bacterial products and regulate epithelial-microbial interactions*. Curr Biol, 2012. 22(7): p. 627-31.
16. Shifrin, D. A., Jr. and M. J. Tyska, *Ready . . . aim . . . fire into the lumen: a new role for enterocyte microvilli in gut host defense*. Gut Microbes, 2012. 3(5): p. 460-2.
17. Ening, T., et al., *The roles of bacteria and TLR4 in rat and murine models of necrotizing enterocolitis*. J Immunol, 2006. 177(5): p. 3273-82.
18. Leaphart, C. L., et al., *A critical role for TLR4 in the pathogenesis of necrotizing enterocolitis by modulating intestinal injury and repair*. J Immunol, 2007. 179(7): p.4808-20.
19. Gribar, S. C., et al., *Reciprocal expression and signaling of TLR4 and TLR9 in the pathogenesis and treatment of necrotizing enterocolitis*. J Immunol, 2009. 182(1): p. 636-46.
20. Good, M., et al., *Breast milk protects against the development of necrotizing enterocolitis through inhibition of Toll-like receptor 4 in the intestinal epithelium via activation of the epidermal growth factor receptor*. Mucosal Immunol, 2015. 8(5): p. 1166-79.
21. Thomas, D. W. and D. H. Henton, *The use of fecal alkaline phosphatase as an indicator of intestinal damage*. Digestion, 1985. 31(2-3): p. 82-8.
22. Goldman, J., et al., *Development of biomarkers to optimize pediatric patient management: what makes children different?* Biomark Med, 2011. 5(6): p. 781-94.
23. Smith, P. B., et al., *Safety monitoring of drugs receiving pediatric marketing exclusivity Pediatrics*, 2008. 122(3): p. e628-33.
24. Benjamin, D. K., Jr., et al., *Safety and transparency of pediatric drug trials*. Arch Pediatr Adolesc Med, 2009. 163(12): p. 1080-6.
25. Williams, K., et al., *Standard 6: age groups for pediatric trials*. Pediatrics, 2012. 129(Suppl 3): p. S153-60.
26. Laventhal, N., B. A. Tarini, and J. Lantos, *Ethical issues in neonatal and pediatric clinical trials*. Pediatr Clin North Am, 2012. 59(5): p. 1205-20.
27. Joseph, P. D., J. C. Craig, and P. H. Caldwell, *Clinical trials in children*. Br J Clin Pharmacol, 2015. 79(3): p. 357-69.
28. Kern, S. E., *Challenges in conducting clinical trials in children: approaches for improving performance*. Expert Rev Clin Pharmacol, 2009. 2(6): p. 609-617.
29. Institute of Medicine. *Envisioning a Transformed Clinical Trials Enterprise in the United States: Establishing An Agenda for 2020: Workshop Summary*. 2012: Washington (DC); The National Academies Press.
30. Lee, J. S., W. A. Kibbe, and R. L. Grossman, *Data harmonization for a molecularly driven health system*. Cell, 2018. 174(5): p. 1045-1048.
31. Janes, K. A., *An analysis of critical factors for quantitative immunoblotting*. Sci Signal, 2015. 8(371): p. rs2.
32. Lee, J. W., et al., *Fit-for-purpose method development and validation for successful biomarker measurement*. Pharm Res, 2006. 23(2): p. 312-28.
33. Lichtman, J. S., et al., *Host-centric proteomics of stool: a novel strategy focused on intestinal responses to the gut microbiota*. Mol Cell Proteomics, 2013. 12(11): p. 3310-8.
34. Arboleya, S., et al., *Establishment and development of intestinal microbiota in preterm neonates*. FEMS Microbiol Ecol, 2012. 79(3): p. 763-72.
35. Arboleya, S., et al., *Intestinal microbiota development in preterm neonates and effect of perinatal antibiotics*. J Pediatr, 2015. 166(3): p. 538-44.
36. Mulivor, R. A., V. L. Hannig, and H. Harris, *Developmental change in human intestinal alkaline phosphatase*. Proc Natl Acad Sci USA, 1978. 75(8): p. 3909-12.
37. Milani, C., et al., *The first microbial colonizers of the human gut: composition, activities, and health implications of the infant gut microbiota*. Microbiol Mol Biol Rev, 2017. 81(4).
38. Cuna, A., L. George, and V. Sampath, *Genetic predisposition to necrotizing enterocolitis in premature infants: current knowledge, challenges, and future directions*. Semin Fetal Neonatal Med, 2018.
39. Sampath, V., et al., *A functional ATG I6L I (T300A) variant is associated with necrotizing enterocolitis in premature infants*. Pediatr Res, 2017. 81(4): p. 582-588.
40. Sampath, V., et al., N*ecrotizing enterocolitis is not associated with sequence variants in antioxidant response genes in premature infants*. J Pediatr Gastroenterol Nutr, 2016. 62(3): p. 420-3.
41. Franklin, A. L., et al., *Are immune modulating single nucleotide polymorphisms associated with necrotizing enterocolitis?* Sci Rep, 2015. 5: p. 18369.
42. Sampath, V., et al., *SIGIRR genetic variants in premature infants with necrotizing enterocolitis*. Pediatrics, 2015. 135(6): p. e1530-4.
43. Markel, T. A., H. Engelstad, and B. B. Poindexter, *Predicting disease severity of necrotizing enterocolitis: how to identify infants for future novel therapies*. J Clin Neonatol, 2014. 3(1): p. 1-9.

44. Sampath, V., et al., *The NFKB1 (g.-245 I9delATTG) variant is associated with necrotizing enterocolitis (NEC) in premature infants.* J Surg Res, 2011. 169(1): p. e51-7.
45. Bokodi, G., et al., *Association of interferon gamma T+874A and interleukin 12 p40 promoter CTCTAA/GC polymorphism with the need for respiratory support and perinatal complications in low birthweight neonates.* Arch Dis Child Fetal Neonatal Ed, 2007. 92(1): p. F25-9.
46. Richard, J., et al., *Allostery wiring map for kinesin energy transduction and its evolution.* J Biol Chem, 2016. 291(40): p. 20932-20945.
47. Sherry, S. T., et al., *dbSNP: the NCBI database of genetic variation.* Nucleic Acids Res, 2001. 29(1): p. 308-11.
48. Genomes Project, C., et al., *A map of human genome variation from population-scale sequencing.* Nature, 2010. 467(7319): p. 1061-73.
49. International HapMap, C., et al., *Integrating common and rare genetic variation in diverse human populations.* Nature, 2010. 467(7311): p. 52-8.
50. Cooper, G. M. and J. Shendure, *Needles in stacks of needles: finding disease-causal variants in a wealth of genomic data.* Nat Rev Genet, 2011. 12(9): p. 628-40.
51. Ghosh, N. K. and W. H. Fishman, *On the mechanism of inhibition of intestinal alkaline phosphatase by Lphenylalanine. I. Kinetic studies.* J Biol Chem, 1966. 241(11): p. 2516-22.
52. Ghosh, N. K. and W. H. Fishman, *L-phenylalanine inhibiton of rat intestinal alkaline phosphatase: a homosteric phenomenon.* Arch Biochem Biophys, 1968. 126(2): p. 700-6.
53. Le Du, M. H., et al., *Crystal structure of alkaline phosphatase from human placenta at 1.8 A resolution. Implication for a substrate specificity.* J Biol Chem, 2001. 276(12): p. 9158-65.
54. Hoylaerts, M. F., et al., *Mammalian alkaline phosphatase catalysis requires active site structure stabilization via the N-terminal amino acid microenvironment.* Biochemistry, 2006. 45(32): p. 9756-66.
55. Ghosh, K., et al., *Crystal structure of rat intestinal alkaline phosphatase—role of crown domain in mammalian alkaline phosphatases.* J Struct Biol, 2013. 184(2): p. 182-92.
56. Zhi, D. and R. Chen, *Statistical guidance for experimental design and data analysis of mutation detection in rare monogenic mendelian diseases by exome sequencing.* PLoS One, 2012. 7(2): p.e31358.
57. Fosset, M., D. Chappelet-Tordo, and M. Lazdunski, *Intestinal alkaline phosphatase. Physical properties and quaternary structure.* Biochemistry, 1974. 13(9): p. 1783-8.
58. Boycott, K. M., et al., *Rare-disease genetics in the era of next-generation sequencing: discovery to translation.* Nat Rev Genet, 2013. 14(10): p. 681-91.
59. Walsh, T., et al., *Whole exome sequencing and homozygosity mapping identify mutation in the cell polarity protein GPSM2 as the cause of nonsyndromic hearing loss DFNB82.* Am J Hum Genet, 2010. 87(1): p. 90-4.
60. Sunyaev, S. R., *Inferring causality and functional significance of human coding DNA variants.* Hum Mol Genet, 2012. 21(R1): p. R10-7.
61. Ng, S. B., et al., *Exome sequencing identifies the cause of a mendelian disorder.* Nat Genet, 2010. 42(1): p. 30-5.
62. Fiskerstrand, T., et al., *Familial diarrhea syndrome caused by an activating GUCY2C mutation.* N Engl J Med, 2012. 366(17): p. 1586-95.
63. Gibson, W. T., et al., *Mutations in EZH2 cause Weaver syndrome.* Am J Hum Genet, 2012. 90(1): p. 110-8.
64. Hood, R. L., et al., *Mutations in SRCAP, encoding SNF2-related CREBBP activator protein, cause Floating-Harbor syndrome.* Am J Hum Genet, 2012. 90(2): p. 308-13.
65. Schmoor, C., W. Sauerbrei, and M. Schumacher, *Sample size considerations for the evaluation of prognostic factors in survival analysis.* Stat Med, 2000. 19(4): p. 441-52.
66. Tsim, S., et al., *Diagnostic and prognostic biomarkers in the rational assessment of mesothelioma (DIAPHRAGM) study: protocol of a prospective, multicentre, observational study.* BMJ Open, 2016. 6(11): p. e013324.
67. Chen, D. T., et al., *Strategies for power calculations in predictive biomarker studies in survival data.* Oncotarget, 2016. 7(49): p. 80373-80381.
68. Dang, Q., S. Mazumdar, and P. R. Houck, *Sample size and power calculations based on generalized linear mixed models with correlated binary outcomes.* Comput Methods Programs Biomed, 2008. 91(2): p. 122-7.
69. Rose, C., et al., *The characterization of feces and urine: a review of the literature to inform advanced treatment technology.* Crit Rev Environ Sci Technol, 2015. 45(17): p. 1827-1879.
70. Holman, R. C., et al., *Necrotising enterocolitis hospitalisations among neonates in the United States.* Paediatric and perinatal epidemiology, 2006. 20(6): p. 498-506.
71. Flores, R., et al., *Collection media and delayed freezing effects on microbial composition of human stool.* Microbiome, 2015. 3: p. 33.
72. Marcus, E., *Credibility and reproducibility.* Cell, 2014. 159(5): p. 965-966.
73. Olson, B. J. and J. Markwell, *Assays for determination of protein concentration.* Curr Protoc Protein Sci, 2007. Chapter 3: p. Unit 3 4.
74. Bradford, M. M., *A rapid and sensitive method for the quantitation of microgram quantities of protein utilizing the principle of protein-dye binding.* Anal Biochem, 1976. 72: p. 248-54.
75. Zor, T. and Z. Selinger, *Linearization of the Bradford protein assay increases its sensitivity: theoretical and experimental studies.* Anal Biochem, 1996. 236(2): p. 302-8.
76. Jensen, K. J., et al., *An ERK-p38 subnetwork coordinates host cell apoptosis and necrosis during coxsackievirus B3 infection.* Cell Host Microbe, 2013. 13(1): p. 67-76.
77. Kang, B. H., et al., *Simultaneous profiling of 194 distinct receptor transcripts in human cells.* Sci Signal, 2013. 6(287): p. rs13.
78. Bose, A. K. and K. A. Janes, *A high-throughput assay for phosphoprotein-specific phosphatase activity in cellular extracts.* Mol Cell Proteomics, 2013. 12(3): p. 797-806.
79. Eaton, S. L., et al., *Total protein analysis as a reliable loading control for quantitative fluorescent Western blotting.* PLoS One, 2013. 8(8): p. e72457.
80. Collins, M. A., et al., *Total protein is an effective loading control for cerebrospinal fluid western blots.* J Neurosci Methods, 2015. 251: p. 72-82.
81. Moritz, C. P., *Tubulin or Not Tubulin: Heading Toward Total Protein Staining as Loading Control in Western Blots.* Proteomics, 2017. 17(20).
82. Breslow, N. and D. Clayton, *Approximate inference in generalized linear mixed models.* Journal of the American Statistical Association, 1993. 88(421): p. 9-25.
83. Bates, D., et al., *Fitting Linear Mixed-Effects Models Using lme4.* Journal of Statistical Software, 2015. 67(1): p. 1-48.

84. Ohashi, T., *Enzyme replacement therapy for lysosomal storage diseases*. Pediatr Endocrinol Rev, 2012. 10(Suppl 1): p. 26-34.

Statistical Design and Power for Prognostic NEC Clinical Study

Statistical analyses will be conducted using R (R Core Team, 2018. *R: A language and environment for statistical computing*. R Foundation for Statistical Computing, Vienna, Austria). Tests of significance will be two-tailed tests conducted at the 5% significance level. Statistical assumptions will be tested and suitable modifications will be made to the model if necessary. Missing data will be handled with imputation and sensitivity analysis. If the proposed statistical analysis techniques are found to be untenable, we will use alternative techniques, possibly falling back on strategies that are guaranteed to provide appropriate estimates along with non-parametric measures of variability.

Study Design for Aim 2: The study will be a prospective observational study with pre-term infants enrolled as they arrive. Stool samples from disposed diapers will be collected every 3-4 days until the infant reaches 37 weeks post-conceptual age or is discharged. Stool samples for patients with clinically evident NEC will be analyzed along with a random subset of stool samples from control patients.

Sample Size: For aim 2, we will need 150 subjects to achieve 90% power. This is based on simulation results, as existing sample size calculations are only appropriate for differences between two groups [1]. In contrast, our model requires testing the prognostic capability of a continuous biomarker.

We will model the probability that a patient has signs or has been diagnosed with NEC as a function of the iAP content in the stool sample collected 3-5 days prior as well as the iAP content in the stool sample collected 6-8 days prior. We allow for each patient to have an individual level of susceptibility to NEC, captured in the patient's random effect term. The patient's random effect is combined with the iAP content effect and transformed by a function, the inverse of the logit function, which constrains values between zero and one, allowing us to estimate probabilities.

In symbolic terms, we model the probability that a patient has signs of or has been diagnosed with NEC as:

$$\text{logit}\{P[NEC_{t,i}=1]\} = \alpha_1 D_{t-1,i} + \alpha_2 D_{t-2,i} + \beta + \varepsilon_i$$

where $NEC_{t,i}=0$ if patient i is NEC negative at diaper collection time t and 1 if the patient has signs of NEC (Bell stage I) or NEC diagnosis (Bell stage II/III). $D_{t-1,i}$ and $D_{t-2,i}$ are the iAP contents of the last two collected diapers. $\varepsilon_i$ is a subject specific error term that incorporates the correlation within individuals for NEC diagnosis probability. We model the above with a generalized linear mixed model using the R program lme4. To determine how many patients we should enroll, we perform a simulation study to determine how well we can detect significant differences in α4 and α8 (the effect sizes of the last two diapers iAP content on future NEC occurrence probability) from 0, which would show a prognostic effect of iAP content for predicting NEC diagnosis or signs of NEC, based on the last two diapers collected. This information could help clinicians predict whether or not a patient is at high risk for NEC.

We perform a simulation study with four different combinations of (α4,α8) and examine our probability of detecting a significant difference from 0 for these coefficients. These scenarios are shown in FIG. 32, along with the implied probability of NEC diagnosis/suspicion for patients with the mean iAP content for the NEC and non-NEC patient groups, which are 1.59 and 0.02, respectively.

These four scenarios represent different effects of iAP diaper content on the probability of NEC diagnosis. In both scenarios 1 and 2, only the last diaper predicts whether or not a patient will have NEC at the next diaper time since $\alpha_2=0$. Scenario 1 has more separation between the NEC probability for the high iAP group and low iAP group than in scenario 2. Likewise, scenarios 3 and 4 have differing probability differences for the two groups. For scenarios 3 and 4, $\alpha_2=1$, indicating that the iAP content found in the diaper collected two time points prior (six to eight days) is prognostic for NEC status. These values were chosen in part because they resulted in 9-12% of patients in each scenario having NEC diagnosis, which coincided with previously seen incidences of NEC diagnoses. We simulate 1,000 replications of each of the four scenarios for a sample size of n=50, 100, 150, or 200 with simplified assumptions.

For each patient, we assume 2 months of follow-up with bi-weekly diaper collection, totaling about 16 diaper collections for each patient. We will evaluate NEC status at diaper collection days 3-16 to see how the iAP content of the last two diaper cycles predict NEC diagnosis. To conduct the simulation, we first draw a NEC+ indicator from a Bernoulli distribution with probability 0.09, which is the empirical probability of having NEC for all previously assayed diapers. For each NEC patient, we generate their 16 iAP diaper content values $D_{1,i}, \ldots, D_{16,i}$ from a multivariate lognormal distribution with mean vector −3.90, standard deviation 1.69, and positive correlation between each observed iAP value. To generate a multivariate lognormal sample, we generate a multivariate normal distribution with the above mean vector and implied covariance matrix and then exponentiate these values. For individuals that were not considered as NEC positive, we generated their iAP values $D_{1,i}, \ldots, D_{16,i}$ from a multivariate lognormal distribution with mean vector −0.68, standard deviation 1.57, and positive correlation between each observed iAP value. These means and standard deviations were chosen because they were the estimated maximum likelihood estimates for a lognormal distribution using the iAP values from NEC+ and NEC− patients, respectively.

Then we generate the probability of NEC for patient i at time t=3, . . . ,16 as $\alpha_1 D_{t-1,i} + \alpha_2 D_{t-2,i} + \beta$ and the NEC status is drawn from a Bernoulli random variable with this probability. FIG. 33 shows the simulations for correctly declaring $\alpha_1 > 0$ across the simulations for each sample size, the probability of correctly declaring $\alpha_2 > 0$ and the probability of correctly declaring both $\alpha_1 > 0$ and $\alpha_2 > 0$. For scenarios 1 and 2, this triple is listed as $(P_1, -, -)$ and for scenarios 2 and 3, this triple is listed as $(P_1, P_2, P_3)$.

Based on the simulations above, we see that for n=50, none of the 4 scenarios have power above 0.80. For n=100, we achieved above a power of 0.80 for each scenario, but only detected significant differences for both $\alpha_1$ and $\alpha_2$ with probability 0.819 in scenario 3. With n=150, we had power above 0.9 for each of the four scenarios and for n=200 we had power above 0.95 for each of the four scenarios. This power analysis indicates that a sample size of n≥100 is needed and that n=150 can provide a significant benefit compared to n=100.

REFERENCES CITED IN THIS EXAMPLE

1. Dang, Q., S. Mazumdar, and P. R. Houck, *Sample size and power calculations based on generalized linear mixed-*

*models with correlated binary outcomes. Comput Methods Programs Biomed,* 2008. 91(2):p. 122-7.

Example 12

There are four different alkaline phosphatases in humans that are tissue-specific: intestinal alkaline phosphatase, placental-like alkaline phosphatase, tissue nonspecific alkaline phosphatase, and germ-cell alkaline phosphatase. At the amino acid level, tissue-specific alkaline phosphatase isozymes are 86-98% identical to one another, but 52-56% identical when compared to tissue non-specific alkaline phosphatase. Furthermore, the iAP gene, ALPI, has 403 missense polymorphisms that span the entire sequence: more than 50% of the amino acids in iAP have at least one known mutation.

Our innovation is use of two biochemical measures of intestinal alkaline phosphatase (iAP), shed in stool, as a molecular biomarker for NEC in premature infants. The appeal of iAP as a biomarker lies in its tissue-specific expression in the small intestine and its secretion into the gut lumen iAP would only be measurable in stool as a response to controlling bacterial colonization. Also, it is detectable in human stool samples in healthy individuals; responsible for majority of AP enzymatic activity in stool; and used as a measure of toxic damage to the small intestine in animal models.

(A) Immunoassay-based detection of high iAP levels is a biomarker for necrotizing enterocolitis, but not sepsis. Our prospective study evaluated it in human preterm infants. We assessed the independent correlation of 2 stool biomarkers, which comprise NECDetect, in 136 premature infants [median gestational age=28.3 weeks; 50% female; 64% African-American, 32% Caucasian; 4% Hispanic]. High amounts of fecal iAP protein is associated with clinical NEC diagnosis; these levels were equal to or greater than what is found in a human small intestine enterocyte. iAP content in stool is expected to increase from released membrane vesicles loaded with iAP, if there was risk of bacteria-induced inflammation. In contrast, non-diseased patients had very low amounts of iAP protein in stool. Thus, little iAP is shed into the gut lumen, when no dysbiosis is imminent. Sensitivity and specificity of fecal iAP content is >95%. Unlike other candidate NEC biomarkers, fecal iAP levels had no measurable correlation with other non-GI infections or sepsis, a frequent co-morbidity that can confound diagnosis of NEC.

(B) iAP is the only human alkaline phosphatase recoverable from stool proteomics and has several candidate peptides that may be used for absolute quantitative determination of iAP abundance by mass spectrometry. The combination of liquid chromatography and tandem mass spectrometry (LC-MS/MS) provides a flexible, dynamic platform for the simultaneous identification and quantification of up to thousands of proteins in fecal samples. Our initial shotgun proteomic analysis of a preterm infant stool sample showed that 635 human proteins were detected in the contents of the gut lumen, or the secreted host proteome. This is consistent with the (i) 612 proteins identified in gnobiotic mice and (ii) 234 human proteins in adult stool.142 We confirmed that there were 21 unique tryptic iAP peptides (a subsetare shown in FIG. 34) and these peptides covered 50% of the iAP sequence. Our data are consistent with prior Human Proteome Map studies, but exceeds their reported protein coverage of 32%. Importantly, no other human alkaline phosphatase was recovered from infant stool.

(C) High polymorphism frequency of the iAP gene in the African American population, which may be correlated higher disease incidence, may result in spurious results for both affinity-based and MSbased protein measurements. Sequence information from unrelated individuals in order to ascertain the frequency distribution of iAP polymorphisms. Only in the African-American population (n=12,487) were there iAP polymorphisms, or alleles that were greater than 1% of the population (FIG. 34, panel B). Estimated frequencies for common alleles V201, R33L, R92C, R144H, and T2071 were 4.8, 2.6, 1.9, 4.2, and 3.1%, respectively. Polymorphisms in the total population (blue circles, FIG. 34, panel C) give rise to changes in peptide mass by a change in sidechain molecular weight. Two polymorphisms, common in the African-American population (purple circles, FIG. 34, panel C), result in loss of trypsin cleavage sites, which in turn produces a hundredfold change in peptide mass. Peptide mass changes, irrespective of magnitude, preclude MS identification and quantitation of the protein with accuracy. These data raise concerns not only about the validity of correlating SNPs with affinity-based protein measurement, but also for MS techniques that could give spurious results where minor allele frequencies approach 5%.

Example 13

Necrotizing enterocolitis (NEC) is a common neonatal gastrointestinal (GI) tract emergency with a high mortality ratel and long-term morbidities, including short-gut syndrome, nutritional deficiency, and neurodevelopmental delay.2,3 Suspected NEC presents with mild, nonspecific symptoms that frequently resolve with minimal intervention; no clinical test is an established criterion standard for suspected NEC. Radiographic evidence, such as *pneumatosis intestinalis*, is used to diagnose severe or advanced disease but has a sensitivity as low as 44%,4 has limited specificity, 5 and lacks concordance in interpretation.6-8

There have been many efforts to discover a molecular diagnostic biomarker for NEC (FIG. 35A). Despite the publication of more than 2500 prior biomarker studies, meta-analyses have failed to identify an optimal NEC biomarker for routine clinical use.9-11 The design and power of these studies raise concern: fewer than 30 articles in each decade of analysis were deemed appropriate for meta-analysis. The focus on inflammation and repair proteins in these studies is problematic (FIG. 35B). Late-stage disease with systemic inflammatory damage is not ideal for biomarker evaluation because no period of disease reversibility can be defined.12 Furthermore, proteins involved in inflammation have limited positive predictive value because sepsis is a comorbidity in 35% to 60% of NEC cases.13-17

Necrotizing enterocolitis has been argued to be the antecedent of some cases of late-onset neonatal sepsis (LOS). Neonates, particularly very low-birth-weight infants, are susceptible to sepsis owing to prolonged hospitalizations, invasive instrumentation, underdeveloped innate immunity, and altered immunological responses. The latter 2 physiological states, coupled with an immature intestinal barrier function, can give rise to NEC.18,19 From both epidemiological and clinical standpoints, sepsis can confound the use of inflammation proteins as a biomarker for NEC. Sepsis and NEC require careful differential diagnosis, as both may be lethal if not diagnosed and treated appropriately.

This study evaluated the use of intestinal alkaline phosphatase (TAP) as a diagnostic biomarker for NEC. Recent findings indicate that NEC is preceded and accompanied by changes in gut microbiota (FIG. 35C) and that it is associated with host immune pathways responsible for intestinal inflammation.19,20 Intestinal alkaline phosphatase detoxifies the surface lipopolysaccharide (LPS) of harmful bacteria by cleaving inorganic phosphate. A component of gram-negative bacterial cell walls, LPS is a potent inducer of innate immune signaling through toll-like receptor 4. Robust TAP function neutralizes the LPS signal, prevents inappropriate proinflammatory signal cascades in the gut, and contributes to beneficial microbiota maturation.

Because TAP activity precedes the initiation of signaling cascades that trigger inflammation, we evaluated the abundance and enzyme activity of TAP shed in stool as measures of the pathobiological need and ability to maintain host-microbiota homeostasis, respectively. A multicenter, prospective diagnostic study was conducted to assess the association of 2 TAP biochemical measures with disease severity. As a common core protein in the human stool proteome,21 IAP is ideal for noninvasive testing. Content of IAP in stool is expected to increase from released membrane vesicles loaded with IAP if there were risk of bacterial-induced inflammation.22,23

Methods

Study Design. During a 3-year period (May 2015 to November 2018), preterm infants born younger than 37 weeks gestational age with a birth weight less than 1500 grams were enrolled at Children's Hospital of New Orleans (n=29; New Orleans, Louisiana) and Touro Infirmary Hospital (n=68; New Orleans, Louisiana). Preterm infants born younger than 37 weeks gestational age were enrolled at St Louis Children's Hospital (n=39; St Louis, Missouri). Written informed consent of study participants was obtained from a parent or guardian. All infants were sought for study inclusion, thereby forming a consecutive sampling series.

Deidentified Clinical Data. Clinical data, which included gestational age, birthweight, Apgar scores, delivery type, race/ethnicity, sex, and disposition (ie, death, discharge, or transfer to another facility), were extracted from medical records every 3 months. Of these, only race/ethnicity was defined by a parent. In-hospital data included feeding, antibiotic treatment, laboratory and radiology results, and surgical notes. Clinical findings of NEC (modified Bell stage 1-3), sepsis, and other confirmed non-GI tract infections were reviewed by attending physicians.

To protect confidentiality and anonymity, each enrolled patient was provided a code, which allowed for research tracking and removed any clues to the individual's identity. Every three months, patient records were evaluated to determine clinical correlatives. Clinical data were extracted from medical records into a relational clinical database. Demographic information and initial clinical data included gestational age, birth weight, Apgar scores, delivery type, race, gender, and final outcome (death, discharge, or transfer). Lastly, a second set of clinical information was obtained: antibiotic use, diet, serum AP, radiology reports, length of stay in NICU, surgery, and mortality. Human milk exposure is calculated as the mean percent of feeding from human milk as a function of the total days that the subjects were in the study. For NEC cases, only pre-event exposures were considered for human milk. Antibiotic exposures were considered in aggregate; antibiotics were always parentally administered to subjects. Percent of days of age on antibiotics is related to the number of days that the subjects were in the study. For NEC cases, only pre-event exposures were considered for antibiotics.

Disease Definitions. Different definitions of NEC have been suggested.26-29 For this study, 2 categories of NEC, derived from clinical documentation, were used (eTable 1). Radiological signs were defining criteria for our NEC categories; abdominal signs and clinical and laboratory findings were secondary criteria. Suspected NEC was defined as concern for disease based on abnormal clinical and laboratory findings without evidence of *pneumatosis intestinalis* or portal venous gas on abdominal radiographic images. Severe NEC was defined by radiologic evidence of *pneumatosis intestinalis* and/or portal venous gas. Patients diagnosed with spontaneous intestinal perforation (SIP) were excluded from the study (eTable 2). Diagnosis of neonatal LOS required the appearance of abnormal clinical findings at least 72 hours after birth and blood cultures positive for bacteria not considered a contaminant30,31 (eTable 3). Infants with other confirmed non-GI tract infections had clinical findings with bacterial, viral, or fungal infections identified in body fluids other than blood. The summary of cohorts and diagnoses of NEC, SIP, sepsis, and non-GI tract infections are provided in eTable 4 to eTable 11.

Clinical findings of NEC diagnosis, NEC suspicion, sepsis, and other confirmed non-GI infections were identified from review of clinical documentation. The research definition of NEC did not always align with the clinical diagnosis of the patient. For this study, NEC and suspected NEC were physician-directed clinical diagnoses in which radiologic signs were the defining criteria and abdominal signs, clinical findings, and lab findings further confirmed diagnosis (eTable 1). NEC suspicion (eTable 1) was defined as an infant with concern for early disease based on clinical and laboratory abnormalities without evidence of *pneumatosis intestinalis* on radiography. Instead, infants suspected of NEC exhibited one or more radiologic signs including mild intestinal dilation, mild intestinal ileus, thickened bowel walls, or paucity/absence of bowel gas. One or more of the clinical or abdominal signs and symptoms in addition to one or more laboratory finding(s) including decreased platelets, decreased or increased white blood cells, decreased absolute neutrophil count, increase in number of immature neutrophils, heme-positive stool, metabolic acidosis) were also required. Clinical and abdominal signs and symptoms included bilious aspirates, emesis, bloody stool, feeding intolerance, increased pre-feed gastric residual volume, increased apneas and/or bradycardias, temperature instability, lethargy, generalized clinically ill appearing, mild to moderate abdominal distention and, abdominal wall discoloration.

Severe NEC (eTable 1) was defined by radiological evidence of *pneumatosis intestinalis* and/or portal venous gas or pathological findings on surgical or postmortem intestinal samples. Pneumoperitoneum, which is free intra-bdominal air resulting from a perforation, was considered NEC when accompanied by evidence of *pneumatosis intestinalis* on radiography, as well as abdominal signs found in definite NEC. Additional signs included moderate to severe abdominal distention and/or abdominal tenderness and/or hypoactivity/absence of bowel sounds and/or abdominal wall discoloration, abdominal cellulitis, fixed right lower quadrant abdominal mass, and or signs of peritonitis. NEC diagnosis was categorized by at least one senior clinician and two additional senior research clinicians by case review, note review, x-ray and operative findings.

Although clinical presentation and medical management is similar to that of NEC, patients with spontaneous intestinal perforation (SIP), which is thought to be a different disease altogether (eTable 2), were excluded from the study. Key differences distinguishing SIP from NEC include absence of *pneumatosis intestinalis* on abdominal radiography, an earlier onset of symptoms, focal hemorrhagic intestinal necrosis (rather than coagulative necrosis characteristic of NEC) on pathologic specimen, and an overall, more benign clinical course, both preceding and following diagnosis. Overlapping medical management of both SIP and NEC processes include cessation of enteral feeds, gastric decompression, intravenous antibiotics, and peritoneal drainage if indicated. S8, S9

Diagnosis of neonatal sepsis is variable and complicated by the usage of biomarkers with overall low sensitivity, such as alterations in white blood cell count indices, low absolute neutrophil counts, high immature-to-total (I:T) neutrophil ratio, and elevated serum C-reactive protein levels.S10 Positive blood cultures at 3 or more days of age for late-onset septicemia is considered the gold standard for diagnosis of neonatal sepsis. However, cultures are frequently negative, likely related to low inoculated blood volume that may not fully represent a true bacteremia and exposure to prenatal antibiotics that may suppress bacterial growth.S11-S13

In this study, infants diagnosed with sepsis include only those with laboratory and clinical findings that are confirmed after seventy-two hours of age (eTable 3). Laboratory findings included blood culture or non-culture microbial testing that confirmed the presence of bacteria in blood that was not considered a contaminant.S14,S15 Clinical findings that were used to support the diagnosis of sepsis included a range of criteria from temperature instability and respiratory distress to abnormal perfusion, bleeding issues, and unexplained jaundice.

In addition, infants with other confirmed non-GI infections and infants who were infection-negative were classified and documented in this study (eTable 3). Other confirmed infections were those confirmed bacterial, viral or fungal infections identified in normally sterile body fluids. Clinical findings were similar to those diagnosed with sepsis. An infection-negative classification was comprised of infants with suspected, but not confirmed, infections and infants not suspected of any infections for which no laboratory tests were ordered concerning an infection and were asymptomatic. Those suspected of infections had laboratory findings that included, but were not limited to, leukocytosis or leukopenia, elevated immature neutrophil counts, low absolute neutrophil counts, and elevated C-reactive protein and serum alkaline phosphate. Clinical findings for these infants were identical to those with confirmed sepsis diagnosis.

Sample Collection and Extraction of Soluble Gut Lumen Contents. A simple protocol for stool handling was developed for evaluation of IAP processes in the gut lumen. After written parental consent was obtained, samples were collected biweekly from infant diapers and stored in a 4° C. specimen refrigerator at hospital sites until transport to the laboratory. On receipt, stool samples were prepared for luminal content analyses, and a 200 mg/mL slurry was made with molecular grade water in a sterile microfuge tube. Following vortexing and centrifugation, the supernatant was collected, aliquoted, and banked at −80° C. (FIG. 35E).

Stool samples were collected serially from disposed diapers of study subjects after spontaneous stooling. Initial collection at St. Louis Children's Hospital was only one sample per patient, but shifted to weekly collections per patient. From Children's Hospital of New Orleans and Touro Infirmary Hospital, samples were collected prospectively. Stooling frequency from enrolled infants matched those reported in the literature: for the general pediatric population, the mean bowel frequency is greater than 8 evacuations per week and does not vary in the first 2 years of life.S16 Upon documentation of patient code and date of sample acquisition by nursing staff, stool was stored briefly in hospital specimen 4° C. refrigerators, until transport to the lab in cooler boxes. Stool samples from NEC and from non-NEC patients had a pH between 6 and 7 (ColorpHast pH 0-14 indicator strips, Sigma), consistent with reported median pH of 6.64 for stool.S17

WORKFLOW FOR FECAL MATERIAL FROM GUT LUMEN: Without being bound by theory, specific proteins should shift between insoluble and soluble fractions of stool in a stimulus-dependent manner, such as epithelial release of luminal vesicles from the small intestine microvilli into the lumen. Therefore, stool preparation is a critical factor for accurate quantitative analyses. Stool is a complex matrix: not only is there a variety of biological material (cells from the host infant gut, bacteria, mucin, proteolytic enzymes, etc.), but the different types of biochemical and cellular structures are not represented in equivalent stoichiometry. For example, proteins most biologically relevant to host responses are unlikely to be identified, due to the expected modest representation of host-derived gut proteins in the total stool proteome,S18 partial proteolysis that occurs during gut transit, and a large and ill-defined microbiota proteome.

Furthermore, prior gut proteome investigationsS19-S21 identified or recovered far fewer proteins than typical cell or tissue-based analyses. To cope with these challenges, we first standardized our assay protocol to the fecal weight of a homogenous patient sample, as it is the most commonly used parameter to evaluate fecal properties. S22-S25 Two hundred mg of fresh stool, which typically is 75% water,S17 was weighed (FIG. 35E). Sterile, deionized water, free from proteases and DNases water (Sigma Aldrich), was added to make a slurry at 200 mg/mL (weight stool:volume), as buffer composition substantially affects the results of quantitative immunoblotting and activity assay measurements.S26 Then, after quick vortexing, we applied a centrifugation protocol (FIG. 35E) that separated intact free-living cells, complexes associated with cell membrane surfaces, and other large particular matter in the pellet.S27,S28 The supernatant contained proteins secreted in the gut lumen, on which our analysis is focused. As such, mass spectral analysis confirmed that iAP was found in the supernatant and was readily detectable (eTable 16). We note that cell lysis, for which conditions can have a profound impact on proteins extracted, is not a variable in this study. The supernatant was aliquoted, snap frozen in liquid nitrogen, and stored at −80° C. until use.

Protein Concentration. Total protein concentration in the stool supernatant was determined by Bradford assay(ThermoFisher Scientific). Total protein was used to standardize biochemical activity measurements and protein load for quantitative IAP abundance via immunoblot analyses. Protein concentration measurement was reproducible and accurate between replicates and different operators32 (FIG. 39, eTable 12).

BIOCHEMICAL MEASUREMENTS OF SECRETED PROTEINS IN GUT LUMEN. Three different protein assays were performed on one aliquot of supernatant (FIG. 35E): determination of total protein, enzyme activity assays monitoring alkaline phosphatase catalysis, and detection of intestinal alkaline phosphatase by immunoblot. Intestinal alkaline phosphatase is resistant to intestinal degradation by host digestive enzymesS29 and thermostable.S30 For all three assays, quantitative measurements required standard curves, which were evaluated in replicate on each platform daily. Instrument and pipette calibration were performed every six months by external vendors.

Protein concentration. The concentration of total protein in final stool supernatant was determined by Bradford assay (Coomassie Plus Protein Assay Reagent, Thermo-Scientific) on either a Spectra Max M2e or Spectra Max i3x spectrophotometer (Molecular Devices). Protein standards (bovine serum albumin, Pierce) and patient samples were prepared, using molecular grade water (Millipore) as the diluent. Five-point standard curves were generated for each day of measurement; daily $r^2$ values ≥0.994 were indicative of linearity of protein abundance measurements. A second measure of analytical validity was the mean error from ideal values of standards used.

Fecal IAP Catalytic Activity. Alkaline phosphatase activity was measured with use of 4-methylumbelliferyl phosphate (Abcam) substrate in the presence and absence of L-phenylalanine, an inhibitor of IAP.33,34 Relative fluorescence units at 360/440 nm were measured in a multiwell format on either a Spectra Max M2e or i3x spectrophotometer (Molecular Devices). Total alkaline phosphatase catalysis and 10 mM phenylalanine-inhibited alkaline phosphatase catalysis were measured in triplicate and averaged. Reported IAP activity represents the difference between these 2 averages. We reported IAP activity as 1 μmol of 4-methylumbelliferyl phosphate hydrolysis per minute per gram of total protein in stool supernatant at pH 10.0; individual measurements are in eTable 13, eTable 14, and eTable 15. Intestinal alkaline phosphatase activity was reproducible between users and on different days (FIG. 39, eTable 12).

Activity assays are a measure of enzymatic catalysis as a function of time and as a ratio of protein in the stool supernatant. Alkaline phosphatase activity can be measured using a number of different substrates. The substrate employed determines the dynamic range and sensitivity of the enzymatic reaction. AP activity in this work was measured with use of 4-methylumbelliferyl phosphate (MUP) as a fluorescent substrate (Abcam, ab83371) in the presence and absence of L-phenylalanine, an inhibitor of iAP. Use of MUP has technical advantages for our study. Fluorogenic substrates enable catalytic activity of AP to be measured with high sensitivity and accuracy, attributes which are ideal for basic research and biotechnology applications. Second, fluorogenic substrates typically have a detection range that is 100X-1000X greater than chromogenic substrates, for which product precipitates are detected after reduction of tetrazolium salts or production of colored diazo compounds. S31 The 4-MUP substrate has a lower Km than other native substrates found in human samples.S32 Determination of Vmax using 4-MUP is pH-independent.S33,S34 Lastly, its hydrolysis products do not lead to strong inhibition of alkaline phosphatase,S32 which would lower the measurement range and limit accuracy.

Relative fluorescence units (RFUs) at 360 nm excitation/440 nm emission were measured using a Spectra Max M2e spectrophotometer or Spectra Max i3x (Molecular Devices). Ninety-six-well black optical bottom plates (ThermoScientific) were used. Standards and negative controls were prepared for each plate run. A 100 mM stock of L-phenylalanine (purity >98%; Sigma Aldrich) was freshly prepared in molecular grade water each day of use. A final assay concentration of 10 mM Phe was used to assess inhibition of iAPspecific activity.

Denaturing Gel Electrophoresis and Immunoblot. We determined IAP abundance using affinity-based methods and reported abundance relative to IAP measured in control human small intestine lysate of equivalent protein load. Duplicate, precast denaturing SDS-PAGE gels (ThermoFisher Scientific) were used to visualize proteins prior to immunoblotting detection of IAP; 5 μg total protein was run per sample. To confirm relative protein abundance35-37 of IAP, 2 loading controls were run on each gel. The positive control was a single lot of human small intestinal lysate (Abcam). Purified bovine alkaline phosphatase from intestinal mucosa (Sigma) was our negative control. Immunoblotting was performed using traditional or iBlot-iBind methods (ThermoFisher Scientific).38-40 The amount of IAP in clinical samples was reported as a percent of the detected protein in an immunoblot relative to the difference in densitometric pixel count in a fixed area (Amersham Imager 600; GE Healthcare) that captured the IAP signal in the positive and negative controls. A single lot of primary antibody against human IAP, which did not cross-react with other human alkaline phosphatase or negative control proteins (FIG. 39C), and a single lot of horseradish peroxidase—conjugated secondary antibody (Abcam) were used for all analyses. Determinations of IAP content were linear up to 1 μg small intestinal lysate (FIG. 39D).

The approach was to compare the amount of fecal iAP, which reflects the abundance of protein in the gut lumen, relative to iAP protein in the human intestinal epithelium standard. Supernatant of stool samples were mixed with gel loading buffer (375 mM Tris pH 6.8, 50% (w/v) glycerol, 600 mM dithiothreitol, 420 mM sodium dodecyl sulfate) and boiled for 5 mins. Sample loads per lane were prepared according to total protein.S35-S37 A total of 5 μg of total protein was loaded per lane of a denaturing 4-12% iBolt Bis-Tris gel (Novex, Life Technologies). Duplicate gels were run: one was Coomassie-stained to visualize all proteins in each lane and the second was used for immunoblotting.

Akin to ELISA measurements, more than one reference was used for quantitation of relative iAP content in stool samples in our immunoblots. This approach mitigates the danger of single-variable normalization, long recognized in data from microarrays38 and quantitative PCR.S39 Thus, our positive control was human small intestinal tissue lysate (Abcam). Purified bovine alkaline phosphatase from intestinal mucosa (Sigma Aldrich) was used as a negative control. The primary antibody used was specific for the human intestinal isoform of iAP (FIG. 39C), when evaluated against human small intestine lysate (Abcam; ab29276), purified human placental alkaline phosphatase (ab114268), purified human tissue non-specific alkaline phosphatase (ab114267), and bovine intestinal alkaline phosphatase (Sigma, P5521). Our positive control from a single lot, as well as a single lot of negative control, served as calibrators for all quantitations in the manuscript; both are loaded on each and every gel with patient samples. These two standards were used to define the linear relationship of our anti-iAP signal for patient samples.

Transfer of proteins in gel matrix was performed using one of two techniques: either (1) a semi-dry transfer apparatus (FisherScientific) at a constant 5V for 1 hour or (2) the iBlot 2 (ThermoFisher) dry blotting system at starting at 20V and ending at 25V for a total of 7 min. Western blotting techniques were performed either using traditional methods S40-S42 or with use of an iBind system (ThermoFisher). Membranes were either serially blocked in 5% (w/v) nonfat dry milk in 50 mM Tris-HCl pH 7.5, 150 mM NaCl, and 0.1% Tween or with the iBind solution kit (ThermoFisher) reagents. At room temperature, membranes were incubated with primary rabbit polyclonal antibodies against human iAP (Abcam, ab7322) at a 1:13,000 dilution, washed, and incubated with horseradish peroxidase-conjugated goat anti-rabbit secondary antibodies (Abcam, ab6721) at a 1:20,000 dilution.

Bands were quantified on an Amersham Imager 600 (GE Healthcare); its CCD chip and large aperture FujiIon f/0.85 43 mm lens allows for greater sensitivity for low-light applications. The iAP protein in the positive control lane was manually defined. Equivalent areas were quantitated for each lane of the immunoblot, including the negative control and patient samples. The resulting signal for each patient sample was divided by the difference between the positive control and the negative control to give a final percentage of the positive control standard. To account for sample prep, detection scheme, and normalization approach in our hands, a calibration curve of a lysate of human intestinal epithelium (FIG. 39D), our positive control, showed overlap between linear portion of anti-human iAP signal detection and our working range.S43

Accuracy and reproducibility measurements. Although five different operators performed these assays, examination of replicates showed clear reproducibility (FIG. 39A and FIG. 39B) suggesting that biological signal can be differentiated from noise in these assays.

Accuracy and reliability of each biochemical test used to calculate iAP biomarker sensitivity and specificity were assessed (Table e16). To minimize the impact of batch effects,44 five independent measurements of known analyte concentrations for each biochemical assay were selected randomly from an eight-month period by three different operators. Accuracy was assessed by comparing the experimental measurement of the analyte and the absolute measure as defined by the manufacturer and reported as a percent of the absolute value (FIG. 39A and FIG. 39B). The absolute value of each concentration of alkaline phosphatase used for activity assays was measured on the Tecan Infinite M1000 Pro (personal communication from the supplier; Abcam). Experimental measurement of the analyte was performed on the SpectraMax i3x (Molecular Devices) with a photometric range of 0-0.4 OD and a photometric resolution of 0.001 OD. For the Bradford assay, the extinction coefficient for bovine serum albumin (BSA; 43,824 M-1) and Beer's law equation were used to calculate the absolute value for each dilution of BSA used for the standard curve measured on the SpectraMax i3x. Accuracy was calculated using the equation: accuracy=[(absolute value—measurement value)/absolute value]×100%. The reliability, or how reproducibly a measurement of an analyte compared to the absolute value of the analyte, was determined by calculating the standard error and reporting the p-value. As the p-value indicates whether measurements deviate significantly from each other, it can be used to indicate whether inter-operator measurements for calibrators are either statistically similar (p-value<0.05) or are dissimilar (p-value >0.05). For all measurements of patient samples, dilutions of the sample were performed to ensure the experimental measurement value fell in the middle of the linear range between the highest and lowest analyte concentration used for the standard curve.

MASS SPECTROMETRY. MS1 scans on 0.5 μg/μL processed stool sample, that was subsequently reduced, alkylated, and trypsinized, were performed in a Fusion Tribrid Orbitrap (Thermo Fisher Dionex, Sunnyvale, CA) utilizing a resolution of 240,000, following liquid chromatography separation on a Dionex U3000 HPLC system (Thermo Fisher Dionex, Sunnyvale, CA). The MS2 scans were performed in the Orbitrap using High Energy Collision Dissociation (HCD) setting of 30% and a resolution of 30,000. This was repeated for a total of three technical replicates. Data analysis was performed using Proteome Discoverer 2.2 using SEQUEST HT scoring. The Protein FASTA database was *H. sapiens* version 2017-07-05. Static modifications included carbamidomethyl on cysteines (=57.021) and dynamic modification of oxidation of methionine (=15.9949). Parent ion tolerance was 10 ppm, fragment mass tolerance was 0.02 Da, and the maximum number of missed cleavages was set to 2. Only high scoring peptides were considered utilizing a false discovery rate (FDR) of 1%.

Statistical Analysis. Sample size and power calculations for planning this study were based on preliminary data acquired from 6 NEC and 12 non-NEC stool samples from premature infants. From this initial evaluation of the effect size of IAP abundance and dysfunction, it was determined that at least 12 patients with NEC were needed to demonstrate significant difference (ie, with a 5% CI, 2-sided, 2-sample t test, and 95% power).41 With an assumed event rate of dichotomous outcome of 10% (ie, percent preterm infants born≤1.5 kg who develop NEC) and a 10% attrition rate, our target enrollmentwas 130 very lowbirth-weight infants.

Associations between inflammatory disease (NEC and non-GI tract infections), neonatal variables, and hospital course were evaluated (FIG. 36 and FIG. 37). When characteristics or conditions were considered antecedent or concurrent with disease modality, adjusted associations were evaluated using logistic regression models fit to the binary disease outcome. If the outcome was continuous (eg, the association of sepsis with the number of days in hospital), adjusted associations were evaluated by linear regression; an analysis of variance, t test, or Kruskal-Wallis and Wilcoxon test was adopted, depending on the validation of data normality. For unadjusted comparisons or very small counts, statistical significance was determined by $\chi^2$ or Fisher exact tests. All analyses were completed using SAS version 9.4 (SAS Institute).

Each clinical modality was treated as a binary variable to age-appropriate controls. Differences in medians between NEC and control groups for IAP activity and abundancewere tested using Mann-Whitney U test; a 2-tailed P<0.05 was considered statistically significant in highlighting categorical differences. Potential biomarker efficacy was assessed via sensitivity (true-positive rate) and specificity (true-negative rate) calculation. For each variable of interest, specificity and sensitivity were initially obtained using a simple threshold-based classifier. Receiver operating characteristic curve analysis was used to evaluate sensitivity and specificity of the biomarker for the best discrimination between infant samples with or without disease. The Wilson-Brown method for confidence interval determination was used. These statistical calculations were performed using Prism version 8.1.2 (GraphPad). All figures were generated in Igor Pro version 8.0 (Wavemetric).

Results

A total of 136 infants were enrolled (68 [50.0%] male infants), with a median (interquartile range [IQR]) birth weight of 1050 (790-1350) g and a median (IQR) gestational age of 28.4 (26.0-30.9) weeks. A total of 25 (18.4%) were classified as having severe NEC, 19 (14.0%) were suspected of having NEC, and 92 (66.9%) had no NEC (ie, control) (FIG. 35D). Of the infants with severe NEC, 19 events (76.0%) took place between 26 and 35 weeks' postconceptual age (PCA), and 6 (24.0%) took place between 36 and 40 or more weeks' PCA. For infants classified with suspected NEC, 16 events (84.2%) took place between 26 and 30 weeks' PCA, and 3 (15.8%) took place between 31 and 35 weeks' PCA. Study participants had other forms of confirmed infections besides NEC; 26 (19.1%) were diagnosed with LOS, and 14 (10.3%) had a non-GI tract infection (FIG. 35D). An equivalent number of male and female infants were enrolled.

Attrition rate was 11.0% (ie, 15 infants), resulting from enrollment changes, medical changes, or inadequate biospecimen collection (FIG. 35D). A total of 6 (4.4%) patients were excluded because of withdrawal of parental consent or death (pulmonary or multiorgan failure not related to NEC) before sample collection. A total of 9 (6.6%) enrollees were removed because of diagnosis of SIP, inadequate stool collection, or no stool collection during the episode of suspected or severe NEC. The number of remaining enrollees was 121.

Demographic data and clinical histories were reviewed after stool analyses (FIG. 35E). We compiled 5400 demographic and clinical-course characteristics (FIG. 36 and FIG. 37). Potentially confounding variables were cross-tabulated for disease. Postconceptual age and weight were the only pre-event clinical variables associated with NEC (FIG. 36), supporting postnatal disease development as a consistent risk factor (median [IQR] PCA at first NEC episode: severe NEC, 33.9 [31.0-35.7] weeks; suspected NEC, 29.4 [28.4-30.9] weeks; P=0.02; median [IQR] weight at first NEC episode: severe NEC, 1620 [1110-2050] g; suspected NEC, 1015 [860-1377] g; P<0.001).18 In contrast, birth weight and gestational age were strongly associated with risk of LOS (median [IQR] birth weight: LOS, 790 [670-1010] g; other non-GI tract infections, 830 [700-915] g; no other non-GI tract infection, 1165 [912.5-1410] g; P<0.001; median [IQR] gestational age at birth: LOS, 25.9 [25.0-29.7] weeks; other non-GI tract infections, 26.4 [25.0-27.1] weeks; no other non-GI tract infection, 29.3 [26.9-32.2] weeks; P<0.001) (Table 2).14

Abundance of IAP Protein and IAP Enzyme Activity in Patients With Severe NEC, Suspected NEC, and No NEC. Infants with NEC had high relative IAP content in their stool samples at the time of clinical diagnosis (FIG. 38A). Samples collected at the time of severe NEC had a median (IQR) IAP content of 99.0% (51.0%-187.8%) (95% CI, 54.0%-163.0%), whereas control samples had a median (IQR) IAP content of 4.8%(2.4%-9.8%) (95% CI, 3.4%-5.9%). Increased fecal IAP proteinwas associated not only with severe NEC but also suspected disease. Stool samples collected at the time of NEC suspicion had a median (IQR) IAP content of 123.0%(31.0%-224.0%) (95% CI, 31.0%-224.0%) (FIG. 38A).

The median IAP abundance in stool at the time of severe NEC and suspected NEC was increased 20-fold compared with stool collected from age-matched controls with no NEC.

Activity of IAP in samples collected during episodes of suspected and severe NEC was significantly lower compared with samples from infants who did not have NEC (FIG. 38A). However, different levels of IAP enzyme dysfunctionwere found between patients with suspected and severe NEC. Samples at the time of severe NEC had a median (IQR) IAP activity of 183 (56-507) µmol/min/g (95% CI, 63-478 µmol/min/g) of stool protein. Samples at the time of suspected NEC had a median (IQR) IAP activity of 355 (172-608) µmol/min/g (95% CI, 172-608 µmol/min/g) of stool protein, and IAP activity in PCA-matched control samples had a median (IQR) of 613 (210-1465) µmol/min/g (95% CI, 386-723 µmol/min/g) of stool protein. Thus, infants with severe NEC had only a quarter of the ability to modulate aberrant bacterial colonization as their counterparts with suspected or no NEC, indicating a dysfunction in host-microbial crosstalk.

Sensitivity, Specificity, and Positive Predictive Value of Fecal IAP Measures. Accuracy, or area under the curve, of the single biochemical measure of IAP was evaluated using a receiver operating characteristic curve, a common tool used to calculate clinical prediction rules (FIG. 38B). Mean (SE) accuracy using IAP content as a marker for severe NEC was 0.97 (0.02) (95% CI, 0.93-1.00; P<0.001), and mean (SE) accuracy using IAP activity as a marker for severe NEC was 0.76 (0.06) (95% CI, 0.64-0.86; P<0.001). Similar mean (SE) accuracy values of 0.97 (0.02) (95% CI, 0.93-1.00; P<0.001) for IAP content and 0.62 (0.07) (95% CI, 0.48-0.77; P=0.13) for IAP activity were obtained for suspected NEC.

In contrast, IAP content and activity lacked accuracy in the diagnosis of sepsis and other non-GI tract infections (FIG. 38C). There was negligible IAP shed in stool collected at the time of clinically defined sepsis (median [IQR], 6.5%[2.2%-23.1%]; 95% CI, 2.2%-19.8%), other non-GI tract infections (median [IQR], 3.1% [0.8%-10.9%]; 95% CI, 0.6%-15.2%), and controls (median [IQR], 6.2%[2.7%-40.0%]; 95% CI, 4.6%-11.0%). Enzymatic ability of IAP did not differ statistically between samples collected from these 3 cohorts (FIG. 38C); median (IQR) activity for sepsis was 575 (338-1122) µmol/min/g (95% CI, 355-1073 µmol/min/g) of stool protein, for other non-GI tract infections, 319 (207-961) µmol/min/g (95% CI, 172-1193 µmol/min/g) of stool protein, and, for the control group, 519 (180-1243) µmol/min/g (95% CI, 350-695 µmol/min/g) of stool protein. Area under the receiver operating characteristic curves showed that use of fecal IAP content or activity would randomly assign culture-confirmed bacterial sepsis and other non-GI infection as positives or negatives for these inflammatory conditions (FIG. 38D). Mean (SE) accuracy scores for IAP content were 0.52 (0.07) (95% CI, 0.38-0.66; P=0.75) at the time of sepsis and 0.58 (0.08) (95% CI, 0.42-0.75; P=0.06) at the time of other non-GI infection. Mean (SE) accuracy scores for IAP activity were 0.52 (0.07) (95% CI, 0.39-0.67; P=0.68) at the time of sepsis and 0.57 (0.08) (95% CI, 0.39-0.69; P=0.66) at the time of other non-GI infection.

Necrotizing enterocolitis and LOS in neonates have exaggerated inflammatory responses and a number of common attributes. Differential diagnosis is complicated by their overlapping presentations, diagnostic tools with limited sensitivity, and even their evolving definitions.42,43 Current criterion standards are abdominal radiography for NEC and positive blood culture for sepsis. Yet both standards suffer from low sensitivity and the possibility of causing harm from excessive radiation exposure or blood sampling. Lastly, outcome reports are problematic: interpretations of subtle radiological findings are subjective and may vary, whereas culture results may take up to 48 to 72 hours.

There have been numerous attempts to identify candidate markers of gut injury that discriminate NEC from other inflammatory conditions.44-48 Animal NEC models suggest that the immune dysregulation and microbial dysbiosis associated with severe NEC are tandem host-bacterial missteps owing to excessive toll-like receptor 4 signaling in response to bacterial LPS.19,49-52 The majority of candidate NEC biomarkers are proteins further downstream from the initial host signaling steps. Elevations in platelet activating factor,3,53 inter-α inhibitor protein,54 calprotectin, claudin,48 intestinal fatty acid binding protein,55 and C-reactive protein56 in plasma have been associated with NEC onset. Taken together, current literature points toward the idea that diagnosis of advanced NEC is a clinical descriptor of terminal-stage pathologic processes,29,57 suggesting that an NEC biomarker may always be confounded by sepsis.

This study challenged these theories. Biomarkers, such as calprotectin, are reliable indicators of intestinal inflammation in general but provide no understanding of the dominant inflammatory pathways at work in the intestinal mucosa of a patient. Our study required prospective inclusion of infants with NEC and concurrently tested healthy and unhealthy controls with several inflammatory conditions in the neonatal intensive care unit. Under these real-life conditions, estimates of biomarker reliability more accurately reflected potential performance in clinical application. Examination of proteins involved in organ-specific modulation of microbiota homeostasis and response distinguished NEC from other forms of inflammation. As such, IAP is the first candidate diagnostic biomarker, unique in its high positive predictive value for NEC. Importantly, IAP is associated with NEC and not associated with sepsis or other non-GI tract infections.

Using a protein that is an established antecedent to inflammation, induced by LPS, as a biomarker has support from prior studies. There are several models of IAP activation in gut dysbiosis: exosomes, increased gut permeability, and/or intestinal epithelial injury. It has not been clarified whether the bacterial translocation across the gut epithelium that can give rise to LOS is a native outcome from altered gut epithelial permeability or a result of gut barrier deterioration. Our IAP study does not address whether there is deterioration of the gut endothelium in NEC or sepsis. However, detection of IAP in such high abundance in our stool samples during NEC episodes suggested that there is active regulation of lipid vesicle secretion into the gut lumen during active NEC disease; such secretion of IAP is not detectable in stool during LOS. This investigation does not support the idea that NEC shares the same pathobiological mechanism as neonatal sepsis.

The IAP biomarker is associated with disease severity; IAP biochemistry differentiates advanced NEC, flagged by portal venous gas or *pneumatosis intestinalis*, from suspected disease, for which there are no reliably observable signs by radiology. Our results also showed that this classification of NEC suspicion is supported as an explicit disease state. Our approach differed from other candidate biomarker studies. This work diverges not only by the target protein of interest but also by our use of a disease severity catalog, biospecimen choice, and molecular method of detection. We were able to segregate NEC suspicion from severe cases of NEC. There has been great effort to identify commonalities in clinical criteria to define severe NEC. Very few reports on NEC suspicion are published because of the absence of a molecular diagnostic test and lack of definition consensus. This study showed that suspected and severe NEC were associated with the active release of IAP in infant stool. It also demonstrated that there were clear differences in IAP function in these 2 disease categories. Advanced NEC was associated with severe biochemical dysfunction of host IAP, whereas suspected NEC has only partial loss of IAP enzyme activity. In contrast, C-reactive protein and other biomarkers are not associated with Bell staging,11 and importantly, the values do not significantly vary between suspected and severe NEC.

The findings discussed in this example did differ from the other studies evaluating IAP as a biomarker for NEC. Our research report used not 1 but 2 measures to evaluate IAP biochemistry in patient samples, as follows: (1) immunoblotting to quantify its relative abundance in comparison with the amount of IAP found in human small intestine and (2) enzymatic activity to identify whether the protein is functional and capable of modulating microbial dysbiosis. Both approaches are necessary to distinguish disease pathways and differences between individuals. Serological tests58 of alkaline phosphatase as an NEC biomarker reported that the amount of IAP in blood was increased in infants with NEC compared with controls, suggesting that IAP may play a role in NEC pathogenesis. Serum is not an ideal sampling source, as 4 different alkaline phosphatases are present, and their relative levels in serum are known to change during gestation59 (FIG. 39 and FIG. 40). Although prior conclusions drawn58 support our findings, sole use of denaturing protein gels cannot provide equivalent evidence that IAP was identified nor is it capable of quantifying the amount of alkaline phosphatase in general.

In conclusion, the results of this study indicated that the measurement of IAP dysfunction in stool is a biomarker for NEC with better sensitivity and specificity than other candidates previously reported in the literature. Although promising, use of fecal IAP as a biomarker should be considered an adjunct in establishing the diagnosis of severe NEC, monitoring disease progression, and surveilling high-risk infant groups. Normative data across different PCAs are needed for appropriate design and analysis of future biomarker studies to determine whether fecal IAP can serve as a diagnostic proxy at the molecular level. The clinical potential of this noninvasive tool lies in its ability to identify infants most at risk of developing NEC, to facilitate management of feeding and antibiotic regimens, and to monitor response to treatment.

REFERENCES CITED IN THIS EXAMPLE

1. Lin P W, Stoll B J. Necrotising enterocolitis. *Lancet.* 2006; 368(9543):1271-1283. doi:10.1016/S0140-6736 (06)69525-1
2. Yee W H, Soraisham A S, Shah V S, Aziz K, YoonW, Lee S K; Canadian Neonatal Network. Incidence and timing of presentation of necrotizing enterocolitis in preterm infants. *Pediatrics.* 2012; 129(2):e298-e304. doi:10.1542/peds.2011-2022
3. Young C, Sharma R, Handfield M, Mai V, Neu J. Biomarkers for infants at risk for necrotizing enterocolitis: clues to prevention? *Pediatr Res.* 2009; 65(5 Pt 2):91R-97R. doi:10.1203/PDR.0b013e31819dba7d
4. Tam A L, Camberos A, Applebaum H. Surgical decision making in necrotizing enterocolitis and focal intestinal perforation: predictive value of radiologic findings. *J Pediatr Surg.* 2002; 37(12):1688-1691. doi: 10.1053/j psu.2002.36696
5. Hoehn T, Stover B, Buhrer C. Colonic *pneumatosis intestinalis* in preterm infants: different to necrotizing enterocolitis with a more benign course? *Eur J Pediatr.* 2001; 160(6):369-371. doi:10.1007/s004310100757
6. Mata A G, Rosengart R M. Interobserver variability in the radiographic diagnosis of necrotizing enterocolitis. *Pediatrics.* 1980; 66(1):68-71.
7. Rehan V K, Seshia M M, Johnston B, Reed M, Wilmot D, Cook V. Observer variability in interpretation of abdominal radiographs of infants with suspected necrotizing enterocolitis. *Clin Pediatr (Phila).* 1999; 38(11):637-643. doi:10.1177/000992289903801102

8. Di Napoli A, Di Lallo D, Perucci C A, et al. Inter-observer reliability of radiological signs of necrotising enterocolitis in a population of high-risk newborns. *Paediatr Perinat Epidemiol.* 2004; 18(1):80-87. doi:10.1111/j.1365-3016. 2003.00517.x
9. Evennett N J, PetrovMS, Mittal A, Windsor J A. Systematic review and pooled estimates for the diagnostic accuracy of serological markers for intestinal ischemia. *World J Surg.* 2009; 33 (7): 1374-1383. doi:10.1007/s00268-009-0074-7
10. Terrin G, Stronati L, Cucchiara S, De Curtis M. Serum markers of necrotizing enterocolitis: a systematic review. *J Pediatr Gastroenterol Nutr.* 2017; 65(6):e120-e132. doi:10.1097/MPG.0000000000001588
11. Rusconi B, Good M,Warner B B. The microbiome and biomarkers for necrotizing enterocolitis: are we any closer to prediction? *J Pediatr.* 2017; 189:40-47.e2.
12. Garg B D, Sharma D, Bansal A. Biomarkers of necrotizing enterocolitis: a review of literature. *J Matern Fetal Neonatal Med.* 2018; 31(22):3051-3064. doi:10.1080/14767058.2017.1361925
13. Uauy R D, Fanaroff A A, Korones S B, Phillips E A, Phillips J B, Wright L L; National Institute of Child Health and Human Development Neonatal Research Network. Necrotizing enterocolitis in very low birth weight infants: biodemographic and clinical correlates. *J Pediatr.* 1991; 119(4):630-638. doi:10.1016/50022-3476(05) 82418-7
14. Stoll B J, Hansen N, Fanaroff A A, et al. Late-onset sepsis in very low birth weight neonates: the experience of the NICHD Neonatal Research Network. *Pediatrics.* 2002; 110(2 Pt 1):285-291. doi:10.1542/peds.110.2.285
15. Kaufman D, Fairchild K D. Clinical microbiology of bacterial and fungal sepsis in very-low-birth-weight infants. *Clin Microbiol Rev.* 2004; 17(3): 638-680. doi: 10.1128/CMR.17.3.638-680.2004
16. Sharma R, Tepas J J III, Hudak M L, et al. Neonatal gut injury and infection rate: impact of surgical debridement on outcome. *Pediatr Surg Int.* 2005; 21(12):977-982. doi:10.1007/s00383-005-1539-x
17. Cole C R, Hansen N I, Higgins R D, et al; Eunice Kennedy Shriver National Institute of Child Health and Human Development's Neonatal Research Network. Bloodstream infections in very low birth weight infants with intestinal failure. *J Pediatr* 2012; 160(1):54-9.e2.
18. Neu J, Walker W A. Necrotizing enterocolitis. *N Engl J Med.* 2011; 364(3):255-264. doi:10.1056/NEJMra1005408
19. Nanthakumar N, Meng D, Goldstein A M, et al. The mechanism of excessive intestinal inflammation in necrotizing enterocolitis: an immature innate immune response. *PLoS One.* 2011; 6(3):e17776. doi:10.1371/journal.pone.0017776
20. Mai V, Young C M, Ukhanova M, et al. Fecal microbiota in premature infants prior to necrotizing enterocolitis. *PLoS One.* 2011; 6(6):e20647. doi:10.1371/journal.pone.0020647
21. Lichtman J S, Marcobal A, Sonnenburg J L, Elias J E. Host-centric proteomics of stool: a novel strategy focused on intestinal responses to the gut microbiota. *Mol Cell Proteomics.* 2013; 12(11):3310-3318. doi:10.1074/mcp.M113.029967
22. Shifrin D A Jr, McConnell R E, Nambiar R, Higginbotham J N, Coffey R J, Tyska M J. Enterocyte microvillus-derived vesicles detoxify bacterial products and regulate epithelial-microbial interactions. *Curr Biol.* 2012; 22(7):627-631. doi:10.1016/j.cub.2012.02.022
23. Shifrin D A Jr, Tyska M J. Ready . . . aim . . . fire into the lumen: a new role for enterocyte microvilli in gut host defense. *Gut Microbes.* 2012; 3(5):460-462. doi:10.4161/gmic.21247
24. Cohen J F, Korevaar D A, Altman D G, et al. STARD 2015 guidelines for reporting diagnostic accuracy studies: explanation and elaboration. *BMJ Open.* 2016; 6(11): e012799. doi:10.1136/bmj open-2016-012799
25. Bossuyt P M, Cohen J F, Gatsonis C A, Korevaar D A; STARD group. STARD 2015: updated reporting guidelines for all diagnostic accuracy studies. *Ann Transl Med.* 2016; 4(4):85.
26. Bell M J. Neonatal necrotizing enterocolitis. *N Engl J Med.* 1978; 298(5):281-282. doi:10.1056/NEJM197802022980519
27. Gephart S M, Spitzer A R, Effken J A, Dodd E, Halpern M, McGrath J M. Discrimination of GutCheck(NEC): a clinical risk index for necrotizing enterocolitis. *J Perinatol.* 2014; 34(6):468-475. doi:10.1038/jp.2014.37
28. Battersby C, Longford N, Costeloe K, Modi N; U K Neonatal Collaborative Necrotising Enterocolitis Study Group. Development of a gestational age-specific case definition for neonatal necrotizing enterocolitis. *JAMA Pediatr.* 2017; 171(3):256-263. doi: 10.1001/j amapediatrics.2016.3633
29. Gephart S M, Gordon P V, Penn A H, et al. Changing the paradigm of defining, detecting, and diagnosing NEC: perspectives on Bell's stages and biomarkers for NEC. *Semin Pediatr Surg.* 2018; 27(1):3-10. doi:10.1053/j.sempedsurg.2017.11.002
30. Buhimschi C S, Bhandari V, Hamar B D, et al. Proteomic profiling of the amniotic fluid to detect inflammation, infection, and neonatal sepsis. *PLoS Med.* 2007; 4(1):e18. doi: 10.1371/j ournal.pmed.0040018
31. Buhimschi C S, Buhimschi I A, Abdel-Razeq S, et al. Proteomic biomarkers of intra-amniotic inflammation: relationship with funisitis and early-onset sepsis in the premature neonate. *Pediatr Res.* 2007; 61(3):318-324. doi: 10.1203/01.pdr.0000252439.48564.37
32. Marcus E. Credibility and reproducibility. *Cell.* 2014; 159(5):965-966. doi:10.1016/j.ce11.2014.11.016
33. Fishman W H, Green S, Inglis N I. L-phenylalanine: an organ specific, stereospecific inhibitor of human intestinal alkaline phosphatase. *Nature.* 1963; 198:685-686. doi: 10.1038/198685b0
34. Fernley H N, Walker P G. Inhibition of alkaline phosphatase by L-phenylalanine. *Biochem J.* 1970; 116(3): 543-544. doi:10.1042/bj1160543
35. Jensen K J, Garmaroudi F S, Zhang J, et al. An ERK-p38 subnetwork coordinates host cell apoptosis and necrosis during coxsackievirus B3 infection. *Cell Host Microbe.* 2013; 13(1):67-76. doi:10.1016/j.chom.2012.11.009
36. Kang B H, Jensen K J, Hatch J A, Janes K A. Simultaneous profiling of 194 distinct receptor transcripts in human cells. *Sci Signal.* 2013; 6(287):rs13. doi:10.1126/scisignal.2003624
37. Bose A K, Janes K A. A high-throughput assay for phosphoprotein-specific phosphatase activity in cellular extracts. *Mol Cell Proteomics.* 2013; 12(3):797-806. doi: 10.1074/mcp.0112.024059
38. Towbin H, Staehelin T, Gordon J. Electrophoretic transfer of proteins from polyacrylamide gels to nitrocellulose sheets: procedure and some applications. *Proc Natl Acad Sci USA.* 1979; 76(9):4350-4354. doi:10. 1073/pnas.76.9.4350
39. Burnette W N. "Western blotting": electrophoretic transfer of proteins from sodium dodecyl sulfate-polyacrylamide gels to unmodified nitrocellulose and radiographic detection with antibody and radioiodinated protein A. *Anal Biochem.* 1981; 112(2):195-203. doi: 10.1016/0003-2697(81)90281-5

40. Spinola S M, Cannon J G. Different blocking agents cause variation in the immunologic detection of proteins transferred to nitrocellulose membranes. *J Immunol Methods.* 1985; 81(1):161-165. doi:10.1016/0022-1759(85)90132-2

41. Dang Q, Mazumdar S, Houck P R. Sample size and power calculations based on generalized linear mixed models with correlated binary outcomes. *Comput Methods Programs Biomed.* 2008; 91(2):122-127. doi: 10.1016/j.cmpb. 2008.03.001

42. Wynn J L. Defining neonatal sepsis. *Curr Opin Pediatr.* 2016; 28(2):135-140. doi:10.1097/MOP.0000000000000315

43. Marik P E, Taeb A M. SIRS, qSOF A and new sepsis definition. *J Thorac Dis.* 2017; 9(4):943-945. doi: 10.21037/jtd. 2017.03.125

44. Hintz S R, Kendrick D E, Stoll B J, et al; NICHD Neonatal Research Network. Neurodevelopmental and growth outcomes of extremely low birth weight infants after necrotizing enterocolitis. *Pediatrics.* 2005; 115(3): 696-703. doi:10.1542/peds.2004-0569

45. Derikx J P, Evennett N J, Degraeuwe P L, et al. Urine based detection of intestinal mucosal cell damage in neonates with suspected necrotising enterocolitis. *Gut.* 2007; 56(10):1473-1475. doi:10.1136/gut.2007.128934

46. Guthmann F, Borchers T, Wolfrum C, Wustrack T, Bartholomaus S, Spener F. Plasma concentration of intestinal- and liver-FABP in neonates suffering from necrotizing enterocolitis and in healthy preterm neonates. *Mol Cell Biochem.* 2002; 239(1-2):227-234. doi: 10.1023/A: 1020508420058

47. Sylvester K G, Ling X B, Liu G Y, et al. A novel urine peptide biomarker-based algorithm for the prognosis of necrotising enterocolitis in human infants. *Gut.* 2014; 63(8):1284-1292. doi:10.1136/gutjn1-2013-305130

48. Thuijls G, Derikx J P, van Wijck K, et al. Non-invasive markers for early diagnosis and determination of the severity of necrotizing enterocolitis. *Ann Surg.* 2010; 251(6):1174-1180. doi:10.1097/SLA.0b013e3181d778c4

49. Afrazi A, Sodhi C P, RichardsonW, et al. New insights into the pathogenesis and treatment of necrotizing enterocolitis: Toll-like receptors and beyond. *Pediatr Res.* 2011; 69(3):183-188. doi:10.1203/PDR. 0b013e3182093280

50. Morowitz M J, Poroyko V, Caplan M, Alverdy J, Liu D C. Redefining the role of intestinal microbes in the pathogenesis of necrotizing enterocolitis. *Pediatrics.* 2010; 125(4):777-785. doi:10.1542/peds.2009-3149

51. Sodhi C P, Neal M D, Siggers R, et al. Intestinal epithelial Toll-like receptor 4 regulates goblet cell development and is required for necrotizing enterocolitis in mice. *Gastroenterology.* 2012; 143(3):708-718.e5, e705.

52. Nanthakumar N N, Fusunyan R D, Sanderson I, WalkerWA. Inflammation in the developing human intestine: a possible pathophysiologic contribution to necrotizing enterocolitis. *Proc Natl Acad Sci USA.* 2000; 97(11): 6043-6048. doi:10.1073/pnas.97.11.6043

53. Rabinowitz S S, Dzakpasu P, Piecuch S, Leblanc P, Valencia G, Kornecki E. Platelet-activating factor in infants at risk for necrotizing enterocolitis. *J Pediatr.* 2001; 138(1):81-86. doi:10.1067/mpd.2001.110132

54. Chaaban H, Shin M, Sirya E, Lim Y P, Caplan M, Padbury J F. Inter-alpha inhibitor protein level in neonates predicts necrotizing enterocolitis. *J Pediatr.* 2010; 157(5): 757-761. doi:10.1016/j.jpeds.2010.04.075

55. Evennett N J, Hall N J, Pierro A, Eaton S. Urinary intestinal fatty acid-binding protein concentration predicts extent of disease in necrotizing enterocolitis. *J Pediatr Surg.* 2010; 45(4):735-740. doi:10.1016/j.jpedsurg.2009.09.024

56. Pourcyrous M, Korones S B, YangW, Boulden T F, Bada H S. C-reactive protein in the diagnosis, management, and prognosis of neonatal necrotizing enterocolitis. *Pediatrics.* 2005; 116(5):1064-1069. doi:10.1542/peds. 2004-1806

57. Gordon P, Christensen R, Weitkamp J H, Maheshwari A. Mapping the new world of necrotizing enterocolitis (NEC): review and opinion. *EJ Neonatol Res.* 2012; 2(4):145-172.

58. Kampanatkosol R, Thomson T, Habeeb 0, et al. The relationship between reticulated platelets, intestinal alkaline phosphatase, and necrotizing enterocolitis. *J Pediatr Surg.* 2014; 49(2):273-276. doi:10.1016/j.jpedsurg.2013.11.037

59. McLachlan R, Coakley J, Murton L, Campbell N. Plasma intestinal alkaline phosphatase isoenzymes in neonates with bowel necrosis. *J Clin Pathol.* 1993; 46(7): 654-659. doi:10.1136/jcp.46.7.654

SUPPLEMENTAL (S) REFERENCES

S1. Gupta A, Paria A. Etiology and medical management of NEC. *Early Hum Dev.* 2016; 97:17-23.

S2. Gephart S M, Gordon P V, Penn A H, et al. Changing the paradigm of defining, detecting, and diagnosing NEC: Perspectives on Bell's stages and biomarkers for NEC. *Semin Pediatr Surg.* 2018; 27(1):3-10.

S3. Center for Disease Control and Prevention. CDC/NHSN surveillance definitions for specific types of infections. In 2018 *NHSN Patient Safety Component Manual.* U S Department of Health and Human Services National Healthcare SafetyNetwork, 2018 edition:17.11-17.30.

S4. Singer M, Deutschman C S, Seymour C W, et al. The third international consensus definitions for sepsis and septic shock (Sepsis-3). *JAMA.* 2016; 315(8):801-810.

S5. Henthorn P S, Raducha M, Edwards Y H, et al. Nucleotide and amino acid sequences of human intestinal alkaline phosphatase: close homology to placental alkaline phosphatase. *Proc Natl Acad Sci USA.* 1987; 84(5):1234-1238.

S6. Henthorn P S, Raducha M, Kadesch T, Weiss M J, Harris H. Sequence and characterization of the human intestinal alkaline phosphatase gene. *J Blot Chem.* 1988; 263(24): 12011-12019.

S7. Miki K, Suzuki H, Iino S, Oda T, Hirano K, Sugiura M. Human fetal intestinal alkaline phosphatase. *Clin Chim Acta.* 1977; 79(1):21-30.

S8. Shah J, Singhal N, da Silva 0, et al. Intestinal perforation in very preterm neonates: risk factors and outcomes. *J Perinatol.* 2015; 35(8):595-600.

59. Attridge J T, Herman A C, Gurka M J, Griffin M P, McGahren E D, Gordon P V. Discharge outcomes of extremely low birth weight infants with spontaneous intestinal perforations. *J Perinatol.* 2006; 26(1):49-54.

S10. Hornik C P, Benjamin D K, Becker K C, et al. Use of the complete blood cell count in late-onset neonatal sepsis. *Pediatr Infect Dis J.* 2012; 31(8):803-807.

S11. Wynn J L. Defining neonatal sepsis. *Curr Opin Pediatr.* 2016; 28(2):135-140.

S12. Marik P E, Taeb A M. SIRS, qSOF A and new sepsis definition. *J Thorac Dis.* 2017; 9(4):943-945.

S13. Wynn J L, Polin R A. Progress in the management of neonatal sepsis: the importance of a consensus definition. *Pediatr Res.* 2018; 83(1-1):13-15.

S14. Buhimschi C S, Bhandari V, Hamar B D, et al. Proteomic profiling of the amniotic fluid to detect inflammation, infection, and neonatal sepsis. *PLoS Med.* 2007; 4(1):e18.

S15. Buhimschi C S, Buhimschi I A, Abdel-Razeq S, et al. Proteomic biomarkers of intra-amniotic inflammation: relationship with funisitis and early-onset sepsis in the premature neonate. *Pediatr Res.* 2007; 61(3):318-324.

S16. Corazziari E, Staiano A, Miele E, Greco L, Italian Society of Pediatric Gastroenterology H, Nutrition. Bowel frequency and defecatory patterns in children: a prospective nationwide survey. *Clin Gastroenterol Hepatol.* 2005; 3 (11): 1101-1106.

S17. Rose C, Parker A, Jefferson B, Cartmell E. The characterization of feces and urine: a review of the literature to inform advanced treatment technology. *Crit Rev Environ Sci Technol.* 2015; 45(17):1827-1879.

S18. Consortium U. Reorganizing the protein space at the Universal Protein Resource (UniProt). *Nucleic Acids Res.* 2012; 40(Database issue):$D_{71}$-75.

S19. Verberkmoes N C, Russell A L, Shah M, et al. Shotgun metaproteomics of the human distal gut microbiota. *ISME J.* 2009; 3(2):179-189.

S20. Mahowald M A, Rey F E, Seedorf H, et al. Characterizing a model human gut microbiota composed of members of its two dominant bacterial phyla. *Proc Natl Acad Sci USA.* 2009; 106(14):5859-5864.

S21. Erickson A R, Cantarel B L, Lamendella R, et al. Integrated metagenomics/metaproteomics reveals human host-microbiota signatures of Crohn's disease. *PLoS One.* 2012; 7(11):e49138.

S22. Flynn M A, Gehrke C, Maier B R, Tsutakawa R K, Hentges D J. Effect of diet on fecal nutrients. *J Am Diet Assoc.* 1977; 71(5):521-526.

S23. Beyer P L, Flynn M A. Effects of high- and low-fiber diets on human feces. *J Am Diet Assoc.* 1978; 72(3):271-277.

S24. Cummings J H, Branch W, Jenkins D J, Southgate D A, Houston H, James W P. Colonic response to dietary fibre from carrot, cabbage, apple, bran. *Lancet.* 1978; 1(8054): 5-9.

525. Stephen A M, Wiggins H S, Cummings J H. Effect of changing transit time on colonic microbial metabolism in man. *Gut.* 1987; 28(5):601-609.

S26. Janes K A. An analysis of critical factors for quantitative immunoblotting. *Sci Signal.* 2015; 8(371):r52.

S27. Peterson B W, Sharma P K, van der Mei H C, Busscher H J. Bacterial cell surface damage due to centrifugal compaction. *Appl Environ Microbiol.* 2012; 78(1):120-125.

S28. Livshits M A, Khomyakova E, Evtushenko E G, et al. Isolation of exosomes by differential centrifugation: Theoretical analysis of a commonly used protocol. *Sci Rep.* 2015; 5:17319.

S29. Goldberg R F, Austen W G, Jr., Zhang X, et al. Intestinal alkaline phosphatase is a gut mucosal defense factor maintained by enteral nutrition. *Proc Natl Acad Sci USA.* 2008; 105(9):3551-3556.

S30. PetitClerc C. Quantitative fractionation of alkaline phosphatase isoenzymes according to their thermostability. *Clin Chem.* 1976; 22(1):42-48.

S31. O'Brien P J, Herschlag D. Alkaline phosphatase revisited: hydrolysis of alkyl phosphates. *Biochemistry.* 2002; 41(9):3207-3225.

S32. Bale J R, Chock P B, Huang C Y. The nature of negative cooperativity in alkaline phosphatase: kinetic patterns contrary to the flip-flop model. *J Biol Chem.* 1980; 255(18):8424-8430.

S33. Fernley H N, Walker P G. Kinetic behaviour of calf-intestinal alkaline phosphatase with 4-methylumbelliferyl phosphate. *Biochem J.* 1965; 97(1):95-103.

S34. Levine M N, Raines R T. Sensitive fluorogenic substrate for alkaline phosphatase. *Anal Biochem.* 2011; 418(2):247-252.

S35. Olson B J, Markwell J. Assays for determination of protein concentration. *Curr Protoc Protein Sci.* 2007; Chapter 3:Unit 3 4.

S36. Bradford M M. A rapid and sensitive method for the quantitation of microgram quantities of protein utilizing the principle of protein-dye binding. *Anal Biochem.* 1976; 72:248-254.

S37. Zor T, Selinger Z. Linearization of the Bradford protein assay increases its sensitivity: theoretical and experimental studies. *Anal Biochem.* 1996; 236(2):302-308.

S38. Brody J P, Williams B A, Wold B J, Quake S R. Significance and statistical errors in the analysis of DNA microarray data. *Proc Natl Acad Sci USA.* 2002; 99(20): 12975-12978.

S39. Tricarico C, Pinzani P, Bianchi S, et al. Quantitative real-time reverse transcription polymerase chain reaction: normalization to rRNA or single housekeeping genes is inappropriate for human tissue biopsies. *Anal Biochem.* 2002; 309(2):293-300.

S40. Towbin H, Staehelin T, Gordon J. Electrophoretic transfer of proteins from polyacrylamide gels to nitrocellulose sheets: procedure and some applications. *Proc Natl Acad Sci USA.* 1979; 76(9):4350-4354.

S41. Burnette W N. "Western blotting": electrophoretic transfer of proteins from sodium dodecyl sulfate—polyacrylamide gels to unmodified nitrocellulose and radiographic detection with antibody and radioiodinated protein A. *Anal Biochem.* 1981; 112(2):195-203.

S42. Spinola S M, Cannon J G. Different blocking agents cause variation in the immunologic detection of proteins transferred to nitrocellulose membranes. *J Immunol Methods.* 1985; 81(1):161-165.

S43. Lee J W, Devanarayan V, Barrett Y C, et al. Fit-for-purpose method development and validation for successful biomarker measurement. *Pharm Res.* 2006; 23(2):312-328.

S44. Leek J T, Scharpf R B, Bravo H C, et al. Tackling the widespread and critical impact of batch effects in high-throughput data. *Nat Rev Genet.* 2010; 11(10):733-739.

ETable 1
Study Criteria Used to Classify Diagnosis and Suspicion of Neonatal Necrotizing Enterocolitis

| STUDY CLASSIFICATION | RADIOLOGIC SIGNS | ABDOMINAL SIGNS | CLINICAL FINDINGS | LABORATORY FINDINGS |
|---|---|---|---|---|
| SEVERE NEC | | | | |
| radiologically-confirmed disease | pneumatosis intestinalis, portal venous gas, pneumoperitoneum, intestinal perforation | moderate to severe abdominal distention, tenderness, and/or discoloration, abdominal cellulitis, hypoactivity/absence of bowel sounds, fixed right lower quadrant abdominal mass, signs of peritonitis | bilious aspirate, emesis, bloody stool, feeding intolerance, increased pre-feed gastric residual volume, increased apneas and/or bradycardias, temperature instability, lethargy, generalized clinically ill-appearing, systemic instability (severe apnea, bradycardia, shock, DIC, hypotension, respiratory failure) | coagulopathy, thrombocytopenia, leukocytosis or leukopenia, neutropenia, bandemia, heme-positive stool, metabolic acidosis |
| SUSPECTED NEC | | | | |
| disease not confirmed by radiology | no pneumatosis intestinalis, mild intestinal dilation, mild intestinal ileus, thickened bowel walls, paucity/absence of bowel gas | mild to moderate abdominal distention | identical to above clinical finding criteria for NEC diagnosis | thrombocytopenia, leukocytosis or leukopenia, neutropenia, bandemia, heme-positive stool, metabolic acidosis |

Study classifications result from minimum, common requirements for disease severity definitions.[1,2] Ranked order of study criteria met was (1) radiological signs, (2) abdominal signs, (3) clinical findings, and (4) lab findings; one radiological sign and one criteria from the other groups were identified for each patient classified as NEC.

ETable 2
Study Criteria Used for Focal or Spontaneous Intestinal Perforation

| STUDY CLASSIFICATION | RADIOLOGIC SIGNS | ABDOMINAL SIGNS | CLINICAL FINDINGS | LABORATORY FINDINGS |
|---|---|---|---|---|
| Focal or spontaneous intestinal perforation | intestinal perforation, pneumoperitoneum, no pneumatosis intestinalis | abdominal distention, abdominal wall discoloration | asymptomatic, hypotension | leukocytosis |

Ranked order of study criteria met was (1) radiological signs, (2) abdominal signs, (3) clinical findings, and (4) lab findings.

ETable 3
Study Criteria Used to Define Pathogenic Infection Outside the Gastrointestinal Tract

| STUDY CLASSIFICATION | LABORATORY FINDINGS | CLINICAL FINDINGS |
|---|---|---|
| NEONATAL SEPSIS, LATE-ONSET | After seventy-two hours of age: bacterial, viral, or fungal pathogen, which is not included on the NHSN common commensal list, confirmed in 1 or more blood or serum specimens confirmation obtained by culture or non-culture microbiological testing methods organism identified is not related to an infection at another site | nonspecific, including but not limited to: temperature irregularity, respiratory distress, hypotension, feeding intolerance, glucose intolerance, neurological changes (lethargy/irritability, seizures, hypotonia), abnormal perfusion, bleeding issues, unexplained jaundice |

ETable 3
Study Criteria Used to Define Pathogenic Infection Outside the Gastrointestinal Tract

| STUDY CLASSIFICATION | LABORATORY FINDINGS | CLINICAL FINDINGS |
|---|---|---|
| OTHER CONFIRMED NON-GI INFECTIONS | confirmed bacterial, viral, or fungal pathogen in sterile body fluids, such as cerebrospinal fluid (CSF), tracheal aspirate, urine, and/or joint fluid | identical to above clinical finding criteria for sepsis |
| INFECTION NEGATIVE | | |
| suspected infection | leukocytosis or leukopenia, elevated immature neutrophil counts, low absolute neutrophil count, thrombocytopenia, serial elevated C-reactive protein serum alkaline phosphatase | identical to above clinical finding criteria for sepsis |
| no concern regarding infection | no laboratory tests were ordered | asymptomatic |

Study classifications follow infection definitions from the US Center for Disease Control/National Healthcare Safety Network (CDC/NHSN). Ranked order of study criteria met was (1) laboratory findings and (2) clinical findings. Four types of infection are excluded and not reported in this study: (i) early onset sepsis (before 72 hrs age), as antibiotics were prophylactically administered to infants at birth in all three hospital centers; (ii) a bloodstream infection that is identified secondary to another site of infection; (iii) infections associated with use of a central line; and (iv) laboratory detection of the genera *Blastomyces*, *Histoplasma*, *Coccidioides*, *Paracoccidioides*, *Cryptococcus*, and *Pneumocystis*, which typically give rise to community-associated infections and are rarely known to cause healthcare-associated infections.

ETABLE 4

Summary of NEC Cohorts at Different Clinical Sites

The number of enrolled infants who were clinically designated as NEC suspicion or severe NEC are provided per hospital site. Cohort values shown are the total number of subjects enrolled at each site, grouped by gestational age (GA) bin and the number of cases requiring surgical intervention (peritoneal drain or laparotomy). Percentages, in italics and within parentheses, are related to the number of cases divided by all subjects by cohort and gestational age at birth. Number of NEC cases and suspicion was stratified by either being <27 weeks or ≥27 weeks GA at birth. Median and accompanying interquartile values, in italics and parentheses, are used to identify the post-conceptual age and day of age for cohorts and gestational age at birth. Values and relative percentages are provided for the number of mortalities associated with necrotizing enterocolitis. Abbreviations: surg inter, surgical intervention; CH, Children's Hospital of New Orleans, LA; TI, Touro Infirmary, New Orleans, LA; WU, Washington University in St. Louis, St. Louis, Missouri.

| | | COHORT | | SUSPECTED NEC | | | | SEVERE NEC | | | |
|---|---|---|---|---|---|---|---|---|---|---|---|
| | | | | | at time of initial episode | | | | at time of initial episode | | |
| site | GA (wks) | # infants at risk | # surg inter | # infants | PCA (wks) | day of age | weight (g) | # infants | PCA (wks) | day of age | weight (g) |
| CH | <27 | 14* | 2 (14%) | 1 (7%) | 29.3 | 37 | 901 | 2 (14%) | 32.6 (31.8-33.4) | 49 (47-50) | 1463 (1274-1651) |
| | ≥27 | 15 | 2 (13%) | 5 (33%) | 33.6 (30.9-35.4) | 27 (23-29) | 1464 (1130-1600) | 3 (20%) | 33.1 (32.1-33.7) | 31 (19-32) | 1620 (1390-1705) |
| | total | 29 | 3 (14%) | 6 (21%) | 32.2 (29.7-35.0) | 28 (24-35) | 1297 (958-1566) | 5 (17%) | 33.1 (31.0-34.1) | 33 (31-45) | 1620 (1159-1790) |
| TI | <27 | 22 | 0 | 1 (4%) | 26.9 | 13 | 553 | 2 (9%) | 34.7 | 66 | 1913 |
| | ≥27 | 46 | 3 (7%) | 9 (20%) | 29.9 (29-30.7) | 9 (5-12) | 1043 (994-1105) | 4 (9%) | 32.4 (30.7-34.6) | 13 (9-16) | 1310 (1165-1480) |
| | total | 68 | 3 (4%) | 10 (15%) | 29.9 (28.6-30.7) | 9 (5-12) | 1043 (894-1104) | 6 (9%) | 33.8 (31.7-35.0) | 17 (11-49) | 1516 (1250-1623) |
| WU | <27 | 17 | 4 (24%) | 3 (18%) | 26.9 (26.9-27.9) | 19 (16-20) | 820 (765-860) | 8 (47%) | 27.1 (26.9-34.0) | 21 (16-59) | 1075 (704-1491) |
| | ≥27 | 22** | 0 | 0 | — | — | — | 6 (27%) | 37.7 (35.6-40.1) | 17 (9-41) | 2310 (2093-2565) |
| | total | 39 | 4 (10%) | 3 (8%) | 26.9 (26.9-27.9) | 19 (16-20) | 820 (765-860) | 14 (36%) | 35 (27.0-37.5) | 21 (10-46) | 1705 (1040-2255) |

ETABLE 4-continued

Summary of NEC Cohorts at Different Clinical Sites
The number of enrolled infants who were clinically designated as NEC suspicion or severe NEC are provided per hospital site. Cohort values shown are the total number of subjects enrolled at each site, grouped by gestational age (GA) bin and the number of cases requiring surgical intervention (peritoneal drain or laparotomy). Percentages, in italics and within parentheses, are related to the number of cases divided by all subjects by cohort and gestational age at birth. Number of NEC cases and suspicion was stratified by either being <27 weeks or ≥27 weeks GA at birth. Median and accompanying interquartile values, in italics and parentheses, are used to identify the post-conceptual age and day of age for cohorts and gestational age at birth. Values and relative percentages are provided for the number of mortalities associated with necrotizing enterocolitis. Abbreviations: surg inter, surgical intervention; CH, Children's Hospital of New Orleans, LA; TI, Touro Infirmary, New Orleans, LA; WU, Washington University in St. Louis, St. Louis, Missouri.

| | COHORT | | | SUSPECTED NEC | | | | SEVERE NEC | | | |
|---|---|---|---|---|---|---|---|---|---|---|---|
| | | | | | at time of initial episode | | | | at time of initial episode | | |
| site | GA (wks) | # infants at risk | # surg inter | # infants | PCA (wks) | day of age | weight (g) | # infants | PCA (wks) | day of age | weight (g) |
| All | <27 | 53 | 6 (11%) | 5 (9%) | 26.9 (26.9-28.4) | 19 (13-21) | 820 (710-880) | 12 (22%) | 32.4 (27.1-34.3) | 49 (20-62) | 1265 (960-1739) |
| | ≥27 | 83 | 5 (6%) | 14 (17%) | 30.7 (29.1-32.9) | 12 (6-26) | 1103 (999-1421) | 13 (16%) | 34.3 (33.1-37.0) | 16 (9-31) | 1650 (1430-2220) |
| | total | 136 | 11 (8%) | 19 (14%) | 29.4 (28.6-30.9) | 13 (8-25) | 1015 (873-1254) | 25 (18%) | 33.9 (31.0-35.7) | 21 (10-52) | 1620 (1110-2050) |

*Records and samples for one enrollee were removed from the study after custodial transfer of infant to state care.
**Two infants discontinued participation in the study at PCA week 32 at parental request: data (disease, surgery, mortality, etc.) after PCA wk 32 were not included. Neither infant had NEC, sepsis, confirmed infection at non-GI site, or SIP.

ETABLE 5

List of 25 Radiologically Confirmed (Severe) Cases of Necrotizing Enterocolitis Enrolled
Criteria for defining severe NEC are shown in Table e1; primary criteria was confirmation by radiographic evidence. Abbreviations for parent race/ethnicity self-identification: B = African American/Black; W = Caucasian/White; and H = Hispanic. Other abbreviations are: GA = gestational age; M = male; F = female; C = Cesarean delivery; V = vaginal delivery

| | birth | | | | | at time of initial NEC diagnosis | | | | |
|---|---|---|---|---|---|---|---|---|---|---|
| subject ID | GA (wks) | weight (g) | sex | race/ ethnicity | birth delivery | PCA (wks) | day of life | weight (g) | Bell stage | demise in NICU |
| C1 | 29.9 | 700 | F | B | C | 34.3 | 31 | 1159 | 2 A | no |
| C2 | 24.6 | 650 | F | B | C | 31.0 | 45 | 1085 | 2 B | no |
| C3 | 26.9 | 991 | M | B | V | 34.1 | 52 | 1840 | 2 A | no |
| C4 | 28.4 | 1013 | F | B | V | 33.1 | 33 | 1790 | 2 B | no |
| C5 | 30.1 | 1620 | M | B | V | 31.0 | 7 | 1620 | 3 B | no |
| T1 | 30.0 | 1240 | M | W | C | 31.0 | 7 | 1190 | 2 B | no |
| T2 | 28.7 | 1010 | F | H | C | 29.9 | 9 | 1090 | 2 B | no |
| T3 | 32.4 | 1440 | F | B | V | 33.9 | 16 | 1430 | 3 B | no |
| T4 | 25.3 | 815 | M | B | C | 33.7 | 59 | 1602 | 2 A | no |
| T5* | 25.0 | 855 | M | B | C | 35.7 | 73 | 2234 | 2 A | no |
| T6 | 34.6 | 1380 | M | H | C | 37.0 | 17 | 1630 | 3 B | no |
| W1 | 34.0 | 2360 | F | W | C | 35.1 | 9 | 2050 | 2 A | no |
| W2 | 24.3 | 700 | F | B | C | 25.1 | 7 | 720 | 2 B | no |
| W3 | 31.1 | 1190 | F | W | C | 34.3 | 24 | 1650 | 2 B | no |
| W4 | 26.0 | 480 | M | W | C | 33.7 | 55 | 1420 | 2 B | yes |
| W5 | 36.7 | 2565 | M | W | V | 43.1 | 46 | 2620 | 2 B | no |
| W6 | 36.3 | 2330 | F | W | C | 37.0 | 6 | 2220 | 2 B | no |
| W7 | 24.3 | 750 | M | W | C | 27.1 | 21 | 1110 | 3 B | no |
| W8 | 24.3 | 650 | F | W | C | 27.1 | 21 | 1040 | 3 A | yes |
| W9 | 24.7 | 640 | M | W | C | 27.1 | 18 | 630 | 2 B | no |
| W10* | 24.6 | 630 | F | W | C | 25.9 | 10 | 655 | 3 A | yes |
| W11 | 27.6 | 790 | M | W | C | 40.7 | 93 | 2700 | 3 B | yes |
| W12*⁻ | 37.1 | 2530 | F | W | C | 38.4 | 10 | 2400 | 2 A | no |
| W13* | 25.0 | 760 | M | B | C | 34.9 | 69 | 2255 | 2 A | no |
| W14* | 23.6 | 430 | M | W | C | 37.6 | 99 | 1705 | 2 B | no |

*No samples were obtained during NEC period. If a sample was not obtained during the radiologically- and clinically-defined period of NEC, all samples from the infant were excluded from cross-sectional analyses.
⁻Study subject was excluded due to gestational age >37 weeks at time of enrollment

ETABLE 6

List of 19 Suspected Necrotizing Enterocolitis Cases Enrolled
Criteria for defining suspected NEC are shown in eTable 1; these cases could not be confirmed by radiographic evidence. Bell stage documented by attending neonatologist in medical record is shown and may differ from our manuscript criteria. Abbreviations for parent race/ethnicity self-identification: B = African American/Black; W = Caucasian/White; and H = Hispanic. Other abbreviations: GA = gestational age; M = male; F = female; C = Cesarean delivery; V = vaginal delivery

| | birth | | | | | at time of clinical diagnosis of NEC suspicion | | | | |
|---|---|---|---|---|---|---|---|---|---|---|
| subject ID | GA (wk) | weight (g) | sex | race/ ethnicity | birth delivery | PCA (wks) | day of life | weight (g) | Bell stage | demise in NICU |
| C6 | 28.0 | 810 | M | B | V | 28.9 | 8 | 885 | 1 | no |
| C7 | 29.4 | 1340 | M | B | V | 33.6 | 29 | 1740 | 1 | no |
| C8* | 29.4 | 1130 | F | W | C | 35.4 | 42 | 1600 | 1 | no |
| C9 | 24.0 | 715 | M | B | V | 29.3 | 37 | 901 | 1 | no |
| C10 | 32.7 | 1170 | F | B | C | 36.0 | 23 | 1464 | 1 | no |
| C11* | 27.0 | 850 | M | B | C | 30.9 | 27 | 1130 | 1 | no |
| T7* | 30.0 | 1200 | F | W | C | 30.7 | 6 | 1105 | 1 | no |
| T8 | 28.7 | 1120 | M | B | C | 29.4 | 5 | 1070 | 1 | no |
| T9 | 29.1 | 1485 | M | B | C | 30.7 | 11 | 1435 | 1 | no |
| T10 | 32.3 | 1420 | M | B | C | 35.0 | 2 | 1377 | 1 | no |
| T11 | 29.6 | 1170 | M | B | C | 30.3 | 5 | 994 | 1 | no |
| T12* | 28.9 | 1190 | F | W | V | 30.6 | 12 | 1100 | 1 | no |
| T13 | 25.0 | 560 | F | B | V | 26.9 | 13 | 553 | 1 | no |
| T14 | 26.7 | 531 | F | B | C | 27.7 | 7 | 490 | 1 | no |
| T15 | 26.7 | 860 | M | B | C | 28.4 | 12 | 860 | 1 | no |
| T16 | 26.9 | 940 | M | W | C | 29.0 | 29 | 1015 | 1 | no |
| W15** | 24.3 | 700 | M | W | C | 26.9 | 19 | 900 | 3 B | yes |
| W16 | 26.0 | 830 | F | B | C | 28.9 | 21 | 710 | 1 | no |
| W17 | 25.1 | 790 | M | B | C | 26.9 | 13 | 820 | 1 | no |

*No samples were obtained during NEC period. If a sample was not obtained during the radiologically- and clinically-defined period of NEC, all samples from the infant were excluded from cross-sectional analyses.
**No abdominal radiographic evidence nor abdominal ultrasound evidence of pneumatosis intestinalis, portal venous gas, or pneumoperitoneum on multiple evaluations.

ETABLE 7

List of 3 Enrolled Infants With Spontaneous Intestinal Perforation (SIP) and Necrotizing Enterocollitis
Abbreviations for parent race/ethnicity self-identification: B = African American/Black; W = Caucasian/White; and H = Hispanic. Other abbreviations: GA = gestational age at birth; M = male; F = female; C = Cesarean delivery; V = vaginal delivery; and NA = not applicable

| | | | | | at time of SIP diagnosis | | | At time of NEC diagnosis or suspicion | | | | |
|---|---|---|---|---|---|---|---|---|---|---|---|---|
| subject ID | GA (wk) | birth weight (g) | sex | race | PCA (wks) | day of life | weight (g) | # days after SIP | PCA (wks) | day of life | weight (g) | study classifi- cation | Bell stage |
| C1 | 29.9 | 700 | F | B | 30.4 | 5 | 800 | 26 | 34.3 | 31 | 1159 | diagnosis | 2A |
| C7 | 29.4 | 1340 | M | B | 30.4 | 7 | 1360 | 22 | 33.6 | 29 | 1740 | suspicion | 1 |
| W11 | 27.6 | 790 | M | W | 28.4 | 7 | 940 | 86 | 40.7 | 93 | 2700 | diagnosis | 3B |

ETABLE 8

List of 86 Enrolled Infants Who Were Neither Clinically Diagnosed With or Suspected of Having Necrotizing Enterocolitis
Abbreviations for parent race/ethnicity self-identification: B = African American/Black; W = Caucasian/White; and H = Hispanic. Other abbreviations: GA = gestational age; M = male; F = female; C = Cesarean delivery; V = vaginal delivery

| subject ID | GA (wks) | birth weight (g) | sex | race/ ethnicity | birth delivery | demise in NICU |
|---|---|---|---|---|---|---|
| C13 | 25.0 | 710 | F | B | C | no |
| C14 | 24.4 | 710 | F | B | C | no |
| C15 | 24.6 | 715 | M | B | C | no |
| C16 | 27.1 | 915 | F | B | V | no |
| C17 | 23.9 | 490 | F | B | V | no |
| C18 | 26.0 | 855 | M | B | C | no |
| C19 | 27.0 | 950 | F | H | C | no |
| C20 | 31.7 | 1289 | M | W | C | no |

ETABLE 8-continued

List of 86 Enrolled Infants Who Were Neither Clinically Diagnosed With or Suspected of Having Necrotizing Enterocolitis
Abbreviations for parent race/ethnicity self-identification:
B = African American/Black; W = Caucasian/White; and H = Hispanic. Other abbreviations: GA = gestational age;
M = male; F = female; C = Cesarean delivery; V = vaginal delivery

| subject ID | GA (wks) | birth weight (g) | sex | race/ ethnicity | birth delivery | demise in NICU |
|---|---|---|---|---|---|---|
| C21 | 30.9 | 1390 | M | B | C | no |
| C22 | 24.1 | 630 | M | W | C | no |
| C23 | 27.0 | 1075 | F | H | C | no |
| C24 | 30.0 | 1489 | M | B | V | no |
| C25 | 26.0 | 589 | F | B | C | no |
| C26 | 31.6 | 1435 | F | W | C | no |
| T17 | 24.6 | 655 | M | B | V | no |
| T18 | 25.9 | 845 | M | B | V | no |
| T19 | 25.1 | 680 | M | W | V | no |
| T20 | 29.7 | 1035 | M | B | C | no |
| T21 | 29.9 | 1075 | F | B | C | no |
| T22 | 30.0 | 790 | F | W | C | no |
| T23 | 25.3 | 540 | F | B | C | no |
| T24 | 23.6 | 540 | M | B | C | no |
| T25 | 27.4 | 1500 | F | B | V | no |
| T26 | 28.7 | 1100 | M | B | C | no |
| T27 | 26.9 | 800 | F | W | C | no |
| T28 | 25.6 | 805 | F | B | C | no |
| T29 | 24.6 | 655 | M | W | V | no |
| T30 | 26.9 | 1025 | F | B | C | yes |
| T31 | 35.3 | 1240 | F | B | C | no |
| T32 | 30.0 | 850 | M | H | C | no |
| T33 | 30.0 | 1330 | M | B | C | no |
| T34 | 34.1 | 2450 | F | B | C | no |
| T35 | 34.1 | 2520 | F | B | C | no |
| T36 | 30.9 | 1390 | M | B | C | no |
| T37 | 26.4 | 910 | F | B | V | no |
| T38 | 26.0 | 915 | F | B | C | no |
| T39 | 25.0 | 625 | M | B | C | no |
| T40 | 26.9 | 1000 | M | W | C | no |
| T41 | 26.4 | 985 | M | B | V | no |
| T42 | 37.0 | 2703 | F | B | V | no |
| T43 | 28.1 | 1050 | M | B | C | no |
| T44 | 29.1 | 1310 | F | B | C | no |
| T45 | 29.1 | 1265 | M | B | C | no |
| T46 | 29.7 | 1350 | M | B | V | no |
| T47 | 26.4 | 845 | F | B | C | no |
| T48 | 28.4 | 1135 | M | B | C | no |
| T49 | 29.6 | 1291 | M | W | C | no |
| T50 | 29.3 | 1270 | M | B | C | no |
| T51 | 30.3 | 1150 | M | B | C | no |
| T52 | 32.1 | 1450 | M | B | V | no |
| T53 | 30.3 | 1020 | F | B | C | no |
| T54 | 32.4 | 1050 | F | B | V | no |
| T55 | 32.6 | 1525 | F | B | C | no |
| T56 | 32.6 | 1490 | F | B | C | no |
| T57 | 32.4 | 1220 | F | B | C | no |
| T58 | 32.3 | 1140 | F | B | C | no |
| T59 | 31.1 | 1335 | F | B | C | no |
| T60 | 32.4 | 1160 | F | B | C | no |
| T61 | 32.3 | 1770 | M | W | C | no |
| T62 | 34.1 | 1470 | F | B | C | no |
| T63 | 34.3 | 1230 | M | B | C | no |
| T64 | 35.6 | 1210 | M | B | C | no |
| T65 | 37.1 | 2320 | M | B | C | no |
| T66 | 32.3 | 1380 | M | B | C | no |
| W18 | 26.7 | 930 | F | W | C | yes |
| W19 | 29.9 | 1700 | F | W | V | no |
| W20 | 25.0 | 670 | F | B | C | no |
| W21 | 26.4 | 790 | F | B | V | no |
| W22 | 29.4 | 1150 | F | W | C | no |
| W23 | 29.3 | 1400 | M | W | V | no |
| W24 | 27.3 | 1160 | M | W | C | no |
| W25 | 27.3 | 1060 | M | W | C | no |
| W26 | 29.3 | 1580 | F | W | C | no |
| W27 | 31.9 | 2200 | M | W | V | no |
| W28 | 27.4 | 1110 | F | W | V | no |
| W29 | 31.9 | 1565 | F | B | V | no |
| W30 | 26.0 | 1030 | F | B | V | no |
| W31 | 29.1 | 1400 | M | W | V | no |
| W32 | 29.1 | 1370 | F | W | V | no |
| W33 | 26.6 | 890 | F | B | V | no |
| W34 | 29.6 | 1515 | F | W | V | no |
| W35 | 28.1 | 1200 | M | W | C | no |
| W36 | 27.9 | 1050 | M | B | V | no |
| W37 | 27.9 | 1140 | F | B | V | no |
| W38 | 25.4 | 630 | F | B | C | no |
| W39 | 36.4 | 3161 | M | W | C | no |

ETABLE 9

Summary of Sepsis and Other Non-GI Tract Infection Cohorts at Different Clinical Sites
The number of enrolled infants who were clinically designated as having sepsis or other non-GI infection are provided per hospital site.[3, 4] Cohort values shown are the total number of subjects enrolled at each site, grouped by gestational age (GA) bin. Percentages, in italics and within parentheses, are related to the number of cases divided by all subjects by cohort and gestational age at birth. Median and accompanying interquartile values, in italics and parentheses, are used to identify the post-conceptual age, day of age, and weight at time of infection. Abbreviations: GA = gestational age at birth; CH, Children's Hospital of New Orleans, LA; TI, Touro Infirmary, New Orleans, LA; WU, Washington University in St. Louis, St. Louis, Missouri.

| COHORT | | | OTHER NON-GI INFECTIONS | | | | SEPSIS | | | |
|---|---|---|---|---|---|---|---|---|---|---|
| | | | | episode closest to NEC | | | | episode closest to NEC | | |
| site | GA (wks) | # infants at risk | # infants | PCA (wks) | day of age | weight (g) | # infants | PCA (wks) | day of age | weight (g) |
| CH | <27 | 14 | 4 (21%) | 28.4 (26.9-30.4) | 17 (12-38) | 900 (780-1130) | 4 (29%) | 31.6 (27.8-35.9) | 46 (13-80) | 1375 (978-1725) |
| | ≥27 | 15 | 4 (27%) | 31.6 (30.9-32) | 32 (25-34) | 1154 (1061-1198) | 0 | 0 | 0 | 0 |
| | total | 29 | 8 (28%) | 31.6 (28.6-32) | 31 (12-37) | 1030 (878-1219) | 4 (14%) | 31.6 (27.8-35.9) | 46 (13-80) | 1375 (978-1725) |

ETABLE 9-continued

Summary of Sepsis and Other Non-GI Tract Infection Cohorts at Different Clinical Sites
The number of enrolled infants who were clinically designated as having sepsis or other non-GI infection
are provided per hospital site.[3, 4] Cohort values shown are the total number of subjects
enrolled at each site, grouped by gestational age (GA) bin. Percentages, in italics and within parentheses,
are related to the number of cases divided by all subjects by cohort and gestational age at birth. Median
and accompanying interquartile values, in italics and parentheses, are used to identify the post-conceptual
age, day of age, and weight at time of infection. Abbreviations: GA = gestational age at birth; CH,
Children's Hospital of New Orleans, LA; TI, Touro Infirmary, New Orleans, LA; WU, Washington
University in St. Louis, St. Louis, Missouri.

| COHORT | | | OTHER NON-GI INFECTIONS | | | | SEPSIS | | |
|---|---|---|---|---|---|---|---|---|---|
| | | | | episode closest to NEC | | | | episode closest to NEC | |
| site | GA (wks) | # infants at risk | # infants | PCA (wks) | day of age | weight (g) | # infants | PCA (wks) | day of age | weight (g) |
| TI | <27 | 22 | 5 (23%) | 29 (28.6-29.6) | 26 (26-28) | 960 (955-1030) | 6 (27%) | 28.3 (27.3-28.9) | 16 (9-27) | 820 (623-926) |
| | ≥27 | 46 | 2 (4%) | 32.2 | 29 | 2045 | 6 (13%) | 32.3 (31.8-33) | 17 (13-22) | 1303 (1200-1407) |
| | total | 68 | 7 (10%) | 29.6 (28.8-32.2) | 26 (25-33) | 1030 (958-1565) | 12 (18%) | 30.6 (28.4-32.1) | 17 (10-24) | 1140 (830-1266) |
| WU | <27 | 17 | 1 (6%) | 25.3 | 8 | 720 | 8 (47%) | 30 (28.6-33.6) | 41 (24-56) | 1070 (958-1310) |
| | ≥27 | 22 | 0 | 0 | 0 | 0 | 2 (9%) | 35.6 (34.8-36.3) | 19 (13-24) | 2150 (2115-2185) |
| | total | 39 | 1 (3%) | 25.3 | 8 | 720 | 10 (26%) | 32 (28.7-35.4) | 32 (22-51) | 1108 (980-2034) |
| All | <27 | 53 | 7 (13%) | 28.4 (26.4-28.8) | 23 (13-26) | 900 (708-958) | 18 (34%) | 28.8 (28-32) | 27 (15-51) | 1000 (810-1194) |
| | ≥27 | 83 | 6 (7%) | 31.6 (31.6-32.6) | 32 (23-37) | 1219 (1142-1575) | 8 (10%) | 33 (31.8-34.8) | 17 (12-24) | 1397 (1220-2115) |
| | total | 136 | 15 (11%) | 29 (28.4-31.7) | 26 (17-32) | 960 (855-1260) | 26 (19%) | 31.1 (28.5-33.8) | 22 (13-45) | 1108 (951-1630) |

ETABLE 10

List of All 26 Late-Onset Neonatal Sepsis Cases Enrolled
Sepsis event was either closest in time to NEC episode or after study enrollment.
Abbreviations: GA = gestational age at birth; M = male; F = female; B = African
American/Black, W = Caucasian/White, H = Hispanic, C = Cesarean
delivery; V = vaginal delivery; NA = not applicable.

| subject ID | GA (wk) | birth weight (g) | sex | race/ ethnicity | birth delivery | at time of sepsis PCA (wks) | day of life | total no. days antibiotics received (% of NICU stay) | NEC Bell stage (if applicable) | demise in NICU |
|---|---|---|---|---|---|---|---|---|---|---|
| C3* | 26.9 | 991 | M | B | V | 28 | 8 | 19 (25%) | 2 A | no |
| C13 | 25.0 | 710 | F | B | C | 27.1 | 15 | 28 (30%) | NA | no |
| C14 | 24.4 | 710 | F | B | C | 35.3 | 76 | 31 (20%) | NA | no |
| C15 | 24.6 | 715 | M | B | C | 37.6 | 91 | 61 (33%) | NA | no |
| T2 | 28.7 | 1010 | F | H | C | 29.9 | 9 | 23 (12%) | 2 B | no |
| T4 | 25.3 | 815 | M | B | C | 28.4 | 22 | 20 (23%) | 2 A | no |
| T6 | 34.6 | 1380 | M | H | C | 41.1 | 46 | 44 (17%) | 3 B | no |
| T7 | 30.0 | 1200 | F | W | C | 31.9 | 13 | 30 (5%) | 1 | no |
| T13 | 25.0 | 560 | F | B | V | 29.0 | 28 | 19 (22%) | 1 | no |
| T14 | 26.7 | 531 | F | B | C | 28.1 | 10 | 32 (39%) | 1 | no |
| T17 | 24.6 | 655 | M | B | V | 25.6 | 7 | 30 (16%) | NA | no |
| T18 | 25.9 | 845 | M | B | V | 27.0 | 8 | 18 (19%) | NA | no |
| T19* | 25.1 | 680 | M | W/B | V | 31.3 | 43 | 47 (29%) | NA | no |
| T20 | 29.7 | 1305 | M | B | C | 32.7 | 21 | 6 (12%) | NA | no |
| T21 | 29.9 | 1075 | F | B | C | 31.7 | 13 | 10 (27%) | NA | no |
| T22 | 30.0 | 790 | F | W | C | 33.1 | 22 | 17 (30%) | NA | no |
| W2* | 24.3 | 700 | F | B | C | 29.1 | 34 | 20 (20%) | 2 B | no |
| W4* | 26.0 | 480 | M | W | C | 32.9 | 48 | 36 (46%) | 2 B | yes |
| W6 | 36.3 | 2330 | F | W | C | 37.1 | 7 | 8 (57%) | 2 B | no |
| W8 | 24.3 | 650 | F | W | C | 27.1 | 21 | 10 (48%) | 3 A | yes |
| W14* | 23.6 | 430 | M | W | C | 31.0 | 52 | 49 (31%) | 2 B | no |
| W17* | 25.1 | 790 | M | B | C | 35.9 | 75 | 14 (14%) | 1 B | no |
| W18* | 26.7 | 930 | F | W | C | 36.0 | 66 | 17 (23%) | NA | yes |

ETABLE 10-continued

List of All 26 Late-Onset Neonatal Sepsis Cases Enrolled
Sepsis event was either closest in time to NEC episode or after study enrollment.
Abbreviations: GA = gestational age at birth; M = male; F = female; B = African American/Black, W = Caucasian/White, H = Hispanic, C = Cesarean delivery; V = vaginal delivery; NA = not applicable.

| subject ID | GA (wk) | birth weight (g) | sex | race/ ethnicity | birth delivery | at time of sepsis PCA (wks) | day of life | total no. days antibiotics received (% of NICU stay) | NEC Bell stage (if applicable) | demise in NICU |
|---|---|---|---|---|---|---|---|---|---|---|
| W19* | 29.9 | 1700 | F | W | V | 34.0 | 30 | 10 (20%) | NA | no |
| W20* | 25.0 | 670 | F | B | C | 25.0 | 1 | 25 (19%) | NA | no |
| W21* | 26.4 | 790 | F | B | V | 28.6 | 16 | 31 (22%) | NA | no |

*No samples were obtained during sepsis period. If a sample was not obtained during disease, all samples from the infant were excluded only from cross-sectional analyses of sepsis.

ETABLE 11

List of All 14 Cases of Confirmed, Non-GI Tract Infections in Urine, Bone, or Trachea
Abbreviations: GA = gestational age at birth; PCA = post-conceptual age; M = male; F = female; C = Cesarean delivery; V = vaginal delivery; T = trachea; B = bone; U = urine; S = skin.

| subject ID | GA (wk) | birth weight (g) | sex | race/ ethnicity | birth delivery | at time of infection PCA (wks) | day of life | total no. days antibiotics received (% of NICU stay) | NEC Bell stage (if applicable) | site of infection |
|---|---|---|---|---|---|---|---|---|---|---|
| C6 | 28.0 | 810 | M | B | V | 28.7 | 5 | 13 (11%) | 1 | T |
| C11 | 27.0 | 850 | M | B | C | 32.9 | 41 | 18 (18%) | 1 | T |
| C16 | 27.1 | 915 | F | B | V | 31.6 | 31 | 25 (19%) | 1 | B, T |
| C17 | 23.9 | 490 | F | B | V | 32.3 | 59 | 36 (27%) | NA | T |
| C18 | 26.0 | 855 | M | B | C | 28.4 | 17 | 30 (19%) | NA | T |
| C19 | 27.0 | 950 | F | H | C | 31.7 | 32 | 7 (10%) | NA | T |
| T5 | 25.0 | 855 | M | B | C | 28.6 | 23 | 13 (15%) | 2 A | T |
| T23 | 25.3 | 540 | F | B | C | 29.0 | 26 | 15 (18%) | NA | T |
| T24* | 23.6 | 540 | M | B | C | 27.3 | 26 | 30 (18%) | NA | T |
| T25* | 27.4 | 1500 | F | B | V | 32.9 | 38 | 8 (16%) | NA | S |
| T26* | 28.7 | 1100 | M | B | C | 31.6 | 20 | 18 (21%) | NA | T |
| T27 | 26.9 | 800 | F | W | C | 34.3 | 52 | 8 (8%) | NA | U |
| T28 | 25.6 | 805 | F | B | C | 29.6 | 28 | 10 (13%) | NA | S |
| W2* | 24.3 | 700 | F | B | C | 25.3 | 8 | 20 (10%) | 2 B | T |

*No samples were obtained during non-GI infection period. If a sample was not obtained during infection, all samples from the infant were excluded only from cross-sectional analyses of sepsis.

ETABLE 12

Accuracy and Reproducibility of In Vitro Measurements of Gut Lumen Content
Reference standard for total protein concentration was bovine serum albumin; expected absorbance (ABS) calibration standard was determined using the extinction coefficient for bovine serum albumin (43,824 $M^{-1}$ $cm^{-1}$) and Beer's law.
Reference standard for biochemical activity was 4-methylumbelliferyl phosphate; expected relative fluorescence units were provided by kit manufacturer. Median experimental measurement, reproducibility, and accuracy for each analyte are shown. P-values $\geq 0.05$ indicate there is no significant difference between measurements. Abbreviations: ABS = absorbance; RFU = relative fluorescence units; SE = standard error; SI = small intestine; ND = not determined

| ASSAY | RAW DATA | | | REPRODUCIBILITY | | ACCURACY | |
|---|---|---|---|---|---|---|---|
| | reference standard (mg/ml) | expected $ABS_{595\,nm}$ | median experimental $ABS_{595\,nm}$ | inter-operator SE | p-value | % deviation from absolute value | p-value |
| total protein concentration in stool | 0.750 | 0.166 | 0.176 | 0.010 | 0.52 | 4 | 0.52 |
| | 0.500 | 0.111 | 0.123 | 0.007 | 0.43 | 1 | 0.81 |
| | 0.250 | 0.055 | 0.055 | 0.003 | 0.52 | 10 | 0.18 |

ETABLE 12-continued

Accuracy and Reproducibility of In Vitro Measurements of Gut Lumen Content
Reference standard for total protein concentration was bovine serum albumin; expected
absorbance (ABS) calibration standard was determined using the extinction coefficient
for bovine serum albumin (43,824 $M^{-1}$ $cm^{-1}$) and Beer's law.
Reference standard for biochemical activity was 4-methylumbelliferyl phosphate; expected
relative fluorescence units were provided by kit manufacturer. Median experimental
measurement, reproducibility, and accuracy for each analyte are shown. P-values ≥ 0.05
indicate there is no significant difference between measurements. Abbreviations: ABS = absorbance;
RFU = relative fluorescence units; SE = standard error; SI = small intestine; ND = not determined

|  | | | | | | | |
|---|---|---|---|---|---|---|---|
| supernatant | 0.125 | 0.027 | 0.220 | 0.002 | 0.72 | 28 | 0.0003 |
| (Bradford | 0.025 | 0.004 | 0.002 | 0.001 | 0.10 | 70 | <0.0001 |
| assay) | 0.000 | 0.000 | 0.001 | 0.001 | 0.22 | 50 | 0.0002 |

|  | reference standard (nmol) | expected RFU | median experimental RFU | inter-operator SE | p-value | % deviation from absolute value | p-value |
|---|---|---|---|---|---|---|---|
| iAP biochemical activity (MUP assay) | 0.5 | 20,957,775 | 19,915,897 | 1,685,719 | 0.28 | 5 | 0.55 |
| | 0.4 | 16,951,461 | 16,448,436 | 839,613 | 0.45 | 2 | 0.72 |
| | 0.3 | 12,945,147 | 12,900,112 | 757,993 | 0.27 | 1 | 0.90 |
| | 0.2 | 8,938,833 | 8,419,157 | 630,068 | 0.47 | 3 | 0.70 |
| | 0.1 | 4,932,519 | 4,555,401 | 298,513 | 0.34 | 0 | 0.99 |
| | 0 | 926,205 | 85,588 | 2,049 | 0.88 | 91 | 0.008 |

|  | reference standard | expected concentration (µg) | median experimental RFU | inter-operator SE | p-value | % deviation from absolute value | p-value |
|---|---|---|---|---|---|---|---|
| iAP abundance (immunoblot) | human SI lysate | 3.75 | 207,055 | 31,862 | 0.72 | ND | ND |
| | purified calf iAP | 3.00 | 703 | 113 | 0.11 | ND | ND |

ETABLE 13

IAP Measurements From 20 Stool Samples at the
Time of Severe Necrotizing Enterocolitis

| subject ID | PCA at time of sample collection (wk) | weight at sample collection (g) | iAP activity (µmol $min^{-1}$ $g^{-1}$ stool protein) | relative iAP content (% human SI) |
|---|---|---|---|---|
| C1 | 34.3 | 1159 | 575 | 95.5 |
| C2 | 31.0 | 1085 | 441 | 132.7 |
| C3 | 34.3 | 1840 | 2195 | 30.8 |
| C4 | 43.3 | 2825 | 70 | 162.8 |
| C5 | 31.0 | 1620 | 217 | 50.0 |
| T1 | 31.0 | 1190 | 222 | 103.4 |
| T2 | 29.9 | 1090 | 648 | 10.2 |
| T3 | 33.9 | 1430 | 135 | 71.0 |
| T4 | 34.0 | 1641 | 478 | 216.3 |
| T6 | 38.6 | 2580 | 54 | 213.2 |
| W1 | 35.1 | 2050 | 23 | 242.2 |
| W2 | 26.1 | 900 | 48 | 153.8 |
| W3 | 34.3 | 1650 | 127 | 48.7 |
| W4 | 34.6 | 1300 | 517 | 68.7 |
| W5 | 43.9 | 3040 | 18 | 79.0 |
| W6 | 37.1 | 2220 | 29 | 196.1 |
| W7 | 27.7 | 1330 | 63 | 144.6 |
| W8 | 27.1 | 1040 | 519 | 32.9 |
| W9 | 39.6 | 2400 | 284 | 54.0 |
| W11 | 40.9 | 2700 | 148 | 328.0 |

ETABLE 14

IAP Measurements From 15 Stool Samples at the
Time of Necrotizing Enterocolitis Suspicion

| subject ID | PCA at time of sample collection (wk) | weight at sample collection (g) | iAP activity (µmol $min^{-1}$ $g^{-1}$ stool protein) | relative iAP content (% human SI) |
|---|---|---|---|---|
| C6 | 29.1 | 855 | 6 | 317.8 |
| C7 | 33.6 | 1740 | 227 | 129.5 |
| C9 | 29.6 | 920 | 272 | 39.5 |
| C10 | 36.0 | 1464 | 172 | 123.0 |
| T8 | 29.4 | 1070 | 424 | 30.9 |
| T9 | 30.7 | 1435 | 2075 | 366.9 |
| T10 | 35.1 | 1378 | 520 | 212.9 |
| T11 | 30.3 | 970 | 127 | 223.8 |
| T13 | 26.9 | 553 | 460 | 28.3 |
| T14 | 28.1 | 495 | 355 | 85.5 |
| T15 | 28.7 | 870 | 608 | 158.3 |
| T16 | 29.1 | 1005 | 970 | 14.7 |
| W15 | 29.1 | 1305 | 2 | 584.5 |
| W16 | 30.4 | 860 | 2307 | 117.7 |
| W17 | 26.9 | 820 | 268 | 19.8 |

ETABLE 15

IAP Measurements From 86 Enrolled Infants Who
Were Neither Clinically Diagnosed With nor Suspected
of Having Necrotizing Enterocolitis.

| subject ID | PCA at time of sample collection (wk) | weight at sample collection (g) | iAP activity (µmol $min^{-1}$ $g^{-1}$ stool protein) | relative iAP content (% human SI) |
|---|---|---|---|---|
| C13 | 31.3 | 1580 | 1231 | 0.1 |
| C14 | 39.0 | 2560 | 723 | 2.8 |
| C15 | 40.1 | 2170 | 3195 | 10.7 |
| C16 | 40.4 | 2950 | 1872 | 7.6 |

ETABLE 15-continued

IAP Measurements From 86 Enrolled Infants Who Were Neither Clinically Diagnosed With nor Suspected of Having Necrotizing Enterocolitis.

| subject ID | PCA at time of sample collection (wk) | weight at sample collection (g) | iAP activity (μmol min$^{-1}$ g$^{-1}$ stool protein) | relative iAP content (% human SI) |
|---|---|---|---|---|
| C17 | 35.1 | 1440 | 9752 | 0.9 |
| C18 | 27.0 | 810 | 463 | 5.6 |
| C19 | 34.1 | 1210 | 622 | 2.5 |
| C20 | 33.6 | 1370 | 805 | 3.7 |
| C21 | 28.9 | 780 | 786 | 7.4 |
| C22 | 29.7 | 1090 | 784 | 4.4 |
| C23 | 37.9 | 2725 | 1848 | 2.4 |
| C24 | 30.7 | 1296 | 2695 | 9.5 |
| C25 | 38.1 | 2270 | 7495 | 1.2 |
| C26 | 39.3 | 2390 | 1243 | 0.7 |
| T17 | 25.4 | 595 | 554 | 26.3 |
| T18 | 26.9 | 840 | 470 | 27.9 |
| T19 | 42.7 | 2660 | 6922 | 2.7 |
| T20 | 30.4 | 1040 | 175 | 4.5 |
| T21 | 30.7 | 1025 | 995 | 5.0 |
| T22 | 31.9 | 900 | 1477 | 2.6 |
| T23 | 26.7 | 600 | 405 | 5.9 |
| T24 | 32.0 | 1705 | 2787 | 2.1 |
| T25 | 31.3 | 1960 | 875 | 2.4 |
| T26 | 37.3 | 1513 | 7393 | 4.6 |
| T27 | 27.7 | 650 | 884 | 1.9 |
| T28 | 27.0 | 790 | 344 | 0.3 |
| T29 | 25.6 | 500 | 144 | 14.2 |
| T30 | 28.0 | 990 | 386 | 4.2 |
| T31 | 38.4 | 1660 | 2268 | 3.2 |
| T32 | 30.0 | 850 | 83 | 2.6 |
| T33 | 32.6 | 1727 | 669 | 3.4 |
| T34 | 35.0 | 2285 | 1608 | 5.3 |
| T35 | 34.7 | 2415 | 2303 | 6.3 |
| T36 | 32.7 | 1476 | 61 | 3.8 |
| T37 | 26.4 | 910 | 714 | 6.8 |
| T38 | 26.7 | 750 | 354 | 11.0 |
| T39 | 29.7 | 990 | 409 | 5.7 |
| T40 | 31.3 | 1450 | 1219 | 26.5 |
| T41 | 34.0 | 2160 | 723 | 0.9 |
| T42 | 37.0 | 2703 | 170 | 4.6 |
| T43 | 29.0 | 965 | 63 | 11.6 |
| T44 | 29.6 | 1165 | 305 | 6.2 |
| T45 | 34.0 | 2084 | 2244 | 6.5 |
| T46 | 32.0 | 1450 | 350 | 1.0 |
| T47 | 28.0 | 850 | 148 | 51.1 |
| T48 | 35.9 | 2428 | 6904 | 0.8 |
| T49 | 31.3 | 1270 | 603 | 3.2 |
| T50 | 30.7 | 1215 | 660 | 11.0 |
| T51 | 31.7 | 1180 | 180 | 2.9 |
| T52 | 35.0 | 1790 | 337 | 2.1 |
| T53 | 32.4 | 1122 | 117 | 2.5 |
| T54 | 34.0 | 1114 | 1461 | 4.1 |
| T55 | 38.6 | 2269 | 291 | 3.5 |
| T56 | 33.9 | 1478 | 1898 | 1.5 |
| T57 | 35.9 | 1809 | 2618 | 1.1 |
| T58 | 33.1 | 1230 | 6310 | 15.6 |
| T59 | 36.0 | 1837 | 80 | 7.9 |
| T60 | 34.1 | 1299 | 654 | 2.7 |
| T61 | 36.4 | 2357 | 383 | 1.0 |
| T62 | 35.3 | 2040 | 7386 | 4.6 |
| T63 | 35.4 | 1277 | 136 | 5.4 |
| T64 | 37.9 | 1423 | 211 | 1.0 |
| T65 | 37.7 | 2836 | 544 | 17.2 |
| T66 | 34.9 | 1550 | 1527 | 22.6 |
| W18 | 29.9 | 1240 | 40 | 4.9 |
| W19 | 31.6 | 1600 | 132 | 17.8 |
| W20 | 28.3 | 960 | 176 | 12.7 |
| W21 | 30.0 | 1090 | 919 | 7.5 |
| W22 | 33.4 | 1680 | 39 | 49.1 |
| W23 | 31.4 | 1520 | 97 | 6.1 |
| W24 | 31.0 | 1560 | 714 | 140.6 |
| W25 | 31.0 | 1460 | 357 | 46.3 |
| W26 | 35.6 | 2550 | 656 | 5.1 |
| W27 | 31.4 | 2040 | 214 | 3.2 |
| W28 | 29.0 | 970 | 695 | 15.7 |
| W29 | 33.4 | 1670 | 239 | 5.2 |
| W30 | 26.6 | 960 | 376 | 12.7 |
| W31 | 33.7 | 2070 | 76 | 6.0 |
| W32 | 33.7 | 1924 | 172 | 6.6 |
| W33 | 33.9 | 1875 | 40 | 7.4 |
| W34 | 40.4 | 3720 | 2275 | 0.5 |
| W35 | 28.6 | 1150 | 474 | 14.3 |
| W36 | 30.7 | 1320 | 547 | 0.4 |
| W37 | 28.7 | 1095 | 170 | 2.4 |
| W38 | 26.1 | 565 | 205 | 209.0 |
| W39 | 36.9 | 3260 | 916 | 0.3 |

ETABLE 16

Proteins Identified in Preterm Gut Lumen (N = 635)

Collected from non-NEC infant, who was 32.57 weeks (wk) postconceptual age and 1000 g weight, a stool sample was analyzed by shotgun mass spectrometry. Proteins are ordered by sumPEP score. Shown are descriptions and Uniprot ID of proteins with MS sumPEP scores of 1400 to 96.

| UniProt ID | Description |
|---|---|
| Q9Y6R7 | IgGFc-binding protein |
| P02768 | serum albumin |
| P02787 | serotransferrin |
| P01024 | complement C3 |
| P00450 | ceruloplasmin |
| P14410 | sucrase-isomaltase, intestinal |
| P98088 | mucin-5AC |
| P01009 | alpha-1-antitrypsin |
| P15144 | aminopeptidase N |
| Q9HC84 | mucin-5B |
| P02751 | fibronectin |
| P01011 | alpha-1-antichymotrypsin |
| P01008 | antithrombin-III |
| P0DOX5 | immunoglobulin gamma-1 heavy chain |
| A8K7I4 | calcium-activated Cl channel regulator 1 |
| P02538 | keratin, type II cytoskeletal 6A |
| P19835 | bile salt-activated lipase |
| P48668 | keratin, type II cytoskeletal 6C |
| Q9BYF1 | angiotensin-converting enzyme 2 |
| P28838 | cytosol aminopeptidase |
| P30740 | leukocyte elastase inhibitor |
| P13645 | keratin, type I cytoskeletal 10 |
| P00738 | haptoglobin |
| P04259 | keratin, type II cytoskeletal 6B |
| P02763 | alpha-1-acid glycoprotein 1 |
| P01861 | immunoglobulin heavy constant gamma 4 |
| A8K2U0 | alpha-2-macroglobulin-like protein 1 |
| P29508 | serpin B3 |
| P02790 | hemopexin |
| P35527 | keratin, type I cytoskeletal 9 |

ETABLE 16-continued

Proteins Identified in Preterm Gut Lumen (N = 635)

| UniProt ID | Description | UniProt ID | Description |
|---|---|---|---|
| P12821 | angiotensin-converting enzyme | P06702 | protein S100-A9 |
| P02788 | lactotransferrin | P01833 | polymeric immunoglobulin receptor |
| Q9UGM3 | deleted in malignant brain tumors 1 protein | P15085 | carboxypeptidase A1 |
| Q02817 | mucin-2 | Q9H3R2 | mucin-13 |
| Q16819 | meprin A subunit alpha | Q9BYE9 | cadherin-related family member 2 |
| P01859 | immunoglobulin heavy constant gamma 2 | P05543 | thyroxine-binding globulin |
| P01023 | alpha-2-macroglobulin | P20742 | pregnancy zone protein |
| P25311 | zinc-alpha-2-glycoprotein | P04217 | alpha-1B-glycoprotein |
| P00747 | plasminogen | Q13228 | selenium-binding protein 1 |
| Q6UWV6 | ectonucleotide pyrophosphatase-phosphodiesterase family member 7 | P09848 | lactase-phlorizin hydrolase |
|  |  | P01031 | complement C5 |
| P09923 | intestinal-type alkaline phosphatase | P01876 | immunoglobulin heavy constant alpha 1 |
| O43895 | Xaa-Pro aminopeptidase 2 | P08779 | keratin, type I cytoskeletal 16 |
| P0DOX7 | immunoglobulin kappa light chain | Q6UX06 | olfactomedin-4 |
| P27487 | dipeptidyl peptidase 4 | P27216 | annexin A13 |
| P08473 | neprilysin [OS = *Homo sapiens*] | P02533 | keratin, type I cytoskeletal 14 |
| P04264 | keratin, type II cytoskeletal 1 | P16444 | dipeptidase 1 |
| Q8TDL5 | BPI fold-containing family B member 1 | P09525 | annexin A4 |
| P01834 | immunoglobulin kappa constant | P02771 | alpha-fetoprotein |
| P01860 | immunoglobulin heavy constant gamma 3 | O75882 | attractin |
| P55259 | pancreatic secretory granule membrane major glycoprotein GP2 | P19652 | alpha-1-acid glycoprotein 2 |
|  |  | Q04609 | glutamate carboxypeptidase 2 |
| P02760 | protein AMBP | P08697 | alpha-2-antiplasmin |
| P07911 | uromodulin | P51884 | lumican |
| P13646 | keratin, type I cytoskeletal 13 | P15086 | carboxypeptidase B |
| P02766 | transthyretin | P69892 | hemoglobin subunit gamma-2 |
| P35237 | serpin B6 | P29622 | kallistatin |
| Q08380 | galectin-3-binding protein | P06748 | nucleophosmin |
| P0C0L4 | complement C4-A | P13647 | keratin, type II cytoskeletal 5 |
| P60174 | triosephosphate isomerase |  |  |
| P47989 | xanthine dehydrogenase/oxidase |  |  |

Shown are descriptions and Uniprot ID of proteins with MS sumPEP scores of 95.0 to 47.9.

| UniProt ID | Description | UniProt ID | Description |
|---|---|---|---|
| P05155 | plasma protease C1 inhibitor | Q2M2H8 | probable maltase-glucoamylase 2 |
| P02753 | retinol-binding protein 4 | P04083 | annexin A1 |
| P06733 | alpha-enolase | P62736 | actin, aortic smooth muscle |
| P0DOX8 | immunoglobulin lambda-1 light chain | P02675 | fibrinogen beta chain |
| P0DOX2 | immunoglobulin alpha-2 heavy chain | P08582 | melanotransferrin |
| P69891 | hemoglobin subunit gamma-1 | P10643 | complement component C7 |
| P0DOY2 | immunoglobulin lambda constant 2 | P62979 | ubiquitin-40S ribosomal protein S27a |
| P07148 | fatty acid-binding protein, liver | Q13867 | bleomycin hydrolase |
| Q9BXP8 | pappalysin-2 | P15941 | mucin-1 |
| P04406 | glyceraldehyde-3-phosphate dehydrogenase | P09622 | dihydrolipoyl dehydrogenase, mitochondrial |
| P15586 | N-acetylglucosamine-6-sulfatase | Q9UBG3 | cornulin |
| P12830 | cadherin-1 | Q8NFJ5 | retinoic acid-induced protein 3 |
| Q12864 | cadherin-17 | P09093 | chymotrypsin-like elastase 3A |
| P05120 | plasminogen activator inhibitor 2 | Q9NQ84 | G-protein coupled receptor family C group 5 member C |
| P62158 | calmodulin |  |  |
| P19440 | glutathione hydrolase 1 proenzyme | Q07075 | glutamyl aminopeptidase |
| P08185 | corticosteroid-binding globulin | Q07654 | trefoil factor 3 |
| P17931 | galectin-3 | Q07837 | neutral and basic amino acid transport protein rBAT |
| P19013 | keratin, type II cytoskeletal 4 |  |  |
| P60709 | actin, cytoplasmic 1 | Q03154 | aminoacylase-1 |
| P07858 | cathepsin B | Q10588 | ADP-ribosyl cyclase/cyclic ADP-ribose hydrolase 2 |
| P19801 | amiloride-sensitive amine oxidase |  |  |
| P49747 | cartilage oligomeric matrix protein | Q9Y646 | carboxypeptidase Q |
| P07477 | trypsin-1 | P01042 | kininogen-1 |
| P07478 | trypsin-2 | P04179 | superoxide dismutase [Mn], mitochondrial |
| P35908 | keratin, type II cytoskeletal 2 epidermal | P13727 | bone marrow proteoglycan |
| O95497 | pantetheinase | Q6UXC1 | apical endosomal glycoprotein |
| O14983 | sarcoplasmic/ER calcium ATPase 1 | P17538 | chymotrypsinogen B |
| P05090 | apolipoprotein D | P04114 | apolipoprotein B-100 |
| P07998 | ribonuclease pancreatic | P00390 | glutathione reductase, mitochondrial |
| P07686 | beta-hexosaminidase subunit beta | Q6FI13 | histone H2A type 2-A |
| P54802 | alpha-N-acetylglucosaminidase | O75369 | filamin-B |
| P41222 | prostaglandin-H2 D-isomerase | Q04695 | keratin, type I cytoskeletal 17 |
| Q15493 | regucalcin | P00338 | L-lactate dehydrogenase A chain |
| P02749 | beta-2-glycoprotein 1 | O43451 | maltase-glucoamylase, intestinal |
| P02748 | complement component C9 | O14818 | proteasome subunit alpha type-7 |
| P07093 | glia-derived nexin | P12955 | Xaa-Pro dipeptidase |
| P07996 | thrombospondin-1 | Q9ULA0 | aspartyl aminopeptidase |
| Q9Y2T3 | guanine deaminase | Q99895 | chymotrypsin-C |
| P48052 | carboxypeptidase A2 | P50995 | annexin A11 |
| P05787 | keratin, type II cytoskeletal 8 | P04040 | catalase |
| P05109 | protein S100-A8 | P04196 | histidine-rich glycoprotein |

ETABLE 16-continued

Proteins Identified in Preterm Gut Lumen (N = 635)

| UniProt ID | Description | UniProt ID | Description |
|---|---|---|---|
| Q12805 | EGF-containing fibulin-like extracellular matrix protein 1 | P15311 | ezrin |
| | | P35555 | fibrillin-1 |
| P04118 | colipase | P07225 | vitamin K-dependent protein S |
| | | Q12929 | epidermal growth factor receptor kinase substrate 8 |
| | | O43707 | alpha-actinin-4 |

Shown are descriptions and Uniprot ID of proteins with MS sumPEP scores of 47.6 to 13.0.

| UniProt ID | Description | UniProt ID | Description |
|---|---|---|---|
| P05154 | plasma serine protease inhibitor | P40199 | carcinoembryonic antigen-related cell adhesion molecule 6 |
| Q9HBB8 | cadherin-related family member 5 | | |
| P13929 | beta-enolase | Q08188 | protein-glutamine gamma-glutamyltransferase E |
| P04908 | histone H2A type 1-B/E | | |
| O43280 | trehalase | P00751 | complement factor B |
| A0A0C4DH31 | immunoglobulin heavy variable 1-18 | P21589 | 5'-nucleotidase |
| P02750 | leucine-rich alpha-2-glycoprotein | P69905 | hemoglobin subunit alpha |
| Q14624 | inter-alpha-trypsin inhibitor heavy chain H4 | P27105 | erythrocyte band 7 integral membrane protein |
| P07093 | glia-derived nexin | P01871 | immunoglobulin heavy constant mu |
| P20933 | N(4)-(beta-N-acetylglucosaminyl)-L-asparaginase | P06744 | glucose-6-phosphate isomerase |
| | | P28799 | granulins |
| Q9H6S3 | epidermal growth factor receptor kinase substrate 8-like protein 2 | P00734 | prothrombin |
| | | P16930 | fumarylacetoacetase |
| P08727 | keratin, type I cytoskeletal 19 | P12429 | annexin A3 |
| Q92820 | gamma-glutamyl hydrolase | P04054 | phospholipase A2 |
| P23142 | fibulin-1 | Q99828 | calcium and integrin-binding protein 1 |
| P12532 | creatine kinase U-type, mitochondrial | Q9UQQ1 | N-acetylated-alpha-linked acidic dipeptidase-like protein |
| P61916 | epididymal secretory protein E1 | | |
| Q01546 | keratin, type II cytoskeletal 2 oral | P43652 | afamin |
| Q92485 | acid sphingomyelinase-like phosphodiesterase 3B | Q14520 | hyaluronan-binding protein 2 |
| | | P07339 | cathepsin D |
| P08861 | chymotrypsin-like elastase family member 3B | P12273 | prolactin-inducible protein |
| | | P02765 | alpha-2-HS-glycoprotein |
| P31151 | protein S100-A7 | A0A0B4J1X5 | immunoglobulin heavy variable 3-74 |
| Q03403 | trefoil factor 2 | P16422 | epithelial cell adhesion molecule |
| P24855 | deoxyribonuclease | Q53GD3 | choline transporter-like protein 4 |
| P04004 | vitronectin | P04432 | immunoglobulin kappa variable 1D-39 |
| Q96DA0 | zymogen granule protein 16 homolog | O00391 | sulfhydryl oxidase 1 |
| P31025 | lipocalin-1 | Q96KP4 | cytosolic non-specific dipeptidase |
| Q9UGM5 | fetuin-B | P08253 | 72 kDa type IV collagenase |
| Q13822 | ectonucleotide pyrophosphatase-phosphodiesterase family member 2 | A0A0C4DH29 | immunoglobulin heavy variable 1-3 |
| | | Q03591 | complement factor H-related protein 1 |
| P08236 | beta-glucuronidase | P05556 | integrin beta-1 |
| P02774 | vitamin D-binding protein | Q9H0W9 | ester hydrolase C11orf54 |
| P04278 | sex hormone-binding globulin | Q9NR71 | neutral ceramidase |
| Q9UHL4 | dipeptidyl peptidase 2 | P40925 | malate dehydrogenase, cytoplasmic |
| P13866-1 | sodium/glucose cotransporter 1 | Q13162 | peroxiredoxin |
| P00441 | superoxide dismutase | Q6EMK4 | vasorin |
| P63104 | 14-3-3 protein zeta/delta | P06731 | carcinoembryonic antigen-related cell adhesion molecule 5 |
| P80188 | neutrophil gelatinase-associated lipocalin | | |
| Q9H3G5 | probable serine carboxypeptidase | | |

Shown are descriptions and Uniprot ID of proteins with MS sumPEP scores of 30.8 to 21.3.

| UniProt ID | Description | UniProt ID | Description |
|---|---|---|---|
| Q06830 | peroxiredoxin-1 | Q8WUM4 | programmed cell death 6-interacting protein |
| P06865 | beta-hexosaminidase subunit alpha | | |
| P09211 | glutathione S-transferase | Q14315 | filamin-C |
| P04745 | alpha-amylase 1 | P29377 | protein S100-G |
| Q695T7 | sodium-dependent neutral amino acid transporter B(0)AT1 | P04066 | tissue alpha-L-fucosidase |
| | | P08174 | complement decay-accelerating factor |
| P02489 | alpha-crystallin A chain | P61626 | lysozyme c |
| Q6UWP2 | dehydrogenase/reductase SDR family member 11 | P36222 | chitinase-3-like protein 1 |
| | | Q86SQ4 | adhesion G-protein coupled receptor |
| P36980 | complement factor H-related protein 2 | Q14002 | carcinoembryonic antigen-related cell adhesion molecule 7 |
| P03973 | antileukoproteinase | | |
| O60494 | cubilin | P09972 | fructose-bisphosphate aldolase C |
| Q6P1J6 | phospholipase B1, membrane-associated | P01743 | immunoglobulin heavy variable 1-46 |
| | | Q01518 | adenylyl cyclase-associated protein 1 |
| Q9HAT2 | sialate O-acetylesterase | P25788 | proteasome subunit alpha type-3 |
| P01780 | immunoglobulin heavy variable 3-7 | O43490 | prominin-1 |
| P01824 | immunoglobulin heavy variable 4-39 | P98160 | basement membrane-specific heparan sulfate proteoglycan core protein |
| O14745 | Na(+)/H(+) exchange regulatory cofactor NHE-RF1 | | |
| | | Q9NP55 | BPI fold-containing family A member 1 |
| P25789 | proteasome subunit alpha type-4 | P26038 | moesin |
| P05546 | heparin cofactor 2 | P53990 | IST1 homolog |
| P17900 | ganglioside GM2 activator | P01614 | immunoglobulin kappa variable 2D-40 |

ETABLE 16-continued

Proteins Identified in Preterm Gut Lumen (N = 635)

| UniProt ID | Description | UniProt ID | Description |
|---|---|---|---|
| P60900 | proteasome subunit alpha type-6 | P28066 | proteasome subunit alpha type-5 |
| Q5T2W1 | Na/H exchange regulatory cofactor | P62937 | peptidyl-prolyl cis-trans isomerase A |
| P02679 | fibrinogen gamma chain | Q99497 | protein/nucleic acid deglycase DJ-1 |
| P12882 | myosin-1 | P11047 | laminin subunit gamma-1 |
| P07358 | complement component C8 β chain | A0A0C4DH38 | immunoglobulin heavy variable 5-51 |
| P19827 | inter-alpha-trypsin inhibitor heavy chain H1 | P01624 | immunoglobulin kappa variable 3-15 |
| A0A0B4J1Y9 | immunoglobulin heavy variable 3-72 | Q8TE67 | epidermal growth factor receptor kinase substrate 8-like protein 3 |
| Q14508 | WAP four-disulfide core domain protein 2 | P62258 | 14-3-3 protein epsilon |
| | | O00754 | lysosomal alpha-mannosidase |
| P01782 | immunoglobulin kappa variable 3-9 | P16233 | pancreatic triacylglycerol lipase |
| P22352 | glutathione peroxidase 3 | A0A087WSY6 | immunoglobulin kappa variable 3D-15 |
| O14638 | ectonucleotide pyrophosphatase-phosphodiesterase family member 3 | Q01459 | di-N-acetylchitobiase |
| | | P01591 | immunoglobulin J chain |
| Q8N4F0 | BPI fold-containing family B member 2 | A0A0C4DH73 | immunoglobulin kappa variable 1-12 |
| P13688 | carcinoembryonic antigen-related cell adhesion molecule 1 | A0A0B4J1X8 | immunoglobulin heavy variable 3-43 |
| | | P20618 | proteasome subunit beta type-1 |
| Q99715 | collagen alpha-1(XII) chain | P01764 | immunoglobulin heavy variable 3-23 |
| Q8TE67 | epidermal growth factor receptor kinase substrate 8-like protein 3 | | |
| P12111 | collagen alpha-3(VI) chain | | |
| P01019 | angiotensinogen | | |
| P07195 | L-lactate dehydrogenase B chain | | |

Shown are descriptions and Uniprot ID of proteins with MS sumPEP scores of 21.2 to 13.1.

| UniProt ID | Description | UniProt ID | Description |
|---|---|---|---|
| A0A0C4DH67 | immunoglobulin kappa variable 1-8 | P12814 | alpha-actinin-1 |
| A0A0B4J1V2 | immunoglobulin heavy variable 2-26 | P27482 | calmodulin-like protein 3 |
| P01619 | immunoglobulin kappa variable 3-20 | Q13277 | syntaxin-3 |
| O75830 | serpin I2 | P61981 | 14-3-3 protein gamma |
| P61224 | Ras-related protein Rap-1b | P09327 | villin-1 |
| P06576 | ATP synthase subunit beta | P08962 | CD63 antigen |
| P01594 | immunoglobulin kappa variable 1-33 | O43653 | prostate stem cell antigen |
| P11678 | eosinophil peroxidase | O00584 | ribonuclease T2 |
| A0A0C4DH25 | immunoglobulin kappa variable 3D-20 | A0A075B6S6 | immunoglobulin kappa variable 2D-30 |
| Q16651 | prostasin | Q6UXY8 | transmembrane channel-like protein 5 |
| P62805 | histone H4 | Q8WWA0 | intelectin-1 |
| O60635 | tetraspanin-1 | Q9HD89 | resistin |
| P29992 | guanine nucleotide-binding protein subunit alpha-11 | P45880 | voltage-dependent anion-selective channel protein 2 |
| P78324 | tyrosine-protein phosphatase non-receptor type substrate 1 | P21796 | voltage-dependent anion-selective channel protein 1 |
| P00915 | carbonic anhydrase 1 | P17050 | alpha-N-acetylgalactosaminidase |
| P0DOX6 | immunoglobulin mu heavy chain | Q53R12 | transmembrane 4 |
| Q15113 | procollagen C-endopeptidase enhancer 1 | P11279 | lysosome-associated membrane glycoprotein 1 |
| Q9NZH0 | G-protein coupled receptor family C group 5 member B | Q86VB7 | scavenger receptor cysteine-rich type 1 protein |
| Q6YHK3 | CD109 antigen | Q9Y624 | junctional adhesion molecule A |
| P01766 | immunoglobulin heavy variable 3-13 | A0A075B6S2 | immunoglobulin kappa variable 2D-29 |
| A0A0A0MRZ8 | immunoglobulin kappa variable 3D-11 | Q14533 | keratin, type II cuticular Hb1 |
| P53634 | dipeptidyl peptidase 1 | P00505 | aspartate aminotransferase |
| A0A0B4J1V0 | immunoglobulin heavy variable 3-15 | P01700 | immunoglobulin lambda variable 1-47 |
| P01040 | cystatin-A | P11142 | heat shock cognate 71 kDa protein |
| Q6W4X9 | mucin-6 | P62070 | Ras-related protein R-Ras2 |
| P23083 | immunoglobulin heavy variable 1-2 | P43251 | biotinidase |
| Q15848 | adiponectin | P80748 | immunoglobulin lambda variable 3-21 |
| Q15274 | nicotinate-nucleotide pyrophosphorylase | Q9Y5Y7 | lymphatic vessel endothelial hyaluronic acid receptor 1 |
| A0A0A0MS15 | immunoglobulin heavy variable 3-49 | | |
| P05156 | complement factor I | P06396 | gelsolin |
| A0A0J9YXX1 | immunoglobulin heavy variable 5-10-1 | Q96NY7 | chloride intracellular channel protein 6 |
| P13671 | complement component c6 | P01034 | cystatin-C |
| P05121 | plasminogen activator inhibitor 1 | P12277 | creatine kinase B-type |
| Q13219 | pappalysin-1 | Q14393 | growth arrest-specific protein 6 |
| P31947 | 14-3-3 protein sigma | P01704 | immunoglobulin lambda variable 2-14 |
| Q9H4M9 | EH domain-containing protein 1 | P04632 | calpain small subunit 1 |
| P08294 | extracellular superoxide dismutase | P55287 | cadherin-11 |
| P01599 | immunoglobulin kappa variable 1-17 | Q14CN2 | Ca-activated chloride channel regulator |
| P31949 | protein S100-A11 | O75131 | copine-3 |

ETABLE 16-continued

Proteins Identified in Preterm Gut Lumen (N = 635)

| UniProt ID | Description | UniProt ID | Description |
|---|---|---|---|
| P04155 | trefoil factor 1 | P28070 | proteasome subunit beta type-4 |
| Q96A32 | myosin regulatory light chain 2, skeletal muscle | P25786 | proteasome subunit alpha type-1 |
| | | Q9UK41 | vacuolar protein sorting-associated protein |

Shown are descriptions and Uniprot ID of proteins with MS sumPEP scores of 13.0 to 8.1.

| UniProt ID | Description | UniProt ID | Description |
|---|---|---|---|
| P0C0S5 | histone H2A.Z | P10619 | lysosomal protective protein |
| P06312 | immunoglobulin kappa variable 4-1 | P01701 | immunoglobulin lambda variable 1-51 |
| O94760 | N(G),N(G)-dimethylarginine dimethylaminohydrolase 1 | Q92484 | acid sphingomyelinase-like phosphodiesterase 3a |
| P36957 | dihydrolipoyllysine-residue succinyltransferase | P22735 | protein-glutamine gamma-glutamyltransferase K |
| A0A0B4J2H0 | immunoglobulin heavy variable 1-69D | Q8NCR9 | clarin-3 |
| Q99102 | mucin-4 | P09466 | glycodelin |
| P12235 | ADP/ATP translocase 1 | P37837 | transaldolase |
| P25774 | cathepsin S | P55058 | phospholipid transfer protein |
| Q8WXI7 | mucin-16 | P08603 | complement factor H |
| P31946 | 14-3-3 protein beta/alpha | P07360 | complement component 08 γ chain |
| Q9UBC5 | unconventional myosin-Ia | P14618 | pyruvate kinase |
| Q9Y376 | calcium-binding protein 39 | P06732 | creatine kinase M-type |
| P10909 | clusterin | P60953 | cell division control protein 42 |
| Q6P4A8 | phospholipase B-like 1 | P30048 | thioredoxin-dependent peroxide reductase, mitochondrial |
| Q9Y6N9 | harmonin | | |
| P61604 | 10 kDa HSP, mitochondrial | P29401 | transketolase |
| P07357 | complement component C8 α chain | Q8IWL2 | pulmonary surfactant-associated protein |
| Q9HCY8 | protein S100-A14 | O75367 | core histone macro-H2A.1 |
| Q92824 | proprotein convertase subtilisin | Q969X1 | protein lifeguard 3 |
| P62873 | guanine nucleotide-binding protein G(I)/G(S)/G(T) subunit beta-1 | O15551 | claudin-3 |
| | | Q92484 | acid sphingomyelinase-like phosphodiesterase 3a |
| Q14CN4 | keratin, type II cytoskeletal 72 | | |
| P09960 | leukotriene A-4 hydrolase | Q16891 | MICOS complex subunit Mic60 |
| P51688 | N-sulphoglucosamine sulphohydrolase | P09668 | pro-cathepsin H |
| P00813 | adenosine deaminase | P43234 | cathepsin O |
| P78417 | glutathione S-transferase omega-1 | P00558 | phosphoglycerate kinase 1 |
| Q5JS37 | NHL repeat-containing protein 3 | Q8TBG9 | synaptoporin |
| P07602 | prosaposin | P56199 | integrin alpha-1 |
| Q01970 | 1-phosphatidylinositol 4,5-bisphosphate phosphodiesterase | P02452 | collagen alpha-1(I) chain |
| | | P13284 | gamma-interferon-inducible lysosomal thiol reductase |
| A0A0C4DH68 | immunoglobulin kappa variable 2-24 | | |
| Q01628 | interferon-induced transmembrane protein 3 | P05783 | keratin, type I cytoskeletal 18 |
| | | P43353 | aldehyde dehydrogenase family 3 member B1 |
| Q96JP2 | unconventional myosin-XVB | | |
| P32119 | peroxiredoxin-2 | Q6P5W5 | zinc transporter ZIP4 |
| P16671 | platelet glycoprotein 4 | P07098-3 | gastric triacylglycerol lipase |
| P21980 | protein-glutamine gamma-glutamyltransferase 2 | P13798 | acylamino-acid-releasing enzyme |
| | | P08833 | insulin-like growth factor-binding protein |
| P50395 | Rab GDP dissociation inhibitor beta | P07237 | protein disulfide-isomerase |
| A0A0A0MT36 | immunoglobulin kappa variable 6D-21 | P18206 | vinculin |
| P23528 | cofilin | P06870 | kallikrein |
| A0A0C4DH24 | immunoglobulin kappa variable 6-21 | Q9H190 | syntenin |
| Q14766 | latent-transforming growth factor beta-binding protein 1 | Q13126 | S-methyl-5'-thioadenosine phosphorylase |
| | | P29972 | aguaporin |
| P51148 | Ras-related protein Rab-5C | | |

Shown are descriptions and Uniprot ID of proteins with MS sumPEP scores of 8.1 to 5.4.

| UniProt ID | Description | UniProt ID | Description |
|---|---|---|---|
| P11234 | Ras-related protein Ral-B | P14384 | carboxypeptidase M |
| O75340 | programmed cell death protein 6 | P08238 | heat shock protein HSP 90-beta |
| P35247 | pulmonary surfactant-associated protein D | Q13443 | disintegrin and metalloproteinase domain-containing protein 9 |
| Q14651 | plastin-1 | P04216 | thy-1 membrane glycoprotein |
| O15484 | calpain-5 | A0A0C4DH34 | immunoglobulin heavy variable 4-28 |
| P05062 | fructose-bisphosphate aldolase B | P32926 | desmoglein-3 |
| Q9H444 | charged multivesicular body protein 4b | P63000 | Ras-related C3 botulinum toxin substrate 1 |
| P01714 | immunoglobulin lambda variable 3-19 | | |
| Q2WGJ9 | fer-1-like protein 6 | Q96RF0 | sorting nexin-18 |
| P55290 | cadherin-13 | P00918 | carbonic anhydrase 2 |
| Q8WTV0 | scavenger receptor class B member 1 | Q08722 | leukocyte surface antigen CD47 |
| P27701 | CD82 antigen | P05451 | lithostathine-1-alpha |
| Q16769 | glutaminyl-peptide cyclotransferase | P09467 | fructose-1,6-bisphosphatase 1 |
| Q9HC38 | glyoxalase domain-containing protein | P16278 | beta-galactosidase |
| P52565 | rho GDP-dissociation inhibitor 1 | A0A0C4DH33 | immunoglobulin heavy variable 1-24 |
| P14618 | pyruvate kinase | P29218 | inositol monophosphatase 1 |
| P36955 | pigment epithelium-derived factor | P35606 | coatomer subunit beta |
| O00560 | syntenin-1 | Q16706 | alpha-mannosidase 2 |
| P0DOX3 | immunoglobulin delta heavy chain | Q16820 | meprin A subunit beta |

ETABLE 16-continued

Proteins Identified in Preterm Gut Lumen (N = 635)

| UniProt ID | Description | UniProt ID | Description |
|---|---|---|---|
| P07108 | acyl-CoA-binding protein | Q14126 | desmoglein-2 |
| P27169 | serum paraoxonase/arylesterase 1 | P84243 | histone H3.3 |
| Q14112 | nidogen-2 | P22304 | iduronate 2-sulfatase |
| Q9UBI6 | guanine nucleotide-binding protein g(i)/g(s)/g(o) subunit gamma-12 | P01703 | immunoglobulin lambda variable 1-40 |
| A0A075B6K0 | immunoglobulin lambda variable 3-16 | O95967 | EGF-containing fibulin-like extracellular matrix protein 2 |
| P01706 | immunoglobulin lambda variable 2-11 | P22079 | lactoperoxidase |
| Q8WW52 | protein FAM151A | P32189 | glycerol kinase |
| Q9NQ38 | serine protease inhibitor Kazal-type 5 | P06753 | tropomyosin alpha-3 chain |
| P02647 | apolipoprotein A-I | O00161 | synaptosomal-associated protein 23 |
| P07988 | pulmonary surfactant-associated protein B | P28074 | proteasome subunit beta type-5 |
| P12931 | proto-oncogene tyrosine-protein kinase Src | P16083 | ribosyldihydronicotinamide dehydrogenase |
| Q9UGT4 | sushi domain-containing protein 2 | Q1EHB4 | sodium-coupled monocarboxylate transporter 2 |
| Q9UBP4 | dickkopf-related protein 3 | O95274 | Iy6/PLAUR domain-containing protein |
| P11217 | glycogen phosphorylase, muscle form | P35556 | fibrillin-2 |
| P04080 | cystatin-B | Q6PIF6 | unconventional myosin-VIIb |
| P28072 | proteasome subunit beta type-6 | Q02505 | mucin-3A |
| Q9BRF8 | serine/threonine-protein phosphatase | Q5SRE5 | nucleoporin NUP188 homolog |
| P56470 | galectin-4 | P01215 | glycoprotein hormones alpha chain |
| Q86XR7 | TIR domain-containing adapter molecule 2 | Q15323 | keratin, type I cuticular Ha1 |
| | | P11021 | 78 kDa glucose-regulated protein |
| Q86UP6 | CUB and zona pellucida-like domain-containing protein 1 | Q12841 | follistatin-related protein 1 |
| | | P02511 | alpha-crystallin B chain |
| O75298 | reticulon-2 | | |

Shown are descriptions and Uniprot ID of proteins with MS sumPEP scores of 5.4 to 2.9.

| UniProt ID | Description | UniProt ID | Description |
|---|---|---|---|
| P02792 | ferritin light chain | Q8N5I2 | arrestin domain-containing protein 1 |
| P59665 | neutrophil defensin 1 | P19021 | peptidyl-glycine alpha-amidating monooxygenase |
| Q9Y6W3 | calpain-7 | | |
| P35243 | recoverin | P80370 | protein delta homolog 1 |
| B0FP48 | uroplakin-3b-like protein 1 | Q16881 | thioredoxin reductase 1, cytoplasmic |
| P63098 | calcineurin subunit B type 1 | Q96P63 | serpin B12 |
| P04075 | fructose-bisphosphate aldolase A | P05164 | myeloperoxidase |
| A0A075B6H9 | immunoglobulin lambda variable 4-69 | O94832 | unconventional myosin-I |
| O75351 | vacuolar protein sorting-associated protein 4B | Q9Y6E0 | serine/threonine-protein kinase 24 |
| | | P50120 | retinol-binding protein 2 |
| P15924 | desmoplakin | P23109 | AMP deaminase 1 |
| P40926 | malate dehydrogenase, mitochondrial | P01033 | metalloproteinase inhibitor 1 |
| Q7Z404 | transmembrane channel-like protein | Q7L5L3 | lysophospholipase D GDPD3 |
| P06681 | complement C2 | Q02487 | desmocollin-2 |
| Q9UM44 | HERV-H LTR-associating protein 2 | Q6UXV4 | MICOS complex subunit MIC27 |
| A5D6W6 | fat storage-inducing transmembrane protein 1 | Q9H1C7 | cysteine-rich and transmembrane domain-containing protein 1 |
| Q96C23 | aldose 1-epimerase | Q99816 | tumor susceptibility gene 101 protein |
| P29279 | connective tissue growth factor | O00115 | deoxyribonuclease-2-alpha |
| O95436 | sodium-dependent phosphate transport protein 2B | P13473 | lysosome-associated membrane glycoprotein 2 |
| Q8NCW5 | NAD(P)H-hydrate epimerase | A0A0J9YX35 | immunoglobulin heavy variable 3-64D |
| P35080 | profilin-2 | P61204 | ADP-ribosylation factor 3 |
| O00462 | beta-mannosidase | O96009 | napsin-A |
| Q16787 | laminin subunit alpha-3 | P50443 | sulfate transporter |
| P01709 | immunoglobulin lambda variable 2-8 | P55064 | aquaporin-5 |
| P08670 | vimentin | A0A0A0MS14 | immunoglobulin heavy variable 1-45 |
| P06703 | protein S100-A6 | Q99436 | proteasome subunit beta type-7 |
| O75015 | low affinity immunoglobulin gamma Fc region receptor III-B | P11717 | cation-independent mannose-6-phosphate receptor |
| Q9BXD5 | N-acetylneuraminate lyase | P48637 | glutathione synthetase |
| P08134 | rho-related GTP-binding protein RhoC | Q9H0E2 | Toll-interacting protein |
| P54727 | UV excision repair protein RAD23 homolog B | P52758 | 2-iminobutanoate/2-iminopropanoate deaminase |
| Q5QNW6 | histone H2B type 2-F | Q9UBC9 | small proline-rich protein 3 |
| P27449 | V-type proton ATPase 16 kDa proteolipid subunit | A0A075B6J9 | immunoglobulin lambda variable 2-18 |
| | | P46459 | vesicle-fusing ATPase |
| O15145 | actin-related protein 2/3 complex subunit 3 | P62330 | ADP-ribosylation factor 6 |
| | | A0A075B6I0 | immunoglobulin lambda variable 8-61 |
| Q9UKN1 | mucin-12 | P17948 | vascular endothelial growth factor receptor 1 |
| O60235 | transmembrane protease serine 11D | | |
| O75629 | protein CREG1 | | |
| P99999 | cytochrome c | | |

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A method for determining the prognosis of necrotizing enterocolitis (NEC) in an infant, the method comprising:
    a) fitting a Markov model using a two state transition matrix and propensity values determined for a plurality of subjects, wherein the two state transition matrix comprises a first state and a second state, wherein the first state comprises a non-necrotizing enterocolitis status, wherein the second state comprises a necrotizing enterocolitis status, wherein a propensity value is a function of intestinal Alkaline Phosphatase (iAP) activity values and the amount of iAP found in a stool sample;
    b) using a propensity value of the infant and the fitted Markov model to estimate a probability of transitioning from the first state to the second state, wherein the fitted model indicates that an increased propensity level of the infant significantly increases the probability of transitioning from the first state to the second state;
    c) Identifying a propensity value of the infant that is greater than or equal to a threshold value of about 0.5, and treating the infant wherein the treating comprises withholding oral feeding, administering an antibiotic, a probiotic, an intravenous fluid, an iAP replacement composition, a small molecule effector of catalytic activity, an anti-inflammatory agent, parenteral or intravenous nutrition, a biologic, or a combination thereof.

2. The method of claim 1, wherein a propensity value comprises a product of a first value and a second value, wherein the first value comprises one (1) minus a first ratio, wherein the first ratio comprise an iAP activity value of a subject of the plurality of subjects divided by a maximum iAP activity value observed among the plurality of subjects, wherein the second value comprises a second ratio, wherein the second ratio comprises an amount of iAP from an immunoassay value of a subject of the plurality of subjects divided by a maximum amount of iAP from an immunoassay value observed in a sample.

3. The method of claim 1, wherein a propensity value comprises a product of a first value and a second value, wherein the first value comprises one (1) minus an iAP activity value of a subject of the plurality of subjects, wherein the second value comprises an amount of iAP from an immunoassay value of a subject of the plurality of subjects.

4. The method of claim 2 or 3, wherein the immunoassay comprises a western blot, an ELISA, or immunoprecipitation.

* * * * *